United States Patent
Shmulevitz et al.

(10) Patent No.: US 12,295,977 B2
(45) Date of Patent: May 13, 2025

(54) ONCOLYTIC REOVIRUS

(71) Applicant: The Governors of the University of Alberta, Edmonton (CA)

(72) Inventors: Maya Shmulevitz, Edmonton (CA); Adil Mohamed, Edmonton (CA); Mary Hitt, Edmonton (CA); Wan Kong Yip, Edmonton (CA)

( * ) Notice: Subject to any disclaimer, the term of this patent is extended or adjusted under 35 U.S.C. 154(b) by 1268 days.

(21) Appl. No.: 16/979,458

(22) PCT Filed: Mar. 13, 2019

(86) PCT No.: PCT/CA2019/050312
§ 371 (c)(1),
(2) Date: Sep. 9, 2020

(87) PCT Pub. No.: WO2019/173919
PCT Pub. Date: Sep. 19, 2019

(65) Prior Publication Data
US 2021/0008136 A1   Jan. 14, 2021

Related U.S. Application Data

(60) Provisional application No. 62/642,881, filed on Mar. 14, 2018.

(51) Int. Cl.
| | | |
|---|---|---|
| A01K 35/00 | (2006.01) | |
| A61K 35/765 | (2015.01) | |
| A61P 35/00 | (2006.01) | |
| A61P 37/02 | (2006.01) | |
| C12N 7/00 | (2006.01) | |

(52) U.S. Cl.
CPC ............ A61K 35/765 (2013.01); A61P 35/00 (2018.01); A61P 37/02 (2018.01); C12N 7/00 (2013.01); *C12N 2720/12221* (2013.01); *C12N 2720/12222* (2013.01); *C12N 2720/12232* (2013.01)

(58) Field of Classification Search
CPC .................................................. A61K 35/765
See application file for complete search history.

(56) References Cited

FOREIGN PATENT DOCUMENTS

| WO | 2015070323 | 5/2015 | | |
|---|---|---|---|---|
| WO | WO-2015070323 A1 | * | 5/2015 | ............ A61K 31/337 |

OTHER PUBLICATIONS

Denzler et al. (1994, Virology, vol. 204, pp. 190-199) (Year: 1994).*
Cristi et al., 2023, Molecular Therapy: Oncolytics, vol. 31, pp. 1-20 (Year: 2023).*
Boehme et al. (2011) "Reverse Genetics for Mammalian Reovirus" Methods, 55:109-113.
Chappell et al. (1998) "Cleavage Susceptibility of Reovirus Attachment Protein σ1 during Proteolytic Disassembly of Virions Is Determined by a Sequence Polymorphism in the σ1 Neck" J. Virol. 72(10):8205-8213.
Clements et al. (2014) "Reovirus in cancer therapy: an evidence-based review" Oncolytic Virotherapy, 3:69-82.
Kobayashi et al. (2007) "A Plasmid-Based Reverse Genetics System for Animal Double Stranded RNA Viruses" Cell Host Microbe, 1:147-157.
Kobayashi et al. (2010) "An improved reverse genetics system for mammalian orthoreoviruses" Virology, 398:194-200.
Komoto et al. (2014) "A plasmid-based reverse genetics system for mammalian orthoreoviruses driven by a plasmid-ncoded T7 RNA polymerase" J. Virol. Methods, 196:36-39.
Mohamed et al. (2015) "Potential for improving potency and specificity of reovirus oncolysis with next-generation reovirus variants" Viruses, 7:6251-6278.
Mohamed et al. (2015) "Reduction of Virion-Associated 1 Fibers on Oncolytic Reovirus Variants Promotes Adaptation toward Tumorigenic Cells" J. Virol., 89:4319-4334.
Mohamed et al. (2019) "Genetic polymorphisms and molecular mechanisms mediating oncolytic potency of reovirus strains" doi: https://doi.org/10.1101/569301, 60 pp.
Phillips et al. (2018) "Current understanding of reovirus oncolysis mechanisms" Oncolytic Virother., 7:53-63.
Shmulevitz et al. (2012) "Reovirus Variants with Mutations in Genome Segments S1 and L2 Exhibit Enhanced Virion Infectivity and Superior Oncolysis" J. Virol., 86(13):7403-7413.
Trask et al. (2013) "Comparative Analysis of Reoviridae Reverse Genetics Methods" Methods, 59:199-206.

* cited by examiner

*Primary Examiner* — Anoop K Singh
*Assistant Examiner* — David A Montanari
(74) *Attorney, Agent, or Firm* — Bennett Jones LLP

(57) ABSTRACT

The present disclosure provides modified reovirus with improved characteristics, including improved oncolytic activity. Reoviruses provided herein include resortant viruses as well as viruses expressing mutated proteins. Methods of using such modified reovirus for inducing cancer cell lysis as well as treatment of cancer are disclosed. Also provided are methods tailored for induction of a desired cytokine profile in conjunction with, e.g., methods of inducing cancer cell oncolysis.

12 Claims, 33 Drawing Sheets
Specification includes a Sequence Listing.

σ1 levels on virions

Post-entry steps: protein expression

Virus titers

SEQUENCE LISTING

<160> NUMBER OF SEQ ID NOS: 38

<210> SEQ ID NO 1
<211> LENGTH: 455
<212> TYPE: PRT
<213> ORGANISM: Artificial sequence
<220> FEATURE:
<223> OTHER INFORMATION: synthetic sequence

<400> SEQUENCE: 1

```
Met Asp Pro Arg Leu Arg Glu Glu Val Val Arg Leu Ile Ile Ala Leu
1               5                   10                  15

Thr Ser Asp Asn Gly Ala Ser Leu Ser Lys Gly Leu Glu Ser Arg Val
            20                  25                  30

Ser Ala Leu Glu Lys Thr Ser Gln Ile His Ser Asp Thr Ile Leu Arg
        35                  40                  45

Ile Thr Gln Gly Leu Asp Asp Ala Asn Lys Arg Ile Ile Ala Leu Glu
    50                  55                  60

Gln Ser Arg Asp Asp Leu Val Ala Ser Val Ser Asp Ala Gln Leu Ala
65                  70                  75                  80

Ile Ser Arg Leu Glu Ser Ser Ile Gly Ala Leu Gln Thr Val Val Asn
                85                  90                  95

Gly Leu Asp Ser Ser Val Thr Gln Leu Gly Ala Arg Val Gly Gln Leu
            100                 105                 110

Glu Thr Gly Leu Ala Glu Leu Arg Val Asp His Asp Asn Leu Val Ala
        115                 120                 125
```

```
Arg Val Asp Thr Ala Glu Arg Asn Ile Gly Ser Leu Thr Thr Glu Leu
    130                 135                 140

Ser Thr Leu Thr Leu Arg Val Thr Ser Ile Gln Ala Asp Phe Glu Ser
145                 150                 155                 160

Arg Ile Ser Thr Leu Glu Arg Thr Ala Val Thr Ser Ala Gly Ala Pro
                165                 170                 175

Leu Ser Ile Arg Asn Asn Arg Met Thr Met Gly Leu Asn Asp Gly Leu
            180                 185                 190

Thr Leu Ser Gly Asn Asn Leu Ala Ile Arg Leu Pro Gly Asn Thr Gly
        195                 200                 205

Leu Asn Ile Gln Asn Gly Gly Leu Gln Phe Arg Phe Asn Thr Asp Gln
    210                 215                 220

Phe Gln Ile Val Asn Asn Leu Thr Leu Lys Thr Thr Val Phe Asp
225                 230                 235                 240

Ser Ile Asn Ser Arg Ile Gly Ala Thr Glu Gln Ser Tyr Val Ala Ser
                245                 250                 255

Ala Val Thr Pro Leu Arg Leu Asn Ser Ser Thr Lys Val Leu Asp Met
            260                 265                 270

Leu Ile Asp Ser Ser Thr Leu Glu Ile Asn Ser Ser Gly Gln Leu Thr
        275                 280                 285

Val Arg Ser Thr Ser Pro Asn Leu Arg Tyr Pro Ile Ala Asp Val Ser
    290                 295                 300

Gly Gly Ile Gly Met Ser Pro Asn Tyr Arg Phe Arg Gln Ser Met Trp
305                 310                 315                 320

Ile Gly Ile Val Ser Tyr Ser Gly Ser Gly Leu Asn Trp Arg Val Gln
                325                 330                 335

Val Asn Ser Asp Ile Phe Ile Val Asp Asp Tyr Ile His Ile Cys Leu
            340                 345                 350

Pro Ala Phe Asp Gly Phe Ser Ile Ala Asp Gly Gly Asp Leu Ser Leu
        355                 360                 365

Asn Phe Val Thr Gly Leu Leu Pro Pro Leu Leu Thr Gly Asp Thr Glu
    370                 375                 380

Pro Ala Phe His Asn Asp Val Val Thr Tyr Gly Ala Gln Thr Val Ala
385                 390                 395                 400

Ile Gly Leu Ser Ser Gly Gly Ala Pro Gln Tyr Met Ser Lys Asn Leu
                405                 410                 415

Trp Val Glu Gln Trp Gln Asp Gly Val Leu Arg Leu Arg Val Glu Gly
            420                 425                 430

Gly Gly Ser Ile Thr His Ser Asn Ser Lys Trp Pro Ala Met Thr Val
        435                 440                 445

Ser Tyr Pro Arg Ser Phe Thr
    450                 455

<210> SEQ ID NO 2
<211> LENGTH: 418
<212> TYPE: PRT
<213> ORGANISM: Artificial sequence
<220> FEATURE:
<223> OTHER INFORMATION: synthetic sequence

<400> SEQUENCE: 2

Met Ala Arg Ala Ala Phe Leu Phe Lys Thr Val Gly Phe Gly Gly Leu
1               5                   10                  15

Gln Asn Val Pro Ile Asn Asp Glu Leu Ser Ser His Leu Leu Arg Ala
            20                  25                  30
```

```
Gly Asn Ser Pro Trp Gln Leu Thr Gln Phe Leu Asp Trp Ile Ser Leu
         35                  40                  45

Gly Arg Gly Leu Ala Thr Ser Ala Leu Val Pro Thr Ala Gly Ser Arg
 50                  55                  60

Tyr Tyr Gln Met Ser Cys Leu Leu Ser Gly Thr Leu Gln Ile Pro Phe
 65                  70                  75                  80

Arg Pro Asn His Arg Trp Gly Asp Ile Arg Phe Leu Arg Leu Val Trp
                 85                  90                  95

Ser Ala Pro Thr Leu Asp Gly Leu Val Val Ala Pro Pro Gln Val Leu
                100                 105                 110

Ala Gln Pro Ala Leu Gln Ala Gln Ala Asp Arg Val Tyr Asp Cys Asp
            115                 120                 125

Asp Tyr Pro Phe Leu Ala Arg Asp Pro Arg Phe Lys His Arg Val Tyr
        130                 135                 140

Gln Gln Leu Ser Ala Val Thr Leu Leu Asn Leu Thr Gly Phe Gly Pro
145                 150                 155                 160

Ile Ser Tyr Val Arg Val Asp Glu Asp Met Trp Ser Gly Asp Val Asn
                165                 170                 175

Gln Leu Leu Met Asn Tyr Phe Gly His Thr Phe Ala Glu Ile Ala Tyr
            180                 185                 190

Thr Leu Cys Gln Ala Ser Ala Asn Arg Pro Trp Glu Tyr Asp Gly Thr
        195                 200                 205

Tyr Ala Arg Met Thr Gln Ile Val Leu Ser Leu Phe Trp Leu Ser Tyr
    210                 215                 220

Val Gly Val Ile His Gln Gln Asn Thr Tyr Arg Thr Phe Tyr Phe Gln
225                 230                 235                 240

Cys Asn Arg Arg Gly Asp Ala Ala Glu Val Trp Ile Leu Ser Cys Ser
                245                 250                 255

Leu Asn His Ser Ala Gln Ile Arg Pro Gly Asn Arg Ser Leu Phe Val
            260                 265                 270

Met Pro Thr Ser Pro Asp Trp Asn Met Asp Val Asn Leu Ile Leu Ser
        275                 280                 285

Ser Thr Leu Thr Gly Cys Leu Cys Ser Gly Ser Gln Leu Pro Leu Ile
290                 295                 300

Asp Asn Asn Ser Val Pro Ala Val Ser Arg Asn Ile His Gly Trp Thr
305                 310                 315                 320

Gly Arg Ala Gly Asn Gln Leu His Gly Phe Gln Val Arg Arg Met Val
                325                 330                 335

Thr Glu Phe Cys Asp Arg Leu Arg Arg Asp Gly Val Met Thr Gln Ala
            340                 345                 350

Gln Gln Asn Gln Val Glu Ala Leu Ala Asp Gln Thr Gln Gln Phe Lys
        355                 360                 365

Arg Asp Lys Leu Glu Thr Trp Ala Arg Glu Asp Asp Gln Tyr Asn Gln
    370                 375                 380

Ala His Pro Asn Ser Thr Met Phe Arg Thr Lys Pro Phe Thr Asn Ala
385                 390                 395                 400

Gln Trp Gly Arg Gly Asn Thr Gly Ala Thr Ser Ala Ala Ile Ala Ala
                405                 410                 415

Leu Ile

<210> SEQ ID NO 3
<211> LENGTH: 366
<212> TYPE: PRT
<213> ORGANISM: Artificial sequence
```

<220> FEATURE:
<223> OTHER INFORMATION: synthetic sequence

<400> SEQUENCE: 3

Met Ala Ser Ser Leu Arg Ala Ala Ile Ser Lys Ile Lys Arg Asp Asp
1               5                   10                  15

Val Gly Gln Gln Val Cys Pro Asn Tyr Val Met Leu Arg Ser Ser Val
            20                  25                  30

Thr Thr Lys Val Val Arg Asn Val Val Glu Tyr Gln Ile Arg Thr Gly
        35                  40                  45

Gly Phe Phe Ser Cys Leu Ala Met Leu Arg Pro Leu Gln Tyr Ala Lys
    50                  55                  60

Arg Glu Arg Leu Leu Gly Gln Arg Asn Leu Glu Arg Ile Ser Thr Arg
65                  70                  75                  80

Asp Ile Leu Gln Thr Arg Asp Leu His Ser Leu Cys Met Pro Thr Pro
                85                  90                  95

Asp Ala Pro Met Ser Asn His Gln Ala Ser Thr Met Arg Glu Leu Ile
            100                 105                 110

Cys Ser Tyr Phe Lys Val Asp His Ala Asp Gly Leu Lys Tyr Ile Pro
        115                 120                 125

Met Asp Glu Arg Tyr Ser Pro Ser Ser Leu Ala Arg Leu Phe Thr Met
130                 135                 140

Gly Met Ala Gly Leu His Ile Thr Thr Glu Pro Ser Tyr Lys Arg Val
145                 150                 155                 160

Pro Ile Met His Leu Ala Ala Asp Leu Asp Cys Met Thr Leu Ala Leu
                165                 170                 175

Pro Tyr Met Ile Thr Leu Asp Gly Asp Thr Val Val Pro Val Ala Pro
            180                 185                 190

Thr Leu Ser Ala Glu Gln Leu Leu Asp Asp Gly Leu Lys Gly Leu Ala
        195                 200                 205

Cys Met Asp Ile Ser Tyr Gly Cys Glu Val Asp Ala Asn Ser Arg Pro
210                 215                 220

Ala Gly Asp Gln Ser Met Asp Ser Ser Arg Cys Ile Asn Glu Leu Tyr
225                 230                 235                 240

Cys Glu Glu Thr Ala Glu Ala Ile Cys Val Leu Lys Thr Cys Leu Val
                245                 250                 255

Leu Asn Cys Met Gln Phe Lys Leu Glu Met Asp Asp Leu Ala His Asn
            260                 265                 270

Ala Ala Glu Leu Asp Lys Ile Gln Met Met Ile Pro Phe Ser Glu Arg
        275                 280                 285

Val Phe Arg Met Ala Ser Ser Phe Ala Thr Ile Asp Ala Gln Cys Phe
    290                 295                 300

Arg Phe Cys Val Met Met Lys Asp Lys Asn Leu Lys Ile Asp Met Arg
305                 310                 315                 320

Glu Thr Thr Arg Leu Trp Thr Arg Ser Ala Ser Asp Ser Val Ala
                325                 330                 335

Thr Ser Ser Leu Ser Ile Ser Leu Asp Arg Gly Arg Trp Val Ala Ala
            340                 345                 350

Asp Ala Ser Asp Ala Arg Leu Leu Val Phe Pro Ile Arg Val
        355                 360                 365

<210> SEQ ID NO 4
<211> LENGTH: 365
<212> TYPE: PRT
<213> ORGANISM: Artificial sequence
<220> FEATURE:
<223> OTHER INFORMATION: synthetic sequence

<400> SEQUENCE: 4

```
Met Glu Val Cys Leu Pro Asn Gly His Gln Val Val Asp Leu Ile Asn
1               5                   10                  15

Asn Ala Phe Glu Gly Arg Val Ser Ile Tyr Ser Ala Gln Glu Gly Trp
            20                  25                  30

Asp Lys Thr Ile Ser Ala Gln Pro Asp Met Met Val Cys Gly Gly Ala
        35                  40                  45

Val Val Cys Met His Cys Leu Gly Val Val Gly Ser Leu Gln Arg Lys
50                  55                  60

Leu Lys His Leu Pro His His Arg Cys Asn Gln Gln Ile Arg His Gln
65                  70                  75                  80

Asp Tyr Val Asp Val Gln Phe Ala Asp Arg Val Thr Ala His Trp Lys
                85                  90                  95

Arg Gly Met Leu Ser Phe Val Ala Gln Met His Glu Met Met Asn Asp
            100                 105                 110

Val Ser Pro Asp Asp Leu Asp Arg Val Arg Thr Glu Gly Gly Ser Leu
        115                 120                 125

Val Glu Leu Asn Arg Leu Gln Val Asp Pro Asn Ser Met Phe Arg Ser
130                 135                 140

Ile His Ser Ser Trp Thr Asp Pro Leu Gln Val Val Asp Asp Leu Asp
145                 150                 155                 160

Thr Lys Leu Asp Gln Tyr Trp Thr Ala Leu Asn Leu Met Ile Asp Ser
                165                 170                 175

Ser Asp Leu Ile Pro Asn Phe Met Met Arg Asp Pro Ser His Ala Phe
            180                 185                 190

Asn Gly Val Lys Leu Lys Gly Asp Ala Arg Gln Thr Gln Phe Ser Arg
        195                 200                 205

Thr Phe Asp Ser Arg Ser Ser Leu Glu Trp Gly Val Met Val Tyr Asp
210                 215                 220

Tyr Ser Glu Leu Asp His Asp Pro Ser Lys Gly Arg Ala Tyr Arg Lys
225                 230                 235                 240

Glu Leu Val Thr Pro Ala Arg Asp Phe Gly His Gly Leu Ser His
                245                 250                 255

Tyr Ser Arg Ala Thr Thr Pro Ile Leu Gly Lys Met Pro Ala Val Phe
            260                 265                 270

Ser Gly Met Leu Thr Gly Asn Cys Lys Met Tyr Pro Phe Ile Lys Gly
        275                 280                 285

Thr Ala Lys Leu Lys Thr Val Arg Lys Leu Val Glu Ala Val Asn His
290                 295                 300

Ala Trp Gly Val Glu Lys Ile Arg Tyr Ala Leu Gly Pro Gly Gly Met
305                 310                 315                 320

Thr Gly Trp Tyr Asn Arg Thr Met Gln Gln Ala Pro Ile Val Leu Thr
                325                 330                 335

Pro Ala Ala Leu Thr Met Phe Pro Asp Thr Ile Lys Phe Gly Asp Leu
            340                 345                 350

Asn Tyr Pro Val Met Ile Gly Asp Pro Met Ile Leu Gly
        355                 360                 365
```

<210> SEQ ID NO 5
<211> LENGTH: 736
<212> TYPE: PRT
<213> ORGANISM: Artificial sequence
<220> FEATURE:
<223> OTHER INFORMATION: synthetic sequence

<400> SEQUENCE: 5

```
Met Ala Tyr Ile Ala Val Pro Ala Val Val Asp Ser Arg Ser Ser Glu
1               5                   10                  15

Ala Ile Gly Leu Leu Glu Ser Phe Gly Val Asp Ala Gly Ala Asp Ala
            20                  25                  30

Asn Asp Val Ser Tyr Gln Asp His Asp Tyr Val Leu Asp Gln Leu Gln
        35                  40                  45

Tyr Met Leu Asp Gly Tyr Glu Ala Gly Asp Val Ile Asp Ala Leu Val
    50                  55                  60

His Lys Asn Trp Leu His His Ser Val Tyr Cys Leu Leu Pro Pro Lys
65                  70                  75                  80

Ser Gln Leu Leu Glu Tyr Trp Lys Ser Asn Pro Ser Ala Ile Pro Asp
                85                  90                  95

Asn Val Asp Arg Arg Leu Arg Lys Arg Leu Met Leu Lys Lys Asp Leu
            100                 105                 110

Arg Lys Asp Asp Glu Tyr Asn Gln Leu Ala Arg Ala Phe Lys Ile Ser
            115                 120                 125

Asp Val Tyr Ala Pro Leu Ile Ser Ser Thr Thr Ser Pro Met Thr Met
        130                 135                 140

Ile Gln Asn Leu Asn Arg Gly Glu Ile Val Tyr Thr Thr Thr Asp Arg
145                 150                 155                 160

Val Ile Gly Ala Arg Ile Leu Leu Tyr Ala Pro Arg Lys Tyr Tyr Ala
                165                 170                 175

Ser Thr Leu Ser Phe Thr Met Thr Lys Cys Ile Ile Pro Phe Gly Lys
            180                 185                 190

Glu Val Gly Arg Val Pro His Ser Arg Phe Asn Val Gly Thr Phe Pro
            195                 200                 205

Ser Ile Ala Thr Pro Lys Cys Phe Val Met Ser Gly Val Asp Ile Glu
210                 215                 220

Ser Ile Pro Asn Glu Phe Ile Lys Leu Phe Tyr Gln Arg Val Lys Ser
225                 230                 235                 240

Val His Ala Asn Ile Leu Asn Asp Ile Ser Pro Gln Ile Val Ser Asp
                245                 250                 255

Met Ile Asn Arg Lys Arg Leu Arg Val His Thr Pro Ser Asp Arg Arg
            260                 265                 270

Ala Ala Gln Leu Met His Leu Pro Tyr His Val Lys Arg Gly Ala Ser
            275                 280                 285

His Val Asp Val Tyr Lys Val Asp Val Asp Met Leu Phe Glu Val
        290                 295                 300

Val Asp Val Ala Asp Gly Leu Arg Asn Val Ser Arg Lys Leu Thr Met
305                 310                 315                 320

His Thr Val Pro Val Cys Ile Leu Glu Met Leu Gly Ile Glu Ile Ala
                325                 330                 335

Asp Tyr Cys Ile Arg Gln Glu Asp Gly Met Leu Thr Asp Trp Phe Leu
            340                 345                 350

Leu Leu Thr Met Leu Ser Asp Gly Leu Thr Asp Arg Arg Thr His Cys
            355                 360                 365

Gln Tyr Leu Ile Asn Pro Ser Ser Val Pro Pro Asp Val Ile Leu Asn
        370                 375                 380

Ile Ser Ile Thr Gly Phe Ile Asn Arg His Thr Ile Asp Val Met Pro
385                 390                 395                 400
```

```
Asp Ile Tyr Asp Phe Val Lys Pro Ile Gly Ala Val Leu Pro Lys Gly
            405                 410                 415

Ser Phe Lys Ser Thr Ile Met Arg Val Leu Asp Ser Ile Ser Ile Leu
            420                 425                 430

Gly Ile Gln Ile Met Pro Arg Ala His Val Val Asp Ser Asp Glu Val
            435                 440                 445

Gly Glu Gln Met Glu Pro Thr Phe Glu Gln Ala Val Met Glu Ile Tyr
            450                 455                 460

Lys Gly Ile Ala Gly Val Asp Ser Leu Asp Asp Leu Ile Lys Trp Val
465                 470                 475                 480

Leu Asn Ser Asp Leu Ile Pro His Asp Asp Arg Leu Gly Gln Leu Phe
            485                 490                 495

Gln Ala Phe Leu Pro Leu Ala Lys Asp Leu Leu Ala Pro Met Ala Arg
            500                 505                 510

Lys Phe Tyr Asp Asn Ser Met Ser Glu Gly Arg Leu Leu Thr Phe Ser
            515                 520                 525

His Ala Asp Ser Glu Leu Leu Asn Ala Asn Tyr Phe Gly His Leu Leu
            530                 535                 540

Arg Leu Lys Ile Pro Tyr Ile Thr Glu Val Asn Leu Met Ile Arg Lys
545                 550                 555                 560

Asn Arg Glu Gly Gly Glu Leu Phe Gln Leu Val Leu Ser Tyr Leu Tyr
            565                 570                 575

Lys Met Tyr Ala Thr Ser Ala Gln Pro Lys Trp Phe Gly Ser Leu Leu
            580                 585                 590

Arg Leu Leu Ile Cys Pro Trp Leu His Met Glu Lys Leu Ile Gly Glu
            595                 600                 605

Ala Asp Pro Ala Ser Thr Ser Ala Glu Ile Gly Trp His Ile Pro Arg
            610                 615                 620

Glu Gln Leu Met Gln Asp Gly Trp Cys Gly Cys Glu Asp Gly Phe Ile
625                 630                 635                 640

Pro Tyr Val Ser Ile Arg Ala Pro Arg Leu Val Ile Glu Glu Leu Met
            645                 650                 655

Glu Lys Asn Trp Gly Gln Tyr His Ala Gln Val Ile Val Thr Asp Gln
            660                 665                 670

Leu Val Val Gly Glu Pro Arg Arg Val Ser Ala Lys Ala Val Ile Lys
            675                 680                 685

Gly Asn His Leu Pro Val Lys Leu Val Ser Arg Phe Ala Cys Phe Thr
            690                 695                 700

Leu Thr Ala Lys Tyr Glu Met Arg Leu Ser Cys Gly His Ser Thr Gly
705                 710                 715                 720

Arg Gly Ala Ala Tyr Ser Ala Arg Leu Ala Phe Arg Ser Asp Leu Ala
            725                 730                 735

<210> SEQ ID NO 6
<211> LENGTH: 708
<212> TYPE: PRT
<213> ORGANISM: Artificial sequence
<220> FEATURE:
<223> OTHER INFORMATION: synthetic sequence

<400> SEQUENCE: 6

Met Gly Asn Ala Ser Ser Ile Val Gln Thr Ile Asn Val Thr Gly Asp
1               5                   10                  15

Gly Asn Val Phe Lys Pro Ser Ala Glu Thr Ser Ser Thr Ala Val Pro
            20                  25                  30
```

```
Ser Leu Ser Leu Ser Pro Gly Met Leu Asn Pro Gly Gly Val Pro Trp
            35                  40                  45

Ile Ala Val Gly Asp Glu Thr Ser Val Thr Ser Pro Gly Ala Leu Arg
 50                  55                  60

Arg Met Thr Ser Lys Asp Ile Pro Asp Thr Ala Ile Ile Asn Thr Asp
 65                  70                  75                  80

Asn Ser Ser Gly Ala Val Pro Ser Glu Ser Ala Leu Val Pro Tyr Ile
                 85                  90                  95

Asp Glu Pro Leu Val Val Val Thr Glu His Ala Ile Thr Asn Phe Thr
            100                 105                 110

Lys Ala Glu Met Ala Leu Glu Phe Asn Arg Glu Phe Leu Asp Lys Met
            115                 120                 125

Arg Val Leu Ser Val Ser Pro Lys Tyr Ser Asp Leu Leu Thr Tyr Val
            130                 135                 140

Asp Cys Tyr Val Gly Val Ser Ala Arg Gln Ala Leu Asn Asn Phe Gln
145                 150                 155                 160

Lys Gln Val Pro Val Ile Thr Pro Thr Arg Gln Thr Met Tyr Val Asp
                165                 170                 175

Ser Ile Gln Ala Ala Leu Lys Ala Leu Glu Lys Trp Glu Ile Asp Leu
            180                 185                 190

Arg Val Ala Gln Thr Leu Leu Pro Thr Asn Val Pro Ile Gly Glu Val
            195                 200                 205

Ser Cys Pro Met Gln Ser Val Val Lys Leu Leu Asp Asp Gln Leu Pro
            210                 215                 220

Asp Asp Ser Leu Ile Arg Arg Tyr Pro Lys Glu Ala Ala Val Ala Leu
225                 230                 235                 240

Ala Lys Arg Asn Gly Gly Ile Gln Trp Met Asp Val Ser Glu Gly Thr
                245                 250                 255

Val Met Asn Glu Ala Val Asn Ala Val Ala Ala Ser Ala Leu Ala Pro
            260                 265                 270

Ser Ala Ser Ala Pro Pro Leu Glu Glu Lys Ser Lys Leu Thr Glu Gln
            275                 280                 285

Ala Met Asp Leu Val Thr Ala Ala Glu Pro Glu Ile Ile Ala Ser Leu
            290                 295                 300

Ala Pro Val Pro Ala Pro Val Phe Ala Ile Pro Pro Lys Pro Ala Asp
305                 310                 315                 320

Tyr Asn Val Arg Thr Leu Arg Ile Asp Glu Ala Thr Trp Leu Arg Met
                325                 330                 335

Ile Pro Lys Ser Met Asn Thr Pro Phe Gln Ile Gln Val Thr Asp Asn
            340                 345                 350

Thr Gly Thr Asn Trp His Leu Asn Leu Arg Gly Gly Thr Arg Val Val
            355                 360                 365

Asn Leu Asp Gln Ile Ala Pro Met Arg Phe Val Leu Asp Leu Gly Gly
            370                 375                 380

Lys Ser Tyr Lys Glu Thr Ser Trp Asp Pro Asn Gly Lys Lys Val Gly
385                 390                 395                 400

Phe Ile Val Phe Gln Ser Lys Ile Pro Phe Glu Leu Trp Thr Ala Ala
                405                 410                 415

Ser Gln Ile Gly Gln Ala Thr Val Val Asn Tyr Val Gln Leu Tyr Ala
            420                 425                 430

Glu Asp Ser Ser Phe Thr Ala Gln Ser Ile Ile Ala Thr Thr Ser Leu
            435                 440                 445
```

Ala Tyr Asn Tyr Glu Pro Glu Gln Leu Asn Lys Thr Asp Pro Glu Met
    450                 455                 460

Asn Tyr Tyr Leu Leu Ala Thr Phe Ile Asp Ser Ala Ala Ile Thr Pro
465                 470                 475                 480

Thr Asn Met Thr Gln Pro Asp Val Trp Asp Ala Leu Leu Thr Met Ser
                485                 490                 495

Pro Leu Ser Ala Gly Glu Val Thr Val Lys Gly Ala Val Val Ser Glu
                500                 505                 510

Val Val Pro Ala Asp Leu Ile Gly Ser Tyr Thr Pro Glu Ser Leu Asn
            515                 520                 525

Ala Ser Leu Pro Asn Asp Ala Ala Arg Cys Met Ile Asp Arg Ala Ser
530                 535                 540

Lys Ile Ala Glu Ala Ile Lys Ile Asp Asp Ala Gly Pro Asp Glu
545                 550                 555                 560

Tyr Ser Pro Asn Ser Val Pro Ile Gln Gly Gln Leu Ala Ile Ser Gln
                565                 570                 575

Leu Glu Thr Gly Tyr Gly Val Arg Ile Phe Asn Pro Lys Gly Ile Leu
                580                 585                 590

Ser Lys Ile Ala Ser Arg Ala Met Gln Ala Phe Ile Gly Asp Pro Ser
            595                 600                 605

Thr Ile Ile Thr Gln Ala Ala Pro Val Leu Ser Asp Lys Asn Asn Trp
610                 615                 620

Ile Ala Leu Ala Gln Gly Val Lys Thr Ser Leu Arg Thr Lys Ser Leu
625                 630                 635                 640

Ser Ala Gly Val Lys Thr Ala Val Ser Lys Leu Ser Ser Ser Glu Ser
                645                 650                 655

Ile Gln Asn Trp Thr Gln Gly Phe Leu Asp Lys Val Ser Ala His Phe
                660                 665                 670

Pro Ala Pro Lys Pro Asp Cys Pro Thr Ser Gly Asp Ser Gly Glu Ser
            675                 680                 685

Ser Asn Arg Arg Val Lys Arg Asp Ser Tyr Ala Gly Val Val Lys Arg
            690                 695                 700

Gly Tyr Thr Arg
705

<210> SEQ ID NO 7
<211> LENGTH: 721
<212> TYPE: PRT
<213> ORGANISM: Artificial sequence
<220> FEATURE:
<223> OTHER INFORMATION: synthetic sequence

<400> SEQUENCE: 7

Met Ala Ser Phe Lys Gly Phe Ser Ala Asn Thr Val Pro Val Ser Lys
1               5                   10                  15

Ala Lys Arg Asp Ile Ser Ser Leu Ala Ala Thr Pro Gly Leu Arg Ser
            20                  25                  30

Gln Ser Phe Thr Pro Ser Val Asp Met Ser Gln Ser Arg Glu Phe Leu
        35                  40                  45

Thr Lys Ala Ile Glu Gln Gly Ser Met Ser Ile Pro Tyr Gln His Val
    50                  55                  60

Asn Val Pro Lys Val Asp Arg Lys Val Val Ser Leu Val Val Arg Pro
65                  70                  75                  80

Phe Ser Ser Gly Ala Phe Ser Ile Ser Gly Val Ile Ser Pro Ala His
                85                  90                  95

```
Ala Tyr Leu Leu Glu Cys Leu Pro Gln Leu Glu Gln Ala Met Ala Phe
            100                 105                 110

Val Ala Ser Pro Glu Ser Phe Gln Ala Ser Asp Val Ala Lys Arg Phe
        115                 120                 125

Ala Ile Lys Pro Gly Met Ser Leu Gln Asp Ala Ile Thr Ala Phe Ile
    130                 135                 140

Asn Phe Val Ser Ala Met Leu Lys Met Thr Val Thr Arg Gln Asn Phe
145                 150                 155                 160

Asp Val Ile Val Ala Glu Ile Glu Arg Leu Ala Ser Thr Ser Val Ser
                165                 170                 175

Val Arg Thr Glu Glu Ala Lys Val Ala Asp Glu Glu Leu Met Leu Phe
            180                 185                 190

Gly Leu Asp His Arg Gly Pro Gln Gln Leu Asp Val Ser Asp Ala Lys
        195                 200                 205

Gly Ile Met Lys Ala Ala Asp Ile Gln Thr Thr His Asp Val His Leu
    210                 215                 220

Ala Pro Gly Val Gly Asn Ile Asp Pro Glu Ile Tyr Asn Glu Gly Arg
225                 230                 235                 240

Phe Met Phe Met Gln His Lys Pro Leu Ala Ala Asp Gln Ser Tyr Phe
                245                 250                 255

Thr Leu Glu Thr Ala Asp Tyr Phe Lys Ile Tyr Pro Thr Tyr Asp Glu
            260                 265                 270

His Asp Gly Arg Met Ala Asp Gln Lys Gln Ser Gly Leu Ile Leu Cys
        275                 280                 285

Thr Lys Asp Glu Val Leu Ala Glu Gln Thr Ile Phe Lys Leu Asp Ala
    290                 295                 300

Pro Asp Asp Lys Thr Val His Leu Leu Asp Arg Asp Asp His Val
305                 310                 315                 320

Val Ala Arg Phe Thr Lys Val Phe Ile Glu Asp Val Ala Pro Gly His
                325                 330                 335

His Ala Ala Gln Arg Ser Gly Gln Arg Ser Val Leu Asp Leu Tyr
            340                 345                 350

Ala Asn Thr Gln Val Ile Ser Ile Thr Ser Ala Ala Leu Lys Trp Val
        355                 360                 365

Val Lys His Gly Val Ser Asp Gly Ile Val Asn Arg Lys Asn Val Lys
    370                 375                 380

Val Cys Val Gly Phe Asp Pro Leu Tyr Thr Leu Ser Thr His Asn Gly
385                 390                 395                 400

Val Ser Leu Cys Ala Leu Leu Met Asp Glu Lys Leu Ser Val Leu Asn
                405                 410                 415

Ser Ala Cys Arg Met Thr Leu Arg Ser Leu Met Lys Thr Gly Arg Asp
            420                 425                 430

Val Asp Ala His Arg Ala Phe Gln Arg Val Leu Ser Gln Gly Tyr Thr
        435                 440                 445

Ser Leu Met Cys Tyr Tyr His Pro Ser Arg Lys Leu Ala Tyr Gly Glu
    450                 455                 460

Val Leu Phe Leu Glu Arg Ser Asn Asp Val Thr Asp Gly Ile Lys Leu
465                 470                 475                 480

Gln Leu Asp Ala Ser Arg Gln Cys His Glu Cys Pro Val Leu Gln Gln
                485                 490                 495

Lys Val Val Glu Leu Glu Lys Gln Ile Ile Met Gln Lys Ser Ile Gln
            500                 505                 510

Ser Asp Pro Thr Pro Val Ala Leu Gln Pro Leu Leu Ser Gln Leu Arg
```

-continued

```
                515                 520                 525
Glu Leu Ser Ser Glu Val Thr Arg Leu Gln Met Glu Leu Ser Arg Ala
            530                 535                 540
Gln Ser Leu Asn Ala Gln Leu Glu Ala Asp Val Lys Ser Ala Gln Ser
545                 550                 555                 560
Cys Ser Leu Asp Met Tyr Leu Arg His His Thr Cys Ile Asn Gly His
                565                 570                 575
Ala Lys Glu Asp Glu Leu Leu Asp Ala Val Arg Val Ala Pro Asp Val
            580                 585                 590
Arg Arg Glu Ile Met Glu Lys Arg Ser Glu Val Arg Gln Gly Trp Cys
            595                 600                 605
Glu Arg Ile Ser Lys Glu Ala Ala Lys Cys Gln Thr Val Ile Asp
            610                 615                 620
Asp Leu Thr Leu Met Asn Gly Lys Gln Ala Gln Glu Ile Thr Glu Leu
625                 630                 635                 640
Arg Asp Ser Ala Glu Lys Tyr Glu Lys Gln Ile Ala Glu Leu Val Ser
                645                 650                 655
Thr Ile Thr Gln Asn Gln Ile Thr Tyr Gln Gln Glu Leu Gln Ala Leu
                660                 665                 670
Val Ala Lys Asn Val Glu Leu Asp Ala Leu Asn Gln Arg Gln Ala Lys
            675                 680                 685
Ser Leu Arg Ile Thr Pro Ser Leu Leu Ser Ala Thr Pro Ile Asp Ser
            690                 695                 700
Val Asp Val Ala Asp Leu Ile Asp Phe Ser Val Pro Thr Asp Glu
705                 710                 715                 720
Leu
```

<210> SEQ ID NO 8
<211> LENGTH: 1267
<212> TYPE: PRT
<213> ORGANISM: Artificial sequence
<220> FEATURE:
<223> OTHER INFORMATION: synthetic sequence

<400> SEQUENCE: 8

```
Met Ser Ser Met Ile Leu Thr Gln Phe Gly Pro Phe Ile Glu Ser Ile
1               5                   10                  15
Ser Gly Ile Thr Asp Gln Ser Asn Asp Val Phe Glu Asp Ala Ala Lys
            20                  25                  30
Ala Phe Ser Met Phe Thr Arg Ser Asp Val Tyr Lys Ala Leu Asp Glu
        35                  40                  45
Ile Pro Phe Ser Asp Asp Ala Met Leu Pro Ile Pro Pro Thr Ile Tyr
    50                  55                  60
Thr Lys Pro Ser His Asp Ser Tyr Tyr Tyr Ile Asp Ala Leu Asn Arg
65                  70                  75                  80
Val Arg Arg Lys Thr Tyr Gln Gly Pro Asp Asp Val Tyr Val Pro Asn
                85                  90                  95
Cys Ser Ile Val Glu Leu Leu Glu Pro His Glu Thr Leu Thr Ser Tyr
            100                 105                 110
Gly Arg Leu Ser Glu Ala Ile Glu Asn Arg Ala Lys Asp Gly Asp Ser
        115                 120                 125
Gln Ala Arg Ile Ala Thr Thr Tyr Gly Arg Ile Ala Glu Ser Gln Ala
    130                 135                 140
Arg Gln Ile Lys Ala Pro Leu Glu Lys Phe Val Leu Ala Leu Leu Val
145                 150                 155                 160
```

```
Ala Glu Ala Gly Gly Ser Leu Tyr Asp Pro Val Leu Gln Lys Tyr Asp
            165                 170                 175

Glu Ile Pro Asp Leu Ser His Asn Cys Pro Leu Trp Cys Phe Arg Glu
            180                 185                 190

Ile Cys Arg His Ile Ser Gly Pro Leu Pro Asp Arg Ala Pro Tyr Leu
            195                 200                 205

Tyr Leu Ser Ala Gly Val Phe Trp Leu Met Ser Pro Arg Met Thr Ser
            210                 215                 220

Ala Ile Pro Pro Leu Leu Ser Asp Leu Val Asn Leu Ala Ile Leu Gln
225                 230                 235                 240

Gln Thr Ala Gly Leu Asp Pro Ser Leu Val Lys Leu Gly Val Gln Ile
            245                 250                 255

Cys Leu His Ala Ala Ala Ser Ser Tyr Ala Trp Phe Ile Leu Lys
            260                 265                 270

Thr Lys Ser Ile Phe Pro Gln Asn Thr Leu His Ser Met Tyr Glu Ser
            275                 280                 285

Leu Glu Gly Gly Tyr Cys Pro Asn Leu Glu Trp Leu Glu Pro Arg Ser
            290                 295                 300

Asp Tyr Lys Phe Met Tyr Met Gly Val Met Pro Leu Ser Ala Lys Tyr
305                 310                 315                 320

Ala Arg Ser Ala Pro Ser Asn Asp Lys Lys Ala Arg Glu Leu Gly Glu
            325                 330                 335

Lys Tyr Gly Leu Ser Ser Val Val Gly Glu Leu Arg Lys Arg Thr Lys
            340                 345                 350

Thr Tyr Val Lys His Asp Phe Ala Ser Val Arg Tyr Ile Arg Asp Ala
            355                 360                 365

Met Ala Cys Thr Ser Gly Ile Phe Leu Val Arg Thr Pro Thr Glu Thr
370                 375                 380

Val Leu Gln Glu Tyr Thr Gln Ser Pro Glu Ile Lys Val Pro Ile Pro
385                 390                 395                 400

Gln Lys Asp Trp Thr Gly Pro Ile Gly Glu Ile Arg Ile Leu Lys Asp
            405                 410                 415

Thr Thr Ser Ser Ile Ala Arg Tyr Leu Tyr Arg Thr Trp Tyr Leu Ala
            420                 425                 430

Ala Ala Arg Met Ala Ala Gln Pro Arg Thr Trp Asp Pro Leu Phe Gln
            435                 440                 445

Ala Ile Met Arg Ser Gln Tyr Val Thr Ala Arg Gly Gly Ser Gly Ala
450                 455                 460

Ala Leu Arg Glu Ser Leu Tyr Ala Ile Asn Val Ser Leu Pro Asp Phe
465                 470                 475                 480

Lys Gly Leu Pro Val Lys Ala Thr Lys Ile Phe Gln Ala Ala Gln
            485                 490                 495

Leu Ala Asn Leu Pro Phe Ser His Thr Ser Val Ala Ile Leu Ala Asp
            500                 505                 510

Thr Ser Met Gly Leu Arg Asn Gln Val Gln Arg Pro Arg Ser Ile
            515                 520                 525

Met Pro Leu Asn Val Pro Gln Gln Val Ser Ala Pro His Thr Leu
            530                 535                 540

Thr Ala Asp Tyr Ile Asn Tyr His Met Asn Leu Ser Thr Thr Ser Gly
545                 550                 555                 560

Ser Ala Val Ile Glu Lys Val Ile Pro Leu Gly Val Tyr Ala Ser Ser
            565                 570                 575
```

```
Pro Pro Asn Gln Ser Ile Asn Ile Asp Ile Ser Ala Cys Asp Ala Ser
            580                 585                 590

Ile Thr Trp Asp Phe Phe Leu Ser Val Ile Met Ala Ala Ile His Glu
        595                 600                 605

Gly Val Ala Ser Ser Ser Ile Gly Lys Pro Phe Met Gly Val Pro Ala
        610                 615                 620

Ser Ile Val Asn Asp Glu Ser Val Val Gly Val Arg Ala Ala Arg Pro
625                 630                 635                 640

Ile Ser Gly Met Gln Asn Met Ile Gln His Leu Ser Lys Leu Tyr Lys
                645                 650                 655

Arg Gly Phe Ser Tyr Arg Val Asn Asp Ser Phe Ser Pro Gly Asn Asp
            660                 665                 670

Phe Thr His Met Thr Thr Thr Phe Pro Ser Gly Ser Thr Ala Thr Ser
        675                 680                 685

Thr Glu His Thr Ala Asn Asn Ser Thr Met Met Glu Thr Phe Leu Thr
    690                 695                 700

Val Trp Gly Pro Glu His Thr Asp Asp Pro Asp Val Leu Arg Leu Met
705                 710                 715                 720

Lys Ser Leu Thr Ile Gln Arg Asn Tyr Val Cys Gln Gly Asp Asp Gly
                725                 730                 735

Leu Met Ile Ile Asp Gly Thr Thr Ala Gly Lys Val Asn Ser Glu Thr
            740                 745                 750

Ile Gln Lys Met Leu Glu Leu Ile Ser Lys Tyr Gly Glu Glu Phe Gly
        755                 760                 765

Trp Lys Tyr Asp Ile Ala Tyr Asp Gly Thr Ala Glu Tyr Leu Lys Leu
770                 775                 780

Tyr Phe Ile Phe Gly Cys Arg Ile Pro Asn Leu Ser Arg His Pro Ile
785                 790                 795                 800

Val Gly Lys Glu Arg Ala Asn Ser Ser Ala Glu Pro Trp Pro Ala
                805                 810                 815

Ile Leu Asp Gln Ile Met Gly Val Phe Phe Asn Gly Val His Asp Gly
            820                 825                 830

Leu Gln Trp Gln Arg Trp Ile Arg Tyr Ser Trp Ala Leu Cys Cys Ala
            835                 840                 845

Phe Ser Arg Gln Arg Thr Met Ile Gly Glu Ser Val Gly Tyr Leu Gln
850                 855                 860

Tyr Pro Met Trp Ser Phe Val Tyr Trp Gly Leu Pro Leu Val Lys Ala
865                 870                 875                 880

Phe Gly Ser Asp Pro Trp Ile Phe Ser Trp Tyr Met Pro Thr Gly Asp
            885                 890                 895

Leu Gly Met Tyr Ser Trp Ile Ser Leu Ile Arg Pro Leu Met Thr Arg
            900                 905                 910

Trp Met Val Ala Asn Gly Tyr Val Thr Asp Arg Cys Ser Pro Val Phe
        915                 920                 925

Gly Asn Ala Asp Tyr Arg Arg Cys Phe Asn Glu Leu Lys Leu Tyr Gln
930                 935                 940

Gly Tyr Tyr Met Ala Gln Leu Pro Arg Asn Pro Lys Lys Ser Gly Arg
945                 950                 955                 960

Ala Ala Pro Arg Glu Val Arg Glu Gln Phe Thr Gln Ala Leu Ser Asp
                965                 970                 975

Tyr Leu Leu Gln Asn Pro Glu Leu Lys Ser Arg Val Leu Arg Gly Arg
            980                 985                 990

Ser Glu Trp Glu Lys Tyr Gly Ala  Gly Ile Ile His Asn  Pro Pro Ser
```

|     |     |     |     |     | 995 |     |     |     | 1000 |     |     |     |     | 1005 |     |
| --- | --- | --- | --- | --- | --- | --- | --- | --- | --- | --- | --- | --- | --- | --- | --- |

```
Leu Phe Asp Val Pro His Lys Trp Tyr Gln Gly Ala Gln Glu Ala
    1010                1015                1020

Ala Ile Ala Thr Arg Glu Glu Leu Ala Glu Met Asp Glu Thr Leu
    1025                1030                1035

Met Arg Ala Arg Arg His Arg Tyr Ser Ser Phe Ser Lys Leu Leu
    1040                1045                1050

Glu Ala Tyr Leu Leu Val Lys Trp Arg Met Cys Glu Ala Arg Glu
    1055                1060                1065

Pro Ser Val Asp Leu Arg Leu Pro Leu Cys Ala Gly Ile Asp Pro
    1070                1075                1080

Leu Asn Ser Asp Pro Phe Leu Lys Met Val Ser Val Gly Pro Met
    1085                1090                1095

Leu Gln Ser Thr Arg Lys Tyr Phe Ala Gln Thr Leu Phe Met Ala
    1100                1105                1110

Lys Thr Val Ser Gly Leu Asp Val Asn Ala Ile Asp Ser Ala Leu
    1115                1120                1125

Leu Arg Leu Arg Thr Leu Gly Ala Asp Lys Lys Ala Leu Thr Ala
    1130                1135                1140

Gln Leu Leu Met Val Gly Leu Gln Glu Ser Glu Ala Asp Ala Leu
    1145                1150                1155

Ala Gly Lys Ile Met Leu Gln Asp Val Asn Thr Val Gln Leu Ala
    1160                1165                1170

Arg Val Val Asn Leu Ala Val Pro Asp Thr Trp Met Ser Leu Asp
    1175                1180                1185

Phe Asp Ser Met Phe Lys His His Val Lys Leu Leu Pro Lys Asp
    1190                1195                1200

Gly Arg His Leu Asn Thr Asp Ile Pro Pro Arg Met Gly Trp Leu
    1205                1210                1215

Arg Ala Ile Leu Arg Phe Leu Gly Ala Gly Met Val Met Thr Ala
    1220                1225                1230

Thr Gly Val Ala Val Asp Ile Tyr Leu Glu Asp Ile His Gly Gly
    1235                1240                1245

Gly Arg Ser Leu Gly Gln Arg Phe Met Thr Trp Met Arg Gln Glu
    1250                1255                1260

Gly Arg Ser Ala
    1265
```

<210> SEQ ID NO 9
<211> LENGTH: 1289
<212> TYPE: PRT
<213> ORGANISM: Artificial sequence
<220> FEATURE:
<223> OTHER INFORMATION: synthetic sequence

<400> SEQUENCE: 9

```
Met Ala Asn Val Trp Gly Val Arg Leu Ala Asp Ser Leu Ser Ser Pro
1               5                   10                  15

Thr Ile Glu Thr Arg Thr Arg Gln Tyr Thr Leu His Asp Leu Cys Ser
            20                  25                  30

Asp Leu Asp Ala Asn Pro Gly Arg Glu Pro Trp Lys Pro Leu Arg Asn
        35                  40                  45

Gln Arg Thr Asn Asn Ile Val Ala Val Gln Leu Phe Arg Pro Leu Gln
    50                  55                  60

Gly Leu Val Leu Asp Thr Gln Leu Tyr Gly Phe Pro Gly Ala Phe Asp
```

```
                    65                  70                  75                  80
Asp Trp Glu Arg Phe Met Arg Glu Lys Leu Arg Val Leu Lys Tyr Glu
                        85                  90                  95

Val Leu Arg Ile Tyr Pro Ile Ser Asn Tyr Ser Asn Glu His Val Asn
                100                 105                 110

Val Phe Val Ala Asn Ala Leu Val Gly Ala Phe Leu Ser Asn Gln Ala
            115                 120                 125

Phe Tyr Asp Leu Leu Pro Leu Leu Ile Ile Asn Asp Thr Met Ile Gly
        130                 135                 140

Asp Leu Leu Gly Thr Gly Ala Ser Leu Ser Gln Phe Gln Ser His
145                 150                 155                 160

Gly Asp Val Leu Glu Val Ala Ala Gly Arg Lys Tyr Leu Gln Met Glu
                165                 170                 175

Asn Tyr Ser Asn Asp Asp Asp Pro Pro Leu Phe Ala Lys Asp Leu
                180                 185                 190

Ser Asp Tyr Ala Lys Ala Phe Tyr Ser Asp Thr Tyr Glu Val Leu Asp
            195                 200                 205

Arg Phe Phe Trp Thr His Asp Ser Ser Ala Gly Val Leu Val His Tyr
        210                 215                 220

Asp Lys Pro Thr Asn Gly His His Tyr Leu Leu Gly Thr Leu Thr Gln
225                 230                 235                 240

Met Val Ser Ala Pro Pro Tyr Ile Ile Asn Ala Thr Asp Ala Met Leu
                245                 250                 255

Leu Glu Ser Cys Leu Glu Gln Phe Ser Ala Asn Val Arg Ala Arg Pro
                260                 265                 270

Ala Gln Pro Val Thr Arg Leu Asp Gln Cys Tyr His Leu Arg Trp Gly
            275                 280                 285

Ala Gln Tyr Val Gly Glu Asp Ser Leu Thr Tyr Arg Leu Gly Val Leu
        290                 295                 300

Ser Leu Leu Ala Thr Asn Gly Tyr Gln Leu Ala Arg Pro Ile Pro Arg
305                 310                 315                 320

Gln Leu Thr Asn Arg Trp Leu Ser Ser Phe Val Ser Gln Ile Met Ser
                325                 330                 335

Asp Gly Val Asn Glu Thr Pro Leu Trp Pro Gln Glu Arg Tyr Val Gln
                340                 345                 350

Ile Ala Tyr Asp Ser Pro Ser Val Val Asp Gly Ala Thr Gln Tyr Gly
            355                 360                 365

Tyr Val Arg Lys Asn Gln Leu Arg Leu Gly Met Arg Ile Ser Ala Leu
        370                 375                 380

Gln Ser Leu Ser Asp Thr Pro Ser Pro Val Gln Trp Leu Pro Gln Tyr
385                 390                 395                 400

Thr Ile Asp Gln Ala Ala Met Asp Glu Gly Asp Leu Met Val Ser Arg
                405                 410                 415

Leu Thr Gln Leu Pro Leu Arg Pro Asp Tyr Gly Asn Ile Trp Val Gly
                420                 425                 430

Asp Ala Leu Ser Tyr Tyr Val Asp Tyr Asn Arg Ser His Arg Val Val
            435                 440                 445

Leu Ser Ser Glu Leu Pro Gln Leu Pro Asp Thr Tyr Phe Asp Gly Asp
        450                 455                 460

Glu Gln Tyr Gly Arg Ser Leu Phe Ser Leu Ala Arg Lys Ile Gly Asp
465                 470                 475                 480

Arg Ser Leu Val Lys Asp Thr Ala Val Leu Lys His Ala Tyr Gln Ala
                485                 490                 495
```

```
Ile Asp Pro Asn Thr Gly Lys Glu Tyr Leu Arg Ser Arg Gln Ser Val
            500                 505                 510

Ala Tyr Phe Gly Ala Ser Ala Gly His Ser Gly Ala Asp Gln Pro Leu
            515                 520                 525

Val Ile Glu Pro Trp Ile Gln Gly Lys Ile Ser Gly Val Pro Pro Pro
            530                 535                 540

Ser Ser Val Arg Gln Phe Gly Tyr Asp Val Ala Arg Gly Ala Ile Val
545                 550                 555                 560

Asp Leu Ala Arg Pro Phe Pro Ser Gly Asp Tyr Gln Phe Val Tyr Ser
                565                 570                 575

Asp Val Asp Gln Val Val Asp Gly His Asp Asp Leu Ser Ile Ser Ser
            580                 585                 590

Gly Leu Val Glu Ser Leu Leu Ser Ser Cys Met His Ala Thr Ala Pro
            595                 600                 605

Gly Gly Ser Phe Val Val Lys Ile Asn Phe Pro Thr Arg Pro Val Trp
            610                 615                 620

His Tyr Ile Glu Gln Lys Ile Leu Pro Asn Ile Thr Ser Tyr Met Leu
625                 630                 635                 640

Ile Lys Pro Phe Val Thr Asn Asn Val Glu Leu Phe Phe Val Ala Phe
                645                 650                 655

Gly Val His Gln His Ser Ser Leu Thr Trp Thr Ser Gly Val Tyr Phe
                660                 665                 670

Phe Leu Val Asp His Phe Tyr Arg Tyr Glu Thr Leu Ser Thr Ile Ser
                675                 680                 685

Arg Gln Leu Pro Ser Phe Gly Tyr Val Asp Asp Gly Ser Ser Val Thr
            690                 695                 700

Gly Ile Glu Thr Ile Ser Ile Glu Asn Pro Gly Phe Ser Asn Met Thr
705                 710                 715                 720

Gln Ala Ala Arg Ile Gly Ile Ser Gly Leu Cys Ala Asn Val Gly Asn
                725                 730                 735

Ala Arg Lys Ser Ile Ala Ile Tyr Glu Ser His Gly Ala Arg Val Leu
                740                 745                 750

Thr Ile Thr Ser Arg Arg Ser Pro Ala Ser Ala Arg Arg Lys Ser Arg
            755                 760                 765

Leu Arg Tyr Leu Pro Leu Ile Asp Pro Arg Ser Leu Glu Val Gln Ala
770                 775                 780

Arg Thr Ile Leu Pro Ala Asp Pro Val Leu Phe Glu Asn Val Ser Gly
785                 790                 795                 800

Ala Ser Pro His Val Cys Leu Thr Met Met Tyr Asn Phe Glu Val Ser
                805                 810                 815

Ser Ala Val Tyr Asp Gly Asp Val Leu Asp Leu Gly Thr Gly Pro
            820                 825                 830

Glu Ala Lys Ile Leu Glu Leu Ile Pro Ala Thr Ser Pro Val Thr Cys
            835                 840                 845

Val Asp Ile Arg Pro Thr Ala Gln Pro Ser Gly Cys Trp Asn Val Arg
            850                 855                 860

Thr Thr Phe Leu Glu Leu Asp Tyr Leu Ser Asp Gly Trp Ile Thr Gly
865                 870                 875                 880

Val Arg Gly Asp Ile Val Thr Cys Met Leu Ser Leu Gly Ala Ala Ala
                885                 890                 895

Ala Gly Lys Ser Met Thr Phe Asp Ala Ala Phe Gln Gln Leu Ile Lys
            900                 905                 910
```

```
Val Leu Ser Lys Ser Thr Ala Asn Val Val Leu Val Gln Val Asn Cys
        915                 920                 925

Pro Thr Asp Val Val Arg Ser Ile Lys Gly Tyr Leu Glu Ile Asp Ser
930                 935                 940

Thr Asn Lys Arg Tyr Arg Phe Pro Lys Phe Gly Arg Asp Glu Pro Tyr
945                 950                 955                 960

Ser Asp Met Asp Ala Leu Glu Lys Ile Cys Arg Thr Ala Trp Pro Asn
                965                 970                 975

Cys Ser Ile Thr Trp Val Pro Leu Ser Tyr Asp Leu Arg Trp Thr Arg
            980                 985                 990

Leu Ala Leu Leu Glu Ser Thr Thr Leu Ser Ser Ala Ser Ile Arg Ile
            995                 1000                1005

Ala Glu Leu Met Tyr Lys Tyr Met Pro Ile Met Arg Ile Asp Ile
    1010                1015                1020

His Gly Leu Pro Met Glu Lys Arg Gly Asn Phe Ile Val Gly Gln
    1025                1030                1035

Asn Cys Ser Leu Val Ile Pro Gly Phe Asn Ala Gln Asp Val Phe
    1040                1045                1050

Asn Cys Tyr Phe Asn Ser Ala Leu Ala Phe Ser Thr Glu Asp Val
    1055                1060                1065

Asn Ala Ala Met Ile Pro Gln Val Ser Ala Gln Phe Asp Ala Thr
    1070                1075                1080

Lys Gly Glu Trp Thr Leu Asp Met Val Phe Ser Asp Ala Gly Ile
    1085                1090                1095

Tyr Thr Met Gln Ala Leu Val Gly Ser Asn Ala Asn Pro Val Ser
    1100                1105                1110

Leu Gly Ser Phe Val Val Asp Ser Pro Asp Val Asp Ile Thr Asp
    1115                1120                1125

Ala Trp Pro Ala Gln Leu Asp Phe Thr Ile Ala Gly Thr Asp Val
    1130                1135                1140

Asp Ile Thr Val Asn Pro Tyr Tyr Arg Leu Met Thr Phe Val Arg
    1145                1150                1155

Ile Asp Gly Gln Trp Gln Ile Ala Asn Pro Asp Lys Phe Gln Phe
    1160                1165                1170

Phe Ser Ser Ala Ser Gly Thr Leu Val Met Asn Val Lys Leu Asp
    1175                1180                1185

Ile Ala Asp Lys Tyr Leu Leu Tyr Tyr Ile Arg Asp Val Gln Ser
    1190                1195                1200

Arg Asp Val Gly Phe Tyr Ile Gln His Pro Leu Gln Leu Leu Asn
    1205                1210                1215

Thr Ile Thr Leu Pro Thr Asn Glu Asp Leu Phe Leu Ser Ala Pro
    1220                1225                1230

Asp Met Arg Glu Trp Ala Val Lys Glu Ser Gly Asn Thr Ile Cys
    1235                1240                1245

Ile Leu Asn Ser Gln Gly Phe Val Leu Pro Gln Asp Trp Asp Val
    1250                1255                1260

Leu Thr Asp Thr Ile Ser Trp Ser Pro Ser Ile Pro Thr Tyr Ile
    1265                1270                1275

Val Pro Pro Gly Asp Tyr Thr Leu Thr Pro Leu
    1280                1285

<210> SEQ ID NO 10
<211> LENGTH: 1275
<212> TYPE: PRT
```

<213> ORGANISM: Artificial sequence
<220> FEATURE:
<223> OTHER INFORMATION: synthetic sequence

<400> SEQUENCE: 10

```
Met Lys Arg Ile Pro Arg Lys Thr Lys Gly Lys Ser Ser Gly Lys Gly
1               5                   10                  15

Asn Asp Ser Thr Glu Arg Ala Asp Asp Gly Ser Ser Gln Leu Arg Asp
            20                  25                  30

Lys Gln Asn Asn Lys Ala Gly Pro Ala Thr Thr Glu Pro Gly Thr Ser
        35                  40                  45

Asn Arg Glu Gln Tyr Lys Ala Arg Pro Gly Ile Ala Ser Val Gln Arg
    50                  55                  60

Ala Thr Glu Ser Ala Glu Met Pro Met Lys Asn Asn Asp Glu Gly Thr
65                  70                  75                  80

Pro Asp Lys Lys Gly Asn Thr Lys Gly Asp Leu Val Asn Glu His Ser
                85                  90                  95

Glu Ala Lys Asp Glu Ala Asp Glu Ala Thr Lys Lys Gln Ala Lys Asp
            100                 105                 110

Thr Asp Lys Ser Lys Ala Gln Val Thr Tyr Ser Asp Thr Gly Ile Asn
        115                 120                 125

Asn Ala Asn Glu Leu Ser Arg Ser Gly Asn Val Asp Asn Glu Gly Gly
    130                 135                 140

Ser Asn Gln Lys Pro Met Ser Thr Arg Ile Ala Glu Ala Thr Ser Ala
145                 150                 155                 160

Ile Val Ser Lys His Pro Ala Arg Val Gly Leu Pro Pro Thr Ala Ser
                165                 170                 175

Ser Gly His Gly Tyr Gln Cys His Val Cys Ser Ala Val Leu Phe Ser
            180                 185                 190

Pro Leu Asp Leu Asp Ala His Val Ala Ser His Gly Leu His Gly Asn
        195                 200                 205

Met Thr Leu Thr Ser Ser Asp Ile Gln Arg His Ile Thr Glu Phe Ile
    210                 215                 220

Ser Ser Trp Gln Asn His Pro Ile Val Gln Val Ser Ala Asp Val Glu
225                 230                 235                 240

Asn Lys Lys Thr Ala Gln Leu Leu His Ala Asp Thr Pro Arg Leu Val
                245                 250                 255

Thr Trp Asp Ala Gly Leu Cys Thr Ser Phe Lys Ile Val Pro Ile Val
            260                 265                 270

Pro Ala Gln Val Pro Gln Asp Val Leu Ala Tyr Thr Phe Phe Thr Ser
        275                 280                 285

Ser Tyr Ala Ile Gln Ser Pro Phe Pro Glu Ala Ala Val Ser Arg Ile
    290                 295                 300

Val Val His Thr Arg Trp Ala Ser Asn Val Asp Phe Asp Arg Asp Ser
305                 310                 315                 320

Ser Val Ile Met Ala Pro Pro Thr Glu Asn Asn Ile His Leu Phe Lys
                325                 330                 335

Gln Leu Leu Asn Thr Glu Thr Leu Ser Val Arg Gly Ala Asn Pro Leu
            340                 345                 350

Met Phe Arg Ala Asn Val Leu His Met Leu Leu Glu Phe Val Leu Asp
        355                 360                 365

Asn Leu Tyr Leu Asn Arg His Thr Gly Phe Ser Gln Asp His Thr Pro
    370                 375                 380

Phe Thr Glu Gly Ala Asn Leu Arg Ser Leu Pro Gly Pro Asp Ala Glu
```

```
                385                 390                 395                 400
Lys Trp Tyr Ser Ile Met Tyr Pro Thr Arg Met Gly Thr Pro Asn Val
                    405                 410                 415

Ser Lys Ile Cys Asn Phe Val Ala Ser Cys Val Arg Asn Arg Val Gly
                    420                 425                 430

Arg Phe Asp Arg Ala Gln Met Met Asn Gly Ala Met Ser Glu Trp Val
                    435                 440                 445

Asp Val Phe Glu Thr Ser Asp Ala Leu Thr Val Ser Ile Arg Gly Arg
                    450                 455                 460

Trp Met Ala Arg Leu Ala Arg Met Asn Ile Asn Pro Thr Glu Ile Glu
465                 470                 475                 480

Trp Ala Leu Thr Glu Cys Ala Gln Gly Tyr Val Thr Val Thr Ser Pro
                    485                 490                 495

Tyr Ala Pro Ser Val Asn Arg Leu Met Pro Tyr Arg Ile Ser Asn Ala
                    500                 505                 510

Glu Arg Gln Ile Ser Gln Ile Ile Arg Ile Met Asn Ile Gly Asn Asn
                    515                 520                 525

Ala Thr Val Ile Gln Pro Val Leu Gln Asp Ile Ser Val Leu Leu Gln
                    530                 535                 540

Arg Ile Ser Pro Leu Gln Ile Asp Pro Thr Ile Ile Ser Asn Thr Met
545                 550                 555                 560

Ser Thr Val Ser Glu Ser Thr Thr Gln Thr Leu Ser Pro Ala Ser Ser
                    565                 570                 575

Ile Leu Gly Lys Leu Arg Pro Ser Asn Ser Asp Phe Ser Ser Phe Arg
                    580                 585                 590

Val Ala Leu Ala Gly Trp Leu Tyr Asn Gly Val Val Thr Thr Val Ile
                    595                 600                 605

Asp Asp Ser Ser Tyr Pro Lys Asp Gly Gly Ser Val Thr Ser Leu Glu
                    610                 615                 620

Asn Leu Trp Asp Phe Phe Ile Leu Ala Leu Ala Leu Pro Leu Thr Thr
625                 630                 635                 640

Asp Pro Cys Ala Pro Val Lys Ala Phe Met Thr Leu Ala Asn Met Met
                    645                 650                 655

Val Gly Phe Glu Thr Ile Pro Met Asp Asn Gln Ile Tyr Thr Gln Ser
                    660                 665                 670

Arg Arg Ala Ser Ala Phe Ser Thr Pro His Thr Trp Pro Arg Cys Phe
                    675                 680                 685

Met Asn Ile Gln Leu Ile Ser Pro Ile Asp Ala Pro Ile Leu Arg Gln
                    690                 695                 700

Trp Ala Glu Ile Ile His Arg Tyr Trp Pro Asn Pro Ser Gln Ile Arg
705                 710                 715                 720

Tyr Gly Ala Pro Asn Val Phe Gly Ser Ala Asn Leu Phe Thr Pro Pro
                    725                 730                 735

Glu Val Leu Leu Leu Pro Ile Asp His Gln Pro Ala Asn Val Thr Thr
                    740                 745                 750

Pro Thr Leu Asp Phe Thr Asn Glu Leu Thr Asn Trp Arg Ala Arg Val
                    755                 760                 765

Cys Glu Leu Met Lys Asn Leu Val Asp Asn Gln Arg Tyr Gln Pro Gly
                    770                 775                 780

Trp Thr Gln Ser Leu Val Ser Ser Met Arg Gly Thr Leu Asp Lys Leu
785                 790                 795                 800

Lys Leu Ile Lys Ser Met Thr Pro Met Tyr Leu Gln Gln Leu Ala Pro
                    805                 810                 815
```

```
Val Glu Leu Ala Val Ile Ala Pro Met Leu Pro Phe Pro Phe Gln
            820                 825                 830

Val Pro Tyr Val Arg Leu Asp Arg Asp Arg Val Pro Thr Met Val Gly
            835                 840                 845

Val Thr Arg His Ser Arg Asp Thr Ile Thr Gln Pro Ala Leu Ser Leu
    850                 855                 860

Ser Thr Thr Asn Thr Thr Val Gly Val Pro Leu Ala Leu Asp Ala Arg
865                 870                 875                 880

Ala Ile Thr Val Ala Leu Leu Ser Gly Lys Tyr Pro Pro Asp Leu Val
                885                 890                 895

Thr Asn Val Trp Tyr Ala Asp Ala Ile Tyr Pro Met Tyr Ala Asp Thr
            900                 905                 910

Glu Val Phe Ser Asn Leu Gln Arg Asp Met Ile Thr Cys Glu Ala Val
            915                 920                 925

Gln Thr Leu Val Thr Leu Val Ala Gln Ile Ser Glu Thr Gln Tyr Pro
    930                 935                 940

Val Asp Arg Tyr Leu Asp Trp Ile Pro Ser Leu Arg Ala Ser Ala Ala
945                 950                 955                 960

Thr Ala Ala Thr Phe Ala Glu Trp Val Asn Thr Ser Met Lys Thr Ala
                965                 970                 975

Phe Asp Leu Ser Asp Met Leu Leu Glu Pro Leu Leu Ser Gly Asp Pro
            980                 985                 990

Arg Met Thr Gln Leu Ala Ile Gln Tyr Gln Gln Tyr Asn Gly Arg Thr
            995                 1000                1005

Phe Asn Ile Ile Pro Glu Met Pro Gly Ser Val Ile Ala Asp Cys
    1010                1015                1020

Val Gln Leu Thr Ala Glu Val Phe Asn His Glu Tyr Asn Leu Phe
    1025                1030                1035

Gly Ile Ala Arg Gly Asp Ile Ile Gly Arg Val Gln Ser Thr
    1040                1045                1050

His Leu Trp Ser Pro Leu Ala Pro Pro Asp Leu Val Phe Asp
    1055                1060                1065

Arg Asp Thr Pro Gly Val His Ile Phe Gly Arg Asp Cys Arg Ile
    1070                1075                1080

Ser Phe Gly Met Asn Gly Ala Ala Pro Met Ile Arg Asp Glu Thr
    1085                1090                1095

Gly Leu Met Val Pro Phe Glu Gly Asn Trp Ile Phe Pro Leu Ala
    1100                1105                1110

Leu Trp Gln Met Asn Thr Arg Tyr Phe Asn Gln Gln Phe Asp Ala
    1115                1120                1125

Trp Ile Lys Thr Gly Glu Leu Arg Ile Arg Ile Glu Met Gly Ala
    1130                1135                1140

Tyr Pro Tyr Met Leu His Tyr Tyr Asp Pro Arg Gln Tyr Ala Asn
    1145                1150                1155

Ala Trp Asn Leu Thr Ser Ala Trp Leu Glu Glu Ile Thr Pro Thr
    1160                1165                1170

Ser Ile Pro Ser Val Pro Phe Met Val Pro Ile Ser Ser Asp His
    1175                1180                1185

Asp Ile Ser Ser Ala Pro Ala Val Gln Tyr Ile Ile Ser Thr Glu
    1190                1195                1200

Tyr Asn Asp Arg Ser Leu Phe Cys Thr Asn Ser Ser Ser Pro Gln
    1205                1210                1215
```

```
Thr Ile Ala Gly Pro Asp Lys His Ile Pro Val Glu Arg Tyr Asn
    1220                1225                1230

Ile Leu Thr Asn Pro Asp Ala Pro Pro Thr Gln Ile Gln Leu Pro
    1235                1240                1245

Glu Val Val Asp Leu Tyr Asn Val Val Thr Arg Tyr Ala Tyr Glu
    1250                1255                1260

Thr Pro Pro Ile Thr Ala Val Val Met Gly Val Pro
    1265                1270                1275

<210> SEQ ID NO 11
<211> LENGTH: 455
<212> TYPE: PRT
<213> ORGANISM: Artificial sequence
<220> FEATURE:
<223> OTHER INFORMATION: synthetic sequence

<400> SEQUENCE: 11

Met Asp Pro Arg Leu Arg Glu Glu Val Val Arg Leu Ile Ala Leu
1               5                   10                  15

Thr Ser Asp Asn Gly Val Ser Leu Ser Lys Gly Leu Glu Ser Arg Val
                20                  25                  30

Ser Ala Leu Glu Lys Thr Ser Gln Ile His Ser Asp Thr Ile Leu Arg
            35                  40                  45

Ile Thr Gln Gly Leu Asp Asp Ala Asn Lys Arg Ile Ile Ala Leu Glu
    50                  55                  60

Gln Ser Arg Asp Asp Leu Val Ala Ser Val Ser Asp Ala Gln Leu Ala
65                  70                  75                  80

Ile Ser Arg Leu Glu Ser Ser Ile Gly Ala Leu Gln Thr Val Val Asn
                85                  90                  95

Gly Leu Asp Ser Ser Val Thr Gln Leu Gly Ala Arg Val Gly Gln Leu
            100                 105                 110

Glu Thr Gly Leu Ala Glu Leu Arg Val Asp His Asp Asn Leu Val Ala
    115                 120                 125

Arg Val Asp Thr Ala Glu Arg Asn Ile Gly Ser Leu Thr Thr Glu Leu
130                 135                 140

Ser Thr Leu Thr Leu Arg Val Thr Ser Ile Gln Ala Asp Phe Glu Ser
145                 150                 155                 160

Arg Ile Ser Thr Leu Glu Arg Thr Ala Val Thr Ser Ala Gly Ala Pro
                165                 170                 175

Leu Ser Ile Arg Asn Asn Arg Met Thr Met Gly Leu Asn Asp Gly Leu
            180                 185                 190

Thr Leu Ser Gly Asn Asn Leu Ala Ile Arg Leu Pro Gly Asn Thr Gly
    195                 200                 205

Leu Asn Ile Gln Asn Gly Gly Leu Gln Phe Arg Phe Asn Thr Asp Gln
210                 215                 220

Phe Gln Ile Val Asn Asn Asn Leu Thr Leu Lys Thr Thr Val Phe Asp
225                 230                 235                 240

Ser Ile Asn Ser Arg Ile Gly Ala Thr Glu Gln Ser Tyr Val Ala Ser
                245                 250                 255

Ala Val Thr Pro Leu Arg Leu Asn Ser Ser Thr Lys Val Leu Asp Met
            260                 265                 270

Leu Ile Asp Ser Ser Thr Leu Glu Ile Asn Ser Ser Gly Gln Leu Thr
    275                 280                 285

Val Arg Ser Thr Ser Pro Asn Leu Arg Tyr Pro Ile Ala Asp Val Ser
290                 295                 300
```

Gly Gly Ile Gly Met Ser Pro Asn Tyr Arg Phe Arg Gln Ser Met Trp
305                 310                 315                 320

Ile Gly Ile Val Ser Tyr Ser Gly Ser Gly Leu Asn Trp Arg Val Gln
            325                 330                 335

Val Asn Ser Asp Ile Phe Ile Val Asp Asp Tyr Ile His Ile Cys Leu
            340                 345                 350

Pro Ala Phe Asp Gly Phe Ser Ile Ala Asp Gly Gly Asp Leu Ser Leu
            355                 360                 365

Asn Phe Val Thr Gly Leu Leu Pro Pro Leu Leu Thr Gly Asp Thr Glu
            370                 375                 380

Pro Ala Phe His Asn Asp Val Val Thr Tyr Gly Ala Gln Thr Val Ala
385                 390                 395                 400

Ile Gly Leu Ser Ser Gly Gly Thr Pro Gln Tyr Met Ser Lys Asn Leu
            405                 410                 415

Trp Val Glu Gln Trp Gln Asp Gly Val Leu Arg Leu Arg Val Glu Gly
            420                 425                 430

Gly Gly Ser Ile Thr His Ser Asn Ser Lys Trp Pro Ala Met Thr Val
            435                 440                 445

Ser Tyr Pro Arg Ser Phe Thr
450                 455

<210> SEQ ID NO 12
<211> LENGTH: 418
<212> TYPE: PRT
<213> ORGANISM: Artificial sequence
<220> FEATURE:
<223> OTHER INFORMATION: synthetic sequence

<400> SEQUENCE: 12

Met Ala Arg Ala Ala Phe Leu Phe Lys Thr Val Gly Phe Gly Gly Leu
1               5                   10                  15

Gln Asn Val Pro Ile Asn Asp Glu Leu Ser Ser His Leu Leu Arg Ala
            20                  25                  30

Gly Asn Ser Pro Trp Gln Leu Thr Gln Phe Leu Asp Trp Ile Ser Leu
            35                  40                  45

Gly Arg Gly Leu Ala Thr Ser Ala Leu Val Pro Thr Ala Gly Ser Arg
        50                  55                  60

Tyr Tyr Gln Met Ser Cys Leu Leu Ser Gly Thr Leu Gln Ile Pro Phe
65                  70                  75                  80

Arg Pro Asn His Arg Trp Gly Asp Ile Arg Phe Leu Arg Leu Val Trp
                85                  90                  95

Ser Ala Pro Thr Leu Asp Gly Leu Val Val Ala Pro Pro Gln Val Leu
            100                 105                 110

Ala Gln Pro Ala Leu Gln Ala Gln Ala Asp Arg Val Tyr Asp Cys Asp
            115                 120                 125

Asp Tyr Pro Phe Leu Ala Arg Asp Pro Arg Phe Lys His Arg Val Tyr
        130                 135                 140

Gln Gln Leu Ser Ala Val Thr Leu Leu Asn Leu Thr Gly Phe Gly Pro
145                 150                 155                 160

Ile Ser Tyr Val Arg Val Asp Glu Asp Met Trp Ser Gly Asp Val Asn
                165                 170                 175

Gln Leu Leu Met Asn Tyr Phe Gly His Thr Phe Ala Glu Ile Ala Tyr
            180                 185                 190

Thr Leu Cys Gln Ala Ser Ala Asn Arg Pro Trp Glu Tyr Asp Gly Thr
            195                 200                 205

```
Tyr Ala Arg Met Thr Gln Ile Val Leu Ser Leu Phe Trp Leu Ser Tyr
    210                 215                 220

Val Gly Val Ile His Gln Gln Asn Thr Tyr Arg Thr Phe Tyr Phe Gln
225                 230                 235                 240

Cys Asn Arg Arg Gly Asp Ala Ala Glu Val Trp Ile Leu Ser Cys Ser
                245                 250                 255

Leu Asn His Ser Ala Gln Ile Arg Pro Gly Asn Arg Ser Leu Phe Val
            260                 265                 270

Met Pro Thr Ser Pro Asp Trp Asn Met Asp Val Asn Leu Ile Leu Ser
        275                 280                 285

Ser Thr Leu Thr Gly Cys Leu Cys Ser Gly Ser Gln Leu Pro Leu Ile
    290                 295                 300

Asp Asn Asn Ser Val Pro Ala Val Ser Arg Asn Ile His Gly Trp Thr
305                 310                 315                 320

Gly Arg Ala Gly Asn Gln Leu His Gly Phe Gln Val Arg Arg Met Val
                325                 330                 335

Thr Glu Phe Cys Asp Arg Leu Arg Arg Asp Gly Val Met Thr Gln Ala
            340                 345                 350

Gln Gln Asn Gln Val Glu Ala Leu Ala Asp Gln Thr Gln Gln Phe Lys
        355                 360                 365

Arg Asp Lys Leu Glu Thr Trp Ala Arg Glu Asp Asp Gln Tyr Asn Gln
    370                 375                 380

Ala His Pro Asn Ser Thr Met Phe Arg Thr Lys Pro Phe Thr Asn Ala
385                 390                 395                 400

Gln Trp Gly Arg Gly Asn Thr Gly Ala Thr Ser Ala Ala Ile Ala Ala
                405                 410                 415

Leu Ile

<210> SEQ ID NO 13
<211> LENGTH: 365
<212> TYPE: PRT
<213> ORGANISM: Artificial sequence
<220> FEATURE:
<223> OTHER INFORMATION: synthetic sequence

<400> SEQUENCE: 13

Met Glu Val Cys Leu Pro Asn Gly His Gln Val Val Asp Leu Ile Asn
1               5                   10                  15

Asn Ala Phe Glu Gly Arg Val Ser Ile Tyr Ser Ala Gln Glu Gly Trp
                20                  25                  30

Asp Lys Thr Ile Ser Ala Gln Pro Asp Met Met Val Cys Gly Gly Ala
            35                  40                  45

Val Val Cys Met His Cys Leu Gly Val Val Gly Ser Leu Gln Arg Lys
        50                  55                  60

Leu Lys His Leu Pro His His Arg Cys Asn Gln Gln Ile Arg His Gln
65                  70                  75                  80

Asp Tyr Val Asp Val Gln Phe Ala Asp Arg Val Thr Ala His Trp Lys
                85                  90                  95

Arg Gly Met Leu Ser Phe Val Ala Gln Met His Glu Met Met Asn Asp
            100                 105                 110

Val Ser Pro Asp Asp Leu Asp Arg Val Arg Thr Glu Gly Gly Ser Leu
        115                 120                 125

Val Glu Leu Asn Trp Leu Gln Val Asp Pro Asn Ser Met Phe Arg Ser
    130                 135                 140

Ile His Ser Ser Trp Thr Asp Pro Leu Gln Val Val Asp Asp Leu Asp
```

```
145                 150                 155                 160
Thr Lys Leu Asp Gln Tyr Trp Thr Ala Leu Asn Leu Met Ile Asp Ser
            165                 170                 175

Ser Asp Leu Ile Pro Asn Phe Met Met Arg Asp Pro Ser His Ala Phe
            180                 185                 190

Asn Gly Val Lys Leu Gly Gly Asp Ala Arg Gln Thr Gln Phe Ser Arg
            195                 200                 205

Thr Phe Asp Ser Arg Ser Ser Leu Glu Trp Gly Val Met Val Tyr Asp
            210                 215                 220

Tyr Ser Glu Leu Glu His Asp Pro Ser Lys Gly Arg Ala Tyr Arg Lys
225                 230                 235                 240

Glu Leu Val Thr Pro Ala Arg Asp Phe Gly His Phe Gly Leu Ser His
            245                 250                 255

Tyr Ser Arg Ala Thr Thr Pro Ile Leu Gly Lys Met Pro Ala Val Phe
            260                 265                 270

Ser Gly Met Leu Thr Gly Asn Cys Lys Met Tyr Pro Phe Ile Lys Gly
            275                 280                 285

Thr Ala Lys Leu Lys Thr Val Arg Lys Leu Val Glu Ala Val Asn His
            290                 295                 300

Ala Trp Gly Val Glu Lys Ile Arg Tyr Ala Leu Gly Pro Gly Gly Met
305                 310                 315                 320

Thr Gly Trp Tyr Asn Arg Thr Met Gln Gln Ala Pro Ile Val Leu Thr
            325                 330                 335

Pro Ala Ala Leu Thr Met Phe Pro Asp Thr Ile Lys Phe Gly Asp Leu
            340                 345                 350

Asn Tyr Pro Val Met Ile Gly Asp Pro Met Ile Leu Gly
            355                 360                 365

<210> SEQ ID NO 14
<211> LENGTH: 736
<212> TYPE: PRT
<213> ORGANISM: Artificial sequence
<220> FEATURE:
<223> OTHER INFORMATION: synthetic sequence

<400> SEQUENCE: 14

Met Ala Tyr Ile Ala Val Pro Ala Val Val Asp Ser Arg Ser Ser Glu
1               5                   10                  15

Ala Ile Gly Leu Leu Glu Ser Phe Gly Val Asp Ala Gly Ala Asp Ala
            20                  25                  30

Asn Asp Val Ser Tyr Gln Asp His Asp Tyr Val Leu Asp Gln Leu Gln
            35                  40                  45

Tyr Met Leu Asp Gly Tyr Glu Ala Gly Asp Val Ile Asp Ala Leu Val
            50                  55                  60

His Lys Asn Trp Leu His His Ser Val Tyr Cys Leu Leu Pro Pro Lys
65                  70                  75                  80

Ser Gln Leu Leu Glu Tyr Trp Lys Ser Asn Pro Ser Ala Ile Pro Asp
            85                  90                  95

Asn Val Asp Arg Arg Leu Arg Lys Arg Leu Met Leu Lys Lys Asp Leu
            100                 105                 110

Arg Lys Asp Asp Glu Tyr Asn Gln Leu Ala Arg Ala Phe Lys Ile Ser
            115                 120                 125

Asp Val Tyr Ala Pro Leu Ile Ser Ser Thr Ser Pro Met Thr Met
            130                 135                 140

Ile Gln Asn Leu Asn Gln Gly Glu Ile Val Tyr Thr Thr Thr Asp Arg
```

```
                145                 150                 155                 160
        Val Ile Gly Ala Arg Ile Leu Leu Tyr Ala Pro Arg Lys Tyr Tyr Ala
                        165                 170                 175
        Ser Thr Leu Ser Phe Thr Met Thr Lys Cys Ile Ile Pro Phe Gly Lys
                        180                 185                 190
        Glu Val Gly Arg Val Pro His Ser Arg Phe Asn Val Gly Thr Phe Ser
                        195                 200                 205
        Ser Ile Ala Thr Pro Lys Cys Phe Val Met Ser Gly Val Asp Ile Glu
                        210                 215                 220
        Ser Ile Pro Asn Glu Phe Ile Lys Leu Phe Tyr Gln Arg Val Lys Ser
        225                 230                 235                 240
        Val His Ala Asn Ile Leu Asn Asp Ile Ser Pro Gln Ile Val Ser Asp
                        245                 250                 255
        Met Ile Asn Arg Lys Arg Leu Arg Val His Thr Pro Ser Asp Arg Arg
                        260                 265                 270
        Ala Ala Gln Leu Met His Leu Pro Tyr His Val Lys Arg Gly Ala Ser
                        275                 280                 285
        His Val Asp Val Tyr Lys Val Asp Val Asp Met Leu Phe Glu Val
                        290                 295                 300
        Val Asp Val Ala Asp Gly Leu Arg Asn Val Ser Arg Lys Leu Thr Met
        305                 310                 315                 320
        His Thr Val Pro Val Cys Ile Leu Glu Met Leu Gly Ile Glu Ile Ala
                        325                 330                 335
        Asp Tyr Cys Ile Arg Arg Glu Asp Gly Met Leu Thr Asp Trp Phe Leu
                        340                 345                 350
        Leu Leu Thr Met Leu Ser Asp Gly Leu Thr Asp Arg Arg Thr His Cys
                        355                 360                 365
        Gln Tyr Leu Ile Asn Pro Ser Ser Val Pro Pro Asp Val Ile Leu Asn
                        370                 375                 380
        Ile Ser Ile Thr Gly Phe Ile Asn Arg His Thr Ile Asp Val Met Pro
        385                 390                 395                 400
        Asp Ile Tyr Asp Phe Val Lys Pro Ile Gly Ala Val Leu Pro Lys Gly
                        405                 410                 415
        Ser Phe Lys Ser Thr Ile Met Arg Val Leu Asp Ser Ile Ser Ile Leu
                        420                 425                 430
        Gly Ile Gln Ile Met Pro Arg Ala His Val Val Asp Ser Asp Glu Val
                        435                 440                 445
        Gly Glu Gln Met Glu Pro Thr Phe Gly Gln Ala Val Met Glu Ile Tyr
                        450                 455                 460
        Lys Gly Ile Ala Gly Val Asp Ser Leu Asp Asp Leu Ile Lys Trp Val
        465                 470                 475                 480
        Leu Asn Ser Asp Leu Ile Pro His Asp Asp Arg Leu Gly Gln Leu Phe
                        485                 490                 495
        Gln Ala Phe Leu Pro Leu Ala Lys Asp Leu Leu Ala Pro Met Ala Arg
                        500                 505                 510
        Lys Phe Tyr Asp Asn Ser Met Ser Glu Gly Arg Leu Leu Thr Phe Ala
                        515                 520                 525
        His Ala Asp Ser Glu Leu Leu Asn Ala Asn Tyr Phe Gly His Leu Leu
                        530                 535                 540
        Arg Leu Lys Ile Pro Tyr Ile Thr Glu Val Asn Leu Met Ile Arg Lys
        545                 550                 555                 560
        Asn Arg Glu Gly Gly Glu Leu Phe Gln Leu Val Leu Ser Tyr Leu Tyr
                        565                 570                 575
```

```
Lys Met Tyr Ala Thr Ser Ala Gln Pro Lys Trp Phe Gly Ser Leu Leu
            580                 585                 590

Arg Leu Leu Ile Cys Pro Trp Leu His Met Glu Lys Leu Ile Gly Glu
        595                 600                 605

Ala Asp Pro Ala Ser Thr Ser Ala Glu Ile Gly Trp His Ile Pro Arg
610                 615                 620

Gln Gln Leu Met Gln Asp Gly Trp Cys Gly Cys Glu Asp Gly Phe Ile
625                 630                 635                 640

Pro Tyr Val Ser Ile Arg Ala Pro Arg Leu Val Ile Glu Glu Leu Met
                645                 650                 655

Glu Lys Asn Trp Gly Gln Tyr His Ala Gln Val Ile Val Thr Asp Gln
            660                 665                 670

Leu Val Val Gly Glu Pro Arg Arg Val Ser Ala Lys Ala Val Ile Lys
        675                 680                 685

Gly Asn His Leu Pro Val Lys Leu Val Ser Arg Phe Ala Cys Phe Thr
690                 695                 700

Leu Thr Ala Lys Tyr Glu Met Arg Leu Ser Cys Gly His Ser Thr Gly
705                 710                 715                 720

Arg Gly Ala Ala Tyr Ser Ala Arg Leu Ala Phe Arg Ser Asp Leu Ala
                725                 730                 735

<210> SEQ ID NO 15
<211> LENGTH: 708
<212> TYPE: PRT
<213> ORGANISM: Artificial sequence
<220> FEATURE:
<223> OTHER INFORMATION: synthetic sequence

<400> SEQUENCE: 15

Met Gly Asn Ala Ser Ser Ile Val Gln Thr Ile Asn Val Thr Gly Asp
1               5                   10                  15

Gly Asn Val Phe Lys Pro Ser Ala Glu Thr Ser Ser Thr Ala Val Pro
            20                  25                  30

Ser Leu Ser Leu Ser Pro Gly Met Leu Asn Pro Gly Gly Val Pro Trp
        35                  40                  45

Ile Ala Val Gly Asp Glu Thr Ser Val Thr Ser Pro Gly Ala Leu Arg
    50                  55                  60

Arg Met Thr Ser Lys Asp Ile Pro Glu Thr Ala Ile Ile Asn Thr Asp
65                  70                  75                  80

Asn Ser Ser Gly Ala Val Pro Ser Glu Ser Ala Leu Val Pro Tyr Ile
                85                  90                  95

Asp Glu Pro Leu Val Val Val Thr Glu His Ala Ile Thr Asn Phe Thr
            100                 105                 110

Lys Ala Glu Met Ala Leu Glu Phe Asn Arg Glu Phe Leu Asp Lys Met
        115                 120                 125

Arg Val Leu Ser Val Ser Pro Lys Tyr Ser Asp Leu Leu Thr Tyr Val
    130                 135                 140

Asp Cys Tyr Val Gly Val Ser Ala Arg Gln Ala Leu Asn Asn Phe Gln
145                 150                 155                 160

Lys Gln Val Pro Val Ile Thr Pro Thr Arg Gln Thr Met Tyr Val Asp
                165                 170                 175

Ser Ile Gln Ala Ala Leu Lys Ala Leu Glu Lys Trp Glu Ile Asp Leu
            180                 185                 190

Arg Val Ala Gln Thr Leu Leu Pro Thr Asn Val Pro Ile Gly Glu Val
        195                 200                 205
```

```
Ser Cys Pro Met Gln Ser Val Lys Leu Leu Asp Asp Gln Leu Pro
    210                 215                 220

Asp Asp Ser Leu Ile Arg Arg Tyr Pro Lys Glu Ala Ala Val Ala Leu
225                 230                 235                 240

Ala Lys Arg Asn Gly Gly Ile Gln Trp Met Asp Val Ser Glu Gly Thr
                245                 250                 255

Val Met Asn Glu Ala Val Asn Ala Val Ala Ala Ser Ala Leu Ala Pro
            260                 265                 270

Ser Ala Ser Ala Pro Pro Leu Glu Glu Lys Ser Lys Leu Thr Glu Gln
        275                 280                 285

Ala Met Asp Leu Val Thr Ala Ala Glu Pro Glu Ile Ile Ala Ser Leu
    290                 295                 300

Ala Pro Val Pro Ala Pro Val Phe Ala Ile Pro Pro Lys Pro Ala Asp
305                 310                 315                 320

Tyr Asn Val Arg Thr Leu Arg Ile Asp Glu Ala Thr Trp Leu Arg Met
                325                 330                 335

Ile Pro Lys Ser Met Asn Thr Pro Phe Gln Ile Gln Val Thr Asp Asn
            340                 345                 350

Thr Gly Thr Asn Trp His Leu Asn Leu Arg Gly Gly Thr Arg Val Val
        355                 360                 365

Asn Leu Asp Gln Ile Ala Pro Met Arg Phe Val Leu Asp Leu Gly Gly
    370                 375                 380

Lys Ser Tyr Lys Glu Thr Ser Trp Asp Pro Asn Gly Lys Lys Val Gly
385                 390                 395                 400

Phe Ile Val Phe Gln Ser Lys Ile Pro Phe Glu Leu Trp Thr Ala Ala
                405                 410                 415

Ser Gln Ile Gly Gln Ala Thr Val Val Asn Tyr Val Gln Leu Tyr Ala
            420                 425                 430

Glu Asp Ser Ser Phe Thr Ala Gln Ser Ile Ile Ala Thr Thr Ser Leu
        435                 440                 445

Ala Tyr Asn Tyr Glu Pro Glu Gln Leu Asn Lys Thr Asp Pro Glu Met
    450                 455                 460

Asn Tyr Tyr Leu Leu Ala Thr Phe Ile Asp Ser Ala Ala Ile Thr Pro
465                 470                 475                 480

Thr Asn Met Thr Gln Pro Asp Val Trp Asp Ala Leu Leu Thr Met Ser
                485                 490                 495

Pro Leu Ser Ala Gly Glu Val Thr Val Lys Gly Ala Val Val Ser Glu
            500                 505                 510

Val Val Pro Ala Asp Leu Ile Gly Ser Tyr Thr Pro Glu Ser Leu Asn
        515                 520                 525

Ala Ser Leu Pro Asn Asp Ala Ala Arg Cys Met Ile Asp Arg Ala Ser
    530                 535                 540

Lys Ile Ala Glu Ala Ile Lys Ile Asp Asp Ala Gly Pro Asp Glu
545                 550                 555                 560

Tyr Ser Pro Asn Ser Val Pro Ile Gln Gly Gln Leu Ala Ile Ser Gln
                565                 570                 575

Leu Glu Thr Gly Tyr Gly Val Arg Ile Phe Asn Pro Lys Gly Ile Leu
            580                 585                 590

Ser Lys Ile Ala Ser Arg Ala Met Gln Ala Phe Ile Gly Asp Pro Ser
        595                 600                 605

Thr Ile Ile Thr Gln Ala Ala Pro Val Leu Ser Asp Lys Asn Asn Trp
    610                 615                 620
```

-continued

```
Ile Ala Leu Ala Gln Gly Val Lys Thr Ser Leu Arg Thr Lys Ser Leu
625                 630                 635                 640

Ser Ala Gly Val Lys Thr Ala Val Ser Lys Leu Ser Ser Ser Glu Ser
                645                 650                 655

Ile Gln Asn Trp Thr Gln Gly Phe Leu Asp Lys Val Ser Ala His Phe
            660                 665                 670

Pro Ala Pro Lys Pro Asp Cys Pro Thr Ser Gly Asp Ser Gly Glu Ser
        675                 680                 685

Ser Asn Arg Arg Val Lys Arg Asp Ser Tyr Ala Gly Val Val Lys Arg
    690                 695                 700

Gly Tyr Thr Arg
705

<210> SEQ ID NO 16
<211> LENGTH: 721
<212> TYPE: PRT
<213> ORGANISM: Artificial sequence
<220> FEATURE:
<223> OTHER INFORMATION: synthetic sequence

<400> SEQUENCE: 16

Met Ala Ser Phe Lys Gly Phe Ser Ala Asn Thr Val Pro Val Ser Lys
1               5                   10                  15

Ala Lys Arg Asp Ile Ser Ser Leu Ala Ala Thr Pro Gly Leu Arg Ser
            20                  25                  30

Gln Ser Phe Thr Pro Ser Val Asp Met Ser Gln Ser Arg Glu Phe Leu
        35                  40                  45

Thr Lys Ala Ile Glu Gln Gly Ser Met Ser Ile Pro Tyr Gln His Val
    50                  55                  60

Asn Val Pro Lys Val Asp Arg Lys Val Val Ser Leu Val Val Arg Pro
65                  70                  75                  80

Phe Ser Ser Gly Ala Phe Ser Ile Ser Gly Val Ile Ser Pro Ala His
                85                  90                  95

Ala Tyr Leu Leu Glu Cys Leu Pro Gln Leu Glu Gln Ala Met Ala Phe
            100                 105                 110

Val Ala Ser Pro Glu Ser Phe Gln Ala Ser Asp Val Ala Lys Arg Phe
        115                 120                 125

Ala Ile Lys Pro Gly Met Ser Leu Gln Asp Ala Ile Thr Ala Phe Ile
    130                 135                 140

Asn Phe Val Ser Ala Met Leu Lys Met Thr Val Thr Arg Gln Asn Phe
145                 150                 155                 160

Asp Val Ile Val Ala Glu Ile Glu Arg Leu Ala Ser Thr Ser Val Ser
                165                 170                 175

Val Arg Thr Lys Glu Ala Lys Val Ala Asp Glu Glu Leu Met Leu Phe
            180                 185                 190

Gly Leu Asp His Arg Gly Pro Gln Gln Leu Asp Val Ser Asp Ala Lys
        195                 200                 205

Gly Ile Met Lys Ala Ala Asp Ile Gln Thr Thr His Asp Val His Leu
    210                 215                 220

Ala Pro Gly Val Gly Asn Ile Asp Pro Glu Ile Tyr Asn Glu Gly Arg
225                 230                 235                 240

Phe Met Phe Met Gln His Lys Pro Leu Ala Ala Asp Gln Ser Tyr Phe
                245                 250                 255

Thr Leu Glu Thr Ala Asp Tyr Phe Lys Ile Tyr Pro Tyr Asp Glu
            260                 265                 270
```

His Asp Gly Arg Met Ala Asp Gln Lys Gln Ser Gly Leu Ile Leu Cys
            275                 280                 285

Thr Lys Asp Glu Val Leu Ala Glu Gln Thr Ile Phe Lys Leu Asp Ala
            290                 295                 300

Pro Asp Lys Thr Val His Leu Leu Asp Arg Asp Asp His Val
305                 310                 315                 320

Val Ala Arg Phe Thr Lys Val Phe Ile Glu Asp Val Ala Pro Gly His
                325                 330                 335

His Ala Ala Gln Arg Ser Gly Gln Arg Ser Val Leu Asp Leu Tyr
            340                 345                 350

Ala Asn Thr Gln Val Ile Ser Ile Thr Ser Ala Ala Leu Lys Trp Val
            355                 360                 365

Val Lys His Gly Val Ser Asp Gly Ile Val Asn Arg Lys Asn Val Lys
            370                 375                 380

Val Cys Val Gly Phe Asp Pro Leu Tyr Thr Leu Ser Thr His Asn Gly
385                 390                 395                 400

Val Ser Leu Cys Ala Leu Leu Met Asp Glu Lys Leu Ser Val Leu Asn
                405                 410                 415

Ser Ala Cys Arg Met Thr Leu Arg Ser Leu Met Lys Thr Gly Arg Asp
            420                 425                 430

Val Asp Ala His Arg Ala Phe Gln Arg Val Leu Ser Gln Gly Tyr Thr
            435                 440                 445

Ser Leu Met Cys Tyr Tyr His Pro Ser Arg Lys Leu Ala Tyr Gly Glu
            450                 455                 460

Val Leu Phe Leu Glu Arg Ser Asn Asp Val Thr Asp Gly Ile Lys Leu
465                 470                 475                 480

Gln Leu Asp Ala Ser Arg Gln Cys His Glu Cys Pro Val Leu Gln Gln
                485                 490                 495

Lys Val Val Glu Leu Glu Lys Gln Ile Ile Met Gln Lys Ser Ile Gln
            500                 505                 510

Ser Asp Pro Thr Pro Val Ala Leu Gln Pro Leu Leu Ser Gln Leu Arg
            515                 520                 525

Glu Leu Ser Ser Glu Val Thr Arg Leu Gln Met Glu Leu Ser Arg Ala
            530                 535                 540

Gln Ser Leu Asn Ala Gln Leu Glu Ala Asp Val Lys Ser Ala Gln Ser
545                 550                 555                 560

Cys Ser Leu Asp Met Tyr Leu Arg His His Thr Cys Ile Asn Gly His
                565                 570                 575

Ala Lys Glu Asp Glu Leu Leu Asp Ala Val Arg Val Ala Pro Asp Val
            580                 585                 590

Arg Arg Glu Ile Met Glu Lys Arg Ser Glu Val Arg Gln Gly Trp Cys
            595                 600                 605

Glu Arg Ile Ser Lys Glu Ala Ala Lys Cys Gln Thr Val Ile Asp
            610                 615                 620

Asp Leu Thr Leu Met Asn Gly Lys Gln Ala Gln Glu Ile Thr Glu Leu
625                 630                 635                 640

Arg Asp Ser Ala Glu Lys Tyr Glu Lys Gln Ile Ala Glu Leu Val Ser
                645                 650                 655

Thr Ile Thr Gln Asn Gln Ile Thr Tyr Gln Gln Glu Leu Gln Ala Leu
            660                 665                 670

Val Ala Lys Asn Val Glu Leu Asp Ala Leu Asn Gln Arg Gln Ala Lys
            675                 680                 685

Ser Leu Arg Ile Thr Pro Ser Leu Leu Ser Ala Thr Pro Ile Asp Ser

```
                690             695             700
Ala Asp Gly Val Ala Asp Leu Ile Asp Phe Ser Val Pro Thr Asp Glu
705                 710             715             720

Leu

<210> SEQ ID NO 17
<211> LENGTH: 1267
<212> TYPE: PRT
<213> ORGANISM: Artificial sequence
<220> FEATURE:
<223> OTHER INFORMATION: synthetic sequence

<400> SEQUENCE: 17

Met Ser Ser Met Ile Leu Thr Gln Phe Gly Pro Phe Ile Glu Ser Ile
1               5                   10                  15

Ser Gly Ile Thr Asp Gln Ser Asn Asp Val Phe Glu Asp Ala Ala Lys
            20                  25                  30

Ala Phe Ser Met Phe Thr Arg Ser Asp Val Tyr Lys Ala Leu Asp Glu
        35                  40                  45

Ile Pro Phe Ser Asp Asp Ala Met Leu Pro Ile Pro Pro Thr Ile Tyr
    50                  55                  60

Thr Lys Pro Ser His Asp Ser Tyr Tyr Tyr Ile Asp Ala Leu Asn Arg
65                  70                  75                  80

Val Arg Arg Lys Thr Tyr Gln Gly Pro Asp Asp Val Tyr Val Pro Asn
                85                  90                  95

Cys Ser Ile Val Glu Leu Leu Glu Pro His Glu Thr Leu Thr Ser Tyr
            100                 105                 110

Gly Arg Leu Ser Glu Ala Ile Glu Asn Arg Ala Lys Asp Gly Asp Ser
        115                 120                 125

Gln Ala Arg Ile Ala Thr Thr Tyr Gly Arg Ile Ala Glu Ser Gln Ala
    130                 135                 140

Arg Gln Ile Lys Ala Pro Leu Glu Lys Phe Val Leu Ala Leu Leu Val
145                 150                 155                 160

Ala Glu Ala Gly Gly Ser Leu Tyr Asp Pro Val Leu Gln Lys Tyr Asp
                165                 170                 175

Glu Ile Pro Asp Leu Ser His Asn Cys Pro Leu Trp Cys Phe Arg Glu
            180                 185                 190

Ile Cys Arg His Ile Ser Gly Pro Leu Pro Asp Arg Ala Pro Tyr Leu
        195                 200                 205

Tyr Leu Ser Ala Gly Val Phe Trp Leu Met Ser Pro Arg Met Thr Ser
    210                 215                 220

Ala Ile Pro Pro Leu Leu Ser Asp Leu Val Asn Leu Ala Ile Leu Gln
225                 230                 235                 240

Gln Thr Ala Gly Leu Asp Pro Ser Leu Val Lys Leu Gly Val Gln Ile
                245                 250                 255

Cys Leu His Ala Ala Ala Ser Ser Tyr Ala Trp Phe Ile Leu Lys
            260                 265                 270

Thr Lys Ser Ile Phe Pro Gln Asn Thr Leu His Ser Met Tyr Glu Ser
        275                 280                 285

Leu Glu Gly Gly Tyr Cys Pro Asn Leu Glu Trp Leu Glu Pro Arg Ser
    290                 295                 300

Asp Tyr Lys Phe Met Tyr Met Gly Val Met Pro Leu Ser Ala Lys Tyr
305                 310                 315                 320

Ala Arg Ser Ala Pro Ser Asn Asp Lys Lys Ala Arg Glu Leu Gly Glu
                325                 330                 335
```

```
Lys Tyr Gly Leu Ser Ser Val Val Gly Glu Leu Arg Lys Arg Thr Lys
                340                 345                 350

Thr Tyr Val Lys His Asp Phe Ala Ser Val Arg Tyr Ile Arg Asp Ala
            355                 360                 365

Met Ala Cys Thr Ser Gly Ile Phe Leu Val Arg Thr Pro Thr Glu Thr
370                 375                 380

Val Leu Gln Glu Tyr Thr Gln Ser Pro Glu Ile Lys Val Pro Ile Pro
385                 390                 395                 400

Gln Lys Asp Trp Thr Gly Pro Ile Gly Glu Ile Arg Ile Leu Lys Asp
                405                 410                 415

Thr Thr Ser Ser Ile Ala Arg Tyr Leu Tyr Arg Thr Trp Tyr Leu Ala
            420                 425                 430

Ala Ala Arg Met Ala Ala Gln Pro Arg Thr Trp Asp Pro Leu Phe Gln
        435                 440                 445

Ala Ile Met Arg Ser Gln Tyr Val Thr Ala Arg Gly Gly Ser Gly Ala
    450                 455                 460

Ala Leu Arg Glu Ser Leu Tyr Ala Ile Asn Val Ser Leu Pro Asp Phe
465                 470                 475                 480

Lys Gly Leu Pro Val Lys Ala Ala Thr Lys Ile Phe Gln Ala Ala Gln
                485                 490                 495

Leu Ala Asn Leu Pro Phe Ser His Thr Ser Val Ala Ile Leu Ala Asp
            500                 505                 510

Thr Ser Met Gly Leu Arg Asn Gln Val Gln Arg Arg Pro Arg Ser Ile
        515                 520                 525

Met Pro Leu Asn Val Pro Gln Gln Val Ser Ala Pro His Thr Leu
    530                 535                 540

Thr Ala Asp Tyr Ile Asn Tyr His Met Asn Leu Ser Thr Thr Ser Gly
545                 550                 555                 560

Ser Ala Val Ile Glu Lys Val Ile Pro Leu Gly Val Tyr Ala Ser Ser
                565                 570                 575

Pro Pro Asn Gln Ser Ile Asn Ile Asp Ile Ser Ala Cys Asp Ala Ser
            580                 585                 590

Ile Thr Trp Asp Phe Phe Leu Ser Val Ile Met Ala Ala Ile His Glu
        595                 600                 605

Gly Val Ala Ser Ser Ser Ile Gly Lys Pro Phe Met Gly Val Pro Ala
    610                 615                 620

Ser Ile Val Asn Asp Glu Ser Val Val Gly Val Arg Ala Ala Arg Pro
625                 630                 635                 640

Ile Ser Gly Met Gln Asn Met Ile Gln His Leu Ser Lys Leu Tyr Lys
                645                 650                 655

Arg Gly Phe Ser Tyr Arg Val Asn Asp Ser Phe Ser Pro Gly Asn Asp
            660                 665                 670

Phe Thr His Met Thr Thr Thr Phe Pro Ser Gly Ser Thr Ala Thr Ser
        675                 680                 685

Thr Glu His Thr Ala Asn Asn Ser Thr Met Met Glu Thr Phe Leu Thr
    690                 695                 700

Val Trp Gly Pro Glu His Thr Asp Asp Pro Asp Val Leu Arg Leu Met
705                 710                 715                 720

Lys Ser Leu Thr Ile Gln Arg Asn Tyr Val Cys Gln Gly Asp Asp Gly
                725                 730                 735

Leu Met Ile Ile Asp Gly Thr Thr Ala Gly Lys Val Asn Ser Glu Thr
            740                 745                 750
```

-continued

```
Ile Gln Lys Met Leu Glu Leu Ile Ser Lys Tyr Gly Glu Glu Phe Gly
            755                 760                 765
Trp Lys Tyr Asp Ile Ala Tyr Asp Gly Thr Ala Glu Tyr Leu Lys Leu
770                 775                 780
Tyr Phe Ile Phe Gly Cys Arg Ile Pro Asn Leu Ser Arg His Pro Ile
785                 790                 795                 800
Val Gly Lys Glu Arg Ala Asn Ser Ser Ala Glu Pro Trp Pro Ala
                805                 810                 815
Ile Leu Asp Gln Ile Met Gly Val Phe Asn Gly Val His Asp Gly
            820                 825                 830
Leu Gln Trp Gln Arg Trp Ile Arg Tyr Ser Trp Ala Leu Cys Cys Ala
            835                 840                 845
Phe Ser Arg Gln Arg Thr Met Ile Gly Glu Ser Val Gly Tyr Leu Gln
    850                 855                 860
Tyr Pro Met Trp Ser Phe Val Tyr Trp Gly Leu Pro Leu Val Lys Ala
865                 870                 875                 880
Phe Gly Ser Asp Pro Trp Ile Phe Ser Trp Tyr Met Pro Thr Gly Asp
                885                 890                 895
Leu Gly Met Tyr Ser Trp Ile Ser Leu Ile Arg Pro Leu Met Thr Arg
            900                 905                 910
Trp Met Val Ala Asn Gly Tyr Val Thr Asp Arg Cys Ser Pro Val Phe
    915                 920                 925
Gly Asn Ala Asp Tyr Arg Arg Cys Phe Asn Glu Leu Lys Leu Tyr Gln
            930                 935                 940
Gly Tyr Tyr Met Ala Gln Leu Pro Arg Asn Pro Lys Lys Ser Gly Arg
945                 950                 955                 960
Ala Ala Pro Arg Glu Val Arg Glu Gln Phe Thr Gln Ala Leu Ser Asp
                965                 970                 975
Tyr Leu Met Gln Asn Pro Glu Leu Lys Ser Arg Val Leu Arg Gly Arg
            980                 985                 990
Ser Glu Trp Glu Lys Tyr Gly Ala  Gly Ile Ile His Asn  Pro Pro Ser
    995                 1000                1005
Leu Phe  Asp Val Pro His Lys  Trp Tyr Gln Gly Ala  Gln Glu Ala
    1010                1015                1020
Ala Ile  Ala Thr Arg Glu Glu  Leu Ala Glu Met Asp  Glu Thr Leu
    1025                1030                1035
Met Arg  Ala Arg Arg His Ser  Tyr Ser Asn Phe Ser  Lys Leu Leu
    1040                1045                1050
Glu Ala  Tyr Leu Leu Val Lys  Trp Arg Met Cys Glu  Ala Arg Glu
    1055                1060                1065
Pro Ser  Val Asp Leu Arg Leu  Pro Leu Cys Ala Gly  Ile Asp Pro
    1070                1075                1080
Leu Asn  Ser Asp Pro Phe Leu  Lys Met Val Ser Val  Gly Pro Met
    1085                1090                1095
Leu Gln  Ser Thr Arg Lys Tyr  Phe Ala Gln Thr Leu  Phe Met Ala
    1100                1105                1110
Lys Thr  Val Ser Gly Leu Asp  Val Asn Ala Ile Asp  Ser Ala Leu
    1115                1120                1125
Leu Arg  Leu Arg Thr Leu Gly  Ala Asp Lys Lys Ala  Leu Thr Ala
    1130                1135                1140
Gln Leu  Leu Met Val Gly Leu  Gln Glu Ser Glu Ala  Asp Ala Leu
    1145                1150                1155
Ala Gly  Lys Ile Met Leu Gln  Asp Val Asn Thr Val  Gln Leu Ala
```

```
            1160               1165              1170
Arg Val  Val Asn Leu Ala Val  Pro Asp Thr Trp Met  Ser Leu Asp
    1175             1180                 1185

Phe Asp  Ser Met Phe Lys His  His Val Lys Leu Leu  Pro Lys Asp
    1190             1195                 1200

Gly Arg  His Leu Asn Thr Asp  Ile Pro Pro Arg Met  Gly Trp Leu
    1205             1210                 1215

Arg Ala  Ile Leu Arg Phe Leu  Gly Ala Gly Met Val  Met Thr Ala
    1220             1225                 1230

Thr Gly  Val Ala Val Asp Ile  Tyr Leu Glu Asp Ile  His Gly Gly
    1235             1240                 1245

Gly Arg  Ser Leu Gly Gln Arg  Phe Met Thr Trp Met  Arg Gln Glu
    1250             1255                 1260

Gly Arg  Ser Ala
    1265

<210> SEQ ID NO 18
<211> LENGTH: 1289
<212> TYPE: PRT
<213> ORGANISM: Artificial sequence
<220> FEATURE:
<223> OTHER INFORMATION: synthetic sequence

<400> SEQUENCE: 18

Met Ala Asn Val Trp Gly Val Arg Leu Ala Asp Ser Leu Ser Ser Pro
1               5                   10                  15

Thr Ile Glu Thr Arg Thr Arg Gln Tyr Thr Leu His Asp Leu Cys Ser
            20                  25                  30

Asp Leu Asp Ala Asn Pro Gly Arg Glu Pro Trp Lys Pro Leu Arg Asn
        35                  40                  45

Gln Arg Thr Asn Asn Ile Val Ala Val Gln Leu Phe Arg Pro Leu Gln
    50                  55                  60

Gly Leu Val Leu Asp Thr Gln Leu Tyr Gly Phe Pro Gly Ala Phe Asp
65                  70                  75                  80

Asp Trp Glu Arg Phe Met Arg Glu Lys Leu Arg Val Leu Lys Tyr Glu
                85                  90                  95

Val Leu Arg Ile Tyr Pro Ile Ser Asn Tyr Ser Asn Glu His Val Asn
            100                 105                 110

Val Phe Val Ala Asn Ala Leu Val Gly Ala Phe Leu Ser Asn Gln Ala
        115                 120                 125

Phe Tyr Asp Leu Leu Pro Leu Leu Ile Ile Asn Asp Thr Met Ile Gly
    130                 135                 140

Asp Leu Leu Gly Thr Gly Ala Ser Leu Ser Gln Phe Phe Gln Ser His
145                 150                 155                 160

Gly Asp Val Leu Glu Val Ala Ala Gly Arg Lys Tyr Leu Gln Met Glu
                165                 170                 175

Asn Tyr Ser Asn Asp Asp Asp Pro Pro Leu Phe Ala Lys Asp Leu
            180                 185                 190

Ser Asp Tyr Ala Lys Ala Phe Tyr Ser Asp Thr Tyr Glu Val Leu Asp
        195                 200                 205

Arg Phe Phe Trp Thr His Asp Ser Ser Ala Gly Val Leu Val His Tyr
    210                 215                 220

Asp Lys Pro Thr Asn Gly His His Tyr Leu Leu Gly Thr Leu Thr Gln
225                 230                 235                 240

Met Val Ser Ala Pro Pro Tyr Ile Ile Asn Ala Thr Asp Ala Met Leu
```

-continued

```
                245                 250                 255
Leu Glu Ser Cys Leu Glu Gln Phe Ser Ala Asn Val Arg Ala Arg Pro
            260                 265                 270

Ala Gln Pro Val Thr Arg Leu Asp Gln Cys Tyr His Leu Arg Trp Gly
        275                 280                 285

Ala Gln Tyr Val Gly Glu Asp Ser Leu Thr Tyr Arg Leu Gly Val Leu
    290                 295                 300

Ser Leu Leu Ala Thr Asn Gly Tyr Gln Leu Ala Arg Pro Ile Pro Arg
305                 310                 315                 320

Gln Leu Thr Asn Arg Trp Leu Ser Ser Phe Val Ser Gln Ile Met Ser
            325                 330                 335

Asp Gly Val Asn Glu Thr Pro Leu Trp Pro Gln Glu Arg Tyr Val Gln
        340                 345                 350

Ile Ala Tyr Asp Ser Pro Ser Val Val Asp Gly Ala Thr Gln Tyr Gly
    355                 360                 365

Tyr Val Arg Lys Asn Gln Leu Arg Leu Gly Met Arg Ile Ser Ala Leu
370                 375                 380

Gln Ser Leu Ser Asp Thr Pro Ser Pro Val Gln Trp Leu Pro Gln Tyr
385                 390                 395                 400

Thr Ile Asp Gln Ala Ala Met Asp Glu Gly Asp Leu Met Val Ser Arg
            405                 410                 415

Leu Thr Gln Leu Pro Leu Arg Pro Asp Tyr Gly Asn Ile Trp Val Gly
        420                 425                 430

Asp Ala Leu Ser Tyr Tyr Val Asp Tyr Asn Arg Ser His Arg Val Val
    435                 440                 445

Leu Ser Ser Glu Leu Pro Gln Leu Pro Asp Thr Tyr Phe Asp Gly Asp
450                 455                 460

Glu Gln Tyr Gly Arg Ser Leu Phe Ser Leu Ala Arg Lys Ile Gly Asp
465                 470                 475                 480

Arg Ser Leu Val Lys Asp Thr Ala Val Leu Lys His Ala Tyr Gln Ala
            485                 490                 495

Ile Asp Pro Asn Thr Gly Lys Gly Tyr Leu Arg Ser Gly Gln Ser Val
        500                 505                 510

Ala Tyr Phe Gly Ala Ser Ala Gly His Ser Gly Ala Asp Gln Pro Leu
    515                 520                 525

Val Ile Glu Pro Trp Ile Gln Gly Lys Ile Ser Gly Val Pro Pro Pro
530                 535                 540

Ser Ser Val Arg Gln Phe Gly Tyr Asp Val Ala Arg Gly Ala Ile Val
545                 550                 555                 560

Asp Leu Ala Arg Pro Phe Pro Ser Gly Asp Tyr Gln Phe Val Tyr Ser
            565                 570                 575

Asp Val Asp Gln Val Val Asp Gly His Asp Asp Leu Ser Ile Ser Ser
        580                 585                 590

Gly Leu Val Glu Ser Leu Leu Ser Ser Cys Met His Ala Thr Ala Pro
    595                 600                 605

Gly Gly Ser Phe Val Val Lys Ile Asn Phe Pro Thr Arg Pro Val Trp
610                 615                 620

His Tyr Ile Glu Gln Lys Ile Leu Pro Asn Ile Thr Ser Tyr Met Leu
625                 630                 635                 640

Ile Lys Pro Phe Val Thr Asn Asn Val Glu Leu Phe Phe Val Ala Phe
            645                 650                 655

Gly Val His Gln His Ser Ser Leu Thr Trp Thr Ser Gly Val Tyr Phe
        660                 665                 670
```

```
Phe Leu Val Asp His Phe Tyr Arg Tyr Glu Thr Leu Ser Thr Ile Ser
        675                 680                 685

Arg Gln Leu Pro Ser Phe Gly Tyr Val Asp Asp Gly Ser Ser Val Thr
        690                 695                 700

Gly Ile Glu Thr Ile Ser Ile Glu Asn Pro Gly Phe Ser Asn Met Thr
705                 710                 715                 720

Gln Ala Ala Arg Ile Gly Ile Ser Gly Leu Cys Ala Asn Val Gly Asn
                725                 730                 735

Ala Arg Lys Ser Ile Ala Ile Tyr Glu Ser His Gly Ala Arg Val Leu
            740                 745                 750

Thr Ile Thr Ser Arg Arg Ser Pro Ala Ser Ala Arg Arg Lys Ser Arg
        755                 760                 765

Leu Arg Tyr Leu Pro Leu Ile Asp Pro Arg Ser Leu Glu Val Gln Ala
        770                 775                 780

Arg Thr Ile Leu Pro Ala Asp Pro Val Leu Phe Glu Asn Val Ser Gly
785                 790                 795                 800

Ala Ser Pro His Val Cys Leu Thr Met Met Tyr Asn Phe Glu Val Ser
                805                 810                 815

Ser Ala Val Tyr Asp Gly Asp Val Val Leu Asp Leu Gly Thr Gly Pro
            820                 825                 830

Glu Ala Lys Ile Leu Glu Leu Ile Pro Ala Thr Ser Pro Val Thr Cys
        835                 840                 845

Val Asp Ile Arg Pro Thr Ala Gln Pro Ser Gly Cys Trp Asn Val Arg
850                 855                 860

Thr Thr Phe Leu Glu Leu Asp Tyr Leu Ser Asp Gly Trp Ile Thr Gly
865                 870                 875                 880

Val Arg Gly Asp Ile Val Thr Cys Met Leu Ser Leu Gly Ala Ala Ala
                885                 890                 895

Ala Gly Lys Ser Met Thr Phe Asp Ala Ala Phe Gln Gln Leu Ile Lys
            900                 905                 910

Val Leu Ser Lys Ser Thr Ala Asn Val Val Leu Val Gln Val Asn Cys
        915                 920                 925

Pro Thr Asp Val Val Arg Ser Ile Lys Gly Tyr Leu Glu Ile Asp Ser
        930                 935                 940

Thr Asn Lys Arg Tyr Arg Phe Pro Lys Phe Gly Arg Asp Glu Pro Tyr
945                 950                 955                 960

Ser Asp Met Asp Ala Leu Glu Lys Ile Cys Arg Thr Ala Trp Pro Asn
                965                 970                 975

Cys Ser Ile Thr Trp Val Pro Leu Ser Tyr Asp Leu Arg Trp Thr Arg
            980                 985                 990

Leu Ala Leu Leu Glu Ser Thr Thr Leu Ser Ser Ala Ser Ile Arg Ile
        995                 1000                1005

Ala Glu Leu Met Tyr Lys Tyr Met Pro Ile Met Arg Ile Asp Ile
        1010                1015                1020

His Gly Leu Pro Met Glu Lys Arg Gly Asn Phe Ile Val Gly Gln
        1025                1030                1035

Asn Cys Ser Leu Val Ile Pro Gly Phe Asn Ala Gln Asp Val Phe
        1040                1045                1050

Asn Cys Tyr Phe Asn Ser Ala Leu Ala Phe Ser Thr Glu Asp Val
        1055                1060                1065

Asn Ala Ala Met Ile Pro Gln Val Ser Ala Gln Phe Asp Ala Thr
        1070                1075                1080
```

```
Lys Gly Glu Trp Thr Leu Asp Met Val Phe Ser Asp Ala Gly Ile
    1085                1090                1095

Tyr Thr Met Gln Ala Leu Val Gly Ser Asn Ala Asn Pro Val Ser
    1100                1105                1110

Leu Gly Ser Phe Val Val Asp Ser Pro Asp Val Asp Ile Thr Asp
    1115                1120                1125

Ala Trp Pro Ala Gln Leu Asp Phe Thr Ile Ala Gly Thr Asp Val
    1130                1135                1140

Asp Ile Thr Val Asn Pro Tyr Tyr Arg Leu Met Thr Phe Val Arg
    1145                1150                1155

Ile Asp Gly Gln Trp Gln Ile Ala Asn Pro Asp Lys Phe Gln Phe
    1160                1165                1170

Phe Ser Ser Ala Ser Gly Thr Leu Val Met Asn Val Lys Leu Asp
    1175                1180                1185

Ile Ala Asp Lys Tyr Leu Leu Tyr Tyr Ile Arg Asp Val Gln Ser
    1190                1195                1200

Arg Asp Val Gly Phe Tyr Ile Gln His Pro Leu Gln Leu Leu Asn
    1205                1210                1215

Thr Ile Thr Leu Pro Thr Asn Glu Asp Leu Phe Leu Ser Ala Pro
    1220                1225                1230

Asp Met Arg Glu Trp Ala Val Lys Glu Ser Gly Asn Thr Ile Cys
    1235                1240                1245

Ile Leu Asn Ser Gln Gly Phe Val Leu Pro Gln Asp Trp Asp Val
    1250                1255                1260

Leu Thr Asp Thr Ile Ser Trp Ser Pro Ser Ile Pro Thr Tyr Ile
    1265                1270                1275

Val Pro Pro Gly Asp Tyr Thr Leu Thr Pro Leu
    1280                1285

<210> SEQ ID NO 19
<211> LENGTH: 1275
<212> TYPE: PRT
<213> ORGANISM: Artificial sequence
<220> FEATURE:
<223> OTHER INFORMATION: synthetic sequence

<400> SEQUENCE: 19

Met Lys Arg Ile Pro Arg Lys Thr Lys Gly Lys Ser Ser Gly Lys Gly
1               5                   10                  15

Asn Asp Ser Thr Glu Arg Ala Asp Asp Gly Ser Ser Gln Leu Arg Asp
            20                  25                  30

Lys Gln Asn Asn Lys Ala Gly Pro Ala Thr Thr Glu Pro Gly Thr Ser
        35                  40                  45

Asn Arg Glu Gln Tyr Lys Ala Arg Pro Gly Ile Ala Ser Val Gln Arg
    50                  55                  60

Ala Thr Glu Ser Ala Glu Met Pro Met Lys Asn Asn Asp Glu Gly Thr
65                  70                  75                  80

Pro Asp Lys Lys Gly Asn Thr Lys Gly Asp Leu Val Asn Glu His Ser
                85                  90                  95

Glu Ala Lys Asp Glu Ala Asp Glu Ala Thr Lys Lys Gln Ala Lys Asp
            100                 105                 110

Thr Asp Lys Ser Lys Ala Gln Val Thr Tyr Ser Asp Thr Gly Ile Asn
        115                 120                 125

Asn Ala Asn Glu Leu Ser Arg Ser Gly Asn Val Asp Asn Glu Gly Gly
    130                 135                 140
```

```
Ser Asn Gln Lys Pro Met Ser Thr Arg Ile Ala Glu Ala Thr Ser Ala
145                 150                 155                 160

Ile Val Ser Lys His Pro Ala Arg Val Gly Leu Pro Pro Thr Ala Ser
                165                 170                 175

Ser Gly His Gly Tyr Gln Cys His Val Cys Ser Ala Val Leu Phe Ser
            180                 185                 190

Pro Leu Asp Leu Asp Ala His Val Ala Ser His Gly Leu His Gly Asn
        195                 200                 205

Met Thr Leu Thr Ser Ser Asp Ile Gln Arg His Ile Thr Glu Phe Ile
    210                 215                 220

Ser Ser Trp Gln Asn His Pro Ile Val Gln Val Ser Ala Asp Val Glu
225                 230                 235                 240

Asn Lys Lys Thr Ala Gln Leu Leu His Ala Asp Thr Pro Arg Leu Val
                245                 250                 255

Thr Trp Asp Ala Gly Leu Cys Thr Ser Phe Lys Ile Val Pro Ile Val
            260                 265                 270

Pro Ala Gln Val Pro Gln Asp Val Leu Ala Tyr Thr Phe Phe Thr Ser
        275                 280                 285

Ser Tyr Ala Ile Gln Ser Pro Phe Pro Glu Ala Ala Val Ser Arg Ile
    290                 295                 300

Val Val His Thr Arg Trp Ala Ser Asn Val Asp Phe Asp Arg Asp Ser
305                 310                 315                 320

Ser Val Ile Met Ala Pro Pro Thr Glu Asn Asn Ile His Leu Phe Lys
                325                 330                 335

Gln Leu Leu Asn Thr Glu Thr Leu Ser Val Arg Gly Ala Asn Pro Leu
            340                 345                 350

Met Phe Arg Ala Asn Val Leu His Met Leu Leu Glu Phe Val Leu Asp
        355                 360                 365

Asn Leu Tyr Leu Asn Arg His Thr Gly Phe Ser Gln Asp His Thr Pro
    370                 375                 380

Phe Thr Glu Gly Ala Asn Leu Arg Ser Leu Pro Gly Pro Asp Ala Glu
385                 390                 395                 400

Lys Trp Tyr Ser Ile Met Tyr Pro Thr Arg Met Gly Thr Pro Asn Val
                405                 410                 415

Ser Lys Ile Cys Asn Phe Val Ala Ser Cys Val Arg Asn Arg Val Gly
            420                 425                 430

Arg Phe Asp Arg Ala Gln Met Met Asn Gly Ala Met Ser Glu Trp Val
        435                 440                 445

Asp Val Phe Glu Thr Ser Asp Ala Leu Thr Val Ser Ile Arg Gly Arg
    450                 455                 460

Trp Met Ala Arg Leu Ala Arg Met Asn Ile Asn Pro Thr Glu Ile Glu
465                 470                 475                 480

Trp Ala Leu Thr Glu Cys Ala Gln Gly Tyr Val Thr Val Thr Ser Pro
                485                 490                 495

Tyr Ala Pro Ile Val Asn Arg Leu Met Pro Tyr Arg Ile Ser Asn Ala
            500                 505                 510

Glu Arg Gln Ile Ser Gln Ile Ile Arg Ile Met Asn Ile Gly Asn Asn
        515                 520                 525

Ala Thr Val Ile Gln Pro Val Leu Gln Asp Ile Ser Val Leu Leu Gln
    530                 535                 540

Arg Ile Ser Pro Leu Gln Ile Asp Pro Thr Ile Ile Ser Asn Thr Met
545                 550                 555                 560

Ser Thr Val Ser Glu Ser Thr Thr Gln Thr Leu Ser Pro Ala Ser Ser
```

```
                565                 570                 575
Ile Leu Gly Lys Leu Arg Pro Ser Asn Ser Asp Phe Ser Ser Phe Arg
            580                 585                 590

Val Ala Leu Ala Gly Trp Leu Tyr Asn Gly Val Val Thr Thr Val Ile
            595                 600                 605

Asp Ser Ser Tyr Pro Lys Asp Gly Gly Ser Val Thr Ser Leu Glu
            610                 615                 620

Asn Leu Trp Asp Phe Phe Ile Leu Ala Leu Ala Leu Pro Leu Thr Thr
625                 630                 635                 640

Asp Pro Cys Ala Pro Val Lys Ala Phe Met Thr Leu Ala Asn Met Met
                645                 650                 655

Val Gly Phe Glu Thr Ile Pro Met Asp Asn Gln Ile Tyr Thr Gln Ser
            660                 665                 670

Arg Arg Ala Ser Ala Phe Ser Thr Pro His Thr Trp Pro Arg Cys Phe
            675                 680                 685

Met Asn Ile Gln Leu Ile Ser Pro Ile Asp Ala Pro Ile Leu Arg Gln
            690                 695                 700

Trp Ala Glu Ile Ile His Arg Tyr Trp Pro Asn Pro Ser Gln Ile Arg
705                 710                 715                 720

Tyr Gly Ala Pro Asn Val Phe Gly Ser Ala Asn Leu Phe Thr Pro Pro
                725                 730                 735

Glu Val Leu Leu Leu Pro Ile Asp His Gln Pro Ala Asn Val Thr Thr
            740                 745                 750

Pro Thr Leu Asp Phe Thr Asn Glu Leu Thr Asn Trp Arg Ala Arg Val
            755                 760                 765

Cys Glu Leu Met Lys Asn Leu Val Asp Asn Gln Arg Tyr Gln Pro Gly
            770                 775                 780

Trp Thr Gln Ser Leu Val Ser Ser Met Arg Gly Thr Leu Asp Lys Leu
785                 790                 795                 800

Lys Leu Ile Lys Ser Met Thr Pro Met Tyr Leu Gln Gln Leu Ala Pro
                805                 810                 815

Val Glu Leu Ala Val Ile Ala Pro Met Leu Pro Phe Pro Pro Phe Gln
            820                 825                 830

Val Pro Tyr Val Arg Leu Asp Arg Asp Arg Val Pro Thr Met Val Gly
            835                 840                 845

Val Thr Arg Gln Ser Arg Asp Thr Ile Thr Gln Pro Ala Leu Ser Leu
            850                 855                 860

Ser Thr Thr Asn Thr Thr Val Gly Val Pro Leu Ala Leu Asp Ala Arg
865                 870                 875                 880

Ala Ile Thr Val Ala Leu Leu Ser Gly Lys Tyr Pro Pro Asp Leu Val
                885                 890                 895

Thr Asn Val Trp Tyr Ala Asp Ala Ile Tyr Pro Met Tyr Ala Asp Thr
            900                 905                 910

Glu Val Phe Ser Asn Leu Gln Arg Asp Met Ile Thr Cys Glu Ala Val
            915                 920                 925

Gln Thr Leu Val Thr Leu Val Ala Gln Ile Ser Glu Thr Gln Tyr Pro
            930                 935                 940

Val Asp Arg Tyr Leu Asp Trp Ile Pro Ser Leu Arg Ala Ser Ala Ala
945                 950                 955                 960

Thr Ala Ala Thr Phe Ala Glu Trp Val Asn Thr Ser Met Lys Thr Ala
                965                 970                 975

Phe Asp Leu Ser Asp Met Leu Leu Glu Pro Leu Leu Ser Gly Asp Pro
            980                 985                 990
```

Arg Met Thr Gln Leu Ala Ile Gln Tyr Gln Gln Tyr Asn Gly Arg Thr
        995                 1000                1005

Phe Asn Ile Ile Pro Glu Met Pro Gly Ser Val Ile Ala Asp Cys
    1010                1015                1020

Val Gln Leu Thr Ala Glu Val Phe Asn His Glu Tyr Asn Leu Phe
    1025                1030                1035

Gly Ile Ala Arg Gly Asp Ile Ile Gly Arg Val Gln Ser Thr
    1040                1045                1050

His Leu Trp Ser Pro Leu Ala Pro Pro Pro Asp Leu Val Phe Asp
    1055                1060                1065

Arg Asp Thr Pro Gly Val His Ile Phe Gly Arg Asp Cys Arg Ile
    1070                1075                1080

Ser Phe Gly Met Asn Gly Ala Ala Pro Met Ile Arg Asp Glu Thr
    1085                1090                1095

Gly Leu Met Val Pro Phe Glu Gly Asn Trp Ile Phe Pro Leu Ala
    1100                1105                1110

Leu Trp Gln Met Asn Thr Arg Tyr Phe Asn Gln Gln Phe Asp Ala
    1115                1120                1125

Trp Ile Lys Thr Gly Glu Leu Arg Ile Arg Ile Glu Met Gly Ala
    1130                1135                1140

Tyr Pro Tyr Met Leu His Tyr Tyr Asp Pro Arg Gln Tyr Ala Asn
    1145                1150                1155

Ala Trp Asn Leu Thr Ser Ala Trp Leu Glu Glu Ile Thr Pro Thr
    1160                1165                1170

Ser Ile Pro Ser Val Pro Phe Met Val Pro Ile Ser Ser Asp His
    1175                1180                1185

Asp Ile Ser Ser Ala Pro Ala Val Gln Tyr Ile Ile Ser Thr Glu
    1190                1195                1200

Tyr Asn Asp Arg Ser Leu Phe Cys Thr Asn Ser Ser Ser Pro Gln
    1205                1210                1215

Thr Ile Ala Gly Pro Asp Lys His Ile Pro Val Glu Arg Tyr Asn
    1220                1225                1230

Ile Leu Thr Asn Pro Asp Ala Pro Pro Thr Gln Ile Gln Leu Pro
    1235                1240                1245

Glu Val Val Asp Leu Tyr Asn Val Val Thr Arg Tyr Ala Tyr Glu
    1250                1255                1260

Thr Pro Pro Ile Thr Ala Val Val Met Gly Val Pro
    1265                1270                1275

<210> SEQ ID NO 20
<211> LENGTH: 1416
<212> TYPE: DNA
<213> ORGANISM: Artificial sequence
<220> FEATURE:
<223> OTHER INFORMATION: synthetic sequence

<400> SEQUENCE: 20
gctattggtc ggatggatcc tcgcctacgt gaagaagtag tacggctgat aatcgcatta      60
acgagtgata atgagcatc actgtcaaaa gggcttgaat caagggtctc ggcgctcgag     120
aagacgtctc aaatacactc tgatactatc ctccggatca cccagggact cgatgatgca     180
aacaaacgaa tcatcgctct tgagcaaagt cgggatgact tggttgcatc agtcagtgat     240
gctcaacttg caatctccag attggaaagc tctatcggag ccctccaaac agttgtcaat     300
ggacttgatt cgagtgttac ccagttgggt gctcgagtgg acaacttga dacaggactt      360

-continued

```
gcagagctac gcgttgatca cgacaatctc gttgcgagag tggatactgc agaacgtaac      420
attggatcat tgaccactga gctatcaact ctgacgttac gagtaacatc catacaagcg      480
gatttcgaat ctaggatatc cacgttagag cgcacggcgg tcactagcgc gggagctccc      540
ctctcaatcc gtaataaccg tatgaccatg ggattaaatg atggactcac gttgtcaggg      600
aataatctcg ccatccgatt gccaggaaat acgggtctga atattcaaaa tggtggactt      660
cagtttcgat ttaatactga tcaattccag atagttaata ataacttgac tctcaagacg      720
actgtgtttg attctatcaa ctcaaggata ggcgcaactg agcaaagtta cgtggcgtcg      780
gcagtgactc ccttgagatt aaacagtagc acgaaggtgc tggatatgct aatagacagt      840
tcaacacttg aaattaattc tagtggacag ctaactgtta gatcgacatc cccgaatttg      900
aggtatccga tagctgatgt tagcggcggt atcggaatga gtccaaatta taggtttagg      960
cagagcatgt ggataggaat tgtctcctat tctggtagtg ggctgaattg agggtacag     1020 gtgaactccg acattttat tgtagatgat tacatacata tatgtcttcc agcttttgac     1080
ggtttctcta tagctgacgg tggagatcta tcgttgaact ttgttaccgg attgttacca     1140
ccgttactta caggagacac tgagcccgct tttcataatg acgtggtcac atatggagca     1200
cagactgtag ctatagggtt gtcgtcgggt ggtgcgcctc agtatatgag taagaatctg     1260
tgggtggagc agtggcagga tggagtactt cggttacgtg ttgagggggg tggctcaatt     1320
acgcactcaa acagtaagtg gcctgccatg accgtttcgt acccgcgtag tttcacgtga     1380
ggatcagacc accccgcggc actggggcat ttcatc                              1416
```

<210> SEQ ID NO 21
<211> LENGTH: 1331
<212> TYPE: DNA
<213> ORGANISM: Artificial sequence
<220> FEATURE:
<223> OTHER INFORMATION: synthetic sequence

<400> SEQUENCE: 21

```
gctattcgct ggtcagttat ggctcgcgct gcgttcctat tcaagactgt tgggtttggt       60
ggtctgcaaa atgtgccaat taacgacgaa ctatcttcac atctactccg agctggtaat      120
tcaccatggc agttaacaca gttttagac tggataagcc ttgggagggg tttagctaca      180
tcggctctcg ttccgacggc tgggtcaaga tactatcaaa tgagttgcct tctaagtggc      240
actctccaga ttccgttccg tcctaaccac cgatggggag acattaggtt cttacgctta      300
gtgtggtcag ctcctactct cgatggatta gtcgtagctc caccacaagt tttggctcag      360
cccgctttgc aagcacaggc agatcgagtg tacgactgcg atgattatcc atttctagcg      420
cgtgatccaa gattcaaaca tcgggtgtat cagcaattga gtgctgtaac tctacttaac      480
ttgacaggtt ttggcccgat ttcctacgtt cgagtggatg aagatatgtg gagtggagat      540
gtgaaccagc ttctcatgaa ctatttcggg cacacgtttg cagagattgc atacacattg      600
tgtcaagcct cggctaatag gccttgggaa tatgacggta catatgctag gatgactcag      660
attgtgttat ccttgttctg gctatcgtat gtcggtgtaa ttcatcagca gaatacgtat      720
cggacattct attttcagtg taatcggcga ggtgacgccg ctgaggtgtg gattcttcct      780
tgttcgttga accattccgc acaaattaga ccgggtaatc gtagcttatt cgttatgcca      840
actagcccag attggaacat ggacgtcaat ttgatcctga gttcaacgtt gacggggtgt      900
ttgtgttcgg gttcacagct gccactgatt gacaataatt cagtacctgc agtgtcgcgt      960
```

| aacatccatg gctggactgg tagagctggt aaccaattgc atgggttcca ggtgagacga | 1020 |
| atggtgactg aattttgtga caggttgaga cgcgatggtg tcatgaccca agctcagcag | 1080 |
| aatcaagttg aagcgttggc agatcagact caacagttta agagggacaa gctcgaaacg | 1140 |
| tgggcgagag aagacgatca atataatcag gctcatccca actccacaat gttccgtacg | 1200 |
| aaaccattta cgaatgcgca atggggacga ggtaatacgg gggcgactag tgccgcgatt | 1260 |
| gcagccctta tctgatcgtc ttggagtgag ggggtccccc cacacccctc acgactgacc | 1320 |
| acacattcat c | 1331 |

<210> SEQ ID NO 22
<211> LENGTH: 1198
<212> TYPE: DNA
<213> ORGANISM: Artificial sequence
<220> FEATURE:
<223> OTHER INFORMATION: synthetic sequence

<400> SEQUENCE: 22

| gctaaagtca cgcctgtcgt cgtcactatg gcttcctcac tcagagctgc gatctccaag | 60 |
| atcaagaggg atgacgtcgg tcagcaagtt tgtcctaatt atgtcatgct gcggtcctct | 120 |
| gtcacaacaa aggtggtacg aaatgtggtt gagtatcaaa ttcgtacggg cggattcttt | 180 |
| tcgtgcttag ctatgctaag gccactccag tacgctaagc gtgagcgttt gcttggtcag | 240 |
| aggaatctgg aacgtatatc gactagggat atccttcaga ctcgtgattt acactcacta | 300 |
| tgtatgccaa ctcctgatgc gccaatgtct aatcatcaag catccaccat gagagagctg | 360 |
| atttgcagtt acttcaaggt cgatcatgcg gatgggttga aatatatacc catggatgag | 420 |
| agatactctc cgtcatcact tgccagattg tttaccatgg gcatggctgg gctgcacatt | 480 |
| accactgagc catcttataa gcgtgttccg attatgcact tagctgcgga cttggactgt | 540 |
| atgacgctgg ctctacctta catgattacg cttgatggtg atactgtggt tcctgtcgct | 600 |
| ccaacactgt cagcggaaca gcttctggac gacggactca aaggattagc atgcatggat | 660 |
| atctcctatg gatgtgaggt ggacgcgaat agccggccgg ctggtgatca gagtatggac | 720 |
| tcttcacgct gcatcaacga gttgtattgc gaggagacag cagaagccat ctgtgtgctt | 780 |
| aagacatgcc ttgtgttaaa ttgcatgcag tttaaacttg agatggatga cctagcacat | 840 |
| aacgctgctg agctggacaa gatacagatg atgataccct tcagtgagcg tgttttагg | 900 |
| atggcctcgt cctttgcgac tattgatgcc cagtgtttta ggttttgcgt gatgatgaag | 960 |
| gataaaaatc tgaaaataga tatgcgtgaa acgacgagac tgtggactcg ttcagcatca | 1020 |
| gatgattctg tggccacgtc atctttaagt atttccctgg accggggtcg atgggtggcg | 1080 |
| gctgacgcca gtgatgctag actgctggtt tttccgattc gcgtgtaatg ggtgagtgag | 1140 |
| ctgatgtggt cgccaagaca tgtgccggtg tcttggtggt gggtgacgcc taatcatc | 1198 |

<210> SEQ ID NO 23
<211> LENGTH: 1196
<212> TYPE: DNA
<213> ORGANISM: Artificial sequence
<220> FEATURE:
<223> OTHER INFORMATION: synthetic sequence

<400> SEQUENCE: 23

| gctattttg cctcttccca gacgttgtcg caatggaggt gtgcttgccc aacggtcatc | 60 |
| aggtcgtgga cttaattaac aacgcttttg aaggtcgtgt atcaatctac agcgcgcaag | 120 |
| agggatggga caaaacaatc tcagcacagc cagatatgat ggtatgtggt ggcgccgtcg | 180 |

```
tttgcatgca ttgtctaggt gttgttggat ctctacaacg caagctgaag catttgcctc      240
accatagatg taatcaacag atccgtcatc aggattacgt cgatgtacag ttcgcagacc      300
gtgttactgc tcactggaag cggggtatgc tgtccttcgt tgcgcagatg cacgagatga      360
tgaatgacgt gtcgccagat gacctggatc gtgtgcgtac tgagggaggt tcactagtgg      420
agctgaaccg gcttcaggtt gacccaaatt caatgtttag atcaatacac tcaagttgga      480
cagatccttt gcaggtggtg gacgaccttg acactaagct ggatcagtac tggacagcct      540
taaacctgat gatcgactca tccgacttga tacccaactt tatgatgaga gacccatcac      600
acgcgttcaa tggtgtgaaa ctgaagggag atgctcgtca acccaattc tccaggactt       660 ttgattcgag atcgagtttg aatgggtg tgatggttta tgattactct gagctggatc        720
atgatccatc gaagggccgt gcttacagaa aggaattggt gacgccagct cgagatttcg      780
gtcactttgg attatcccat tattctaggg cgactacccc aatccttgga agatgccgg       840 ccgtattctc aggaatgttg actgggaact gtaaaatgta tccattcatt aaaggaacgg      900
ctaagctgaa gacagtgcgc aagctagtgg aggcagtcaa tcatgcttgg ggtgtcgaga      960
agattagata tgctcttggg ccaggtggca tgacgggatg gtacaatagg actatgcaac     1020
aggcccccat tgtgctaact cctgctgctc tcacaatgtt cccagatacc atcaagtttg     1080
gggatttgaa ttatccagtg atgattggcg atccgatgat tcttggctaa acaccccat      1140 cttcacagcg ccgggcttga ccaacctggt gtgacgtggg acaggcttca ttcatc         1196

<210> SEQ ID NO 24
<211> LENGTH: 2304
<212> TYPE: DNA
<213> ORGANISM: Artificial sequence
<220> FEATURE:
<223> OTHER INFORMATION: synthetic sequence

<400> SEQUENCE: 24
gctattcgcg gtcatggctt acatcgcagt tcctgcggtg gtggattcac gttcgagtga       60
ggctattgga ctgctagaat cgtttggagt agacgctggg gctgacgcga atgacgtttc      120
atatcaagat catgactatg tgttggatca gttacagtac atgttagatg gatatgaggc      180
tggtgacgtt atcgatgcac tcgtccacaa gaattggtta catcactctg tctattgctt      240
gttgccgccc aaaagtcaac tattagagta ttggaaaagt aatccttcag cgataccgga      300
caacgttgat cgtcggcttc gtaaacgact aatgctaaag aaagatctca ggaaagatga      360
tgaatacaat cagctagcgc gtgctttcaa gatatcggat gtctacgcac ctctcatctc      420
atccacgacg tcaccgatga caatgataca gaacttgaat cgaggcgaga tcgtgtacac      480
cacgacggac agggtaatag gggctagaat cttgttatat gctcctagaa agtactatgc      540
gtcaactctg tcatttacta tgactaagtg catcattccg tttggtaaag aggtgggtcg      600
tgttcctcac tctcgatta atgttggcac atttccgtca attgctaccc cgaaatgttt      660
tgtcatgagt ggggttgata ttgagtccat cccaaatgaa tttatcaagt tgttttacca      720
gcgcgtcaag agtgttcacg ctaacatact aaatgacata tctcctcaga tcgtctctga      780
catgataaac agaaagcgtc tgcgcgttca tactccatca gatcgtcgag ccgcgcagtt      840
gatgcatttg ccttaccatg ttaaacgagg agcgtctcac gtcgacgttt acaaggtgga      900
tgttgtagac atgttgttcg aggtagtgga tgtggccgat gggttgcgca acgtatctag      960
gaaactaact atgcataccg ttcctgtatg tattcttgaa atgttgggta ttgagattgc     1020
```

```
ggactattgc attcgtcaag aggatggaat gctcacagat tggttcctac tttttaaccat    1080 gctatctgat ggcttgactg atagaaggac gcattgtcaa tacttgatta atccgtcaag    1140
tgtgcctcct gatgtgatac ttaacatctc aattactgga tttataaata gacatacaat    1200
cgatgtcatg cctgacatat atgacttcgt taaacccatt ggcgctgtgc tgcctaaggg    1260
atcatttaaa tcaacaatta tgagagttct tgattcaata tcaatattag gaatccaaat    1320
catgccgcgc gcgcatgtag ttgactcaga tgaggtgggc gagcaaatgg agcctacgtt    1380
tgagcaggcg gttatggaga tatacaaagg gattgctggc gttgactcgc tggatgatct    1440
catcaagtgg gtgttgaact cggatctcat tccgcatgat gacaggcttg gtcaattatt    1500
tcaagcgttt ttgcctctcg caaaggactt attagctcca atggccagaa agttttatga    1560
taactcaatg agtgagggta gattgctaac attctctcat gccgacagtg agttgctgaa    1620
cgcaaattat tttggtcatt tattgcgact aaaaatacca tatattacag aggttaatct    1680
gatgattcgc aagaatcgtg agggtggaga gctatttcag ctcgtgttat cttatctata    1740
taaaatgtat gctactagcg cgcagcctaa atggtttgga tcattattgc gattgttaat    1800
atgtccctgg ttacatatgg agaaattaat aggagaagca gacccggcat ctacgtcggc    1860
tgaaattggg tggcatatcc ctcgtgaaca gctgatgcaa gatggatggt gtggatgtga    1920
agacggattc attccctatg ttagcatacg tgcgccaaga ctggttatag aggagttgat    1980
ggagaagaac tggggccaat atcatgccca agttattgtc actgatcagc ttgtcgtagg    2040
cgaaccgcgg agggtatctg ctaaggctgt gatcaagggt aaccacttac cagttaagtt    2100
agtttcacga tttgcatgtt tcacattgac ggcgaagtat gagatgaggc tttcgtgcgg    2160
ccatagcact ggacgtggag ctgcatacag tgcgagacta gctttccgat ctgacttggc    2220
gtgatccgtg acatgcgtag tgtgacacct gctcctaggt caatgggggt aggggcggg    2280 ctaggactac gtacgcgctt catc    2304
```

<210> SEQ ID NO 25
<211> LENGTH: 2203
<212> TYPE: DNA
<213> ORGANISM: Artificial sequence
<220> FEATURE:
<223> OTHER INFORMATION: synthetic sequence

<400> SEQUENCE: 25

```
gctaatctgc tgaccgttac tctgcaaaga tggggaacgc ttcctctatc gttcagacga     60
tcaacgtcac tggagatggc aatgtattta aaccatcagc tgaaacttca tctaccgctg    120
taccatcgtt aagcttatca cctggaatgc tgaatcccgg aggggtacca tggattgctg    180
ttggagatga cacatctgtg acttcaccag gcgcattacg tcgaatgacg tcaaaggaca    240
tcccggacac ggcaataatc aacacagaca attcatcagg cgccgtgcca agcgaatcag    300
ccttggtgcc ctacatcgat gagccgctgg tagtggttac agagcatgct attaccaact    360
tcaccaaagc tgagatggca cttgaattca atcgtgagtt ccttgacaag atgcgtgtgc    420
tgtcagtgtc accaaaatat tcggatcttc tgacctatgt tgactgctac gtcggtgtgt    480
ctgctcgtca ggctttaaac aatttttcaga acaagtgcc tgtgattaca cctactaggc    540
agacgatgta tgtcgactcg atacaagcgg ccttgaaagc tttagaaaag tgggagattg    600
atctgagagt ggctcaaacg ttgctgccta cgaacgttcc gattggagaa gtctcttgtc    660
caatgcagtc ggtagtgaaa ctgctggatg atcagctgcc agatgacagc tgatacggaa    720
ggtatcccaa ggaagccgcc gtcgctttgg ctaaacgaaa cggggaata caatggatgg    780
```

```
acgtatcaga aggcaccgtg atgaacgagg ctgtcaacgc tgttgcagct agtgcactgg    840
caccttcagc atcagcccca cccttagaag agaagtcaaa gttaaccgaa caagcgatgg    900
atctcgtgac cgcggctgag cctgagataa ttgcctcact cgcgccagtt cccgcacccg    960
tgtttgccat accacctaaa ccagcagatt ataatgtgcg tactctgagg atcgacgagg   1020
ccacttggct gcgaatgatt ccaaaatcaa tgaacacacc ttttcaaatc caggtgactg   1080
ataacacagg aactaattgg catctcaatt tgaggggggg gactcgtgta gtgaatctgg   1140
accaaatcgc tccgatgcgg tttgtattag atctaggggg aaagagttat aaagagacga   1200
gctgggatcc aaacggcaag aaggtcggat tcatcgtttt tcaatcgaag ataccattcg   1260
aactttggac tgctgcttca cagatcggtc aagccacggt ggttaactat gtccaactat   1320
acgctgaaga cagctcattt accgcgcagt ctatcattgc tactacctct ttggcttata   1380
actatgagcc tgagcagttg aataagactg accctgagat gaattattat cttttggcga   1440
cctttataga ctcagccgct ataacgccaa cgaatatgac acagcctgat gtttgggatg   1500
ccttgctgac gatgtcccca ctatcagctg gcgaggtgac agtgaagggt gcggtagtga   1560
gtgaagtagt ccctgcagac ttgataggta gctacactcc agaatcccta aacgcctcac   1620
ttccgaatga tgctgctaga tgcatgatcg atagagcttc gaagatagcc gaagcaatca   1680
agattgatga tgatgctgga ccagatgaat attcccccaaa ctctgtacca attcaaggtc   1740
agcttgctat ctcgcaactc gaaactggat atggtgtgcg aatattcaac cctaaaggga   1800
tcctttccaa aattgcatct agggcaatgc aggctttcat tggtgacccg agcacaatca   1860
tcacgcaggc ggcgccagtg ttatcagaca agaataattg gattgcattg gcacagggag   1920
tgaaaactag tctgcgtact aaaagtctat cagcgggagt gaagactgca gtgagtaagc   1980
tgagctcatc tgagtctatc cagaattgga ctcaaggatt cttggataaa gtgtcagcgc   2040
attttccagc accaaagccc gattgtccga ctagcggaga tagtggtgaa tcgtctaatc   2100
gccgagtgaa gcgcgactca tacgcaggag tggtcaaacg tgggtacaca cgttaggccg   2160
ctcgccctgg tgacgcgggg ttaagggatg caggcaaatc atc                     2203
```

<210> SEQ ID NO 26  
<211> LENGTH: 2241  
<212> TYPE: DNA  
<213> ORGANISM: Artificial sequence  
<220> FEATURE:  
<223> OTHER INFORMATION: synthetic sequence

<400> SEQUENCE: 26

```
gctaaagtga ccgtggtcat ggcttcattc aagggattct ccgccaacac tgttccagtt     60
tctaaggcca agcgtgacat atcatctctt gccgctactc ctggacttcg ttcacaatcc    120
ttcactccgt ctgtggatat gtctcaatcg cgtgaattcc tcacaaaggc aattgagcaa    180
gggtccatgt ctataccttta tcagcatgtg aatgtaccga agttgatcg taaagttgtt    240
agcctggtag tgcgaccttt ctcttcaggt gctttctcta tctctggagt gatttcgcca    300
gcccatgcct atctactaga gtgtctaccc cagcttgagc aggcgatggc ttttgtcgct    360
tcacctgagt ctttccaggc ttccgacgtc gcgaagcgct tgccataaa gccaggtatg    420
agcctccagg atgccatcac tgcctttatt aactttgtgt ccgcgatgct gaaaatgacg    480
gtgactcgtc aaaactttga cgttattgtg gctgagatcg agaggcttgc ttcaaccagc    540
gtgtccgtca ggactgaaga agcgaaggtt gctgatgagg agctaatgct attcgggtta    600
```

```
gatcatagag ggccacagca gctggatgtt tctgacgcta aagggataat gaaggctgct    660
gatattcaga caactcatga tgtccatttg gcaccaggcg ttggtaatat tgatcctgaa    720
atctataacg aggggcggtt catgttcatg cagcacaagc cacttgcggc ggatcaatcg    780
tatttcacct tggagactgc ggattatttc aagatttatc caacatacga tgaacatgat    840
ggcaggatgg ctgaccaaaa gcagtcggga ttgatactgt gtactaagga cgaggtattg    900
gctgagcaaa ctatatttaa actggacgcc cctgatgaca agactgttca tctgttggat    960
cgcgatgacg accacgttgt tgccagattt actaaggtat ttatagagga cgtggctccc   1020
gggcatcatg ctgctcaaag atcgggacaa cgctctgtgc ttgatgacct atatgcgaat   1080
acgcaagtga tttccattac ttctgctgct ttaaagtggg tggtcaagca cggcgtatct   1140
gatggaatcg tgaacaggaa gaatgtcaaa gtgtgtgttg gttttgaccc cctgtacacc   1200
ttgtctacac ataacggggt gtccttatgt gccctgctga tggacgaaaa actctctgtg   1260
ctgaacagtg cgtgtcgtat gacgttacgc tcactcatga agaccggacg cgacgttgat   1320
gcacacagag cttttcagcg agtcctctct caaggataca catcgctaat gtgctactat   1380
catccttcac ggaagttggc atatggtgag gtgctctttc tagaacgatc caatgacgtg   1440
acagatggga tcaagcttca gttggacgca tctagacagt gtcatgaatg tcctgtgttg   1500
cagcagaaag tggttgagtt agagaaacag attattatgc agaagtcaat ccagtcagac   1560
cctaccccag tggcgctgca accattgttg tctcagttgc gtgagttgtc tagtgaagtt   1620
actaggctac agatggagtt gagtcgagct cagtccctga atgctcagtt ggaggcggat   1680
gtcaagtcag ctcaatcatg tagcttggat atgtatctga gacaccacac ttgcattaat   1740
ggtcatgcta agaagatga attgcttgac gctgtgcgtg tcgcgccgga tgtgaggaga   1800
gaaatcatgg aaaagaggag tgaagtgaga caaggttggt gcgaacgtat ttctaaggaa   1860
gcagctgcca aatgtcaaac tgttattgat gacctgactt tgatgaatgg aaagcaagca   1920
caagagataa cagaattacg tgattcggct gaaaaatatg agaaacagat tgcagagctg   1980
gtgagtacca tcacccaaaa ccagataacg tatcagcaag agctacaagc cttggtagcg   2040
aaaaatgtgg aattggacgc gttgaatcag cgtcaggcta agtctttgcg tattactccc   2100
tctcttctat cagccactcc tatcgattca gttgatgatg ttgctgactt aattgatttc   2160
tctgttccaa ctgatgagtt gtaaataatc cgtgatgcag tgttgcccta atcccttaag   2220
ccttcccgac ccccattcat c                                              2241
```

<210> SEQ ID NO 27
<211> LENGTH: 3854
<212> TYPE: DNA
<213> ORGANISM: Artificial sequence
<220> FEATURE:
<223> OTHER INFORMATION: synthetic sequence

<400> SEQUENCE: 27

```
gctacacgtt ccacgacaat gtcatccatg atactgactc agtttggacc gttcattgag     60
agcatttcag gtatcactga tcaatcgaat gacgtgtttg aagatgcagc aaaagcattc    120
tctatgttta ctcgcagcga tgtctacaag gcgctggatg aaataccttt ctctgatgat    180
gcgatgcttc caatccctcc aactatatat acgaaaccat ctcacgattc atattattac    240
attgatgctc taaaccgtgt gcgtcgcaaa acatatcagg gccctgatga cgtgtacgta    300
cctaattgtt ctattgttga attgctggag ccacatgaga ctctgacatc ttatgggcgg    360
ttgtccgagg ccatcgagaa tcgtgccaag gatggggaca gccaagccag aatcgccaca    420
```

```
acgtatggta gaatcgctga atctcaagct cgacagatta aggctccatt ggagaagttt    480
gtgttggcac tattagtggc cgaagcaggg gggtctttat atgatccagt tttgcagaag    540
tatgatgaga ttccagatct atcgcataat tgcccttta ggtgttttag agagatctgt     600
cgtcacatat ctggtccatt accagatcgg gcaccttatc tttacttatc tgcaggggtt    660
ttctggttaa tgtcaccacg aatgacgtct gcaatccctc cgctactatc cgatcttgtt    720
aatttagcta ttttgcaaca aactgcgggt ttagatccat cattagtgaa attgggagta    780
cagatatgcc ttcatgcagc agctagctca agttatgcat ggtttatctt aaagactaag    840
tctattttc ctcaaaacac gttgcacagt atgtatgaat ctctagaagg gggatactgt     900
cctaatcttg aatggttaga gcctagatca gactataagt tcatgtacat gggagtcatg    960
ccattgtccg ctaagtatgc taggtcggcg ccgtccaatg ataagaaagc gcgggaactt   1020
ggcgagaaat atggactgag ctcagtcgtc ggtgagcttc gtaaacggac aaagacgtat   1080
gttaaacatg actttgcttc agtgaggtac attcgtgacg ctatggcatg tactagcggt   1140
attttcttgg taagaacacc caccgaaacg gtattgcaag aatatacgca gagtccggag   1200
attaaggttc ccattcccca gaaagactgg acaggcccaa taggtgaaat cagaattcta   1260
aaagatacaa caagttccat cgcgcgttac ttatatagaa catggtactt ggcagcggcg   1320
agaatggcgg ctcaaccacg tacgtgggat ccattgtttc aagcgattat gagatctcaa   1380
tacgtgacag ctaggggtgg atctggcgca gcactccgcg aatctttgta tgcaatcaat   1440
gtgtcgttac ctgatttcaa gggcttacca gtgaaggcag caactaagat attccaggcg   1500
gcacaattag cgaacttgcc gttctcccac acatcagtgg ctatactagc tgacacttca   1560
atgggattgc gaaatcaggt gcagaggcgg ccacgatcca ttatgccatt aaatgtgccc   1620
cagcagcagg tttcggcgcc ccatacattg acagcggatt acattaacta ccacatgaat   1680
ctatcaacca cgtctggtag tgcggtcatt gagaaggtga ttcctttagg tgtatacgct   1740
tcgagccctc ctaaccagtc gatcaacatt gacatatctg cgtgtgacgc tagtattact   1800
tgggatttct ttctgtcagt gattatggcg gctatacacg aaggtgtcgc tagtagctcc   1860
attggaaaac catttatggg ggttcctgca tccattgtaa atgatgagtc tgtcgttgga   1920
gtgagagctg ctaggccgat atcgggaatg cagaacatga ttcagcatct atcgaaacta   1980
tataaacgtg gattttcata tagagtaaac gattctttt ctccaggtaa cgatttact    2040
catatgacta ccactttccc gtcaggttca acagccacct ctactgagca tactgctaat   2100
aatagtacga tgatggaaac tttcctgaca gtatggggac ccgaacatac tgacgaccct   2160
gacgtcttac gtttaatgaa gtctttaact attcaaagga attacgtatg tcaaggtgat   2220
gatgagttaa tgattatcga tgggactact gctggtaagg tgaacagtga aactattcag   2280
aagatgctag aattaatctc aaaatatggt gaggaattcg gatggaaata tgacatagcg   2340
tacgatggga ctgccgaata cttaaagcta tacttcatat ttggctgtcg aattccaaat   2400
cttagtcgcc atccaatcgt ggggaaagaa cgggcgaatt cttcagcaga ggagccatgg   2460
ccagcaattc tagatcagat tatgggtgtc ttctttaatg gtgttcatga tgggttacag   2520
tggcagcggt ggatacgtta ttcatgggct ctatgctgtg ctttctcacg tcaaagaaca   2580
atgattggtg agagcgtggg ttaccttcaa tatcctatgt ggtcttttgt ctactgggga   2640
ttaccactgg ttaaagcgtt tgggtcagac ccatggatat tttcttggta catgcctact   2700
ggagatctgg gaatgtatag ttggattagc ttgatacgcc ctctgatgac aagatggatg   2760
```

```
gtggctaatg gttacgtaac tgacagatgc tcacccgtat tcgggaacgc agattatcgc    2820
aggtgtttca atgaacttaa actatatcaa ggttattata tggcacaatt gcccaggaat    2880
cctaagaagt ctggacgagc ggcccctcgg gaggtaagag aacaattcac tcaggcatta    2940
tccgactatc tactgcaaaa tccagagctg aagtcacgtg tgctacgtgg tcgtagtgag    3000
tgggagaaat atggagcggg gataattcac aatcctccgt cattattcga tgtgccccat    3060
aaatggtatc agggtgcgca agaggcagca atcgctacga gaagagct ggcagaaatg    3120 gatgagacat taatgcgcgc tcgaaggcac agatattcga gcttttcaaa gttattagag    3180
gcgtatctgc tcgtgaaatg gcgaatgtgc gaggcccgcg aaccgtcggt ggatttgcga    3240
ttaccattat gtgcgggtat tgacccatta aactcagatc cttttctcaa gatggtaagc    3300
gttggaccaa tgctccagag tacgagaaag tactttgctc agacactatt catggcaaag    3360
acggtgtcgg gtcttgacgt taacgcgatt gatagcgcgt tattacgact gcgaacatta    3420
ggtgctgata agaaagcatt aacggcgcag ttattaatgg tggggcttca ggagtcagaa    3480
gcggacgcat tggccgggaa gataatgcta caggatgtga atactgtgca attagccaga    3540
gtggttaact tagctgtgcc agatacttgg atgtcgttag actttgactc tatgttcaaa    3600
caccacgtca agctgcttcc caaagatgga cgtcatctaa atactgatat tcctcctcga    3660
atgggatggt tacgggccat tttacgattc ttaggtgccg aatggtaat gactgcgact    3720 ggagttgctg tcgacatcta tctggaggat atacatggcg gtggtcggtc acttggacag    3780
agattcatga cttggatgcg acaggaagga cggtcagcgt gagtctacca tgggtcgtgg    3840
tgcgtcaact catc                                                     3854

<210> SEQ ID NO 28
<211> LENGTH: 3916
<212> TYPE: DNA
<213> ORGANISM: Artificial sequence
<220> FEATURE:
<223> OTHER INFORMATION: synthetic sequence

<400> SEQUENCE: 28
gctaaatggc gcgatggcga acgtttgggg ggtgagactt gcagactcgt tatcttcacc      60
cactattgag acacgaacgc gtcagtatac cttacacgat ctttgctcag acctagatgc     120
taatccgggg agggaaccgt ggaaacctct gcgtaatcag cgtactaata atattgtggc     180
tgtgcaatta ttcagaccat tgcagggttt agttttagat acccagcttt atggatttcc     240
aggagcattt tgatgactggg agcgattcat gagagagaag ctgcgtgtgc taaagtatga     300
agtattgcgc atctatccaa tcagcaacta tagcaatgaa catgtcaacg tcttcgtggc     360
caatgctttg gtgggcgctt tcctgtcgaa tcaagctttc tatgacctgc taccgttgtt     420
gataattaat gacactatga ttggtgatct acttggcacg ggggcatcgc tatcacagtt     480
ctttcaatct catggagatg tgctggaagt cgcagctggt cgtaagtatc tgcagatgga     540
aaactactcc aacgatgacg atgatcctcc attatttgcg aaagaccgt cagattatgc     600 taaagcattc tacagtgaca catatgaagt gttggacagg ttcttttgga cgcatgactc     660
ttcagcgggg gtcttagtgc attatgataa gccaacgaat ggtcatcact atctgctggg     720
tactttgact cagatggtca gtgcacctcc ttatattatt aacgctactg acgcaatgtt     780
gcttgaatcc tgtctagaac agttctcagc taatgtgcgt gcgagacctg cgcaacccgt     840
tacacgctta gaccaatgct atcatttaag atggggagca caatatgtag gagaagattc     900
actgacatat cggttggggg tgttatcctt gctggctacc aatggatatc aattagctag     960
```

```
accgattcca agacagttga cgaatcgatg gttgtcgagc tttgtgagtc aaattatgtc    1020
tgacggcgtc aacgagactc cactgtggcc ccaagaaagg tatgtgcaga tcgcttatga    1080
ttcaccatcc gttgttgatg gggctacgca atatggctat gtcaggaaga atcaactcag    1140
actcggcatg agaatatcgg cgctgcaatc gctgagtgat acgccctcgc cggtacagtg    1200
gcttccacaa tacaccatcg accaggcagc gatggacgaa ggcgatctga tggttagtcg    1260
gcttacgcaa ctcccgttac gtcctgatta tggtaatatc tgggtcggcg atgcgctatc    1320
ctattatgtg gactacaatc ggagtcatcg agtcgtgctt tcatcggaac ttcctcagct    1380
tccggacaca tattttgatg gcgatgaaca gtatgggcgc agcctgttct cactagctcg    1440
taagattggt gaccgctcgt tagtgaaaga tacggctgtc ttgaagcacg cttaccaagc    1500
catcgatcca aatactggta aggagtatct gagatctcgg caatctgtcg catattttgg    1560
tgcatcagcg ggtcattctg gtgccgacca gccgttagtc atagagccct ggattcaagg    1620
gaaaatcagt ggtgtgccgc caccctcctc agtgcgacag ttcggctatg atgttgcccg    1680
tggcgcgatc gtcgatctgg cgagaccatt tccttctgga gattatcaat tgtctattc    1740 ggatgttgac caggtggtcg atggccatga cgatctgagt atatcatctg gactggtgga    1800
gagccttttg tcttcatgca tgcacgccac agcacccggg ggctcatttg ttgttaagat    1860
aaattttccg actagacccg tatggcacta catcgaacag aagatcttgc ccaatattac    1920
gtcatacatg ttgatcaagc ctttcgtcac caacaacgtc gaattgttct tcgtcgcttt    1980
cggtgtgcat caacactcat cacttacttg gacatctgga gtgtacttct tcttggtgga    2040
ccatttttat cgttatgaga ctttatctac gatctcacga caattgccgt cttttgggta    2100
tgttgatgat gggtcttccg tgactggtat cgagacaatt agtattgaga ccctggctt    2160 ctcgaatatg acccaggccg ctcgcattgg tatctcagga ttgtgtgcta atgtaggtaa    2220
cgcgcgtaag tccattgcca tttacgaatc tcatggggcc agagtattaa ctatcacatc    2280
aaggagatct ccggcatcag ctagaagaaa gtctaggttg cgatatttgc cattaataga    2340
ccctaggtcg ttagaggtac aggcgcgcac tattctgcca gctgatccag tgttatttga    2400
aaacgtgagc ggagcgtcac cccatgtttg tctgacaatg atgtacaact tcgaagtgtc    2460
gtcagcggta tatgatggag acgttgtgct agatcttggg acgggaccag aggctaaaat    2520
ccttgaactg atacccgcaa cctctccagt cacatgcgtg gacatacggc ctacagcgca    2580
gcctagtgga tgttggaacg ttcgtaccac gttccttgag ttagattatt tgagcgatgg    2640
atggatcact ggggtgcgtg gggacatagt tacttgtatg ttatctttgg gggccgctgc    2700
cgctggaaaa tcaatgactt ttgacgctgc gtttcagcaa ttaatcaaag tattatccaa    2760
gagtacggct aatgttgtgc tggtgcaggt taactgccct acagacgtgg tgaggagcat    2820
taagggctac ctagagatag attcgactaa caagaggtat aggttccccaa aatttggtcg    2880 agacgagccg tactctgaca tggatgcgct ggagaaaata tgtcgtaccg cctggccaaa    2940
ctgctcaatt acctgggttc cattgtcata cgacttgcgg tggactagac tggcattatt    3000
agagtccacg acattgagta gcgcgtcgat tagaattgct gagctgatgt ataaatacat    3060
gcctattatg aggattgata ttcatggact acccatggaa aagcgaggta acttcatagt    3120
ggggcagaac tgctcattag taatccctgg ttttaatgcg caggatgtct ttaactgtta    3180
tttcaattcc gccctcgctt tctcgactga agatgtcaat gctgcgatga ttccccaagt    3240
gtctgcgcag tttgatgcga ctaagggtga gtggacgttg gatatggtct tctccgacgc    3300
```

```
aggaatctat accatgcagg ctctagtggg atctaatgct aatccagtct ctttgggttc    3360
ctttgtagtt gattctccag atgtagatat aactgacgct tggccagctc agttagactt    3420
tacgatcgcg ggaactgatg tcgatataac agttaatcct tattaccgtc tgatgacctt    3480
tgtaaggatc gatggacagt ggcagattgc caatccagac aaatttcaat tcttttcgtc    3540
ggcgtctggg acgttagtga tgaacgtcaa attagatatc gcagataaat atctactata    3600
ctatatacga gatgtccagt ctcgagatgt tggcttttac attcagcatc cacttcaact    3660
tttgaatacg atcacattgc caaccaacga ggaccttttt ctgagcgcac ctgacatgcg    3720
agagtgggca gttaaggaaa gcggtaacac gatatgtata ctcaatagtc aagggtttgt    3780
gctacctcaa gattgggatg tgttaacaga taccataagt tggtccccat cgatacccac    3840
atacattgtg ccaccgggtg attataacctt gactcctctg taactcactg tccctcgtga    3900
gcgcgcctaa ttcatc                                                    3916
```

<210> SEQ ID NO 29
<211> LENGTH: 3901
<212> TYPE: DNA
<213> ORGANISM: Artificial sequence
<220> FEATURE:
<223> OTHER INFORMATION: synthetic sequence

<400> SEQUENCE: 29

```
gctaatcgtc aggatgaagc ggattccaag gaagacaaag gcaaatccaa gcggaaaggg      60
caatgactca acagagagag cggacgatgg ctcgagccaa ttaagagaca agcaaaacaa     120
taaggctggc cccgccacta cggagcctgg cacatccaac cgagagcaat acaaagctcg     180
accaggtatt gcatctgtgc agagggccac tgaaagtgca gaaatgccca tgaagaataa     240
tgacgaaggg acgccagata agaaaggaaa tactaagggc gacctagtta atgagcatag     300
tgaggctaaa gacgaggcgg atgaagcgac gaagaagcag gcaaaggata cagacaaaag     360
taaagcgcaa gtcacatatt cagacactgg tatcaataat gctaatgaac tgtcaagatc     420
tgggaatgtg gataatgagg gtggaagtaa tcagaagccg atgtctacca gaatagctga     480
ggcaacgtct gctatagtgt cgaaacatcc tgcgcgtgtt gggctgccac ctaccgctag     540
cagtggtcat gggtatcagt gccatgtctg ttctgcagtc ctgtttagtc ctttagacct     600
agatgcccac gtcgcctcac atggtttgca tggtaacatg acattaacat cgagtgatat     660
ccagcgacat ataactgagt tcatcagctc atggcaaaat catcctattg ttcaagtttc     720
ggctgatgtc gaaaataaga aaactgctca attgcttcac gctgacactc ctcgactcgt     780
cacttgggat gctggtttgt gtacttcatt caaaatcgtc ccgattgtgc cagctcaggt     840
gccgcaggat gtactggcct atacgttttt cacctcttca tacgctatcc aatcaccgtt     900
tccagaggcg gcagtgtcta ggattgtggt gcatacgaga tgggcatcta atgttgactt     960
tgaccgagac tcgtctgtca tcatggcgcc acctacagaa aacaatatcc atttgtttaa    1020
acagttacta aatactgaaa ccctgtctgt aaggggggct aatccgctaa tgttcagggc    1080
gaatgtgttg catatgttgc tagagttcgt attagataac ttgtatctga acagacatac    1140
gggattctct caagaccaca cgccatttac tgagggtgct aatttgcgtt cacttcctgg    1200
ccccgatgct gagaaatggt actcgattat gtatccaacg cgcatgggaa cgccgaatgt    1260
atccaaaata tgtaatttcg tcgcctcttg tgtgcgaaat cgggttggac ggtttgatcg    1320
agcacagatg atgaacggag ctatgtcaga gtgggtggat gtcttcgaga cttcagacgc    1380
gctaaccgtc tccattcgag gtcgatggat ggctagacta gctcgcatga acataaatcc    1440
```

```
aacagagatc gaatgggcat tgactgaatg tgcacaagga tatgtgactg tcacaagtcc    1500
ttacgctcct agcgtaaata gattgatgcc ctatcgtatc tccaacgctg agcggcaaat    1560
atcacagata atcaggatca tgaacattgg caataacgcg acggtgatac aacctgttct    1620
gcaagatatt tcggtactcc ttcaacgcat atcaccactc caaatagatc caactattat    1680
ttccaacact atgtcaacag tctcggagtc tactactcag accctcagcc ccgcgtcctc    1740
aattttgggt aaactacgac caagcaactc agatttttct agttttagag tcgcgttggc    1800
tggatggctt tataatgggg ttgtgacgac ggtgattgat gatagttcat atccaaaaga    1860
cggcggcagc gtgacctcac ttgaaaatct gtgggatttc ttcatccttg cgcttgctct    1920
accactgaca actgacccct gtgcacctgt gaaagcattc atgaccctag ccaacatgat    1980
ggttggtttc gagacaatcc ctatggataa tcagatctat actcaatcga gacgcgcgag    2040
tgctttctca acgcctcaca cgtggccacg atgctttatg aacatccagt taatttctcc    2100
aatcgacgct cccatcttgc gacagtgggc tgaaattatt catagatact ggcctaaccc    2160
ttcacagatt cgttatggtg caccgaacgt tttcggctcg gcaaatttgt tcactccacc    2220
tgaggtgctg ttattgccaa tcgatcatca accagctaat gtaacaacgc caacgctgga    2280
cttcaccaat gagttaacta attggcgcgc tcgtgtctgt gagcttatga agaatctcgt    2340
tgataaccaa agatatcaac ctggatggac acaaagtcta gtctcgtcaa tgcgcggaac    2400
gctagacaaa ttgaagttga ttaaatcgat gacaccaatg tatctgcaac agctggctcc    2460
ggtagagtta gcagtgatag ctcccatgtt gccttttcca cctttccagg tgccatacgt    2520
ccgtctcgat cgtgacagag ttccaacaat ggttggagta acacgacatt cacgagatac    2580
tattactcag ccggcgctat cgctgtcgac aaccaatact actgttggcg tgccactagc    2640
tctagacgcg agggctatca ccgttgcgct gttgtcaggg aaatatccgc cggatttggt    2700
gacaaatgta tggtacgctg atgccattta cccaatgtat gcagacacgg aggtgttctc    2760
taatcttcag agagacatga ttacctgcga ggccgtgcag acattagtga ctctggtggc    2820
gcaaatatca gagacccagt atcctgtaga taggtatctt gattggatcc catcactgag    2880
agcatcggcg gcgacggcgg cgacatttgc tgagtgggtt aatacttcaa tgaagacggc    2940
gtttgatttg tctgatatgc tgttagagcc tctcctaagc ggtgatccga ggatgactca    3000
actagcgatt cagtatcagc agtacaatgg cagaacgttt aatatcatac ctgaaatgcc    3060
aggttcagta attgctgact gcgttcaatt aacagcagaa gtctttaatc acgaatataa    3120
cctgtttggg attgcgcggg gtgatatcat cattggccgt gttcagtcga cacatttgtg    3180
gtcaccgctg gctcctccac ctgacctggt gtttgatcgt gataccctg tgttcacat     3240 cttcggacga gattgccgta tatcgtttgg aatgaatggc gccgcgccaa tgattagaga    3300
tgagactgga ctgatggtgc cttttgaagg aaattggatt tcccactgg cgctttggca     3360 aatgaataca cgatattta atcaacagtt cgacgcgtgg attaagacag agagttgcg     3420 aatccgcatt gagatgggcg cgtatccata tatgttgcat tactatgatc cacgtcagta    3480
cgctaatgca tggaatttaa catccgcctg gcttgaagaa attacgccga cgagcatccc    3540
atccgtgcct tcatggtgc ccatttcaag tgatcatgac atttcctctg ccccagctgt     3600
ccaatatatc atttcaactg aatataatga tcggtctctg ttctgcacta actcatcatc    3660
tccccaaacc atcgctggac cagacaaaca cattccagtt gagagatata acattctgac    3720
caaccccgac gctccaccca cgcagataca actgcctgaa gtcgttgact tgtacaacgt    3780
```

| cgtcacacgc tatgcgtatg agactccgcc tattaccgct gttgttatgg gtgttccttg | 3840 |
| atcctcatcc tcccaacagg tgctagagca ttgcgctcaa tgctagttgg gccgattcat | 3900 |
| c | 3901 |

<210> SEQ ID NO 30
<211> LENGTH: 1416
<212> TYPE: DNA
<213> ORGANISM: Artificial sequence
<220> FEATURE:
<223> OTHER INFORMATION: synthetic sequence

<400> SEQUENCE: 30

| gctattggtc ggatggatcc tcgcctacgt gaagaagtag tacggctgat aatcgcatta | 60 |
| acgagtgata atggagtatc actgtcaaaa gggcttgaat caagggtctc ggcgctcgag | 120 |
| aagacgtctc aaatacactc tgatactatc ctccggatca cccagggact cgatgatgca | 180 |
| aacaaacgaa tcatcgctct tgagcaaagt cgggatgact tggttgcatc agtcagtgat | 240 |
| gctcaacttg caatctccag attggaaagc tctatcggag ccctccaaac agttgtcaat | 300 |
| ggacttgatt cgagtgttac ccagttgggt gctcgagtgg gacaacttga gacaggactt | 360 |
| gcagagctac gcgttgatca cgacaatctc gttgcgagag tggatactgc agaacgtaac | 420 |
| attggatcat tgaccaccga gctatcaact ctgacgttac gagtaacatc catacaagcg | 480 |
| gatttcgaat ctaggatatc cacattagag cgcacggcgg tcactagcgc gggagctccc | 540 |
| ctctcaatcc gtaataaccg tatgaccatg ggattaaatg atggactcac gttgtcaggg | 600 |
| aataatctcg ccatccgatt gccaggaaat acgggtctga atattcaaaa tggtggactt | 660 |
| cagtttcgat ttaatactga tcaattccag atagttaata ataacttgac tctcaagacg | 720 |
| actgtgtttg attctatcaa ctcaaggata ggcgcaactg agcaaagtta cgtggcgtcg | 780 |
| gcagtgactc ccttgagatt aaacagtagc acgaaggtgc tggatatgct aatagacagt | 840 |
| tcaacacttg aaattaattc tagtggacag ctaactgtta gatcgacatc cccgaatttg | 900 |
| aggtatccga tagctgatgt tagcggcggt atcggaatga gtccaaatta taggtttagg | 960 |
| cagagcatgt ggataggaat tgtctcctat tctggtagtg ggctgaattg gagggtacag | 1020 |
| gtgaactccg acatttttat tgtagatgat tacatacata tatgtcttcc agcttttgac | 1080 |
| ggtttctcta tagctgacgg tggagatcta tcgttgaact tgttaccgg attgttacca | 1140 |
| ccgttactta caggagacac tgagcccgct tttcataatg acgtggtcac atatggagca | 1200 |
| cagactgtag ctatagggtt gtcgtcgggt ggtacgcctc agtatatgag taagaatctg | 1260 |
| tgggtggagc agtggcagga tggagtactt cggttacgtg ttgaggggg tggctcaatt | 1320 |
| acgcactcaa acagtaagtg gcctgccatg accgtttcgt acccgcgtag tttcacgtga | 1380 |
| ggatcagacc accccgcggc actggggcat tcatc | 1416 |

<210> SEQ ID NO 31
<211> LENGTH: 1331
<212> TYPE: DNA
<213> ORGANISM: Artificial sequence
<220> FEATURE:
<223> OTHER INFORMATION: synthetic sequence

<400> SEQUENCE: 31

| gctattcgct ggtcagttat ggctcgcgct gcgttcctat tcaagactgt tgggtttggt | 60 |
| ggtctgcaaa atgtgccaat taacgacgaa ctatcttcac atctactccg agctggtaat | 120 |
| tcaccatggc agttaacaca gttttagac tggataagcc ttgggagggg tttagctaca | 180 |

```
tcggctctcg ttccgacggc tgggtcaaga tactatcaaa tgagttgcct tctaagtggc      240
actctccaga ttccgttccg tcctaaccac cgatggggag acattaggtt cttacgctta      300
gtgtggtcag ctcctactct cgatggatta gtcgtagctc caccacaagt tttggctcag      360
cccgctttgc aagcacaggc agatcgagtg tacgactgcg atgattatcc atttctagcg      420
cgtgatccaa gattcaaaca tcgggtgtat cagcaattga gtgctgtaac tctacttaac      480
ttgacaggtt ttggcccgat ttcctacgtt cgagtggatg aagatatgtg gagtggagat      540
gtgaaccagc ttctcatgaa ctatttcggg cacacgtttg cagagattgc atacacattg      600
tgtcaagcct cggctaatag gccttgggaa tatgacggta catatgctag gatgactcag      660
attgtgttat ccttgttctg gctatcgtat gtcggtgtaa tccatcagca gaatacgtat      720
cggacattct attttcagtg taatcggcga ggtgacgccg ctgaggtgtg gattcttcct      780
tgttcgttga accattccgc acaaattaga ccgggtaatc gtagcttatt cgttatgcca      840
actagcccag attggaacat ggacgtcaat ttgatcctga gttcaacgtt gacggggtgt      900
ttgtgttcgg gttcacagct gccactgatt gacaataatt cagtacctgc agtgtcgcgc      960
aacatccatg gctggactgg tagagctggt aaccaattgc atgggttcca ggtgagacga     1020
atggtgactg aattttgtga caggttgaga cgcgatggtg tcatgaccca agctcagcag     1080
aatcaagttg aagcgttggc agatcagact caacagttta gagggacaa gctcgaaacg     1140 tgggcgagag aagacgatca atataatcag gctcatccca actccacaat gttccgtacg     1200
aaaccattta cgaatgcgca atggggacga ggtaatacgg gggcgactag tgccgcgatt     1260 gcagcctta tctgatcgtc ttggagtgag ggggtccccc cacacccctc acgactgacc     1320
acacattcat c                                                          1331
```

<210> SEQ ID NO 32
<211> LENGTH: 1196
<212> TYPE: DNA
<213> ORGANISM: Artificial sequence
<220> FEATURE:
<223> OTHER INFORMATION: synthetic sequence

<400> SEQUENCE: 32

```
gctattttg cctcttccca gacgttgtcg caatggaggt gtgcttgccc aacggtcatc       60
aggtcgtgga cttgattaac aacgcttttg aaggtcgtgt atcaatctac agcgcgcaag     120
agggatggga caaaacaatc tcagcacagc cagatatgat ggtatgtggt ggcgccgtcg     180
tttgcatgca ttgtctaggt gttgtcggat ctctacaacg caagctgaag catttgcctc     240
accatagatg taatcaacag atccgtcatc aggattacgt cgatgtacag ttcgcagacc     300
gtgttactgc tcactggaag cggggtatgc tgtccttcgt tgcgcagatg cacgagatga     360
tgaatgacgt gtcgccagat gacctggatc gtgtgcgtac tgagggaggt tcactagtgg     420
agctgaactg gcttcaggtt gacccaaatt caatgtttag atcaatacac tcaagttgga     480
cagatccttt gcaggtggtg gacgaccttg acactaagct ggatcagtac tggacagcct     540
taaacctgat gatcgactca tccgacttga tacccaactt tatgatgaga gacccatcac     600
acgcgttcaa tggtgtgaaa ctgggggag atgctcgtca aacccaattc tccaggactt     660
ttgattcgag atcgagtttg gaatgggtg tgatggttta tgattactct gagctggagc     720
atgatccatc gaagggccgt gcttacagaa aggaattggt gacgccagct cgagatttcg     780
gtcactttgg attatcccat tattctaggg cgactacccc aatccttgga aagatgccgg     840
```

```
ccgtattctc aggaatgttg actgggaact gtaaaatgta tccattcatt aaaggaacgg    900
ctaagctgaa gacagtgcgc aagctagtgg aggcagtcaa tcatgcttgg ggtgtcgaga    960
agattagata tgctcttggg ccaggtggca tgacgggatg gtacaatagg actatgcaac  1020
aggcccccat tgtgctaact cctgctgctc tcacaatgtt cccagatacc atcaagtttg  1080
gggatttgaa ttatccagtg atgattggcg atccgatgat tcttggctaa acaccccat  1140
cttcacagcg ccgggcttga ccaacctggt gtgacgtggg acaggcttca ttcatc       1196
```

<210> SEQ ID NO 33
<211> LENGTH: 2304
<212> TYPE: DNA
<213> ORGANISM: Artificial sequence
<220> FEATURE:
<223> OTHER INFORMATION: synthetic sequence

<400> SEQUENCE: 33

```
gctattcgcg gtcatggctt acatcgcagt tcctgcggtg gtggattcac gttcgagtga    60
ggctattgga ctgctagaat cgtttggagt agacgctggg gctgacgcga atgacgtttc   120
atatcaagat catgactatg tgttggatca gttacagtac atgttagatg gatatgaggc   180
tggtgacgtt atcgatgcac tcgtccacaa gaattggtta catcactctg tctattgctt   240
gttgccaccc aaaagtcaac tattagagta ttggaaaagt aatccttcag cgataccgga   300
caacgttgat cgtcggcttc gtaaacgact aatgctaaag aaagatctca ggaaagatga   360
tgaatacaat cagctagcgc gtgctttcaa gatatcggat gtctacgcac ctctcatctc   420
atccacgacg tcaccgatga caatgataca gaacttgaat caaggcgaga tcgtgtacac   480
cacgacggac agggtaatag gggctagaat cttgttatat gctcctagaa agtactatgc   540
gtcaactctg tcatttacta tgactaagtg catcattccg tttggtaaag aggtgggtcg   600
tgttcctcac tctcgattta atgttggcac attttcgtca attgctaccc cgaaatgttt   660
tgtcatgagt ggggttgata ttgagtccat cccaaatgaa tttatcaagt tgttttacca   720
gcgcgtcaag agtgttcacg ctaacatact aaatgacata tctcctcaga tcgtctctga   780
catgataaac agaaagcgtc tgcgcgttca tactccatca gatcgtcgag ccgcgcagtt   840
gatgcatttg ccttaccatg ttaaacgagg agcgtctcac gtcgacgttt acaaggtgga   900
tgttgtagac atgttgttcg aggtagtgga tgtggccgat gggttgcgca acgtatctag   960
gaaactaact atgcataccg ttccggtatg tattcttgaa atgttgggta ttgagattgc  1020
ggactattgc attcgtcgag aggatggaat gctcacagat tggttcctac ttttaaccat  1080
gctatctgat ggcttgactg atagaaggac gcattgtcaa tacttgatta atccgtcaag  1140
tgtgcctcct gatgtgatac ttaacatctc aattactgga tttataaata gacatacaat  1200
cgatgtcatg cctgacatat atgactttgt taaacccatt ggcgctgtgc tgcctaaggg  1260
atcatttaaa tcaacaatta tgagagttct tgattcaata tcaatattag gaatccaaat  1320
catgccgcgc gcgcatgtag ttgactcaga tgaggtgggc gagcaaatgg agcctacgtt  1380
tgagcaggcg gttatggaga tatacaaagg gattgctggc gttgactcgc tggatgatct  1440
catcaagtgg gtgctgaact cggatctcat tccgcatgat gacaggcttg gtcaattatt  1500
tcaagcgttt ttgcctctcg caaaggactt attagctcca atggccagaa agttttatga  1560
taactcaatg agtgagggta gattgctaac attcgctcat gccgacagtg agttgctgaa  1620
cgcaaattat tttggtcatt tattgcgact aaaaatacca tatattacag aggttaatct  1680
gatgattcgc aagaatcgtg agggtggaga gctatttcag cttgtgttat cttatctata  1740
```

| | | | | |
|---|---|---|---|---|
| taaaatgtat | gctactagcg | cgcagcctaa | atggtttgga | tcattattgc | gattgttaat | 1800 |
| atgtccctgg | ttacatatgg | agaaattaat | aggagaagca | gacccggcat | ctacgtcggc | 1860 |
| tgaaattggg | tggcatatcc | ctcgtgaaca | gctgatgcaa | gatggatggt | gtggatgtga | 1920 |
| agacggattc | attccctatg | ttagcatacg | tgcgccaaga | ctggttatag | aggagttgat | 1980 |
| ggagaagaac | tggggccaat | atcatgccca | agttattgtc | actgatcagc | ttgtcgtagg | 2040 |
| cgaaccgcgg | agggtatctg | ctaaggctgt | gatcaagggt | aaccacttac | cagttaagtt | 2100 |
| agtttcacga | tttgcatgtt | tcacattgac | ggcgaagtat | gagatgaggc | tttcgtgcgg | 2160 |
| ccatagcact | ggacgtggag | ctgcatacag | tgcgagacta | gctttccgat | ctgacttggc | 2220 |
| gtgatccgtg | acatgcgtag | tgtgacacct | gctcctaggt | caatgggggt | aggggcggg | 2280 |
| ctaagactac | gtacgcgctt | catc | | | | 2304 |

<210> SEQ ID NO 34
<211> LENGTH: 2203
<212> TYPE: DNA
<213> ORGANISM: Artificial sequence
<220> FEATURE:
<223> OTHER INFORMATION: synthetic sequence

<400> SEQUENCE: 34

| | | | | | | |
|---|---|---|---|---|---|---|
| gctaatctgc | tgaccgttac | tctgcaaaga | tggggaacgc | ttcctctatc | gttcagacga | 60 |
| tcaacgtcac | tggagatggc | aatgtattta | accatcagc | tgaaacttca | tctaccgctg | 120 |
| taccatcgtt | aagcttatca | cctggaatgc | tgaatcccgg | aggggtacca | tggattgctg | 180 |
| ttggagatga | gacatctgtg | acttcaccag | gcgcattacg | tcgaatgacg | tcaaaggaca | 240 |
| tcccggaaac | ggcaataatc | aacacagaca | attcatcagg | cgccgtgcca | agcgaatcag | 300 |
| ccttggtgcc | ctacatcgat | gagccgctgg | tagtggttac | agagcatgct | attaccaact | 360 |
| tcaccaaagc | tgagatggca | cttgaattca | atcgtgagtt | ccttgacaag | atgcgtgtgc | 420 |
| tgtcagtgtc | accaaaatat | tcggatcttc | tgacctatgt | tgactgctac | gtcggtgtgt | 480 |
| ctgctcgtca | ggctttaaac | aattttcaga | acaagtgcc | tgtgattaca | cctactaggc | 540 |
| agacgatgta | tgtcgactcg | atacaagcgg | ccttgaaagc | tttagaaaag | tgggagattg | 600 |
| atctgagagt | ggctcaaacg | ttgctgccta | cgaacgttcc | gattggagaa | gtctcttgtc | 660 |
| caatgcagtc | ggtagtgaaa | ctgctggatg | atcagctgcc | agatgacagc | tgatacgga | 720 |
| ggtatcccaa | ggaagccgcc | gtcgctttgg | ctaaacgaaa | cggggaata | caatggatgg | 780 |
| acgtatcaga | aggcaccgtg | atgaacgagg | ctgtcaacgc | tgttgcagct | agtgcactgg | 840 |
| caccttcagc | atcagcccca | cccttagaag | agaagtcaaa | gttaaccgaa | caagcgatgg | 900 |
| atctcgtgac | cgcggctgag | cctgagataa | ttgcctcact | cgcgccagtt | cccgcacccg | 960 |
| tgtttgccat | accacctaaa | ccagcagatt | ataatgtgcg | tactctgagg | atcgacgagg | 1020 |
| ccacttggct | gcgaatgatt | ccaaaatcaa | tgaacacacc | ttttcaaatc | caggtgactg | 1080 |
| ataacacagg | aactaattgg | catctcaatt | tgagggggg | gactcgtgta | gtgaatctgg | 1140 |
| accaaatcgc | tccgatgcgg | tttgtattag | atttaggggg | aaagagttat | aaagagacga | 1200 |
| gctgggatcc | aaacggcaag | aaggtcgat | tcatcgtttt | tcaatcgaag | ataccattcg | 1260 |
| aactttggac | tgctgcttca | cagatcggtc | aagccacggt | ggttaactat | gtccaactat | 1320 |
| acgctgaaga | cagctcattt | accgcgcagt | ctatcattgc | tactacctct | ttggcttata | 1380 |
| actatgagcc | tgagcagttg | aataagactg | accctgagat | gaattattat | cttttggcga | 1440 |

```
cctttataga ctcagccgct ataacgccaa cgaatatgac acagcctgat gtttgggatg    1500
ccttgctgac gatgtcccca ctatcagctg gcgaggtgac agtgaagggt gcggtagtga    1560
gtgaagtagt ccctgcagac ttgataggta gctacactcc agaatcccta aacgcctcac    1620
ttccgaatga tgctgctaga tgcatgatcg atagagcttc gaagatagcc gaagcaatca    1680
agattgatga tgatgctgga ccagatgaat attccccaaa ctctgtacca attcaaggtc    1740
agcttgctat ctcgcaactc gaaactggat atggtgtgcg aatattcaac cctaaaggga    1800
tcctttctaa aattgcatct agggcaatgc aggctttcat tggtgacccg agcacaatca    1860
tcacgcaggc ggcgccagtg ttatcagaca agaataattg gattgcattg gcacagggag    1920
tgaaaactag tctgcgtact aaaagtctat cagcgggagt gaagactgca gtgagtaagc    1980
tgagctcatc tgagtctatc cagaattgga ctcaaggatt cttggataaa gtgtcagcgc    2040
attttccagc accaaagccc gattgtccga ctagcggaga tagtggtgaa tcgtctaatc    2100
gccgagtgaa gcgcgactca tacgcaggag tggtcaaacg tgggtacaca cgttaggccg    2160
ctcgccctgg tgacgcgggg ttaagggatg caggcaaatc atc                      2203
```

<210> SEQ ID NO 35
<211> LENGTH: 2241
<212> TYPE: DNA
<213> ORGANISM: Artificial sequence
<220> FEATURE:
<223> OTHER INFORMATION: synthetic sequence

<400> SEQUENCE: 35

```
gctaaagtga ccgtggtcat ggcttcattc aagggattct ccgccaacac tgttccagtt      60
tctaaggcca agcgtgacat atcatctctt gccgctactc ctggacttcg ttcacaatcc     120
ttcactccgt ctgtggatat gtctcaatcg cgtgaattcc tcacaaaggc aattgagcaa     180
gggtccatgt ctatacctta tcagcatgtg aatgtaccga aagttgatcg taaagttgtt     240
agcctggtag tgcgaccttt ctcttcaggt gctttctcta tctctggagt gatttcgcca     300
gcccatgcct atctactaga gtgtctaccc cagcttgagc aggcgatggc ttttgttgct     360
tcacctgagt ctttccaggc ttccgacgtc gcgaagcgct ttgccataaa gccaggtatg     420
agcctccagg atgccatcac tgcctttatt aactttgtgt ccgcgatgct gaaaatgacg     480
gtgactcgtc aaaactttga cgttattgtg gctgagatcg agaggcttgc ttcaaccagc     540
gtgtccgtca ggactaaaga agcgaaggtt gctgatgagg agctaatgct attcgggtta     600
gatcatagag ggccacagca gctggatgtt tctgacgcta aagggataat gaaggctgct     660
gatattcaga caactcatga tgtccatttg gcaccaggcg ttggtaatat tgatcctgaa     720
atctataacg aggggcggtt catgttcatg cagcacaagc cacttgcggc ggatcaatcg     780
tatttcacct tggagactgc ggattatttc aagatttatc aacatacga tgaacatgat     840 ggcaggatgg ctgaccaaaa gcagtcggga ttgatactgt gtactaagga cgaggtattg     900
gctgagcaaa ctatatttaa actggacgcc cctgatgaca agactgttca tctgttggat     960
cgcgatgacg accacgttgt tgccagattt actaaggtat ttatagagga cgtggctccc    1020
gggcatcatg ctgctcaaag atcgggacaa cgctctgtgc ttgatgacct atatgcgaat    1080
acgcaagtga tttccattac ttctgctgct ttaaagtggg tggtcaagca cggcgtatct    1140
gatggaatcg tgaacaggaa gaatgtcaaa gtgtgtgttg gttttgaccc cctgtacacc    1200
ttgtctacac ataacggggt gtccttatgt gccctgctga tggacgaaaa actctctgtg    1260
ctgaacagtg cgtgtcgtat gacgttacgc tcactcatga agaccggacg cgacgttgat    1320
```

| | |
|---|---:|
| gcacacagag cttttcagcg agtcctctct caaggataca catcgctaat gtgctactat | 1380 |
| catccttcac ggaagttggc atatggtgag gtgctctttc tagaacgatc caatgacgtg | 1440 |
| acagatggga tcaagcttca gttggacgca tctagacagt gtcatgaatg tcctgtgttg | 1500 |
| cagcagaaag tggttgagtt agagaaacag attattatgc agaagtcaat ccagtcagac | 1560 |
| cctaccccag tggcgctgca accattgttg tctcagttgc gtgagttgtc tagtgaagtt | 1620 |
| actaggctac agatggagtt gagtcgagct cagtccctga atgctcagtt ggaggcggat | 1680 |
| gtcaagtcag ctcaatcatg tagcttggat atgtatctga gacaccacac ttgcattaat | 1740 |
| ggtcatgcta aagaagatga attgcttgac gctgtgcgtg tcgcgccgga tgtgaggaga | 1800 |
| gaaatcatgg aaaagaggag tgaagtgaga caaggttggt gcgaacgtat ttctaaggaa | 1860 |
| gcagctgcca aatgtcaaac tgttattgat gacctgactt tgatgaatgg aaagcaagca | 1920 |
| caagagataa cagaattacg tgattcggct gaaaaatatg agaaacagat tgcagagctg | 1980 |
| gtgagtacca tcacccaaaa ccagataacg tatcagcaag agctacaagc cttggtagcg | 2040 |
| aaaaatgtgg aattggacgc gttgaatcag cgtcaggcta agtctttgcg tattactccc | 2100 |
| tctcttctat cagccactcc tatcgattca gctgatggtg ttgctgactt aattgatttc | 2160 |
| tctgttccaa ctgatgagtt gtaaataatc cgtgatgcag tgttgcccta atcccttaag | 2220 |
| ccttcccgac ccccattcat c | 2241 |

<210> SEQ ID NO 36
<211> LENGTH: 3854
<212> TYPE: DNA
<213> ORGANISM: Artificial sequence
<220> FEATURE:
<223> OTHER INFORMATION: synthetic sequence

<400> SEQUENCE: 36

| | |
|---|---:|
| gctacacgtt ccacgacaat gtcatccatg atactgactc agtttggacc gttcattgag | 60 |
| agcatttcag gtatcactga tcaatcgaat gacgtgtttg aagatgcagc aaaagcattc | 120 |
| tctatgttta ctcgcagcga tgtctacaag gcgctggatg aaataccttt ctctgatgat | 180 |
| gcgatgcttc caatccctcc aactatatat acgaaaccat ctcacgattc atattattac | 240 |
| attgatgctc taaaccgtgt gcgtcgcaaa acatatcagg gccctgatga cgtgtacgta | 300 |
| cctaattgtt ctattgttga attgctggag ccacatgaga ctctgacatc ttatgggcgg | 360 |
| ttgtccgagg ccatcgagaa tcgtgccaag gatggggaca gccaagccag aatcgcccaca | 420 |
| acgtatggta gaatcgctga atctcaagct cgacagatta aggctccatt ggagaagttt | 480 |
| gtgttggcac tattagtggc gaagcaggg gggtctttat atgatccagt tttgcagaag | 540 |
| tatgatgaga ttccagatct atcgcataat tgcccttat ggtgttttag agagatctgt | 600 |
| cgtcacatat ctggtccatt accagatcgg gcaccttatc tttacttatc tgcaggggtt | 660 |
| ttctggttaa tgtcaccacg aatgacgtct gcaatccctc cgctactatc cgatcttgtt | 720 |
| aatttagcta ttttgcaaca aactgcgggt ttagatccat cattagtgaa attgggagta | 780 |
| cagatatgcc ttcatgcagc agctagctca agttatgcat ggtttatctt aaagactaag | 840 |
| tctatttttc ctcaaaacac gttgcacagt atgtatgaat ctctagaagg gggatactgt | 900 |
| cctaatcttg aatggttaga gcctagatca gactataagt tcatgtacat gggagtcatg | 960 |
| ccattgtccg ctaagtatgc taggtcggcg ccgtccaatg ataagaaagc gcgggaactt | 1020 |
| ggcgagaaat atggactgag ctcagtcgtc ggtgagcttc gtaaacggac aaagacgtat | 1080 |

```
gttaaacatg actttgcttc agtgaggtac attcgtgacg ctatggcatg tactagcggt   1140
attttcttgg taagaacacc caccgaaacg gtattgcaag aatatacgca gagtccggag   1200
attaaggttc ccattcccca gaaagactgg acaggcccaa taggtgaaat cagaattcta   1260
aaagatacaa caagttccat cgcgcgttac ttatatagaa catggtactt ggcagcggcg   1320
agaatggcgg ctcaaccacg tacgtgggat ccattgtttc aagcgattat gagatctcaa   1380
tacgtgacag ctaggggtgg atctggcgca gcactccgcg aatctttgta tgcgatcaat   1440
gtgtcgttac ctgatttcaa gggcttacca gtgaaggcag caactaagat attccaggcg   1500
gcacaattag cgaacttgcc gttctcccac acatcagtgg ctatactagc tgacacttca   1560
atgggattgc gaaatcaggt gcagaggcgg ccacgatcca ttatgccatt aaatgtgccc   1620
cagcagcagg tttcggcgcc ccatacattg acagcggatt acattaacta ccacatgaat   1680
ctatcaacca cgtctggtag tgcggtcatt gagaaggtga ttcctttagg tgtatacgct   1740
tcgagccctc ctaaccagtc gatcaacatt gacatatctg cgtgtgacgc tagtattact   1800
tgggatttct ttctgtcagt gattatggcg gctatacacg aaggtgtcgc tagtagctcc   1860
attggaaaac catttatggg ggttcctgca tccattgtaa atgatgagtc tgtcgttgga   1920
gtgagagctg ctaggccgat atcgggaatg cagaacatga ttcagcatct atcgaaacta   1980
tataaacgtg gattttcata tagagtaaac gattctttt ctccaggtaa cgatttttact   2040 catatgacta ccactttccc gtcaggttca acagccacct ctactgagca tactgctaat   2100
aatagtacga tgatggaaac tttcctgaca gtatggggac ccgaacatac tgacgaccct   2160
gacgtcttac gtttaatgaa gtcttttaact attcaaagga attacgtatg tcaaggtgat   2220
gatggattaa tgattatcga tgggactact gctggtaagg tgaacagtga actattcag   2280 aagatgctag aattaatctc aaaatatggt gaggaattcg gatggaaata tgacatagcg   2340
tacgatggga ctgccgaata cttaaagcta tacttcatat ttggctgtcg aattccaaat   2400
cttagtcgcc atccaatcgt ggggaaagaa cgggcgaatt cttcagcaga ggagccatgg   2460
ccagcaattc tagatcagat tatgggtgtc ttctttaatg gtgttcatga tgggttacag   2520
tggcagcggt ggatacgtta ttcatgggct ctatgctgtg cttctcacg tcaaagaaca   2580 atgattggtg agagcgtggg ttaccttcaa tatcctatgt ggtcttttgt ctactgggga   2640
ttaccactgt ttaaagcgtt tgggtcagac ccatggatat tttcttggta catgcctact   2700
ggagatctgg gaatgtatag ttggattagc ttgatacgcc ctctgatgac aagatggatg   2760
gtggctaatg gttacgtaac tgacagatgc tcaccgtat tcgggaacgc agattatcgc   2820
aggtgtttca atgaacttaa actatatcaa ggttattata tggcacaatt gcccaggaat   2880
cctaagaagt ctggacgagc ggcccctcgg gaggtaagag aacaattcac tcaggcatta   2940
tccgactatc taatgcaaaa tccagaactg aagtcacgtg tgctacgtgg tcgtagtgag   3000
tgggagaaat atggagcggg gataattcac aatcctccgt cattattcga tgtgccccat   3060
aaatggtatc agggtgcgca agaggcagca atcgctacga gagaagagct ggcagaaatg   3120
gatgagacat taatgcgcgc tcgaaggcac agctattcga acttttcaaa gttattagag   3180
gcgtatctgc tcgtgaaatg gcgaatgtgc gaggcccgcg aaccgtcggt tgatttgcga   3240
ttaccattat gtgcgggtat tgacccatta aactcagatc cttttctcaa gatggtaagc   3300
gttggaccaa tgctccagag tacgagaaag tactttgctc agacactatt catggcaaag   3360
acggtgtcgg gtcttgacgt taacgcgatt gatagcgcgt tattacgact gcgaacatta   3420
ggtgctgata agaaagcatt aacggcgcag ttattaatgg tggggcttca ggagtcagaa   3480
```

```
gcggacgcat tggccgggaa gataatgcta caggatgtga atactgtgca attagccaga    3540
gtggttaact tagctgtgcc agatacttgg atgtcgttag actttgactc tatgttcaaa    3600
caccacgtca agctgcttcc caaagatgga cgtcatctaa atactgatat tcctcctcga    3660
atgggatggt tacgggccat tttacgattc ttaggtgccg gaatggtaat gactgcgact    3720
ggagttgctg tcgacatcta tctggaggat atacatggcg gtggtcggtc acttggacag    3780
agattcatga cttggatgcg acaggaagga cggtcagcgt gagtctacca tgggtcgtgg    3840
tgcgtcaact catc                                                       3854
```

<210> SEQ ID NO 37
<211> LENGTH: 3916
<212> TYPE: DNA
<213> ORGANISM: Artificial sequence
<220> FEATURE:
<223> OTHER INFORMATION: synthetic sequence

<400> SEQUENCE: 37

```
gctaaaaggc gcgatggcga acgtttgggg ggtgagactt gcagactcgt tatcttcacc      60
cactattgag acacgaacgc gtcagtatac cttacacgat ctttgctcag acctagatgc     120
taatccgggg agggaaccgt ggaaacctct gcgtaatcag cgtactaata atattgtggc     180
tgtgcaatta ttcagaccat tgcagggttt agttttagat acccagcttt atggatttcc     240
aggagcattt gatgactggg agcgattcat gagagagaag ctgcgtgtgc taaagtatga     300
agtattgcgc atctatccaa tcagcaacta tagcaatgaa catgtcaacg tcttcgtggc     360
caatgctttg gtgggcgctt tcctgtcgaa tcaagctttc tatgacctgc taccgttgtt     420
gataattaat gacactatga ttggtgatct acttggcacg ggggcatcgc tatcacagtt     480
ctttcaatct catggagatg tgctggaagt cgcagctggt cgtaagtatc tgcagatgga     540
aaactactcc aacgatgacg atgatcctcc attatttgcg aaagacctgt cagattatgc     600
taaagcattc tacagtgaca catatgaagt gttggacagg ttcttttgga cgcatgactc     660
ttcagcgggg gtcttagtgc attatgataa gccaacgaat ggtcatcact atctgctggg     720
tactttgact cagatggtca gtgcacctcc ttatattatt aacgctactg acgcaatgtt     780
gcttgaatcc tgtctagaac agttctcagc taatgtgcgt gcgagacctg cgcaacccgt     840
tacacgctta gaccaatgct atcatttaag atggggagca caatatgtag gagaagattc     900
actgacatat cggttggggg tgttatcctt gctggctacc aatggatatc aattagctag     960
accgattcca agacagttga cgaatcgatg gttgtcgagc tttgtgagtc aaattatgtc    1020
tgacggcgtc aacgagactc cactgtggcc ccaagaaagg tatgtgcaga tcgcttatga    1080
ttcaccatcc gttgttgatg gggctacgca atatggctat gtcaggaaga atcaactcag    1140
actcggcatg agaatatcgg cgctgcaatc gctgagtgat acgccctcgc cggtacagtg    1200
gcttccacaa tacaccatcg accaggcagc gatggacgaa ggcgatctga tggttagtcg    1260
gcttacgcaa ctcccgttac gtcctgatta tggtaatatc tgggtcggcg atgcgctatc    1320
ctattatgtg gactacaaatc ggagtcatcg agtcgtgctt tcatcggaac ttcctcagct    1380
tccggacaca tattttgatg gcgatgaaca gtatgggcgc agcctgttct cactagctcg    1440
taagattggt gaccgctcgt tagtgaaaga tacggctgtc ttgaagcacg cttaccaagc    1500
catcgatcca aatactggta agggtatcct gagatctggg caatctgtcg catattttgg    1560
tgcatcagcg ggtcattctg gtgccgacca gccgttagtc atagagccct ggattcaagg    1620
```

```
gaaaatcagt ggtgtgccgc caccctcctc agtgcgacag ttcggctatg atgttgcccg   1680
tggcgcgatc gtcgatctgg cgagaccatt tccttctgga gattatcaat ttgtctattc   1740
ggatgttgac caggtggtcg atggccatga cgatctgagt atatcatctg gactggtgga   1800
gagccttttg tcttcatgca tgcacgccac agcacccggg ggctcatttg ttgttaagat   1860
aaattttccg actagacccg tatggcacta catcgaacag aagatcttgc ccaatattac   1920
gtcatacatg ttgatcaagc ctttcgtcac caacaacgtc gaattgttct tcgtcgcttt   1980
cggtgtgcat caacactcat cacttacttg gacatctgga gtgtacttct tcttggtgga   2040
ccattttat cgttatgaga ctttatctac gatctcacga caattgccgt cttttgggta   2100
tgttgatgat gggtcttccg tgactggtat cgagacaatt agtattgaga accctggctt   2160
ctcgaatatg acccaggccg ctcgcattgg tatctcagga ttgtgtgcta atgtaggtaa   2220
cgcgcgtaag tccattgcca tttacgaatc ccatggggcc agagtattaa ctatcacatc   2280
aaggagatct ccggcatcag ctagaagaaa gtctaggttg cgatatttgc cattaataga   2340
ccctaggtcg ttagaggtac aggcgcgcac tattctgcca gctgatccag tgttatttga   2400
aaacgtgagc ggagcgtcac cccatgtttg tctgacaatg atgtacaact tcgaagtgtc   2460
gtcagcggta tatgatggag acgttgtgct agatcttggg acgggaccag aggctaaaat   2520
ccttgaactg atacccgcaa cctctccagt cacatgcgtg gacatacggc ctacagcgca   2580
gcctagtgga tgttggaacg ttcgtaccac gttccttgag ttagattatt tgagcgatgg   2640
atggatcact ggggtgcgtg gggacatagt tacttgtatg ttatctttgg gggccgctgc   2700
cgctggaaaa tcaatgactt ttgacgctgc gtttcagcaa ttaatcaaag tattatccaa   2760
gagtacggct aatgttgtgc tggtgcaggt taactgccct acagacgtgg tgaggagcat   2820
taagggctac ctagagatag attcgactaa caagaggtat aggttcccca aatttggtcg   2880
agacgagccg tactctgaca tggatgcgct ggagaaaata tgtcgtaccg cctggccaaa   2940
ctgctcaatt acctgggttc cattgtcata cgacttgcgg tggactagac tggcattatt   3000
agagtccacg acattgagta gcgcgtcgat tagaattgct gagctgatgt ataaatacat   3060
gcctattatg aggattgaca ttcatggact acccatggaa aagcgaggta acttcatagt   3120
ggggcagaac tgctcattag taatccctgg ttttaatgcg caggatgtct ttaactgtta   3180
tttcaattcc gccctcgctt tctcgactga agatgtcaat gctgcgatga ttccccaagt   3240
gtctgcgcag tttgatgcga ctaagggtga gtggacgttg gatatggtct ctccgacgc   3300
aggaatctat accatgcagg ctctagtggg atctaatgct aatccagtct ctttgggttc   3360
cttttgtagtt gattctccag atgtagatat aactgacgct tggccagctc agttagactt   3420
tacgatcgcg ggaactgatg tcgatataac agttaatcct tattaccgtc tgatgacctt   3480
tgtaaggatc gatggacagt ggcagattgc caatccagac aaatttcaat tcttttcgtc   3540
ggcgtctggg acgttagtga tgaacgtcaa attagatatc gcagataaat atctactata   3600
ctatatacga gatgtccagt ctcgagatgt tggcttttac attcagcatc cacttcaact   3660
tttgaatacg atcacattgc caaccaacga ggacttttt ctgagcgcac ctgacatgcg   3720
agagtgggca gttaaggaaa gcggtaacac gatatgtata ctcaatagtc aagggtttgt   3780
gctacctcaa gattgggatg tgttaacaga taccataagt tggtccccat cgatacccac   3840
atacattgtg ccaccgggtg attataccct gactcctctg taactcactg tccctcgtga   3900
gcgcgcctaa ttcatc                                                   3916
```

```
<210> SEQ ID NO 38
<211> LENGTH: 3901
<212> TYPE: DNA
<213> ORGANISM: Artificial sequence
<220> FEATURE:
<223> OTHER INFORMATION: synthetic sequence

<400> SEQUENCE: 38
```

| | | | | | |
|---|---|---|---|---|---|
| gctaatcgtc | aggatgaagc | ggattccaag | gaagacaaag | ggcaaatcca | gcggaaaggg | 60 |
| caatgactca | acagagagag | cggacgatgg | ctcgagccaa | ttaagagaca | agcaaaacaa | 120 |
| taaggctggc | cccgccacta | cggagcctgg | cacatccaac | cgagagcaat | acaaagctcg | 180 |
| accaggtatt | gcatctgtgc | agagggccac | tgaaagtgca | gaaatgccca | tgaagaataa | 240 |
| tgacgaaggg | acgccagata | agaaaggaaa | tactaagggc | gacctagtta | atgagcatag | 300 |
| tgaggctaaa | gacgaggcgg | atgaagcgac | gaagaagcag | gcaaaggata | cagacaaaag | 360 |
| taaagcgcaa | gtcacatatt | cagacactgg | tatcaataat | gctaatgaac | tgtcaagatc | 420 |
| tgggaatgtg | gataatgagg | gtggaagtaa | tcagaagccg | atgtctacca | gaatagctga | 480 |
| ggcaacgtct | gctatagtgt | cgaaacatcc | tgcgcgtgtt | gggctgccac | ctaccgctag | 540 |
| cagtggtcat | gggtatcagt | gccatgtctg | ttctgcagtc | ctgtttagtc | ctttagacct | 600 |
| agatgcccac | gtcgcctcac | atggtttgca | tggtaacatg | acattaacat | cgagtgatat | 660 |
| ccagcgacat | ataactgagt | tcatcagctc | atggcaaaat | catcctattg | ttcaagtttc | 720 |
| ggctgatgtc | gaaaataaga | aaactgctca | attgcttcac | gctgacactc | ctcgactcgt | 780 |
| cacttgggat | gctggtttgt | gtacttcatt | caaaatcgtc | ccgattgtgc | cagctcaggt | 840 |
| gccgcaggat | gtactggcct | atacgttttt | cacctcttca | tacgctatcc | aatcaccgtt | 900 |
| tccagaggcg | gcagtgtcta | ggattgtggt | gcatacgaga | tggcatctca | atgttgactt | 960 |
| tgaccgagac | tcgtctgtca | tcatggcgcc | acctacagaa | aacaatatcc | atttgtttaa | 1020 |
| acagttacta | aatactgaaa | ccctgtctgt | aagggggggct | aatccgctaa | tgttcagggc | 1080 |
| gaatgtgttg | catatgttgc | tagagttcgt | attagataac | ttgtatctga | acagacatac | 1140 |
| gggattctct | caagaccaca | cgccatttac | tgagggtgct | aatttgcgtt | cacttcctgg | 1200 |
| ccccgatgct | gagaaatggt | actcgattat | gtatccaacg | cgcatgggaa | cgccgaatgt | 1260 |
| atccaaaata | tgtaatttcg | tcgcctcttg | tgtgcgaaat | cgggttggac | ggtttgatcg | 1320 |
| agcacagatg | atgaacggag | ctatgtcaga | gtgggtggat | gtcttcgaga | cttcagacgc | 1380 |
| gctaaccgtc | tccattcgag | gtcgatggat | ggctagacta | gctcgcatga | acataaatcc | 1440 |
| aacagagatc | gaatgggcat | tgactgaatg | tgcacaagga | tatgtgactg | tcacaagtcc | 1500 |
| ttacgctcct | atcgtaaata | gattgatgcc | ctatcgtatc | tccaacgctg | agcggcaaat | 1560 |
| atcacagata | atcaggatca | tgaacattgg | caataacgcg | acggtgatac | aacctgttct | 1620 |
| gcaagatatt | tcggtactcc | ttcaacgcat | atcaccactc | caaatagatc | caactattat | 1680 |
| ttccaacact | atgtcaacag | tctcggagtc | tactactcag | accctcagcc | ccgcgtcctc | 1740 |
| aattttgggt | aaactacgac | caagcaactc | agatttttct | agttttagag | tcgcgttggc | 1800 |
| tggatggctt | tataatgggg | ttgtgacgac | ggtgattgat | gatagttcat | atccaaaaga | 1860 |
| cggcggcagc | gtgacctcac | ttgaaaatct | gtgggatttc | ttcatccttg | cgcttgctct | 1920 |
| accactgaca | actgacccct | gtgcacctgt | gaaagcattc | atgaccctag | ccaacatgat | 1980 |
| ggttggtttc | gagacaatcc | ctatggataa | tcagatctat | actcaatcga | gacgcgcgag | 2040 |
| tgctttctca | acgcctcaca | cgtggccacg | atgctttatg | aacatccagt | taatttctcc | 2100 |

```
aatcgacgct cccatcttgc gacagtgggc tgaaattatt catagatact ggcctaaccc    2160
ttcacagatt cgttatggtg caccgaacgt tttcggctcg gcaaatttgt tcactccacc    2220
tgaggtgctg ttattgccaa tcgatcatca accagctaat gtaacaacgc caacgctgga    2280
cttcaccaat gagttaacta attggcgcgc tcgtgtctgt gagcttatga agaatctcgt    2340
tgataatcaa agatatcaac ctggatggac acaaagtcta gtctcgtcaa tgcgcggaac    2400
gctagacaaa ttgaagttga ttaaatcgat gacaccaatg tatctgcaac agctggctcc    2460
ggtagagtta gcagtgatag ctcccatgtt gccttttcca cctttccagg tgccatacgt    2520
ccgtctcgat cgtgacagag ttccaacaat ggttggagta acacgacagt cacgagatac    2580
tattactcag ccggcgctat cgctgtcgac aaccaatact actgttggcg tgccactagc    2640
tctagacgcg agggctatca ccgttgcgct gttgtcaggg aaatatccgc cggatttggt    2700
gacaaatgta tggtacgctg atgccattta cccaatgtat gcagacacgg aggtgttctc    2760
taatcttcag agagacatga ttacctgcga ggccgtgcag acattagtga ctctggtggc    2820
gcaaatatca gagacccagt atcctgtaga taggtatctt gattggatcc catcactgag    2880
agcatcggcg gcgacggcgg cgacatttgc tgagtgggtt aatacttcaa tgaagacggc    2940
gtttgatttg tctgatatgc tgttagagcc tctcctaagc ggtgatccga ggatgactca    3000
actagcgatt cagtatcagc agtacaatgg cagaacgttt aatatcatac ctgaaatgcc    3060
aggttcagta attgctgact gcgttcaatt aacagcagaa gtctttaatc acgaatataa    3120
cctgtttggg attgcgcggg gtgatatcat cattggccgt gttcagtcga cacatttgtg    3180
gtcaccgctg gctcctccac ctgacctggt gtttgatcgt gataccccctg gtgttcacat    3240
cttcggacga gattgccgta tatcgtttgg aatgaatggc gccgcgccaa tgattagaga    3300
tgagactgga ctgatggtgc cttttgaagg aaattggatt ttcccactgg cgctttggca    3360
aatgaataca cgatattta atcaacagtt cgacgcgtgg attaagacag gagagttgcg    3420
aatccgcatt gagatgggcg cgtatccata tatgttgcat tactatgatc cacgtcagta    3480
cgctaatgca tggaatttaa catccgcctg gcttgaagaa attacgccga cgagcatccc    3540
atccgtgcct ttcatggtgc ccatttcaag tgatcatgac atttcctctg ccccagctgt    3600
ccaatatatc atttcaactg aatataatga tcggtctctg ttctgcacta actcatcatc    3660
tccccaaacc atcgctggac cagacaaaca cattccagtt gagagatata acattctgac    3720
caaccccgac gctccaccca cgcagataca actgcctgaa gtcgttgact tgtacaacgt    3780
cgtcacacgc tatgcgtatg agactccgcc tattaccgct gttgttatgg gtgttccttg    3840
atcctcatcc tcccaacagg tgctagagca ttgcgctcaa tgctagttgg gccgattcat    3900
c                                                                    3901
```

ONCOLYTIC REOVIRUS

INCORPORATION BY REFERENCE OF SEQUENCE LISTING

A Sequence Listing is provided herewith as a text file, "UALB-042WO Seq List_ST25.txt" created on Mar. 8, 2019 and having a size of 188 KB. The contents of the text file are incorporated by reference herein in their entirety.

CROSS-REFERENCE

This application claims the benefit of U.S. Provisional Patent Application No. 62/642,881, filed Mar. 14, 2018, which application is incorporated herein by reference in its entirety.

INTRODUCTION

Mammalian orthoreovirus (reovirus) is a non-enveloped, icosahedral virus in the Reoviridae family Reovirus is ubiquitously found in bodies of water around the world, but unlike rotavirus and bluetongue virus in the same family, reovirus causes only mild enteric and respiratory infection.

Over the last three decades, interest towards reovirus has increased due to its inherent oncolytic activity. Several viruses including reovirus, vaccinia virus, Newcastle disease virus, adenovirus, Maraba virus and vesicular stomatitis virus demonstrate tumor-specific cytolysis and are therefore candidate cancer therapies. Reovirus replicates robustly in many transformed cancer cells but is strongly restricted in normal cells. Specifically, non-transformed cells restrict reovirus infection through poor uncoating of outercapsid proteins, production of progeny with reduced specific infectivity, reduced cell death and virus release, and high interferon antiviral responses. The existence of multiple barriers in non-transformed cells helps ensure that reovirus replication is tumor-specific.

While reoviruses have been demonstrated to mediate tumor-specific cytolysis, there is a need for modified reovirus with improved oncolytic activity. The modified reoviruses provided herein fulfill these and other needs.

SUMMARY

The present disclosure provides modified reovirus with improved characteristics, including improved oncolytic activity. Reoviruses provided herein include resortant viruses as well as viruses expressing mutated proteins. Methods of using such modified reovirus for inducing cancer cell death as well as treatment of cancer are disclosed. Also provided are methods tailored for induction of a desired cytokine profile in conjunction with methods of inducing cancer cell oncolysis.

A reovirus genetically modified to express at least one protein from the reovirus $T3D^{PL}$, where the protein is $T3D^{PL}$ σ3, $T3D^{PL}$ μ2, or $T3D^{PL}$ λ1 is disclosed. In certain aspects, the reovirus may express $T3D^{PL}$ σ3. In certain aspects, the reovirus may express $T3D^{PL}$ μ1. In certain aspects, the reovirus may express $T3D^{PL}$ λ1. In certain aspects, the reovirus may be a T3D strain other than $T3D^{PL}$. In certain aspects, the reovirus may be $T3D^{TD}$ strain. In certain aspects, the reovirus may be $T3D^{ATTC}$ strain.

In certain aspects, a $T3D^{PL}$ reovirus genetically modified to express a $T3D^{PL}$ reovirus σ3 protein comprising a substitution of lysine at position 198, wherein the numbering of the amino acid position is with reference to the amino acid sequence of $T3D^{PL}$ reovirus σ3 protein set forth in SEQ ID NO:4 is disclosed. The substitution at position 198 may be the substitution K198G. The reovirus may further include a substitution of aspartic acid at position 229, wherein the numbering of the amino acid positions is with reference to the amino acid sequence of $T3D^{PL}$ reovirus σ3 protein set forth in SEQ ID NO:4. The substitution at position at position 229 may be the substitution D229E. The reovirus may be genetically modified to express a $T3D^{PL}$ reovirus σ1 protein comprising a substitution of serine at position 18, wherein the numbering of the amino acid position is with reference to the amino acid sequence of $T3D^{PL}$ reovirus σ1 protein set forth in SEQ ID NO:1. The substitution at position 18 in the $T3D^{PL}$ reovirus σ1 protein may be the substitution S18I.

In certain aspects, a $T3D^{PL}$ reovirus genetically modified to express a $T3D^{PL}$ reovirus σ1 protein comprising a mutation in the tail domain of the σ1 protein, wherein the mutation comprises a substitution of Leucine at position 28 or a substitution of serine at position 66 with reference to the amino acid sequence of wild type $T3D^{PL}$ reovirus σ1 protein set forth in SEQ ID NO:1 is provided. In certain aspects, the substitution may be L28P. In certain aspects, the substitution may be S66I.

In certain aspects, a $T3D^{PL}$ reovirus genetically modified to express a $T3D^{PL}$ reovirus λ2 protein comprising a mutation in a FLAP domain, wherein the FLAP domain comprises amino acids 1023-1274, wherein the numbering of the amino acids is with reference to the amino acid sequence of $T3D^{PL}$ reovirus λ2 protein as set forth in SEQ ID NO:9, wherein the reovirus expresses wild type $T3D^{PL}$ reovirus λ1 and λ3 proteins is provided. In certain aspects, the mutation may be a substitution. In certain aspects, the substitution may be a substitution of isoleucine at position 1274 or aparagine at position 1148 with reference to the amino acid sequence of wild type $T3D^{PL}$ reovirus λ2 protein set forth in SEQ ID NO:9. In certain aspects, the substitution at position 1274 is I1274T. In certain aspects, the substitution at position 1274 is I1274M. In certain aspects, the substitution at position 1148 is N1148S.

In another aspect, this disclosure provides a $T3D^{PL}$ reovirus genetically modified to express a $T3D^{PL}$ reovirus λ2 protein comprising a substitution of isoleucine at position 1274 or aparagine at position 1148 with reference to the amino acid sequence of wild type $T3D^{PL}$ reovirus λ2 protein set forth in SEQ ID NO:9. The substitution at position 1274 may be I1274T or I1274M. The substitution at position 1148 may be N1148S. The reovirus may be further genetically modified to express a $T3D^{PL}$ reovirus λ3 protein comprising a substitution of methionine at position 892 with reference to the amino acid sequence of wild type $T3D^{PL}$ reovirus λ3 protein set forth in SEQ ID NO:8. The substitution at position 892 may be M892I. The reovirus may be further genetically modified to express a $T3D^{PL}$ reovirus σ3 protein comprising a substitution of histidine at position 230 with reference to the amino acid sequence of wild type $T3D^{PL}$ reovirus σ3 protein set forth in SEQ ID NO:4. The substitution at position 230 may be H230Q.

In another aspect, this disclosure provides a $T3D^{PL}$ reovirus genetically modified to express a $T3D^{PL}$ reovirus λ2 protein comprising a substitution of methionine at position 1101 with reference to the amino acid sequence of wild type $T3D^{PL}$ reovirus λ2 protein set forth in SEQ ID NO:9; a $T3D^{PL}$ reovirus λ3 protein comprising a substitution at position 892, wherein the numbering of the amino acid position is with reference to the amino acid sequence of wild type $T3D^{PL}$ reovirus λ3 protein set forth in SEQ ID NO:8;

and a T3D$^{PL}$ reovirus σ3 protein comprising a substitution at position 230, wherein the numbering of the amino acid position is with reference to the amino acid sequence of wild type T3D$^{PL}$ reovirus σ3 protein set forth in SEQ ID NO:4. In certain aspects, the substitution of methionine at position 1101 is M1101I. In certain aspects, the substitution at position 892 is M892I. In certain aspects, the substitution at position 230 is H230Q.

Also provided herein is a T3D$^{PL}$ reovirus genetically modified to express a T3D$^{PL}$ reovirus σ1 protein comprising a mutation in the head domain, body domain, and/or tail domain, wherein the head domain extends from amino acid 296-455, the body domain extends from amino acid 155-289, the tail domain extends from amino acid 28-154, and the numbering of the amino acid positions is with reference to the amino acid sequence of T3D$^{PL}$ reovirus σ1 protein set forth in SEQ ID NO:1. In certain aspects, the T3D$^{PL}$ reovirus σ1 protein comprises a mutation in the head domain of the σ1 protein. The mutation may be a substitution. The substitution may be at amino acid position 312. The substitution may be N312R. In some aspects, the T3D$^{PL}$ reovirus σ1 protein comprises a mutation in the tail domain, wherein the mutation comprises a substitution at S66 and/or L28. In some aspects, the reovirus is further genetically modified to express a T3D$^{PL}$ reovirus µ2 protein comprising a mutation at or adjacent amino acid position 112, 612, and/or 613, wherein the numbering of the amino acid positions is with reference to the amino acid sequence of T3D$^{PL}$ reovirus µ2 protein set forth in SEQ ID NO:5. The substitution may be at position 612 or 613, wherein the numbering of the amino acid positions is with reference to the amino acid sequence of T3D$^{PL}$ reovirus µ2 protein set forth in SEQ ID NO:5. In certain aspects, the substitution is at position 612 and may be A612V. In certain aspects, the substitution is at position 613 and may be S613A. In further embodiments, the T3D$^{PL}$ reovirus σ1 protein comprises a mutation in the body domain of the σ1 protein. The mutation may be a substitution in the body domain of the σ1 protein. The substitution may be at position 217 or 219. In certain aspects, the substitution is at position 217. In certain aspects, the substitution at position 217 may be Q217H. In certain aspects, the substitution is at position 219. In certain aspects, the substitution at position 219 is R219S. In some embodiments, the reovirus may be further genetically modified to express a T3D$^{PL}$ reovirus λ2 protein comprising a mutation in a bridge domain, wherein the bridge domain comprises amino acids 386-433 with reference to the amino acid sequence of wild type T3D$^{PL}$ reovirus λ2 protein set forth in SEQ ID NO:9. In certain aspects, the mutation in the bridge domain comprises a substitution. In certain aspects, the substitution is at amino acid position 408. In certain aspects, the substitution at position 408 is D408N.

In certain cases, a reovirus genetically modified to express a T3D$^{PL}$ reovirus σ1 protein comprising a mutation in the head domain, body domain, and/or tail domain as provided herein may be further is genetically modified to express a T3D$^{PL}$ reovirus µ2 protein comprising a mutation in the a mutation at or adjacent amino acid position 112 and/or 613, wherein the numbering of the amino acid positions is with reference to the amino acid sequence of T3D$^{PL}$ reovirus µ2 protein set forth in SEQ ID NO:5. In certain aspects, the T3D$^{PL}$ reovirus µ2 protein may include a substitution at position 112. In certain aspects, the T3D$^{PL}$ reovirus µ2 protein may include a substitution at position 613. In certain aspects, the 3D$^{PL}$ reovirus µ2 protein may include the substitutions L112F and S613A.

In certain cases, a reovirus genetically modified to express a T3D$^{PL}$ reovirus σ1 protein comprising a mutation in the head domain, body domain, and/or tail domain as provided herein may be further is genetically modified to express a T3D$^{PL}$ reovirus σ1 protein comprising a mutation in the tail domain of the σ1 protein. In certain aspects, the mutation is a substitution in the tail domain of the σ1 protein. In certain aspects, the substitution is at position 114 of the σ1 protein. In certain cases, the substitution is T114P.

In certain aspects, a T3D$^{PL}$ reovirus genetically modified to express a T3D$^{PL}$ reovirus λ1 protein may include a mutation at or adjacent the amino acid position 962 and/or 122 of the λ1 protein, wherein the numbering of the amino acid positions is with reference to the amino acid sequence of T3D$^{PL}$ reovirus λ1 protein set forth in SEQ ID NO:10. In certain aspects, the mutation at or adjacent the amino acid position 962 and/or 122 of the λ1 protein comprises a substitution. The substitution may be at amino acid position 962. In some cases, the substitution may be A962S.

In certain aspects, a T3D$^{PL}$ reovirus genetically modified to express a T3D$^{PL}$ reovirus λ1 protein may include a mutation at or adjacent amino acid position 122 of the λ1 protein, wherein the numbering of the amino acid positions is with reference to the amino acid sequence of T3D$^{PL}$ reovirus λ1 protein set forth in SEQ ID NO:10; T3D$^{PL}$ reovirus λ3 protein comprising a mutation at or adjacent amino acid position 972 of the λ3 protein, wherein the numbering of the amino acid position is with reference to the amino acid sequence of T3D$^{PL}$ reovirus λ3 protein set forth in SEQ ID NO:8; and T3D$^{PL}$ reovirus σ3 protein comprising a mutation at or adjacent amino acid position 64 of the σ3 protein, wherein the numbering of the amino acid position is with reference to the amino acid sequence of T3D$^{PL}$ reovirus σ3 protein set forth in SEQ ID NO:4. In some cases, the mutation in the λ1 protein comprises a substitution at position 122. In some cases, mutation in the λ1 protein comprises the substitution at position 122 is Y122H. In some cases, mutation in the λ3 protein comprises a substitution at position 972. In certain aspects, the substitution at position 972 is Q972R. In some cases, mutation in the σ3 protein comprises a substitution at position 64. In some cases, the substitution at position 64 is K64E.

In some cases, a T3D reovirus, e.g., as T3D$^{PL}$ reovirus is genetically modified to express a mutant σ1 protein that includes a mutation in the body domain of the σ1 protein, wherein the σ1 protein is resistant to cleavage by the metalloprotease. The mutation may be present within amino acids 220-289 of the body domain of the σ1 protein. The mutation may be present within amino acids 222-251 of the body domain of the σ1 protein. The mutation may be present within a metalloprotease cleavage site in the body domain of the σ1 protein. In some aspects, the mutation is present adjacent to a metalloprotease cleavage site in the body domain of the σ1 protein. In some aspects, the mutation includes a substitution at position 249. In some aspects, the substitution is T249L or T249I.

In another aspect, a T3D$^{PL}$ reovirus genetically modified to express T3D$^{TD}$ σ3 protein instead of the endogenous T3D$^{PL}$ σ3 protein is disclosed. In another aspect, a T3D$^{TD}$ reovirus genetically modified to express T3D$^{PL}$ σ3 protein instead of the endogenous T3D$^{TD}$ σ3 protein is provided.

Also disclosed herein is a method for inducing cell death of a cancer cell, the method may include contacting the cancer cell with a reovirus as described in the present disclosure. The cancer cell is may be in vitro, in vivo or ex vivo. In certain aspects, the cancer cell may be in a subject, such as, a human patient.

Also disclosed herein is a method for treating cancer in a subject, the method may include administering therapeutically effective amount of the reovirus as described in the present disclosure to the subject.

Also provided are methods for tailoring immune response to induce a high or a low IFN-dependent cytokine response and/or high or low IFN-independent cytokine response by administering the different virus disclosed herein.

Also provided is a $T3D^{PL}$ reovirus genetically modified to express a $T3D^{PL}$ reovirus σ1 protein comprising a substitution of serine at position 66 in the σ1 protein with reference to the amino acid sequence of wild type $T3D^{PL}$ reovirus σ1 protein set forth in SEQ ID NO:1 and to express a $T3D^{PL}$ reovirus λ2 protein comprising a substitution of isoleucine at position 1274, wherein the numbering of the amino acids is with reference to the amino acid sequence of $T3D^{PL}$ reovirus λ2 protein as set forth in SEQ ID NO:9. In certain aspects, the substitution in the σ1 protein is S66I. In certain aspects, the substitution at position 1274 in the λ2 protein is I1274T.

Also provided is a $T3D^{PL}$ reovirus genetically modified to express a $T3D^{PL}$ reovirus λ2 protein comprising a substitution of isoleucine at position 1274, wherein the numbering of the amino acids is with reference to the amino acid sequence of $T3D^{PL}$ reovirus λ2 protein as set forth in SEQ ID NO:9 and to express a $T3D^{PL}$ reovirus σ1 protein comprising a substitution at amino acid position 312, wherein the numbering of the amino acid position is with reference to the amino acid sequence of $T3D^{PL}$ reovirus σ1 protein set forth in SEQ ID NO:1. In certain aspects, the substitution at position 1274 in the λ2 protein is I1274T. In certain aspects, the substitution in σ1 protein is N312R.

Also provided is a $T3D^{PL}$ reovirus genetically modified to express a $T3D^{PL}$ reovirus σ1 protein comprising the substitution S18I, a $T3D^{PL}$ reovirus σ3 protein comprising the substitution K64E, $T3D^{PL}$ reovirus μ2 protein comprising the substitution A612V, λ2 protein comprising the substitution I1274T, and λ1 protein comprising the substitution A962S.

Also provided is a $T3D^{PL}$ reovirus genetically modified to express a $T3D^{PL}$ reovirus σ1 protein comprising the substitution R219Q, a $T3D^{PL}$ reovirus σ3 protein comprising the substitution K64E, $T3D^{PL}$ reovirus μ2 protein comprising the substitution A612V, λ2 protein comprising the substitution I1274T, and λ1 protein comprising the substitution A962S.

In certain aspects, the $T3D^{PL}$ reovirus may express a $T3D^{PL}$ reovirus σ3 protein comprising a substitution of T249. In certain aspects, the substitution is T249I.

BRIEF DESCRIPTION OF THE DRAWINGS

FIG. 3A. S4 (σ3-encoding), M1 (μ2-encoding) and L3 (λ1 encoding) genes segregate with larger plaque size individually (grey) and even larger plaque size when combined. FIG. 3B. Box and whisker plots showing the distribution of plaque size.

FIG. 5A. Strategy for selecting reovirus mutants with improved replication and/or dissemination in cancer cells. FIG. 5B. Location of mutations in the indicated proteins in $T3D^{PL}$ variants. FIG. 5C. Reovirus variants (T3v1-T3v16) produce larger plaques relative to wild type $T3D^{PL}$ (T3 wt) on two human cancer cell lines. FIG. 5D shows average plaque size for 4 independent experiments. FIG. 5E shows position of mutations in variants T3v1, T3v2, T3v4, T3v5, T3v8, T3v14, T3v16 and characterization of levels of λ2, σ1, and core protein in T3 wt and variants, T3v2, T3v4, T3v5, and T3v14. FIG. 5F depicts analysis of the indicated reovirus by a binding assay. FIG. 5G depicts depicts analysis of the indicated reovirus by an uncoating assay. FIG. 5H. Levels of σ1 on purified virions was assessed with anti-σ1 immunoblotting. FIG. 5I. Levels of reovirus proteins at 12 and 15 hours post-infection were assessed by wester blotting. FIG. 5J. Reovirus titers (MOI 0.01) are higher in T3v10 then T3 wt in the first (24 h) round and subsequent rounds (24-72 h) of infection.

DETAILED DESCRIPTION OF EMBODIMENTS

Figure 1A:
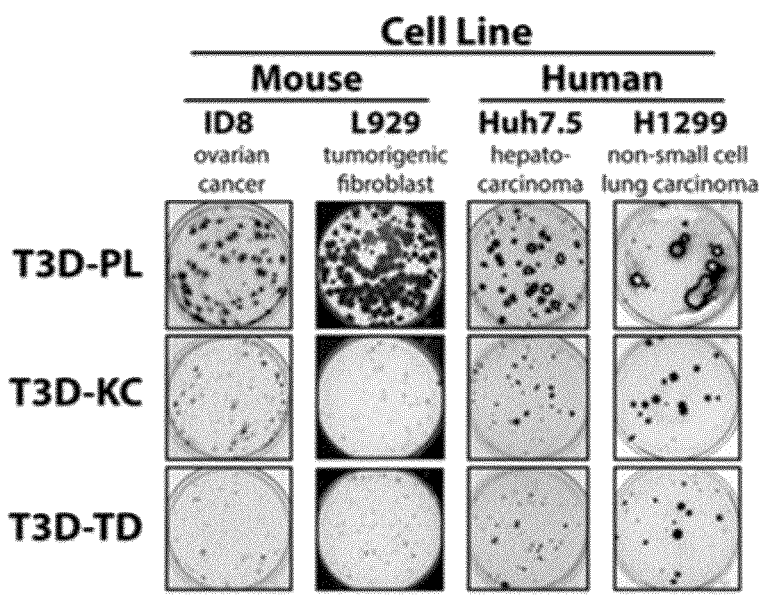
FIG. 1A. Plaque size comparison of $T3D^{PL}$, $T3D^{KC}$ and $T3D^{TD}$ laboratory strains obtained from Drs. Patrick Lee, Kevin Coombs, and Terry Dermody, respectively. $T3D^{PL}$ causes larger plaques on human and mouse cancer cells.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used throughout the entire application, the singular forms "a", "and", and "the" include plural referents unless the context clearly dictates otherwise. Thus, these terms include "at least one," "at least a first," "one or more," or "a plurality" of the referenced components or steps, unless the context clearly dictates otherwise. Thus, for example, reference to "a reovirus" includes a plurality of reoviruses, including mixtures thereof and reference to "the polypeptide" includes reference to one or more polypeptides and equivalents thereof known to those skilled in the art, and so forth.

The publications discussed herein are provided solely for their disclosure prior to the priority date of the present application. Nothing herein is to be construed as an admission that the present invention is not entitled to antedate such publication by virtue of prior invention. Further, the dates of publication provided may be different from the actual publication dates which may need to be independently confirmed.

Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Definitions

The term "and/or" wherever used herein includes the meaning of "and", "or" and "all or any other combination of the elements connected by the term".

The terms "about" or "approximately" as used herein means within 20%, preferably within 10%, and more preferably within 5% of a given value or range.

The terms "obtained from," "derived from" and grammatical equivalents thereof are used to identify the original source of a component (e.g., polypeptide, nucleic acid molecule) but is not meant to limit the method by which the component is made which can be, for example, by chemical synthesis or recombinant means.

As used herein, the term "host cell" should be understood broadly without any limitation concerning particular organization in tissue, organ, or isolated cells. Such cells may be of a unique type of cells or a group of different types of cells such as cultured cell lines, primary cells and dividing cells. In the context of the invention, the term "host cells" include prokaryotic cells, lower eukaryotic cells such as yeast, and other eukaryotic cells such as insect cells, plant and mammalian (e.g. human or non-human) cells as well as cells capable of producing the oncolytic virus. This term also includes cells that can be or has been the recipient of the vectors described herein as well as progeny of such cells.

As used herein, the term "oncolytic reovirus" refers to a reovirus capable of selectively replicating in dividing cells (e.g. a proliferative cell such as a cancer cell) with the aim of slowing the growth and/or lysing the dividing cell, either in vitro or in vivo, while showing no or minimal replication in non-dividing cells. Typically, an oncolytic reovirus contains a reoviral genome packaged into a viral particle (or virion) and is infectious (i.e. capable of infecting and entering into a host cell or subject).

As used herein, the phrase "increased oncolytic activity" or "improved oncolytic activity" in the context of a modified reovirus refers to oncolytic activity that is at least 10% higher than that of a parent strain from which the modified reovirus is derived or a strain that is identical to the modified reovirus other than not having the modification. Oncolytic activity may be measured by any standard method and may be quantitated in terms of number of infectious by viral particles produced by the reovirus, or as iu (infectious unit) or pfu (plaque-forming units). In some embodiments, the modified reovirus of the present disclosure may have oncolytic activity that is at least 20% higher, 30% higher, 40% higher, or even higher than that of a reference strain that only differs from the modified strain in that it lacks the modification present in the modified strain.

The term "administering" (or any form of administration such as "administered") as used herein refers to the delivery to a subject of a therapeutic agent such as the oncolytic reovirus described herein.

As used herein, the term "proliferative disease" encompasses any disease or condition resulting from uncontrolled cell growth including cancers including metastatic cancer. The term "cancer" may be used interchangeably with any of the terms "tumor", "malignancy", "neoplasm", etc. These terms are meant to include any type of tissue, organ or cell, any stage of malignancy (e.g. from a prelesion to stage IV).

As used herein the term, "adjacent" in the context of an amino acid position refers to a region up to 10 amino acids upstream (N-terminus) and up to 10 amino acids downstream (C-terminus) of the reference amino acid position. For example, a region adjacent to amino acid position 18 of SEQ ID NO:1 refers to the region between amino acid positions 8 and 28 of EQ ID NO:1.

The term "combination" or "association" as used herein refers to any arrangement possible of various components (e.g. an oncolytic virus and one or more substance effective in anticancer therapy). Such an arrangement includes mixture of said components as well as separate combinations for concomitant or sequential administrations.

As used herein, the term reovirus refers to oncolytic viruses that infect mammalian cells and are classified as orthoreovirus. The reovirus may be an orthoreovirus of serotype 1 (strain Lang or T1L), serotype 2 (strain Jones, T2J), or serotype 3 (strain Dearing or strain Abney, T3D). The three serotypes are distinguishable on the basis of neutralization and hemagglutinin-inhibition assays (see, for example, Fields, B. N. et al., 1996). Reovirus genomes are composed of 10 dsRNA segments, each encoding 1-2 proteins. Table 1 lists the 10 dsRNA gene segments, the corresponding protein encoded by the dsRNA gene, and function of the protein.

TABLE 1

| Gene Segment | Protein | Virion-associated? | Known functions |
| --- | --- | --- | --- |
| S1 | σ1 | Outer Capsid(O/C) | Cell attachment |
|  | σ1s | No | Cell cycle |
| S2 | σ2 | Core | Core structure |
| S3 | σNS | No | Virus factory formation (RNA recruitment) |
| S4 | σ3 | O/C | O/C structure |
|  |  |  | dsRNA sequestration/signalling modulator |
| M1 | μ2 | Core | Virus factory formation (tubulin association) |
| M2 | μ1 | O/C | O/C structure |
|  |  |  | Cleavage of μ1 mediates uncoating and membrane penetration during entry |
| M3 | μNS | No | Virus factory formation (scaffolds core proteins, σNS) |
| L1 | λ3 | Core | RNA polymerase |
| L2 | λ2 | Core | Vertice channels (holds σ1, permits transport of RNA out of cores) |
| L3 | λ1 | Core | Core structure |

As used herein, the term "reovirus T3D$^{PL}$," "T3D$^{PL}$ reovirus," "T3D$^{PL}$ strain," and grammatical equivalents thereof refer to a serotype 3 mammalian orthoreovirus that includes the genes PL-L1, PL-L2, PL S3, PL-L3, PL-M1, PL-M2, PL-M3, PL-S1, PL-S2, and PL-S4 present in the T3D reovirus from Patrick Lee lab. These genes encode the proteins: PL-λ3, PL-λ2, PL σNS, PL-λ1, PL-μ2, PL-μ1, PL-μNS, PL-σ1, PL-σ2, and PL-σ3, respectively. The sequences of these genes and proteins are provided herein. Also encompassed by these terms are reoviruses that include these genes where one or more of the genes may have a silent mutation which does not result in a change in the amino acid sequence of the protein encoded by the gene. Similarly, a T3D$^{TD}$ reovirus refers to a serotype 3 mammalian orthoreovirus that includes the genes TD-L1, TD-L2, TD S3, TD-L3, TD-M1, TD-M2, TD-M3, TD-S1, TD-S2, and TD-S4 present in the T3D reovirus from Terry Dermody lab. These genes encode the proteins: TD-λ3, TD-λ2, TD σNS, TD-λ1, TD-μ2, TD-μ1, TD-μNS, TD-σ1, TD-σ2, and TD-σ3, respectively. The sequences of these genes and proteins are provided herein.

As used herein, the term "modified reovirus" refers to a reovirus that has been genetically modified to express at least one protein that has an amino acid sequence that is different from the amino acid sequence of the protein in the reovirus from which the modified reovirus is derived. A modified reovirus may be produced from a naturally occurring reovirus or from a reovirus that has previously been genetically modified in a lab. In some cases, a modified reovirus is generated from a parental strain that has been characterized in lab by sequencing its genome.

As used herein, the term "reassortant reovirus" refers to a reovirus that is produced recombinantly and includes one or more genes from another reovirus and lacks the corresponding endogenous gene. For example, a reovirus that includes 9 out of the 10 gene that are native to the reovirus and 1 gene from another reovirus where the gene sequence is different from the native gene and encodes a protein having an amino acid sequence different from that of the corresponding native protein is considered a reassortant reovirus. As used herein, the term modified reovirus encompasses reassortant reovirus.

As used herein, "viral infection" refers to the entry of a virus into a cell and the subsequent replication of the virus in the cell.

As used herein, "multiplicity of infection" refers to the ratio of the number of virus to the number of cells when a virus is used to infect the cells.

As used herein, "cell lysis" refers to the disruption of cell membrane of a cell and the subsequent release of all or part of the content of the cell.

The term "subject" generally refers to an organism for whom any product and method of this disclosure is needed or may be beneficial. Typically, the organism is a mammal, such as, domestic animals, farm animals, sport animals, and primates. In some embodiments, the subject is a human who has been diagnosed as having or at risk of having a proliferative disease such as a cancer. The terms "subject" and "patients" may be used interchangeably when referring to a human and encompasses male and female. The subject to be treated may be a newborn, an infant, a young adult, an adult, or an older adult.

"Conservative amino acid substitution" refers to a substitution of one amino acid residue for another sharing chemical and physical properties of the amino acid side chain (e.g., charge, size, hydrophobicity/hydrophilicity). "Conservative substitutions" are intended to include substitution within the following groups of amino acid residues: (i) gly, ala, val, ile, leu; (ii) asp, glu; (iii) asn, gln; (iv) ser, thr; (v) lys, arg, his; and (vi) phe, tyr. Guidance for such substitutions can be drawn from alignments of amino acid sequences of polypeptides.

"Isolated" refers to an entity of interest that is in an environment different from that in which the entity may naturally occur or occurs during production. "Isolated" is meant to include an entity within a sample that is substantially enriched for the entity of interest. In the context of a reovirus, an isolated reovirus refers to a collection or composition of the reovirus where collection or composition is substantially free of other reovirus, e.g., reovirus having a different genome. Substantially as used in the context of isolated reovirus means that the isolated reovirus has less than 10%, less than 5%, or less than 1% of another virus (e.g., a virus having a different genome).

The terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease. The result of the treatment is to slow down, cure, ameliorate or control the progression of the targeted pathological condition. For example, a subject is successfully treated for a cancer if after administration of an oncolytic virus as described herein, the subject shows an observable improvement of clinical status.

Modified Reovirus

Modified reovirus with improved oncolytic activity are provided. The modified reovirus provided herein include reassortant reovirus that expresses a combination of proteins from at least two different reoviruses, as well as reovirus expressing one or more mutated proteins.

Reassortant Reovirus

In certain embodiments, a reassortant reovirus of this disclosure includes a reovirus that expresses at least one protein from the reovirus T3D$^{PL}$, where the reassortant reovirus is not a T3D$^{PL}$ reovirus. The protein expressed by the reassortant reovirus may be T3D$^{PL}$ σ3, T3D$^{PL}$ μ2, and/or T3D$^{PL}$ λ1. The reassortant reovirus while expressing one or more of T3D$^{PL}$ σ3, T3D$^{PL}$ μ2, and/or T3D$^{PL}$ λ1 may express σ1, σ1s, σ2, σNS, σ3, μ2, μ1, μNS, λ3, λ2, and λ1 proteins that are not from T3D$^{PL}$. In certain embodiments, the reassortant reovirus expresses other proteins from a reovirus strain other than T3D$^{PL}$. In some cases, the other proteins expressed by the reassortant reovirus may be the proteins from a T3D$^{TD}$ strain or a T3D$^{ATCC}$ strain. In some cases, the reassortant reovirus may express a T3D$^{PL}$ σ3, T3D$^{PL}$ μ2, and/or T3D$^{PL}$ λ1, while all other proteins expressed by the virus may be T3D$^{TD}$ proteins. In other words, the reassortant reovirus may be a T3D$^{TD}$ strain that is expressing one or more of T3D$^{PL}$ σ3, T3D$^{PL}$ μ2, and/or T3D$^{PL}$ λ1 instead of the corresponding endogenous protein(s).

In some cases, the reassortant reovirus may express a T3D$^{PL}$ σ3, T3D$^{PL}$ μ2, and/or T3D$^{PL}$ λ1 while all other proteins expressed by the virus may be T3D$^{ATCC}$ proteins. In other words, the reassortant reovirus may be a T3D$^{ATCC}$ strain that is expressing one or more of T3D$^{PL}$ σ3, T3D$^{PL}$ μ2, and/or T3D$^{PL}$ λ1 instead of the endogenous protein(s).

A reassortant reovirus that expresses at least one of T3D$^{PL}$ σ3, T3D$^{PL}$ μ2, and T3D$^{PL}$ λ1 proteins may have at least 10% or higher oncolytic activity as compared to a reference strain that is identical to the reassortant strain except that it expresses the endogenous protein(s) and not a T3D$^{PL}$ σ3, T3D$^{PL}$ μ2, and/or T3D$^{PL}$ λ1 protein.

In some cases, the reassortant reovirus may be generated by using plasmid based reverse genetics system for producing reovirus (e.g., Boehme K W, et al., 2011, Methods 55:109-113; Trask S D, et al., 2013, Methods 59:199-206; Komoto S, et al., 2014, J Virol Methods 196:36-39; Kobayashi T, et al., 2010. Virology 398:194-200; and Kobayashi T, et al., 2007 Cell Host Microbe 1:147-157). In some embodiments, a reassortant reovirus expressing a T3D$^{PL}$ σ3, T3D$^{PL}$ μ2, and/or T3D$^{PL}$ λ1 may be produced by transfecting a cell line (e.g., a mammalian cell line) with plasmids carrying 10 gene segments from a T3D reovirus, where one or more of gene segments encoding σ3, μ2, and λ1 are from T3D$^{PL}$ (i.e., have a sequence that encodes a protein having an amino acid sequence at least 99% or 100% identical to the amino acid sequence of T3D$^{PL}$ σ3, T3D$^{PL}$ μ2, and T3D$^{PL}$ λ1), the remainder of the gene segments are from a different T3D reovirus such as a T3D$^{TD}$ strain or a T3D$^{ATCC}$ strain. The sequences of the 10 gene segments in T3D$^{TD}$ strain and the amino acid sequences of the encoded proteins are set forth in the SEQ ID NOs listed in Table 2. The 10 genes may each be carried on a single plasmid per gene, or two or more genes carried on a single plasmid, e.g., all genes carried using 4 different plasmids. The reovirus genes in the plasmids may be under control of any suitable promoter, e.g., a T7 promoter, CMV promoter, and the like. Any mammalian cell line suitable for producing reovirus may be used and may include human embryonic kidney (HEK293T) cells, monkey kidney (COS-7) cells, BHK-T7 (BHK cell line expressing T7RNAP), and BHK-21 (the parental BHK cell line devoid of T7RNAP).

In certain cases, the reassortant reovirus may be derived from a parent T3D$^{TD}$ strain that is modified to expresses a T3D$^{PL}$ σ3, T3D$^{PL}$ μ2, and/or T3D$^{PL}$ λ1 protein while the remainder of the proteins expressed have the same amino acid sequence as that of the parent T3D$^{TD}$ strain. As used herein, a T3D$^{TD}$ strain refers to a reovirus that expresses the proteins TD σ1, TD σ1s, TD σ2, TD σNS, TD σ3, TD μ2, TD μ1, TD μNS, TD λ3, TD λ2, and TD λ1 having the amino acid sequences as set out in the SEQ ID NOs. listed in Table 2.

TABLE 2

| Protein | SEQ ID NO | Gene | SEQ ID NO |
|---|---|---|---|
| PL-σ1 | 1 | PL-S1 | 20 |
| PL-σ2 | 2 | PL-S2 | 21 |
| PL-σNS and TD-σNS (same sequence) | 3 | PL-S3 and TD-S3 (same sequence) | 22 |
| PL-σ3 | 4 | PL-S4 | 23 |
| PL-μ2 | 5 | PL-M1 | 24 |
| PL-μ1 | 6 | PL-M2 | 25 |
| PL-μNS | 7 | PL-M3 | 26 |
| PL-λ3 | 8 | PL-L1 | 27 |
| PL-λ2 | 9 | PL-L2 | 28 |
| PL-λ1 | 10 | PL-L3 | 29 |
| TD-σ1 | 11 | TD-S1 | 30 |
| TD-σ2 | 12 | TD-S2 | 31 |
| TD-σ3 | 13 | TD-S4 | 32 |
| TD-μ2 | 14 | TD-M1 | 33 |
| TD-μ1 | 15 | TD-M2 | 34 |
| TD-μNS | 16 | TD-M3 | 35 |
| TD-λ3 | 17 | TD-L1 | 36 |
| TD-λ2 | 18 | TD-L2 | 37 |
| TD-λ1 | 19 | TD-L3 | 38 |

A reassortant reovirus from a parent T3D$^{TD}$ strain refers to a reovirus that expresses one or more (e.g., 2, 3, 4, or up to 5) proteins from a different T3D strain while the amino acid sequences of remainder of the proteins are same as that of the proteins expressed by the parent T3D$^{TD}$ strain.

A reassortant reovirus from a parent T3D$^{ATCC}$ strain refers to a reovirus that expresses one or more (e.g., 2, 3, 4, or up to 5) proteins from a different T3D strain while the amino acid sequences of remainder of the proteins are same as that of the proteins expressed by the parent T3D$^{ATCC}$ strain.

The accession numbers for sequences of the 10 gene segments in T3D$^{ATCC}$ strain (also referred to as T3D-Hoeben.R.C (ATCC VR-824)) and the accession numbers for the amino acid sequences of the corresponding proteins are as follows:

| | | T3D-Hoeben.R.C (ATCC VR-824) | | | |
|---|---|---|---|---|---|
| | | S1 | S2 | S3 | S4 |
| Accession # | Gene | GU991665.1 | GU991666.1 | GU991667.1 | GU991668.1 |
| | Protein | ADY80528.1 | ADY80529.1 | ADY80530.1 | ADY80531.1 |
| | | M1 | M2 | M3 | L1 | L2 | L3 |
| Accession # | Gene | GU991662.1 | GU991663.2 | GU991664.1 | GU991659.1 | GU991660.1 | GU991661.1 |
| | Protein | ADY80525.1 | ADY80526.2 | ADY80527.1 | ADY80522.1 | ADY80523.1 | ADY80524.1 |

In certain cases, the reassortant virus may express a T3D$^{PL}$ σ3 protein where the amino acid sequence of the protein is at least 99% or 100% identical to the amino acid sequence of the T3D$^{PL}$ σ3 protein set out in SEQ ID NO:13 and proteins σ1, σ1s, σ2, σNS, μ2, μ1, μNS, λ3, λ2, and λ1 having the same amino acid sequence or at least 99% or 100% identical to the amino acid sequences of these proteins expressed in T3D$^{TD}$ strain or T3D$^{ATTC}$ strain.

In certain cases, the reassortant virus may express a T3D$^{PL}$ μ1 protein where the amino acid sequence of the protein is at least 99% or 100% identical to the amino acid sequence of the T3D$^{PL}$ μ1 protein set out in SEQ ID NO:13 and proteins σ1, σ1s, σ2, σNS, σ3, μ2, μNS, λ3, λ2, and λ1 having the same amino acid sequence or at least 99% or 100% identical to the amino acid sequences of these proteins expressed in T3D$^{TD}$ strain or T3D$^{ATTC}$ strain.

In certain cases, the reassortant virus may express a T3D$^{PL}$ λ1 protein where the amino acid sequence of the protein is at least 99% or 100% identical to the amino acid sequence of the T3D$^{PL}$ λ1 protein set out in SEQ ID NO:13 and proteins σ1, σ1s, σ2, σNS, σ3, μ2, μ1 μNS, λ3, and λ2 having the same amino acid sequence or at least 99% identical to the amino acid sequences of these proteins expressed in T3D$^{TD}$ strain or T3D$^{ATTC}$ strain.

In certain cases, the reassortant virus may express at least one of σ3, μ1, and λ1 protein having the amino acid sequence set forth in SEQ ID NOs: 4, 6, and 10, respectively, and lack the corresponding endogenous gene and the remainder of the proteins expressed by the reassortant virus may have the amino acid sequence of the proteins expressed in T3D$^{TD}$ strain.

In certain cases, the reassortant reovirus may express at least one of σ3, μ1, and λ1 protein having the amino acid sequence set forth in SEQ ID NOs: 4, 6, and 10, respectively, and lack the corresponding endogenous gene and the remainder of the proteins expressed by the reassortant virus may have the amino acid sequence of the proteins expressed in T3D$^{ATTC}$ strain.

In certain cases, the oncolytic activity of the modified viruses disclosed herein is increased by 10% or more compared to the parent virus not having the modification. For example, a T3D$^{TD}$ virus expressing a σ3, μ1, and/or λ1 from T3D$^{PL}$ has an oncolytic activity that is at least 10% higher than the oncolytic activity of the parental T3D$^{TD}$ strain that includes the endogenous proteins.

The name of genes and the proteins expressed in T3D$^{PL}$ strain is referred to by the term "PL". The name of genes and the proteins expressed in T3D$^{TD}$ strain is referred to by the term "TD". The sequence of the genes and the proteins expressed in T3D$^{PL}$ strain are provided:

```
PL-L1Gene Sequence
                                                          (SEQ ID NO: 27)
GCTACACGTTCCACGACAATGTCATCCATGATACTGACTCAGTTTGG

ACCGTTCATTGAGAGCATTTCAGGTATCACTGATCAATCGAATGACGTGTTTGAAG

ATGCAGCAAAAGCATTCTCTATGTTTACTCGCAGCGATGTCTACAAGGCGCTGGAT

GAAATACCTTTCTCTGATGATGCGATGCTTCCAATCCCTCCAACTATATATACGAA

ACCATCTCACGATTCATATTATTACATTGATGCTCTAAACCGTGTGCGTCGCAAAA

CATATCAGGGCCCTGATGACGTGTACGTACCTAATTGTTCTATTGTTGAATTGCTGG

AGCCACATGAGACTCTGACATCTTATGGGCGGTTGTCCGAGGCCATCGAGAATCGT

GCCAAGGATGGGGACAGCCAAGCCAGAATCGCCACAACGTATGGTAGAATCGCTG

AATCTCAAGCTCGACAGATTAAGGCTCCATTGGAGAAGTTTGTGTTGGCACTATTA

GTGGCCGAAGCAGGGGGGTCTTTATATGATCCAGTTTTGCAGAAGTATGATGAGAT

TCCAGATCTATCGCATAATTGCCCTTTATGGTGTTTTAGAGAGATCTGTCGTCACAT

ATCTGGTCCATTACCAGATCGGGCACCTTATCTTTACTTATCTGCAGGGGTTTTCTG

GTTAATGTCACCACGAATGACGTCTGCAATCCCTCCGCTACTATCCGATCTTGTTAA

TTTAGCTATTTTGCAACAAACTGCGGGTTTAGATCCATCATTAGTGAAATTGGGAG

TACAGATATGCCTTCATGCAGCAGCTAGCTCAAGTTATGCATGGTTTATCTTAAAG

ACTAAGTCTATTTTTCCTCAAAACACGTTGCACAGTATGTATGAATCTCTAGAAGG

GGGATACTGTCCTAATCTTGAATGGTTAGAGCCTAGATCAGACTATAAGTTCATGT

ACATGGGAGTCATGCCATTGTCCGCTAAGTATGCTAGGTCGGCGCCGTCCAATGAT

AAGAAAGCGCGGGAACTTGGCGAGAAATATGGACTGAGCTCAGTCGTCGGTGAGC

TTCGTAAACGGACAAAGACGTATGTTAAACATGACTTTGCTTCAGTGAGGTACATT

CGTGACGCTATGGCATGTACTAGCGGTATTTTCTTGGTAAGAACACCCACCGAAAC

GGTATTGCAAGAATATACGCAGAGTCCGGAGATTAAGGTTCCCATTCCCCAGAAA

GACTGGACAGGCCCAATAGGTGAAATCAGAATTCTAAAAGATACAACAAGTTCCA

TCGCGCGTTACTTATATAGAACATGGTACTTGGCAGCGGCGAGAATGGCGGCTCAA
```

-continued

```
CCACGTACGTGGGATCCATTGTTTCAAGCGATTATGAGATCTCAATACGTGACAGC
TAGGGGTGGATCTGGCGCAGCACTCCGCGAATCTTTGTATGCAATCAATGTGTCGT
TACCTGATTTCAAGGGCTTACCAGTGAAGGCAGCAACTAAGATATTCCAGGCGGCA
CAATTAGCGAACTTGCCGTTCTCCCACACATCAGTGGCTATACTAGCTGACACTTC
AATGGGATTGCGAAATCAGGTGCAGAGGCGGCCACGATCCATTATGCCATTAAAT
GTGCCCCAGCAGCAGGTTTCGGCGCCCCATACATTGACAGCGGATTACATTAACTA
CCACATGAATCTATCAACCACGTCTGGTAGTGCGGTCATTGAGAAGGTGATTCCTT
TAGGTGTATACGCTTCGAGCCCTCCTAACCAGTCGATCAACATTGACATATCTGCG
TGTGACGCTAGTATTACTTGGGATTTCTTTCTGTCAGTGATTATGGCGGCTATACAC
GAAGGTGTCGCTAGTAGCTCCATTGGAAAACCATTTATGGGGGTTCCTGCATCCAT
TGTAAATGATGAGTCTGTCGTTGGAGTGAGAGCTGCTAGGCCGATATCGGGAATGC
AGAACATGATTCAGCATCTATCGAAACTATATAAACGTGGATTTTCATATAGAGTA
AACGATTCTTTTTCTCCAGGTAACGATTTTACTCATATGACTACCACTTTCCCGTCA
GGTTCAACAGCCACCTCTACTGAGCATACTGCTAATAATAGTACGATGATGGAAAC
TTTCCTGACAGTATGGGGACCCGAACATACTGACGACCCTGACGTCTTACGTTTAA
TGAAGTCTTTAACTATTCAAAGGAATTACGTATGTCAAGGTGATGATGGATTAATG
ATTATCGATGGGACTACTGCTGGTAAGGTGAACAGTGAAACTATTCAGAAGATGCT
AGAATTAATCTCAAAATATGGTGAGGAATTCGGATGGAAATATGACATAGCGTAC
GATGGGACTGCCGAATACTTAAAGCTATACTTCATATTTGGCTGTCGAATTCCAAA
TCTTAGTCGCCATCCAATCGTGGGAAAGAACGGGCGAATTCTTCAGCAGAGGAG
CCATGGCCAGCAATTCTAGATCAGATTATGGGTGTCTTCTTTAATGGTGTTCATGAT
GGGTTACAGTGGCAGCGGTGGATACGTTATTCATGGGCTCTATGCTGTGCTTTCTC
ACGTCAAAGAACAATGATTGGTGAGAGCGTGGGTTACCTTCAATATCCTATGTGGT
CTTTTGTCTACTGGGGATTACCACTGGTTAAAGCGTTTGGGTCAGACCCATGGATA
TTTTCTTGGTACATGCCTACTGGAGATCTGGGAATGTATAGTTGGATTAGCTTGATA
CGCCCTCTGATGACAAGATGGATGGTGGCTAATGGTTACGTAACTGACAGATGCTC
ACCCGTATTCGGGAACGCAGATTATCGCAGGTGTTTCAATGAACTTAAACTATATC
AAGGTTATTATATGGCACAATTGCCCAGGAATCCTAAGAAGTCTGGACGAGCGGC
CCCTCGGGAGGTAAGAGAACAATTCACTCAGGCATTATCCGACTATCTACTGCAAA
ATCCAGAGCTGAAGTCACGTGTGCTACGTGGTCGTAGTGAGTGGGAGAAATATGG
AGCGGGATAATTCACAATCCTCCGTCATTATTCGATGTGCCCCATAAATGGTATC
AGGGTGCGCAAGAGGCAGCAATCGCTACGAGAGAAGAGCTGGCAGAAATGGATG
AGACATTAATGCGCGCTCGAAGGCACAGATATTCGAGCTTTTCAAAGTTATTAGAG
GCGTATCTGCTCGTGAAATGGCGAATGTGCGAGGCCCGCGAACCGTCGGTGGATTT
GCGATTACCATTATGTGCGGGTATTGACCCATTAAACTCAGATCCTTTTCTCAAGAT
GGTAAGCGTTGGACCAATGCTCCAGAGTACGAGAAAGTACTTTGCTCAGACACTAT
TCATGGCAAAGACGGTGTCGGGTCTTGACGTTAACGCGATTGATAGCGCGTTATTA
CGACTGCGAACATTAGGTGCTGATAAGAAAGCATTAACGGCGCAGTTATTAATGGT
GGGGCTTCAGGAGTCAGAAGCGGACGCATTGGCCGGGAAGATAATGCTACAGGAT
GTGAATACTGTGCAATTAGCCAGAGTGGTTAACTTAGCTGTGCCAGATACTTGGAT
```

-continued

```
GTCGTTAGACTTTGACTCTATGTTCAAACACCACGTCAAGCTGCTTCCCAAAGATG

GACGTCATCTAAATACTGATATTCCTCCTCGAATGGGATGGTTACGGGCCATTTTA

CGATTCTTAGGTGCCGGAATGGTAATGACTGCGACTGGAGTTGCTGTCGACATCTA

TCTGGAGGATATACATGGCGGTGGTCGGTCACTTGGACAGAGATTCATGACTTGGA

TGCGACAGGAAGGACGGTCAGCGTGAGTCTACCATGGGTCGTGGTGCGTCAACTC

ATC
```

PL-λ3 Protein Sequence (SEQ ID NO: 8)

```
MSSMILTQFGPFIESISGITDQSNDVFEDAAKAFSMFTRSDVYKALDEIPF

SDDAMLPIPPTIYTKPSHDSYYYIDALNRVRRKTYQGPDDVYVPNCSIVELLEPHETLTS

YGRLSEAIENRAKDGDSQARIATTYGRIAESQARQIKAPLEKFVLALLVAEAGGSLYDP

VLQKYDEIPDLSHNCPLWCFREICRHISGPLPDRAPYLYLSAGVFWLMSPRMTSAIPPLL

SDLVNLAILQQTAGLDPSLVKLGVQICLHAAASSSYAWFILKTKSIFPQNTLHSMYESL

EGGYCPNLEWLEPRSDYKFMYMGVMPLSAKYARSAPSNDKKARELGEKYGLSSVVG

ELRKRTKTYVKHDFASVRYIRDAMACTSGIFLVRTPTETVLQEYTQSPEIKVPIPQKDW

TGPIGEIRILKDTTSSIARYLYRTWYLAAARMAAQPRTWDPLFQAIMRSQYVTARGGS

GAALRESLYAINVSLPDFKGLPVKAATKIFQAAQLANLPFSHTSVAILADTSMGLRNQV

QRRPRSIIVIPLNVPQQQVSAPHTLTADYINYHMNLSTTSGSAVIEKVIPLGVYASSPPNQ

SINIDISACDASITWDFFLSVIMAAIHEGVASSSIGKPFMGVPASIVNDESVVGVRAARPI

SGMQNMIQHLSKLYKRGFSYRVNDSFSPGNDFTHMTTTFPSGSTATSTEHTANNSTMM

ETFLTVWGPEHTDDPDVLRLMKSLTIQRNYVCQGDDGLMIIDGTTAGKVNSETIQKML

ELISKYGEEFGWKYDIAYDGTAEYLKLYFIFGCRIPNLSRHPIVGKERANSSAEEPWPAI

LDQIMGVFFNGVHDGLQWQRWIRYSWALCCAFSRQRTMIGESVGYLQYPMWSFVYW

GLPLVKAFGSDPWIFSWYMPTGDLGMYSWISLIRPLMTRWMVANGYVTDRCSPVFGN

ADYRRCFNELKLYQGYYMAQLPRNPKKSGRAAPREVREQFTQALSDYLLQNPELKSR

VLRGRSEWEKYGAGIIHNPPSLFDVPHKWYQGAQEAAIATREELAEMDETLMRARRH

RYSSFSKLLEAYLLVKWRMCEAREPSVDLRLPLCAGIDPLNSDPFLKMVSVGPMLQST

RKYFAQTLFMAKTVSGLDVNAIDSALLRLRTLGADKKALTAQLLMVGLQESEADALA

GKIMLQDVNTVQLARVVNLAVPDTWMSLDFDSMFKHHVKLLPKDGRHLNTDIPPRM

GWLRAILRFLGAGMVMTATGVAVDIYLEDIHGGGRSLGQRFMTWMRQEGRSA
```

PL-L2 Gene Sequence (SEQ ID NO: 28)

```
GCTAAATGGCGCGATGGCGAACGTTTGGGGGGTGAGACTTGCAGACT

CGTTATCTTCACCCACTATTGAGACACGAACGCGTCAGTATACCTTACACGATCTTT

GCTCAGACCTAGATGCTAATCCGGGGAGGGAACCGTGGAAACCTCTGCGTAATCA

GCGTACTAATAATATTGTGGCTGTGCAATTATTCAGACCATTGCAGGGTTTAGTTTT

AGATACCCAGCTTTATGGATTTCCAGGAGCATTTGATGACTGGGAGCGATTCATGA

GAGAGAAGCTGCGTGTGCTAAAGTATGAAGTATTGCGCATCTATCCAATCAGCAAC

TATAGCAATGAACATGTCAACGTCTTCGTGGCCAATGCTTTGGTGGGCGCTTTCCT

GTCGAATCAAGCTTTCTATGACCTGCTACCGTTGTTGATAATTAATGACACTATGAT

TGGTGATCTACTTGGCACGGGGGCATCGCTATCACAGTTCTTTCAATCTCATGGAG

ATGTGCTGGAAGTCGCAGCTGGTCGTAAGTATCTGCAGATGGAAAACTACTCCAAC

GATGACGATGATCCTCCATTATTTGCGAAAGACCTGTCAGATTATGCTAAAGCATT
```

-continued

```
CTACAGTGACACATATGAAGTGTTGGACAGGTTCTTTTGGACGCATGACTCTTCAG

CGGGGGTCTTAGTGCATTATGATAAGCCAACGAATGGTCATCACTATCTGCTGGGT

ACTTTGACTCAGATGGTCAGTGCACCTCCTTATATTATTAACGCTACTGACGCAATG

TTGCTTGAATCCTGTCTAGAACAGTTCTCAGCTAATGTGCGTGCGAGACCTGCGCA

ACCCGTTACACGCTTAGACCAATGCTATCATTTAAGATGGGGAGCACAATATGTAG

GAGAAGATTCACTGACATATCGGTTGGGGGTGTTATCCTTGCTGGCTACCAATGGA

TATCAATTAGCTAGACCGATTCCAAGACAGTTGACGAATCGATGGTTGTCGAGCTT

TGTGAGTCAAATTATGTCTGACGGCGTCAACGAGACTCCACTGTGGCCCCAAGAAA

GGTATGTGCAGATCGCTTATGATTCACCATCCGTTGTTGATGGGCTACGCAATAT

GGCTATGTCAGGAAGAATCAACTCAGACTCGGCATGAGAATATCGGCGCTGCAAT

CGCTGAGTGATACGCCCTCGCCGGTACAGTGGCTTCCACAATACACCATCGACCAG

GCAGCGATGGACGAAGGCGATCTGATGGTTAGTCGGCTTACGCAACTCCCGTTACG

TCCTGATTATGGTAATATCTGGGTCGGCGATGCGCTATCCTATTATGTGGACTACA

ATCGGAGTCATCGAGTCGTGCTTTCATCGGAACTTCCTCAGCTTCCGGACACATATT

TTGATGGCGATGAACAGTATGGGCGCAGCCTGTTCTCACTAGCTCGTAAGATTGGT

GACCGCTCGTTAGTGAAAGATACGGCTGTCTTGAAGCACGCTTACCAAGCCATCGA

TCCAAATACTGGTAAGGAGTATCTGAGATCTCGGCAATCTGTCGCATATTTTGGTG

CATCAGCGGGTCATTCTGGTGCCGACCAGCCGTTAGTCATAGAGCCCTGGATTCAA

GGGAAAATCAGTGGTGTGCCGCCACCCTCCTCAGTGCGACAGTTCGGCTATGATGT

TGCCCGTGGCGCGATCGTCGATCTGGCGAGACCATTTCCTTCTGGAGATTATCAAT

TTGTCTATTCGGATGTTGACCAGGTGGTCGATGGCCATGACGATCTGAGTATATCA

TCTGGACTGGTGGAGAGCCTTTTGTCTTCATGCATGCACGCCACAGCACCCGGGGG

CTCATTTGTTGTTAAGATAAATTTTCCGACTAGACCCGTATGGCACTACATCGAAC

AGAAGATCTTGCCCAATATTACGTCATACATGTTGATCAAGCCTTTCGTCACCAAC

AACGTCGAATTGTTCTTCGTCGCTTTCGGTGTGCATCAACACTCATCACTTACTTGG

ACATCTGGAGTGTACTTCTTCTTGGTGGACCATTTTTATCGTTATGAGACTTTATCT

ACGATCTCACGACAATTGCCGTCTTTTGGGTATGTTGATGATGGGTCTTCCGTGACT

GGTATCGAGACAATTAGTATTGAGAACCCTGGCTTCTCGAATATGACCCAGGCCGC

TCGCATTGGTATCTCAGGATTGTGTGCTAATGTAGGTAACGCGCGTAAGTCCATTG

CCATTTACGAATCTCATGGGGCCAGAGTATTAACTATCACATCAAGGAGATCTCCG

GCATCAGCTAGAAGAAAGTCTAGGTTGCGATATTTGCCATTAATAGACCCTAGGTC

GTTAGAGGTACAGGCGCGCACTATTCTGCCAGCTGATCCAGTGTTATTTGAAAACG

TGAGCGGAGCGTCACCCCATGTTTGTCTGACAATGATGTACAACTTCGAAGTGTCG

TCAGCGGTATATGATGGAGACGTTGTGCTAGATCTTGGGACGGGACCAGAGGCTA

AAATCCTTGAACTGATACCCGCAACCTCTCCAGTCACATGCGTGGACATACGGCCT

ACAGCGCAGCCTAGTGGATGTTGGAACGTTCGTACCACGTTCCTTGAGTTAGATTA

TTTGAGCGATGGATGGATCACTGGGGTGCGTGGGGACATAGTTACTTGTATGTTAT

CTTTGGGGGCCGCTGCCGCTGGAAAATCAATGACTTTTGACGCTGCGTTTCAGCAA

TTAATCAAAGTATTATCCAAGAGTACGGCTAATGTTGTGCTGGTGCAGGTTAACTG

CCCTACAGACGTGGTGAGGAGCATTAAGGGCTACCTAGAGATAGATTCGACTAAC
```

-continued

```
AAGAGGTATAGGTTCCCCAAATTTGGTCGAGACGAGCCGTACTCTGACATGGATGC

GCTGGAGAAAATATGTCGTACCGCCTGGCCAAACTGCTCAATTACCTGGGTTCCAT

TGTCATACGACTTGCGGTGGACTAGACTGGCATTATTAGAGTCCACGACATTGAGT

AGCGCGTCGATTAGAATTGCTGAGCTGATGTATAAATACATGCCTATTATGAGGAT

TGATATTCATGGACTACCCATGGAAAAGCGAGGTAACTTCATAGTGGGGCAGAAC

TGCTCATTAGTAATCCCTGGTTTTAATGCGCAGGATGTCTTTAACTGTTATTTCAAT

TCCGCCCTCGCTTTCTCGACTGAAGATGTCAATGCTGCGATGATTCCCCAAGTGTCT

GCGCAGTTTGATGCGACTAAGGGTGAGTGGACGTTGGATATGGTCTTCTCCGACGC

AGGAATCTATACCATGCAGGCTCTAGTGGGATCTAATGCTAATCCAGTCTCTTTGG

GTTCCTTTGTAGTTGATTCTCCAGATGTAGATATAACTGACGCTTGGCCAGCTCAGT

TAGACTTTACGATCGCGGGAACTGATGTCGATATAACAGTTAATCCTTATTACCGT

CTGATGACCTTTGTAAGGATCGATGGACAGTGGCAGATTGCCAATCCAGACAAATT

TCAATTCTTTTCGTCGGCGTCTGGGACGTTAGTGATGAACGTCAAATTAGATATCG

CAGATAAATATCTACTATACTATATACGAGATGTCCAGTCTCGAGATGTTGGCTTTT

ACATTCAGCATCCACTTCAACTTTTGAATACGATCACATTGCCAACCAACGAGGAC

CTTTTTCTGAGCGCACCTGACATGCGAGAGTGGGCAGTTAAGGAAAGCGGTAACA

CGATATGTATACTAATAGTCAAGGGTTTGTGCTACCTCAAGATTGGGATGTGTTA

ACAGATACCATAAGTTGGTCCCCATCGATACCCACATACATTGTGCCACCGGGTGA

TTATACCTTGACTCCTCTGTAACTCACTGTCCCTCGTGAGCGCGCCTAATTCATC
```

PL-λ2 Protein Sequence (SEQ ID NO: 9)

MANVWGVRLADSLSSPTIETRTRQYTLHDLCSDLDANPGREPWKPL

RNQRTNNIVAVQLFRPLQGLVLDTQLYGFPGAFDDWERFMREKLRVLKYEVLRI

YPISNYSNEHVNVFVANALVGAFLSNQAFYDLLPLLIINDTMIGDLLGTGASLSQFF

QSHGDVLEVAAGRKYLQMENYSNDDDDPPLFAKDLSDYAKAFYSDTYEVLDRFF

WTHDSSAGVLVHYDKPTNGHHYLLGTLTQMVSAPPYIINATDAMLLESCLEQFSA

NVRARPAQPVTRLDQCYHLRWGAQYVGEDSLTYRLGVLSLLATNGYQLARPIPR

QLTNRWLSSFVSQIMSDGVNETPLWPQERYVQIAYDSPSVVDGATQYGYVRKNQ

LRLGMRISALQSLSDTPSPVQWLPQYTIDQAAMDEGDLMVSRLTQLPLRPDYGNI<u>WVGDA</u>

<u>LSYYVDYNRSHRVVLSSELPQLPDTYFDGDEQYGRSLFSLARKIGDRSLVKDTAVLKH</u>

<u>AYQAIDPNTGKEYLRSRQSVAYFGASAGHSGADQPLVIEPWIQGKISGVPPPSSVRQFG</u>

<u>YDVARGAIVDLARPFPSGDYQFVYSDVDQVVDGHDDLSISSGLVESLLSSCMHATAPG</u>

<u>GSFVVKINFPTRPVWHYIEQKILPNITSYMLIKPFVTNNVELFFVAFGVHQHSSLTWTSG</u>

<u>VYFFLVDHFY</u>RYETLSTISRQLPSFGYVDDGSSVTGIETISIENPGFSNMTQAARIGISGLCAN

VGNARKSIAIYESHGARVLTITSRRSPASARRKSRLRYLPHDPRSLEVQARTILPADPVLFENVS

GASPHVCLTMMYNFEVSSAVYDGDVVLDLGTGPEAKILELIPATSPVTCVDIRPTAQPS

GCWNVRTTFLELDYLSDGWITGVRGDIVTCMLSLGAAAAGKSMTFDAAFQQLIKVLS

KSTANVVLVQVNCPTDVVRSIKGYLEIDSTNKRYRFPKFGRDEPYSDMDALEKICRTA

WPNCSITWVPLSYDLRWTRLALLESTTLSSASIRIAELMYKYMPIMRIDIHGLPMEKRG

NFIVGQNCSLVIPGFNAQDVFNCYFNSALAFSTEDVNAAMIPQVSAQFDATKGEWTLD

MVFSDAGIYTMQALVGSNANPVSLGSFVVDSPDVDITDAWPAQLDFTIAGTDVDITVN

PYYRLMTFVRIDGQWQIANPDKFQFFSSASGTLVMNVKLDIADKYLLYYIRDVQSRDV

GFYIQHPLQLLNTITLPTNEDLFLSAPDMREWAVKESGNTICILNSQGFVLPQDWDVLT

DTISWSPSIPTYIVPPGDYTLTPL

The domains of PL-λ2 protein are marked as follows: Guanylyltransferase (GTase) domain is in bold; bridge regions are indicated in italics; Methyltransferase (MTase1) domain is underlined; Methyltransferase (MTase2) is marked with squiggled line; and FLAP region is indicated with a dotted line.

PL S3 and TD S3 Gene Sequence (same sequence)
(SEQ ID NO: 22)

GCTAAAGTCACGCCTGTCGTCGTCACTATGGCTTCCTCACTCAGAGCT

GCGATCTCCAAGATCAAGAGGGATGACGTCGGTCAGCAAGTTTGTCCTAATTATGT

CATGCTGCGGTCCTCTGTCACAACAAAGGTGGTACGAAATGTGGTTGAGTATCAAA

TTCGTACGGGCGGATTCTTTTCGTGCTTAGCTATGCTAAGGCCACTCCAGTACGCTA

AGCGTGAGCGTTTGCTTGGTCAGAGGAATCTGGAACGTATATCGACTAGGGATATC

CTTCAGACTCGTGATTTACACTCACTATGTATGCCAACTCCTGATGCGCCAATGTCT

AATCATCAAGCATCCACCATGAGAGAGCTGATTTGCAGTTACTTCAAGGTCGATCA

TGCGGATGGGTTGAAATATATACCCATGGATGAGAGATACTCTCCGTCATCACTTG

CCAGATTGTTTACCATGGGCATGGCTGGGCTGCACATTACCACTGAGCCATCTTAT

AAGCGTGTTCCGATTATGCACTTAGCTGCGGACTTGGACTGTATGACGCTGGCTCT

ACCTTACATGATTACGCTTGATGGTGATACTGTGGTTCCTGTCGCTCCAACACTGTC

AGCGGAACAGCTTCTGGACGACGGACTCAAAGGATTAGCATGCATGGATATCTCCT

ATGGATGTGAGGTGGACGCGAATAGCCGGCCGGCTGGTGATCAGAGTATGGACTC

TTCACGCTGCATCAACGAGTTGTATTGCGAGGAGACAGCAGAAGCCATCTGTGTGC

TTAAGACATGCCTTGTGTTAAATTGCATGCAGTTTAAACTTGAGATGGATGACCTA

GCACATAACGCTGCTGAGCTGGACAAGATACAGATGATGATACCCTTCAGTGAGC

GTGTTTTTAGGATGGCCTCGTCCTTTGCGACTATTGATGCCCAGTGTTTTAGGTTTT

GCGTGATGATGAAGGATAAAAATCTGAAAATAGATATGCGTGAAACGACGAGACT

GTGGACTCGTTCAGCATCAGATGATTCTGTGGCCACGTCATCTTTAAGTATTTCCCT

GGACCGGGGTCGATGGGTGGCGGCTGACGCCAGTGATGCTAGACTGCTGGTTTTC

CGATTCGCGTGTAATGGGTGAGTGAGCTGATGTGGTCGCCAAGACATGTGCCGGTG

TCTTGGTGGTGGGTGACGCCTAATCATC

PL and TD σNS Protein Sequence (same sequence)
(SEQ ID NO: 3)

MASSLRAAISKIKRDDVGQQVCPNYVMLRSSVTTKVVRNVVEYQIRTG

GFFSCLAMLRPLQYAKRERLLGQRNLERISTRDILQTRDLHSLCMPTPDAPMSNHQAST

MRELICSYFKVDHADGLKYIPMDERYSPSSLARLFTMGMAGLHITTEPSYKRVPEVIHL

AADLDCMTLALPYMITLDGDTVVPVAPTLSAEQLLDDGLKGLACMDISYGCEVDANS

RPAGDQSMDSSRCINELYCEETAEAICVLKTCLVLNCMQFKLEMDDLAHNAAELDKIQ

MMIPFSERVFRMASSFATIDAQCFRFCVMMKDKNLKIDMRETTRLWTRSASDDSVATS
SLSISLDRGRWVAADASDARLLVFPIRV

PL-L3 Gene Sequence (SEQ ID NO: 29)

GCTAATCGTCAGGATGAAGCGGATTCCAAGGAAGACAAAGGGCAAA

TCCAGCGGAAAGGGCAATGACTCAACAGAGAGAGCGGACGATGGCTCGAGCCAAT

TAAGAGACAAGCAAAACAATAAGGCTGGCCCCGCCACTACGGAGCCTGGCACATC

CAACCGAGAGCAATACAAAGCTCGACCAGGTATTGCATCTGTGCAGAGGGCCACT

GAAAGTGCAGAAATGCCCATGAAGAATAATGACGAAGGGACGCCAGATAAGAAA

GGAAATACTAAGGGCGACCTAGTTAATGAGCATAGTGAGGCTAAAGACGAGGCGG

ATGAAGCGACGAAGAAGCAGGCAAAGGATACAGACAAAAGTAAAGCGCAAGTCA

CATATTCAGACACTGGTATCAATAATGCTAATGAACTGTCAAGATCTGGGAATGTG

GATAATGAGGGTGGAAGTAATCAGAAGCCGATGTCTACCAGAATAGCTGAGGCAA

CGTCTGCTATAGTGTCGAAACATCCTGCGCGTGTTGGGCTGCCACCTACCGCTAGC

AGTGGTCATGGGTATCAGTGCCATGTCTGTTCTGCAGTCCTGTTTAGTCCTTTAGAC

CTAGATGCCCACGTCGCCTCACATGGTTTGCATGGTAACATGACATTAACATCGAG

TGATATCCAGCGACATATAACTGAGTTCATCAGCTCATGGCAAAATCATCCTATTG

TTCAAGTTTCGGCTGATGTCGAAAATAAGAAAACTGCTCAATTGCTTCACGCTGAC

ACTCCTCGACTCGTCACTTGGGATGCTGGTTTGTGTACTTCATTCAAAATCGTCCCG

ATTGTGCCAGCTCAGGTGCCGCAGGATGTACTGGCCTATACGTTTTTCACCTCTTCA

TACGCTATCCAATCACCGTTTCCAGAGGCGGCAGTGTCTAGGATTGTGGTGCATAC

GAGATGGGCATCTAATGTTGACTTTGACCGAGACTCGTCTGTCATCATGGCGCCAC

CTACAGAAAACAATATCCATTTGTTTAAACAGTTACTAAATACTGAAACCCTGTCT

GTAAGGGGGCTAATCCGCTAATGTTCAGGGCGAATGTGTTGCATATGTTGCTAGA

GTTCGTATTAGATAACTTGTATCTGAACAGACATACGGGATTCTCTCAAGACCACA

CGCCATTTACTGAGGGTGCTAATTTGCGTTCACTTCCTGGCCCCGATGCTGAGAAA

TGGTACTCGATTATGTATCCAACGCGCATGGGAACGCCGAATGTATCCAAAATATG

TAATTTCGTCGCCTCTTGTGTGCGAAATCGGGTTGGACGGTTTGATCGAGCACAGA

TGATGAACGGAGCTATGTCAGAGTGGGTGGATGTCTTCGAGACTTCAGACGCGCTA

ACCGTCTCCATTCGAGGTCGATGGATGGCTAGACTAGCTCGCATGAACATAAATCC

AACAGAGATCGAATGGGCATTGACTGAATGTGCACAAGGATATGTGACTGTCACA

AGTCCTTACGCTCCTAGCGTAAATAGATTGATGCCCTATCGTATCTCCAACGCTGA

GCGGCAAATATCACAGATAATCAGGATCATGAACATTGGCAATAACGCGACGGTG

ATACAACCTGTTCTGCAAGATATTTCGGTACTCCTTCAACGCATATCACCACTCCAA

ATAGATCCAACTATTATTTCCAACACTATGTCAACAGTCTCGGAGTCTACTACTCA

GACCCTCAGCCCCGCGTCCTCAATTTTGGGTAAACTACGACCAAGCAACTCAGATT

TTTCTAGTTTTAGAGTCGCGTTGGCTGGATGGCTTTATAATGGGGTTGTGACGACG

GTGATTGATGATAGTTCATATCCAAAAGACGGCGGCAGCGTGACCTCACTTGAAAA

TCTGTGGGATTTCTTCATCCTTGCGCTTGCTCTACCACTGACAACTGACCCCTGTGC

ACCTGTGAAAGCATTCATGACCCTAGCCAACATGATGGTTGGTTTCGAGACAATCC

CTATGGATAATCAGATCTATACTCAATCGAGACGCGCGAGTGCTTTCTCAACGCCT

CACACGTGGCCACGATGCTTTATGAACATCCAGTTAATTTCTCCAATCGACGCTCC

-continued

```
CATCTTGCGACAGTGGGCTGAAATTATTCATAGATACTGGCCTAACCCTTCACAGA
TTCGTTATGGTGCACCGAACGTTTTCGGCTCGGCAAATTTGTTCACTCCACCTGAGG
TGCTGTTATTGCCAATCGATCATCAACCAGCTAATGTAACAACGCCAACGCTGGAC
TTCACCAATGAGTTAACTAATTGGCGCGCTCGTGTCTGTGAGCTTATGAAGAATCT
CGTTGATAACCAAAGATATCAACCTGGATGGACACAAAGTCTAGTCTCGTCAATGC
GCGGAACGCTAGACAAATTGAAGTTGATTAAATCGATGACACCAATGTATCTGCA
ACAGCTGGCTCCGGTAGAGTTAGCAGTGATAGCTCCCATGTTGCCTTTTCCACCTTT
CCAGGTGCCATACGTCCGTCTCGATCGTGACAGAGTTCCAACAATGGTTGGAGTAA
CACGACATTCACGAGATACTATTACTCAGCCGGCGCTATCGCTGTCGACAACCAAT
ACTACTGTTGGCGTGCCACTAGCTCTAGACGCGAGGGCTATCACCGTTGCGCTGTT
GTCAGGGAAATATCCGCCGGATTTGGTGACAAATGTATGGTACGCTGATGCCATTT
ACCCAATGTATGCAGACACGGAGGTGTTCTCTAATCTTCAGAGAGACATGATTACC
TGCGAGGCCGTGCAGACATTAGTGACTCTGGTGGCGCAAATATCAGAGACCCAGT
ATCCTGTAGATAGGTATCTTGATTGGATCCCATCACTGAGAGCATCGGCGGCGACG
GCGGCGACATTTGCTGAGTGGGTTAATACTTCAATGAAGACGGCGTTTGATTTGTC
TGATATGCTGTTAGAGCCTCTCCTAAGCGGTGATCCGAGGATGACTCAACTAGCGA
TTCAGTATCAGCAGTACAATGGCAGAACGTTTAATATCATACCTGAAATGCCAGGT
TCAGTAATTGCTGACTGCGTTCAATTAACAGCAGAAGTCTTTAATCACGAATATAA
CCTGTTTGGGATTGCGCGGGGTGATATCATCATTGGCCGTGTTCAGTCGACACATTT
GTGGTCACCGCTGGCTCCTCCACCTGACCTGGTGTTTGATCGTGATACCCCTGGTGT
TCACATCTTCGGACGAGATTGCCGTATATCGTTTGGAATGAATGGCGCCGCGCCAA
TGATTAGAGATGAGACTGGACTGATGGTGCCTTTTGAAGGAAATTGGATTTTCCCA
CTGGCGCTTTGGCAAATGAATACACGATATTTTAATCAACAGTTCGACGCGTGGAT
TAAGACAGGAGAGTTGCGAATCCGCATTGAGATGGGCGCGTATCCATATATGTTGC
ATTACTATGATCCACGTCAGTACGCTAATGCATGGAATTTAACATCCGCCTGGCTT
GAAGAAATTACGCCGACGAGCATCCCATCCGTGCCTTTCATGGTGCCCATTTCAAG
TGATCATGACATTTCCTCTGCCCCAGCTGTCCAATATATCATTTCAACTGAATATAA
TGATCGGTCTCTGTTCTGCACTAACTCATCATCTCCCCAAACCATCGCTGGACCAGA
CAAACACATTCCAGTTGAGAGATATAACATTCTGACCAACCCCGACGCTCCACCCA
CGCAGATACAACTGCCTGAAGTCGTTGACTTGTACAACGTCGTCACACGCTATGCG
TATGAGACTCCGCCTATTACCGCTGTTGTTATGGGTGTTCCTTGATCCTCATCCTCC
CAACAGGTGCTAGAGCATTGCGCTCAATGCTAGTTGGGCCGATTCATC
```

PL-λ1 Protein Sequence
(SEQ ID NO: 10)
MKRIPRKTKGKSSGKGNDSTERADDGSSQLRDKQNNKAGPATTEPGTS

NREQYKARPGIASVQRATESAEMPMKNNDEGTPDKKGNTKGDLVNEHSEAKDEADE

ATKKQAKDTDKSKAQVTYSDTGINNANELSRSGNVDNEGGSNQKPMSTRIAEATSAIV

SKHPARVGLPPTASSGHGYQCHVCSAVLFSPLDLDAHVASHGLHGNMTLTSSDIQRHI

TEFISSWQNHPIVQVSADVENKKTAQLLHADTPRLVTWDAGLCTSFKIVPIVPAQVPQD

VLAYTFFTSSYAIQSPFPEAAVSRIVVHTRWASNVDFDRDSSVIMAPPTENNIHLFKQLL

NTETLSVRGANPLMFRANVLHMLLEFVLDNLYLNRHTGFSQDHTPFTEGANLRSLPGP

-continued

DAEKWYSIMYPTRMGTPNVSKICNFVASCVRNRVGRFDRAQMMNGAMSEWVDVFET

SDALTVSIRGRWMARLARMNINPTEIEWALTECAQGYVTVTSPYAPSVNRLMPYRISN

AERQISQIIRIMNIGNNATVIQPVLQDISVLLQRISPLQIDPTIISNTMSTVSESTTQTLSPAS

SILGKLRPSNSDFSSFRVALAGWLYNGVVTTVIDDSSYPKDGGSVTSLENLWDFFILAL

ALPLTTDPCAPVKAFMTLANMMVGFETIPMDNQIYTQSRRASAFSTPHTWPRCFMNIQ

LISPIDAPILRQWAEIIHRYWPNPSQIRYGAPNVFGSANLFTPPEVLLLPIDHQPANVTTP

TLDFTNELTNWRARVCELMKNLVDNQRYQPGWTQSLVSSMRGTLDKLKLIKSMTPM

YLQQLAPVELAVIAPMLPFPPFQVPYVRLDRDRVPTMVGVTRHSRDTITQPALSLSTTN

TTVGVPLALDARAITVALLSGKYPPDLVTNVWYADAIYPMYADTEVFSNLQRDMITCE

AVQTLVTLVAQISETQYPVDRYLDWIPSLRASAATAATFAEWVNTSMKTAFDLSDML

LEPLLSGDPRMTQLAIQYQQYNGRTFNIIPEMPGSVIADCVQLTAEVFNHEYNLFGIAR

GDIIIGRVQSTHLWSPLAPPPDLVFDRDTPGVHIFGRDCRISFGMNGAAPMIRDETGLM

VPFEGNWIFPLALWQMNTRYFNQQFDAWIKTGELRIRIEMGAYPYMLHYYDPRQYAN

AWNLTSAWLEEITPTSIPSVPFMVPISSDHDISSAPAVQYIISTEYNDRSLFCTNSSSPQTI

AGPDKHIPVERYNILTNPDAPPTQIQLPEVVDLYNVVTRYAYETPPITAVVMGVP

PL-M1 Gene Sequence (SEQ ID NO: 24)

GCTATTCGCGGTCATGGCTTACATCGCAGTTCCTGCGGTGGTGGATTC

ACGTTCGAGTGAGGCTATTGGACTGCTAGAATCGTTTGGAGTAGACGCTGGGGCTG

ACGCGAATGACGTTTCATATCAAGATCATGACTATGTGTTGGATCAGTTACAGTAC

ATGTTAGATGGATATGAGGCTGGTGACGTTATCGATGCACTCGTCCACAAGAATTG

GTTACATCACTCTGTCTATTGCTTGTTGCCGCCCAAAAGTCAACTATTAGAGTATTG

GAAAAGTAATCCTTCAGCGATACCGGACAACGTTGATCGTCGGCTTCGTAAACGAC

TAATGCTAAAGAAAGATCTCAGGAAAGATGATGAATACAATCAGCTAGCGCGTGC

TTTCAAGATATCGGATGTCTACGCACCTCTCATCTCATCCACGACGTCACCGATGA

CAATGATACAGAACTTGAATCGAGGCGAGATCGTGTACACCACGACGGACAGGGT

AATAGGGGCTAGAATCTTGTTATATGCTCCTAGAAAGTACTATGCGTCAACTCTGT

CATTTACTATGACTAAGTGCATCATTCCGTTTGGTAAAGAGGTGGGTCGTGTTCCTC

ACTCTCGATTTAATGTTGGCACATTTCCGTCAATTGCTACCCCGAAATGTTTTGTCA

TGAGTGGGGTTGATATTGAGTCCATCCCAAATGAATTTATCAAGTTGTTTTACCAG

CGCGTCAAGAGTGTTCACGCTAACATACTAAATGACATATCTCCTCAGATCGTCTC

TGACATGATAAACAGAAAGCGTCTGCGCGTTCATACTCCATCAGATCGTCGAGCCG

CGCAGTTGATGCATTTGCCTTACCATGTTAAACGAGGAGCGTCTCACGTCGACGTT

TACAAGGTGGATGTTGTAGACATGTTGTTCGAGGTAGTGGATGTGGCCGATGGGTT

GCGCAACGTATCTAGGAAACTAACTATGCATACCGTTCCTGTATGTATTCTTGAAA

TGTTGGGTATTGAGATTGCGGACTATTGCATTCGTCAAGAGGATGGAATGCTCACA

GATTGGTTCCTACTTTTAACCATGCTATCTGATGGCTTGACTGATAGAAGGACGCA

TTGTCAATACTTGATTAATCCGTCAAGTGTGCCTCCTGATGTGACTTAACATCTC

AATTACTGGATTTATAAATAGACATACAATCGATGTCATGCCTGACATATATGACT

TCGTTAAACCCATTGGCGCTGTGCTGCCTAAGGGATCATTTAAATCAACAATTATG

AGAGTTCTTGATTCAATATCAATATTAGGAATCCAAATCATGCCGCGCGCGCATGT

AGTTGACTCAGATGAGGTGGGCGAGCAAATGGAGCCTACGTTTGAGCAGGCGGTT

-continued

```
ATGGAGATATACAAAGGGATTGCTGGCGTTGACTCGCTGGATGATCTCATCAAGTG

GGTGTTGAACTCGGATCTCATTCCGCATGATGACAGGCTTGGTCAATTATTTCAAG

CGTTTTTGCCTCTCGCAAAGGACTTATTAGCTCCAATGGCCAGAAAGTTTTATGATA

ACTCAATGAGTGAGGGTAGATTGCTAACATTCTCTCATGCCGACAGTGAGTTGCTG

AACGCAAATTATTTTGGTCATTTATTGCGACTAAAAATACCATATATTACAGAGGT

TAATCTGATGATTCGCAAGAATCGTGAGGGTGGAGAGCTATTTCAGCTCGTGTTAT

CTTATCTATATAAAATGTATGCTACTAGCGCGCAGCCTAAATGGTTTGGATCATTAT

TGCGATTGTTAATATGTCCCTGGTTACATATGGAGAAATTAATAGGAGAAGCAGAC

CCGGCATCTACGTCGGCTGAAATTGGGTGGCATATCCCTCGTGAACAGCTGATGCA

AGATGGATGGTGTGGATGTGAAGACGGATTCATTCCCTATGTTAGCATACGTGCGC

CAAGACTGGTTATAGAGGAGTTGATGGAGAAGAACTGGGGCCAATATCATGCCCA

AGTTATTGTCACTGATCAGCTTGTCGTAGGCGAACCGCGGAGGGTATCTGCTAAGG

CTGTGATCAAGGGTAACCACTTACCAGTTAAGTTAGTTTCACGATTTGCATGTTTCA

CATTGACGGCGAAGTATGAGATGAGGCTTTCGTGCGGCCATAGCACTGGACGTGG

AGCTGCATACAGTGCGAGACTAGCTTTCCGATCTGACTTGGCGTGATCCGTGACAT

GCGTAGTGTGACACCTGCTCCTAGGTCAATGGGGGTAGGGGGCGGGCTAGGACTA

CGTACGCGCTTCATC
```

PL-μ2 Protein Sequence
(SEQ ID NO: 5)
```
MAYIAVPAVVDSRSSEAIGLLESFGVDAGADANDVSYQDHDYVLDQLQ

YMLDGYEAGDVIDALVHKNWLHHSVYCLLPPKSQLLEYWKSNPSAIPDNVDRRLRKR

LMLKKDLRKDDEYNQLARAFKISDVYAPLISSTTSPMTMIQNLNRGEIVYTTTDRVIGA

RILLYAPRKYYASTLSFTMTKCIIPFGKEVGRVPHSRFNVGTFPSIATPKCFVMSGVDIES

IPNEFIKLFYQRVKSVHANILNDISPQIVSDMINRKRLRVHTPSDRRAAQLMHLPYHVK

RGASHVDVYKVDVVDMLFEVVDVADGLRNVSRKLTMHTVPVCILEMLGIEIADYCIR

QEDGMLTDWFLLLTMLSDGLTDRRTHCQYLINPSSVPPDVILNISITGFINRHTIDVMPD

IYDFVKPIGAVLPKGSFKSTIMRVLDSISILGIQIMPRAHVVDSDEVGEQMEPTFEQAVM

EIYKGIAGVDSLDDLIKWVLNSDLIPHDDRLGQLFQAFLPLAKDLLAPMARKFYDNSM

SEGRLLTFSHADSELLNANYFGHLLRLKIPYITEVNLMIRKNREGGELFQLVLSYLYKM

YATSAQPKWFGSLLRLLICPWLHMEKLIGEADPASTSAEIGWHIPREQLMQDGWCGCE

DGFIPYVSIRAPRLVIEELMEKNWGQYHAQVIVTDQLVVGEPRRVSAKAVIKGNHLPV

KLVSRFACFTLTAKYEMRLSCGHSTGRGAAYSARLAFRSDLA
```

PL-M2 Gene Sequence
(SEQ ID NO: 25)
```
GCTAATCTGCTGACCGTTACTCTGCAAAGATGGGGAACGCTTCCTCT

ATCGTTCAGACGATCAACGTCACTGGAGATGGCAATGTATTTAAACCATCAGCTGA

AACTTCATCTACCGCTGTACCATCGTTAAGCTTATCACCTGGAATGCTGAATCCCG

GAGGGGTACCATGGATTGCTGTTGGAGATGAGACATCTGTGACTTCACCAGGCGCA

TTACGTCGAATGACGTCAAAGGACATCCCGGACACGGCAATAATCAACACAGACA

ATTCATCAGGCGCCGTGCCAAGCGAATCAGCCTTGGTGCCCTACATCGATGAGCCG

CTGGTAGTGGTTACAGAGCATGCTATTACCAACTTCACCAAAGCTGAGATGGCACT

TGAATTCAATCGTGAGTTCCTTGACAAGATGCGTGTGCTGTCAGTGTCACCAAAAT
```

-continued

```
ATTCGGATCTTCTGACCTATGTTGACTGCTACGTCGGTGTGTCTGCTCGTCAGGCTT

TAAACAATTTTCAGAAACAAGTGCCTGTGATTACACCTACTAGGCAGACGATGTAT

GTCGACTCGATACAAGCGGCCTTGAAAGCTTTAGAAAAGTGGGAGATTGATCTGA

GAGTGGCTCAAACGTTGCTGCCTACGAACGTTCCGATTGGAGAAGTCTCTTGTCCA

ATGCAGTCGGTAGTGAAACTGCTGGATGATCAGCTGCCAGATGACAGCCTGATAC

GGAGGTATCCCAAGGAAGCCGCCGTCGCTTTGGCTAAACGAAACGGGGGAATACA

ATGGATGGACGTATCAGAAGGCACCGTGATGAACGAGGCTGTCAACGCTGTTGCA

GCTAGTGCACTGGCACCTTCAGCATCAGCCCCACCCTTAGAAGAGAAGTCAAAGTT

AACCGAACAAGCGATGGATCTCGTGACCGCGGCTGAGCCTGAGATAATTGCCTCA

CTCGCGCCAGTTCCCGCACCCGTGTTTGCCATACCACCTAAACCAGCAGATTATAA

TGTGCGTACTCTGAGGATCGACGAGGCCACTTGGCTGCGAATGATTCCAAAATCAA

TGAACACACCTTTTCAAATCCAGGTGACTGATAACACAGGAACTAATTGGCATCTC

AATTTGAGGGGGGGGACTCGTGTAGTGAATCTGGACCAAATCGCTCCGATGCGGTT

TGTATTAGATCTAGGGGGAAAGAGTTATAAAGAGACGAGCTGGGATCCAAACGGC

AAGAAGGTCGGATTCATCGTTTTTCAATCGAAGATACCATTCGAACTTTGGACTGC

TGCTTCACAGATCGGTCAAGCCACGGTGGTTAACTATGTCCAACTATACGCTGAAG

ACAGCTCATTTACCGCGCAGTCTATCATTGCTACTACCTCTTTGGCTTATAACTATG

AGCCTGAGCAGTTGAATAAGACTGACCCTGAGATGAATTATTATCTTTTGGCGACC

TTTATAGACTCAGCCGCTATAACGCCAACGAATATGACACAGCCTGATGTTTGGGA

TGCCTTGCTGACGATGTCCCCACTATCAGCTGGCGAGGTGACAGTGAAGGGTGCGG

TAGTGAGTGAAGTAGTCCCTGCAGACTTGATAGGTAGCTACACTCCAGAATCCCTA

AACGCCTCACTTCCGAATGATGCTGCTAGATGCATGATCGATAGAGCTTCGAAGAT

AGCCGAAGCAATCAAGATTGATGATGATGCTGGACCAGATGAATATTCCCCAAAC

TCTGTACCAATTCAAGGTCAGCTTGCTATCTCGCAACTCGAAACTGGATATGGTGT

GCGAATATTCAACCCTAAAGGGATCCTTTCCAAAATTGCATCTAGGGCAATGCAGG

CTTTCATTGGTGACCCGAGCACAATCATCACGCAGGCGGCGCCAGTGTTATCAGAC

AAGAATAATTGGATTGCATTGGCACAGGGAGTGAAAACTAGTCTGCGTACTAAAA

GTCTATCAGCGGGAGTGAAGACTGCAGTGAGTAAGCTGAGCTCATCTGAGTCTATC

CAGAATTGGACTCAAGGATTCTTGGATAAAGTGTCAGCGCATTTTCCAGCACCAAA

GCCCGATTGTCCGACTAGCGGAGATAGTGGTGAATCGTCTAATCGCCGAGTGAAGC

GCGACTCATACGCAGGAGTGGTCAAACGTGGGTACACACGTTAGGCCGCTCGCCCT

GGTGACGCGGGGTTAAGGGATGCAGGCAAATCATC
```

PL-μ1 Protein Sequence (SEQ ID NO: 6)

MGNASSIVQTINVTGDGNVFKPSAETSSTAVPSLSLSPGMLNPGGVPWIA

VGDETSVTSPGALRRMTSKDIPDTAIINTDNSSGAVPSESALVPYIDEPLVVVTEHAITN

FTKAEMALEFNREFLDKMRVLSVSPKYSDLLTYVDCYVGVSARQALNNFQKQVPVIT

PTRQTMYVDSIQAALKALEKWEIDLRVAQTLLPTNVPIGEVSCPMQSVVKLLDDQLPD

DSLIRRYPKEAAVALAKRNGGIQWMDVSEGTVMNEAVNAVAASALAPSASAPPLEEK

SKLTEQAMDLVTAAEPEIIASLAPVPAPVFAIPPKPADYNVRTLRIDEATWLRMIPKSM

NTPFQIQVTDNTGTNWHLNLRGGTRVVNLDQIAPMRFVLDLGGKSYKETSWDPNGKK

VGFIVFQSKIPFELWTAASQIGQATVVNYVQLYAEDSSFTAQSIIATTSLAYNYEPEQLN

KTDPEMNYYLLATFIDSAAITPTNMTQPDVWDALLTMSPLSAGEVTVKGAVVSEVVP

ADLIGSYTPESLNASLPNDAARCMIDRASKIAEAIKIDDDAGPDEYSPNSVPIQGQLAIS

QLETGYGVRIFNPKGILSKIASRAMQAFIGDPSTIITQAAPVLSDKNNWIALAQGVKTSL

RTKSLSAGVKTAVSKLSSSESIQNWTQGFLDKVSAHFPAPKPDCPTSGDSGESSNRRVK

RDSYAGVVKRGYTR

PL-M3 Gene Sequence (SEQ ID NO: 26)

GCTAAAGTGACCGTGGTCATGGCTTCATTCAAGGGATTCTCCGCCAA

CACTGTTCCAGTTTCTAAGGCCAAGCGTGACATATCATCTCTTGCCGCTACTCCTGG

ACTTCGTTCACAATCCTTCACTCCGTCTGTGGATATGTCTCAATCGCGTGAATTCCT

CACAAAGGCAATTGAGCAAGGGTCCATGTCTATACCTTATCAGCATGTGAATGTAC

CGAAAGTTGATCGTAAAGTTGTTAGCCTGGTAGTGCGACCTTTCTCTTCAGGTGCTT

TCTCTATCTCTGGAGTGATTTCGCCAGCCCATGCCTATCTACTAGAGTGTCTACCCC

AGCTTGAGCAGGCGATGGCTTTTGTCGCTTCACCTGAGTCTTTCCAGGCTTCCGACG

TCGCGAAGCGCTTTGCCATAAAGCCAGGTATGAGCCTCCAGGATGCCATCACTGCC

TTTATTAACTTTGTGTCCGCGATGCTGAAAATGACGGTGACTCGTCAAAACTTTGA

CGTTATTGTGGCTGAGATCGAGAGGCTTGCTTCAACCAGCGTGTCCGTCAGGACTG

AAGAAGCGAAGGTTGCTGATGAGGAGCTAATGCTATTCGGGTTAGATCATAGAGG

GCCACAGCAGCTGGATGTTTCTGACGCTAAAGGGATAATGAAGGCTGCTGATATTC

AGACAACTCATGATGTCCATTTGGCACCAGGCGTTGGTAATATTGATCCTGAAATC

TATAACGAGGGGCGGTTCATGTTCATGCAGCACAAGCCACTTGCGGCGGATCAATC

GTATTTCACCTTGGAGACTGCGGATTATTTCAAGATTTATCCAACATACGATGAAC

ATGATGGCAGGATGGCTGACCAAAAGCAGTCGGGATTGATACTGTGTACTAAGGA

CGAGGTATTGGCTGAGCAAACTATATTTAAACTGGACGCCCCTGATGACAAGACTG

TTCATCTGTTGGATCGCGATGACGACCACGTTGTTGCCAGATTTACTAAGGTATTTA

TAGAGGACGTGGCTCCCGGGCATCATGCTGCTCAAAGATCGGGACAACGCTCTGTG

CTTGATGACCTATATGCGAATACGCAAGTGATTTCCATTACTTCTGCTGCTTTAAAG

TGGGTGGTCAAGCACGGCGTATCTGATGGAATCGTGAACAGGAAGAATGTCAAAG

TGTGTGTTGGTTTTGACCCCCTGTACACCTTGTCTACACATAACGGGGTGTCCTTAT

GTGCCCTGCTGATGGACGAAAAACTCTCTGTGCTGAACAGTGCGTGTCGTATGACG

TTACGCTCACTCATGAAGACCGGACGCGACGTTGATGCACACAGAGCTTTTCAGCG

AGTCCTCTCTCAAGGATACACATCGCTAATGTGCTACTATCATCCTTCACGGAAGTT

GGCATATGGTGAGGTGCTCTTTCTAGAACGATCCAATGACGTGACAGATGGGATCA

AGCTTCAGTTGGACGCATCTAGACAGTGTCATGAATGTCCTGTGTTGCAGCAGAAA

GTGGTTGAGTTAGAGAAACAGATTATTATGCAGAAGTCAATCCAGTCAGACCCTAC

CCCAGTGGCGCTGCAACCATTGTTGTCTCAGTTGCGTGAGTTGTCTAGTGAAGTTA

CTAGGCTACAGATGGAGTTGAGTCGAGCTCAGTCCCTGAATGCTCAGTTGGAGGCG

GATGTCAAGTCAGCTCAATCATGTAGCTTGGATATGTATCTGAGACACCACACTTG

CATTAATGGTCATGCTAAAGAAGATGAATTGCTTGACGCTGTGCGTGTCGCGCCGG

ATGTGAGGAGAGAAATCATGGAAAAGAGGAGTGAAGTGAGACAAGGTTGGTGCG

AACGTATTTCTAAGGAAGCAGCTGCCAAATGTCAAACTGTTATTGATGACCTGACT

-continued
```
TTGATGAATGGAAAGCAAGCACAAGAGATAACAGAATTACGTGATTCGGCTGAAA

AATATGAGAAACAGATTGCAGAGCTGGTGAGTACCATCACCCAAAACCAGATAAC

GTATCAGCAAGAGCTACAAGCCTTGGTAGCGAAAAATGTGGAATTGGACGCGTTG

AATCAGCGTCAGGCTAAGTCTTTGCGTATTACTCCCTCTCTTCTATCAGCCACTCCT

ATCGATTCAGTTGATGATGTTGCTGACTTAATTGATTTCTCTGTTCCAACTGATGAG

TTGTAAATAATCCGTGATGCAGTGTTGCCCTAATCCCTTAAGCCTTCCCGACCCCCA

TTCATC
```

PL-μNS Protein Sequence (SEQ ID NO: 7)
```
MASFKGFSANTVPVSKAKRDISSLAATPGLRSQSFTPSVDMSQSREFLTK

AIEQGSMSIPYQHVNVPKVDRKVVSLVVRPFSSGAFSISGVISPAHAYLLECLPQLEQA

MAFVASPESFQASDVAKRFAIKPGMSLQDAITAFINFVSAMLKMTVTRQNFDVIVAEIE

RLASTSVSVRTEEAKVADEELMLFGLDHRGPQQLDVSDAKGIMKAADIQTTHDVHLA

PGVGNIDPEIYNEGRFMFMQHKPLAADQSYFTLETADYFKIYPTYDEHDGRMADQKQ

SGLILCTKDEVLAEQTIFKLDAPDDKTVHLLDRDDDHVVARFTKVFIEDVAPGHHAAQ

RSGQRSVLDDLYANTQVISITSAALKWVVKHGVSDGIVNRKNVKVCVGFDPLYTLSTH

NGVSLCALLMDEKLSVLNSACRMTLRSLMKTGRDVDAHRAFQRVLSQGYTSLMCYY

HPSRKLAYGEVLFLERSNDVTDGIKLQLDASRQCHECPVLQQKVVELEKQIIMQKSIQS

DPTPVALQPLLSQLRELSSEVTRLQMELSRAQSLNAQLEADVKSAQSCSLDMYLRHHT

CINGHAKEDELLDAVRVAPDVRREEVIEKRSEVRQGWCERISKEAAAKCQTVIDDLTL

MNGKQAQEITELRDSAEKYEKQIAELVSTITQNQITYQQELQALVAKNVELDALNQRQ

AKSLRITPSLLSATPIDSVDDVADLIDFSVPTDEL
```

PL-S1 Gene Sequence (SEQ ID NO: 20)
```
GCTATTGGTCGGATGGATCCTCGCCTACGTGAAGAAGTAGTACGGCT

GATAATCGCATTAACGAGTGATAATGGAGCATCACTGTCAAAAGGGCTTGAATCA

AGGGTCTCGGCGCTCGAGAAGACGTCTCAAATACACTCTGATACTATCCTCCGGAT

CACCCAGGGACTCGATGATGCAAACAAACGAATCATCGCTCTTGAGCAAAGTCGG

GATGACTTGGTTGCATCAGTCAGTGATGCTCAACTTGCAATCTCCAGATTGGAAAG

CTCTATCGGAGCCCTCCAAACAGTTGTCAATGGACTTGATTCGAGTGTTACCCAGT

TGGGTGCTCGAGTGGGACAACTTGAGACAGGACTTGCAGAGCTACGCGTTGATCA

CGACAATCTCGTTGCGAGAGTGGATACTGCAGAACGTAACATTGGATCATTGACCA

CTGAGCTATCAACTCTGACGTTACGAGTAACATCCATACAAGCGGATTTCGAATCT

AGGATATCCACGTTAGAGCGCACGGCGGTCACTAGCGCGGGAGCTCCCCTCTCAAT

CCGTAATAACCGTATGACCATGGGATTAAATGATGGACTCACGTTGTCAGGGAATA

ATCTCGCCATCCGATTGCCAGGAAATACGGGTCTGAATATTCAAAATGGTGGACTT

CAGTTTCGATTTAATACTGATCAATTCCAGATAGTTAATAATAACTTGACTCTCAAG

ACGACTGTGTTTGATTCTATCAACTCAAGGATAGGCGCAACTGAGCAAAGTTACGT

GGCGTCGGCAGTGACTCCCTTGAGATTAAACAGTAGCACGAAGGTGCTGGATATG

CTAATAGACAGTTCAACACTTGAAATTAATTCTAGTGGACAGCTAACTGTTAGATC

GACATCCCCGAATTTGAGGTATCCGATAGCTGATGTTAGCGGCGGTATCGGAATGA

GTCCAAATTATAGGTTTAGGCAGAGCATGTGGATAGGAATTGTCTCCTATTCTGGT

AGTGGGCTGAATTGGAGGGTACAGGTGAACTCCGACATTTTTATTGTAGATGATTA
```

-continued

CATACATATATGTCTTCCAGCTTTTGACGGTTTCTCTATAGCTGACGGTGGAGATCT

ATCGTTGAACTTTGTTACCGGATTGTTACCACCGTTACTTACAGGAGACACTGAGC

CCGCTTTTCATAATGACGTGGTCACATATGGAGCACAGACTGTAGCTATAGGGTTG

TCGTCGGGTGGTGCGCCTCAGTATATGAGTAAGAATCTGTGGGTGGAGCAGTGGCA

GGATGGAGTACTTCGGTTACGTGTTGAGGGGGTGGCTCAATTACGCACTCAAACA

GTAAGTGGCCTGCCATGACCGTTTCGTACCCGCGTAGTTTCACGTGAGGATCAGAC

CACCCCGCGGCACTGGGGCATTTCATC

PL-σ1 Protein Sequence (SEQ ID NO: 1)

MDPRLREEVVRLIIALTSDNGASLSKGLESRVSALEKTSQIHSDTILRIT

QGLDDANKRIIALEQSRDDLVASVSDAQLAISRLESSIGALQTVVNGLDSSVTQLGARV

GQLETGLAELRVDHDNLVARVDTAERNIGSLTTELSTLTLRVTSI*QADFESRISTLERTA*V

*TSAGAPLSIRNNRMTMGLNDGLTLSGNNLAIRLPGNTGLNIQNGGLQFRFNTDQF*

*QIVNNNLTLK*TTVFDSINSRIGATEQSYVASAVTPLRLNSSTKVLDMLIDSSTLEINSSG

QLTVRSTSPNLRYPIADVSGGIGMSPNYRFRQSMWIGIVSYSGSGLNWRVQVNSDIFIV

DDYIHICLPAFDGFSIADGGDLSLNFVTGLLPPLLTGDTEPAFHNDVVTYGAQTVAIGLS

SGGAPQYMSKNLWVEQWQDGVLRLRVEGGGSITHSNSKWPAMTVSYPRSFT

Anchoring domain of PL-σ1 is indicated in bold; tail (coil-coil) region is single-underlined; flexible 1 linker is italicized; the body domain includes: SA-binding domain which is italicized and in bold; GATE region which is double underlined; β-sheet domain which is underlined with a bold line; neck region is indicated with a dotted line; and the head region is marked with a squiggled line.

PL-S2 Gene Sequence (SEQ ID NO: 21)

GCTATTCGCTGGTCAGTTATGGCTCGCGCTGCGTTCCTATTCAAGACT

GTTGGGTTTGGTGGTCTGCAAAATGTGCCAATTAACGACGAACTATCTTC

ACATCTACTCCGAGCTGGTAATTCACCATGGCAGTTAACACAGTTTTTAG

ACTGGATAAGCCTTGGGAGGGGTTTAGCTACATCGGCTCTCGTTCCGACG

GCTGGGTCAAGATACTATCAAATGAGTTGCCTTCTAAGTGGCACTCTCCA

GATTCCGTTCCGTCCTAACCACCGATGGGGAGACATTAGGTTCTTACGCT

TAGTGTGGTCAGCTCCTACTCTCGATGGATTAGTCGTAGCTCCACCACAA

GTTTTGGCTCAGCCCGCTTTGCAAGCACAGGCAGATCGAGTGTACGACTG

CGATGATTATCCATTTCTAGCGCGTGATCCAAGATTCAAACATCGGGTGT

ATCAGCAATTGAGTGCTGTAACTCTACTTAACTTGACAGGTTTTGGCCCG

ATTTCCTACGTTCGAGTGGATGAAGATATGTGGAGTGGAGATGTGAACCA

GCTTCTCATGAACTATTTCGGGCACACGTTTGCAGAGATTGCATACACAT

TGTGTCAAGCCTCGGCTAATAGGCCTTGGGAATATGACGGTACATATGCT

AGGATGACTCAGATTGTGTTATCCTTGTTCTGGCTATCGTATGTCGGTGT

AATTCATCAGCAGAATACGTATCGGACATTCTATTTTCAGTGTAATCGGC

GAGGTGACGCCGCTGAGGTGTGGATTCTTTCTTGTTCGTTGAACCATTCC

GCACAAATTAGACCGGGTAATCGTAGCTTATTCGTTATGCCAACTAGCCC

AGATTGGAACATGGACGTCAATTTGATCCTGAGTTCAACGTTGACGGGGT

GTTTGTGTTCGGGTTCACAGCTGCCACTGATTGACAATAATTCAGTACCT

GCAGTGTCGCGTAACATCCATGGCTGGACTGGTAGAGCTGGTAACCAATT

GCATGGGTTCCAGGTGAGACGAATGGTGACTGAATTTTGTGACAGGTTGA

GACGCGATGGTGTCATGACCCAAGCTCAGCAGAATCAAGTTGAAGCGTTG

GCAGATCAGACTCAACAGTTTAAGAGGGACAAGCTCGAAACGTGGGCGAG

AGAAGACGATCAATATAATCAGGCTCATCCCAACTCCACAATGTTCCGTA

CGAAACCATTTACGAATGCGCAATGGGGACGAGGTAATACGGGGCGACT

AGTGCCGCGATTGCAGCCCTTATCTGATCGTCTTGGAGTGAGGGGGTCCC

CCCACACCCCTCACGACTGACCACACATTCATC

PL-σ2 Protein Sequence (SEQ ID NO: 2)

MARAAFLFKTVGFGGLQNVPINDELSSHLLRAGNSPWQLTQFLDWISLG

RGLATSALVPTAGSRYYQMSCLLSGTLQIPFRPNHRWGDIRFLRLVWSAP

TLDGLVVAPPQVLAQPALQAQADRVYDCDDYPFLARDPRFKHRVYQQLSA

VTLLNLTGFGPISYVRVDEDMWSGDVNQLLMNYFGHTFAEIAYTLCQASA

NRPWEYDGTYARMTQIVLSLFWLSYVGVIHQQNTYRTFYFQCNRRGDAAE

VWILSCSLNHSAQIRPGNRSLFVMPTSPDWNMDVNLILSSTLTGCLCSGS

QLPLIDNNSVPAVSRNIHGWTGRAGNQLHGFQVRRMVTEFCDRLRRDGVM

TQAQQNQVEALADQTQQFKRDKLETWAREDDQYNQAHPNSTMFRTKPFTN

AQWGRGNTGATSAAIAALI

PL-S4 Gene Sequence (SEQ ID NO: 23)
GCTATTTTTGCCTCTTCCCAGACGTTGTCGCAATGGAGGTGTGCTTGC

CCAACGGTCATCAGGTCGTGGACTTAATTAACAACGCTTTTGAAGGTCGT

GTATCAATCTACAGCGCGCAAGAGGGATGGGACAAAACAATCTCAGCACA

GCCAGATATGATGGTATGTGGTGGCGCCGTCGTTTGCATGCATTGTCTAG

GTGTTGTTGGATCTCTACAACGCAAGCTGAAGCATTTGCCTCACCATAGA

TGTAATCAACAGATCCGTCATCAGGATTACGTCGATGTACAGTTCGCAGA

CCGTGTTACTGCTCACTGGAAGCGGGGTATGCTGTCCTTCGTTGCGCAGA

TGCACGAGATGATGAATGACGTGTCGCCAGATGACCTGGATCGTGTGCGT

ACTGAGGGAGGTTCACTAGTGGAGCTGAACCGGCTTCAGGTTGACCCAAA

TTCAATGTTTAGATCAATACACTCAAGTTGGACAGATCCTTTGCAGGTGG

TGGACGACCTTGACACTAAGCTGGATCAGTACTGGACAGCCTTAAACCTG

ATGATCGACTCATCCGACTTGATACCCAACTTTATGATGAGAGACCCATC

ACACGCGTTCAATGGTGTGAAACTGAAGGGAGATGCTCGTCAAACCCAAT

TCTCCAGGACTTTTGATTCGAGATCGAGTTTGGAATGGGGTGTGATGGTT

TATGATTACTCTGAGCTGGATCATGATCCATCGAAGGGCCGTGCTTACAG

AAAGGAATTGGTGACGCCAGCTCGAGATTTCGGTCACTTTGGATTATCCC

ATTATTCTAGGGCGACTACCCCAATCCTTGGAAAGATGCCGGCCGTATTC

TCAGGAATGTTGACTGGGAACTGTAAAATGTATCCATTCATTAAAGGAAC

GGCTAAGCTGAAGACAGTGCGCAAGCTAGTGGAGGCAGTCAATCATGCTT

GGGGTGTCGAGAAGATTAGATATGCTCTTGGGCCAGGTGGCATGACGGGA

TGGTACAATAGGACTATGCAACAGGCCCCCATTGTGCTAACTCCTGCTGC

TCTCACAATGTTCCCAGATACCATCAAGTTTGGGGATTTGAATTATCCAG

TGATGATTGGCGATCCGATGATTCTTGGCTAAACACCCCCATCTTCACAG

CGCCGGGCTTGACCAACCTGGTGTGACGTGGGACAGGCTTCATTCATC

PL-σ3 Protein Sequence (SEQ ID NO: 4)
MEVCLPNGHQVVDLINNAFEGRVSIYSAQEGWDKTISAQPDMMVCGGA

VVCMHCLGVVGSLQRKLKHLPHHRCNQQIRHQDYVDVQFADRVTAHWKRG

MLSFVAQMHEMMNDVSPDDLDRVRTEGGSLVELNRLQVDPNSMFRSIHSS

WTDPLQVVDDLDTKLDQYWTALNLMIDSSDLIPNFMMRDPSHAFNGVKLK

GDARQTQFSRTFDSRSSLEWGVMVYDYSELDHDPSKGRAYRKELVTPARD

FGHFGLSHYSRATTPILGKMPAVFSGMLTGNCKMYPFIKGTAKLKTVRKL

VEAVNHAWGVEKIRYALGPGGMTGWYNRTMQQAPIVLTPAALTMFPDTIK

FGDLNYPVMIGDPMILG

The sequence of the genes and the proteins expressed in T3D$^{TD}$ strain are provided:

TD-L1 Gene Sequence (SEQ ID NO: 36)
GCTACACGTTCCACGACAATGTCATCCATGATACTGACTCAGTTTGG

ACCGTTCATTGAGAGCATTTCAGGTATCACTGATCAATCGAATGACGTGTTTGAAG

ATGCAGCAAAAGCATTCTCTATGTTTACTCGCAGCGATGTCTACAAGGCGCTGGAT

GAAATACCTTTCTCTGATGATGCGATGCTTCCAATCCCTCCAACTATATATACGAA

ACCATCTCACGATTCATATTATTACATTGATGCTCTAAACCGTGTGCGTCGCAAAA

CATATCAGGGCCCTGATGACGTGTACGTACCTAATTGTTCTATTGTTGAATTGCTGG

AGCCACATGAGACTCTGACATCTTATGGGCGGTTGTCCGAGGCCATCGAGAATCGT

GCCAAGGATGGGGACAGCCAAGCCAGAATCGCCACAACGTATGGTAGAATCGCTG

AATCTCAAGCTCGACAGATTAAGGCTCCATTGGAGAAGTTTGTGTTGGCACTATTA

GTGGCCGAAGCAGGGGGGTCTTTATATGATCCAGTTTTGCAGAAGTATGATGAGAT

TCCAGATCTATCGCATAATTGCCCTTTATGGTGTTTTAGAGAGATCTGTCGTCACAT

ATCTGGTCCATTACCAGATCGGGCACCTTATCTTTACTTATCTGCAGGGGTTTTCTG

GTTAATGTCACCACGAATGACGTCTGCAATCCCTCCGCTACTATCCGATCTTGTTAA

TTTAGCTATTTTGCAACAAACTGCGGGTTTAGATCCATCATTAGTGAAATTGGGAG

TACAGATATGCCTTCATGCAGCAGCTAGCTCAAGTTATGCATGGTTTATCTTAAAG

ACTAAGTCTATTTTTCCTCAAAACACGTTGCACAGTATGTATGAATCTCTAGAAGG

GGGATACTGTCCTAATCTTGAATGGTTAGAGCCTAGATCAGACTATAAGTTCATGT

ACATGGGAGTCATGCCATTGTCCGCTAAGTATGCTAGGTCGGCGCCGTCCAATGAT

AAGAAAGCGCGGGAACTTGGCGAGAAATATGGACTGAGCTCAGTCGTCGGTGAGC

TTCGTAAACGGACAAAGACGTATGTTAAACATGACTTTGCTTCAGTGAGGTACATT

-continued
```
CGTGACGCTATGGCATGTACTAGCGGTATTTTCTTGGTAAGAACACCCACCGAAAC

GGTATTGCAAGAATATACGCAGAGTCCGGAGATTAAGGTTCCCATTCCCCAGAAA

GACTGGACAGGCCCAATAGGTGAAATCAGAATTCTAAAGATACAACAAGTTCCA

TCGCGCGTTACTTATATAGAACATGGTACTTGGCAGCGGCGAGAATGGCGGCTCAA

CCACGTACGTGGGATCCATTGTTTCAAGCGATTATGAGATCTCAATACGTGACAGC

TAGGGGTGGATCTGGCGCAGCACTCCGCGAATCTTTGTATGCGATCAATGTGTCGT

TACCTGATTTCAAGGGCTTACCAGTGAAGGCAGCAACTAAGATATTCCAGGCGGCA

CAATTAGCGAACTTGCCGTTCTCCCACACATCAGTGGCTATACTAGCTGACACTTC

AATGGGATTGCGAAATCAGGTGCAGAGGCGGCCACGATCCATTATGCCATTAAAT

GTGCCCCAGCAGCAGGTTTCGGCGCCCCATACATTGACAGCGGATTACATTAACTA

CCACATGAATCTATCAACCACGTCTGGTAGTGCGGTCATTGAGAAGGTGATTCCTT

TAGGTGTATACGCTTCGAGCCCTCCTAACCAGTCGATCAACATTGACATATCTGCG

TGTGACGCTAGTATTACTTGGGATTTCTTTCTGTCAGTGATTATGGCGGCTATACAC

GAAGGTGTCGCTAGTAGCTCCATTGGAAAACCATTTATGGGGGTTCCTGCATCCAT

TGTAAATGATGAGTCTGTCGTTGGAGTGAGAGCTGCTAGGCCGATATCGGGAATGC

AGAACATGATTCAGCATCTATCGAAACTATATAAACGTGGATTTTCATATAGAGTA

AACGATTCTTTTTCTCCAGGTAACGATTTTACTCATATGACTACCACTTTCCCGTCA

GGTTCAACAGCCACCTCTACTGAGCATACTGCTAATAATAGTACGATGATGGAAAC

TTTCCTGACAGTATGGGGACCCGAACATACTGACGACCCTGACGTCTTACGTTTAA

TGAAGTCTTTAACTATTCAAAGGAATTACGTATGTCAAGGTGATGATGGATTAATG

ATTATCGATGGGACTACTGCTGGTAAGGTGAACAGTGAAACTATTCAGAAGATGCT

AGAATTAATCTCAAAATATGGTGAGGAATTCGGATGGAAATATGACATAGCGTAC

GATGGGACTGCCGAATACTTAAAGCTATACTTCATATTTGGCTGTCGAATTCCAAA

TCTTAGTCGCCATCCAATCGTGGGGAAAGAACGGGCGAATTCTTCAGCAGAGGAG

CCATGGCCAGCAATTCTAGATCAGATTATGGGTGTCTTCTTTAATGGTGTTCATGAT

GGGTTACAGTGGCAGCGGTGGATACGTTATTCATGGGCTCTATGCTGTGCTTTCTC

ACGTCAAAGAACAATGATTGGTGAGAGCGTGGGTTACCTTCAATATCCTATGTGGT

CTTTTGTCTACTGGGGATTACCACTGGTTAAAGCGTTTGGGTCAGACCCATGGATA

TTTTCTTGGTACATGCCTACTGGAGATCTGGGAATGTATAGTTGGATTAGCTTGATA

CGCCCTCTGATGACAAGATGGATGGTGGCTAATGGTTACGTAACTGACAGATGCTC

ACCCGTATTCGGGAACGCAGATTATCGCAGGTGTTTCAATGAACTTAAACTATATC

AAGGTTATTATATGGCACAATTGCCCAGGAATCCTAAGAAGTCTGGACGAGCGGC

CCCTCGGGAGGTAAGAGAACAATTCACTCAGGCATTATCCGACTATCTAATGCAAA

ATCCAGAACTGAAGTCACGTGTGCTACGTGGTCGTAGTGAGTGGGAGAAATATGG

AGCGGGATAATTCACAATCCTCCGTCATTATTCGATGTGCCCCATAAATGGTATC

AGGGTGCGCAAGAGGCAGCAATCGCTACGAGAGAAGAGCTGGCAGAAATGGATG

AGACATTAATGCGCGCTCGAAGGCACAGCTATTCGAACTTTTCAAAGTTATTAGAG

GCGTATCTGCTCGTGAAATGGCGAATGTGCGAGGCCCGCGAACCGTCGGTTGATTT

GCGATTACCATTATGTGCGGGTATTGACCCATTAAACTCAGATCCTTTTCTCAAGAT

GGTAAGCGTTGGACCAATGCTCCAGAGTACGAGAAAGTACTTTGCTCAGACACTAT

TCATGGCAAAGACGGTGTCGGGTCTTGACGTTAACGCGATTGATAGCGCGTTATTA
```

-continued

```
CGACTGCGAACATTAGGTGCTGATAAGAAAGCATTAACGGCGCAGTTATTAATGGT

GGGGCTTCAGGAGTCAGAAGCGGACGCATTGGCCGGGAAGATAATGCTACAGGAT

GTGAATACTGTGCAATTAGCCAGAGTGGTTAACTTAGCTGTGCCAGATACTTGGAT

GTCGTTAGACTTTGACTCTATGTTCAAACACCACGTCAAGCTGCTTCCCAAAGATG

GACGTCATCTAAATACTGATATTCCTCCTCGAATGGGATGGTTACGGGCCATTTTA

CGATTCTTAGGTGCCGGAATGGTAATGACTGCGACTGGAGTTGCTGTCGACATCTA

TCTGGAGGATATACATGGCGGTGGTCGGTCACTTGGACAGAGATTCATGACTTGGA

TGCGACAGGAAGGACGGTCAGCGTGAGTCTACCATGGGTCGTGGTGCGTCAACTC

ATC
```

TD-λ3 Protein Sequence (SEQ ID NO: 17)

```
MSSMILTQFGPFIESISGITDQSNDVFEDAAKAFSMFTRSDVYKALDEIPF

SDDAMLPIPPTIYTKPSHDSYYYIDALNRVRRKTYQGPDDVYVPNCSIVELLEPHETLTS

YGRLSEAIENRAKDGDSQARIATTYGRIAESQARQIKAPLEKFVLALLVAEAGGSLYDP

VLQKYDEIPDLSHNCPLWCFREICRHISGPLPDRAPYLYLSAGVFWLMSPRMTSAIPPLL

SDLVNLAILQQTAGLDPSLVKLGVQICLHAAASSSYAWFILKTKSIFPQNTLHSMYESL

EGGYCPNLEWLEPRSDYKFMYMGVMPLSAKYARSAPSNDKKARELGEKYGLSSVVG

ELRKRTKTYVKHDFASVRYIRDAMACTSGIFLVRTPTETVLQEYTQSPEIKVPIPQKDW

TGPIGEIRILKDTTSSIARYLRTWYLAAARMAAQPRTWDPLFQAIMRSQYVTARGGS

GAALRESLYAINVSLPDFKGLPVKAATKIFQAAQLANLPFSHTSVAILADTSMGLRNQV

QRRPRSIIVIPLNVPQQQVSAPHTLTADYINYHMNLSTTSGSAVIEKVIPLGVYASSPPNQ

SINIDISACDASITWDFFLSVIMAAIHEGVASSSIGKPFMGVPASIVNDESVVGVRAARPI

SGMQNMIQHLSKLYKRGFSYRVNDSFSPGNDFTHMTTTFPSGSTATSTEHTANNSTMM

ETFLTVWGPEHTDDPDVLRLMKSLTIQRNYVCQGDDGLMIIDGTTAGKVNSETIQKML

ELISKYGEEFGWKYDIAYDGTAEYLKLYFIFGCRIPNLSRHPIVGKERANSSAEEPWPAI

LDQIMGVFFNGVHDGLQWQRWIRYSWALCCAFSRQRTMIGESVGYLQYPMWSFVYW

GLPLVKAFGSDPWIFSWYMPTGDLGMYSWISLIRPLMTRWMVANGYVTDRCSPVFGN

ADYRRCFNELKLYQGYYMAQLPRNPKKSGRAAPREVREQFTQALSDYLMQNPELKSR

VLRGRSEWEKYGAGIIHNPPSLFDVPHKWYQGAQEAAIATREELAEMDETLMRARRH

SYSNFSKLLEAYLLVKWRMCEAREPSVDLRLPLCAGIDPLNSDPFLKMVSVGPMLQST

RKYFAQTLFMAKTVSGLDVNAIDSALLRLRTLGADKKALTAQLLMVGLQESEADALA

GKIMLQDVNTVQLARVVNLAVPDTWMSLDFDSMFKHHVKLLPKDGRHLNTDIPPRM

GWLRAILRFLGAGMVMTATGVAVDIYLEDIHGGGRSLGQRFMTWMRQEGRSA
```

TD-L2 Gene Sequence (SEQ ID NO: 37)

```
GCTAAAAGGCGCGATGGCGAACGTTTGGGGGGTGAGACTTGCAGAC

TCGTTATCTTCACCCACTATTGAGACACGAACGCGTCAGTATACCTTACACGATCTT

TGCTCAGACCTAGATGCTAATCCGGGGAGGGAACCGTGGAAACCTCTGCGTAATC

AGCGTACTAATAATATTGTGGCTGTGCAATTATTCAGACCATTGCAGGGTTTAGTTT

TAGATACCCAGCTTTATGGATTTCCAGGAGCATTTGATGACTGGGAGCGATTCATG

AGAGAGAAGCTGCGTGTGCTAAAGTATGAAGTATTGCGCATCTATCCAATCAGCA

ACTATAGCAATGAACATGTCAACGTCTTCGTGGCCAATGCTTTGGTGGGCGCTTTC
```

-continued

```
CTGTCGAATCAAGCTTTCTATGACCTGCTACCGTTGTTGATAATTAATGACACTATG

ATTGGTGATCTACTTGGCACGGGGGCATCGCTATCACAGTTCTTTCAATCTCATGG

AGATGTGCTGGAAGTCGCAGCTGGTCGTAAGTATCTGCAGATGGAAAACTACTCCA

ACGATGACGATGATCCTCCATTATTTGCGAAAGACCTGTCAGATTATGCTAAAGCA

TTCTACAGTGACACATATGAAGTGTTGGACAGGTTCTTTTGGACGCATGACTCTTC

AGCGGGGGTCTTAGTGCATTATGATAAGCCAACGAATGGTCATCACTATCTGCTGG

GTACTTTGACTCAGATGGTCAGTGCACCTCCTTATATTATTAACGCTACTGACGCAA

TGTTGCTTGAATCCTGTCTAGAACAGTTCTCAGCTAATGTGCGTGCGAGACCTGCG

CAACCCGTTACACGCTTAGACCAATGCTATCATTTAAGATGGGGAGCACAATATGT

AGGAGAAGATTCACTGACATATCGGTTGGGGGTGTTATCCTTGCTGGCTACCAATG

GATATCAATTAGCTAGACCGATTCCAAGACAGTTGACGAATCGATGGTTGTCGAGC

TTTGTGAGTCAAATTATGTCTGACGGCGTCAACGAGACTCCACTGTGGCCCCAAGA

AAGGTATGTGCAGATCGCTTATGATTCACCATCCGTTGTTGATGGGGCTACGCAAT

ATGGCTATGTCAGGAAGAATCAACTCAGACTCGGCATGAGAATATCGGCGCTGCA

ATCGCTGAGTGATACGCCCTCGCCGGTACAGTGGCTTCCACAATACACCATCGACC

AGGCAGCGATGGACGAAGGCGATCTGATGGTTAGTCGGCTTACGCAACTCCCGTTA

CGTCCTGATTATGGTAATATCTGGGTCGGCGATGCGCTATCCTATTATGTGGACTAC

AATCGGAGTCATCGAGTCGTGCTTTCATCGGAACTTCCTCAGCTTCCGGACACATA

TTTTGATGGCGATGAACAGTATGGGCGCAGCCTGTTCTCACTAGCTCGTAAGATTG

GTGACCGCTCGTTAGTGAAAGATACGGCTGTCTTGAAGCACGCTTACCAAGCCATC

GATCCAAATACTGGTAAGGGGTATCTGAGATCTGGGCAATCTGTCGCATATTTTGG

TGCATCAGCGGGTCATTCTGGTGCCGACCAGCCGTTAGTCATAGAGCCCTGGATTC

AAGGGAAAATCAGTGGTGTGCCGCCACCCTCCTCAGTGCGACAGTTCGGCTATGAT

GTTGCCCGTGGCGCGATCGTCGATCTGGCGAGACCATTTCCTTCTGGAGATTATCA

ATTTGTCTATTCGGATGTTGACCAGGTGGTCGATGGCCATGACGATCTGAGTATAT

CATCTGGACTGGTGGAGAGCCTTTTGTCTTCATGCATGCACGCCACAGCACCCGGG

GGCTCATTTGTTGTTAAGATAAATTTTCCGACTAGACCCGTATGGCACTACATCGA

ACAGAAGATCTTGCCCAATATTACGTCATACATGTTGATCAAGCCTTTCGTCACCA

ACAACGTCGAATTGTTCTTCGTCGCTTTCGGTGTGCATCAACACTCATCACTTACTT

GGACATCTGGAGTGTACTTCTTCTTGGTGGACCATTTTTATCGTTATGAGACTTTAT

CTACGATCTCACGACAATTGCCGTCTTTTGGGTATGTTGATGATGGGTCTTCCGTGA

CTGGTATCGAGACAATTAGTATTGAGAACCCTGGCTTCTCGAATATGACCCAGGCC

GCTCGCATTGGTATCTCAGGATTGTGTGCTAATGTAGGTAACGCGCGTAAGTCCAT

TGCCATTTACGAATCCCATGGGGCCAGAGTATTAACTATCACATCAAGGAGATCTC

CGGCATCAGCTAGAAGAAAGTCTAGGTTGCGATATTTGCCATTAATAGACCCTAGG

TCGTTAGAGGTACAGGCGCGCACTATTCTGCCAGCTGATCCAGTGTTATTTGAAAA

CGTGAGCGGAGCGTCACCCCATGTTTGTCTGACAATGATGTACAACTTCGAAGTGT

CGTCAGCGGTATATGATGGAGACGTTGTGCTAGATCTTGGGACGGGACCAGAGGC

TAAAATCCTTGAACTGATACCCGCAACCTCTCCAGTCACATGCGTGGACATACGGC

CTACAGCGCAGCCTAGTGGATGTTGGAACGTTCGTACCACGTTCCTTGAGTTAGAT

TATTTGAGCGATGGATGGATCACTGGGGTGCGTGGGGACATAGTTACTTGTATGTT
```

-continued

ATCTTTGGGGGCCGCTGCCGCTGGAAAATCAATGACTTTTGACGCTGCGTTTCAGC

AATTAATCAAAGTATTATCCAAGAGTACGGCTAATGTTGTGCTGGTGCAGGTTAAC

TGCCCTACAGACGTGGTGAGGAGCATTAAGGGCTACCTAGAGATAGATTCGACTA

ACAAGAGGTATAGGTTCCCCAAATTTGGTCGAGACGAGCCGTACTCTGACATGGAT

GCGCTGGAGAAAATATGTCGTACCGCCTGGCCAAACTGCTCAATTACCTGGGTTCC

ATTGTCATACGACTTGCGGTGGACTAGACTGGCATTATTAGAGTCCACGACATTGA

GTAGCGCGTCGATTAGAATTGCTGAGCTGATGTATAAATACATGCCTATTATGAGG

ATTGACATTCATGGACTACCCATGGAAAAGCGAGGTAACTTCATAGTGGGGCAGA

ACTGCTCATTAGTAATCCCTGGTTTTAATGCGCAGGATGTCTTTAACTGTTATTTCA

ATTCCGCCCTCGCTTTCTCGACTGAAGATGTCAATGCTGCGATGATTCCCCAAGTGT

CTGCGCAGTTTGATGCGACTAAGGGTGAGTGGACGTTGGATATGGTCTTCTCCGAC

GCAGGAATCTATACCATGCAGGCTCTAGTGGGATCTAATGCTAATCCAGTCTCTTT

GGGTTCCTTTGTAGTTGATTCTCCAGATGTAGATATAACTGACGCTTGGCCAGCTCA

GTTAGACTTTACGATCGCGGGAACTGATGTCGATATAACAGTTAATCCTTATTACC

GTCTGATGACCTTTGTAAGGATCGATGGACAGTGGCAGATTGCCAATCCAGACAAA

TTTCAATTCTTTTCGTCGGCGTCTGGGACGTTAGTGATGAACGTCAAATTAGATATC

GCAGATAAATATCTACTATACTATATACGAGATGTCCAGTCTCGAGATGTTGGCTT

TTACATTCAGCATCCACTTCAACTTTTGAATACGATCACATTGCCAACCAACGAGG

ACCTTTTTCTGAGCGCACCTGACATGCGAGAGTGGGCAGTTAAGGAAAGCGGTAA

CACGATATGTATACTCAATAGTCAAGGGTTTGTGCTACCTCAAGATTGGGATGTGT

TAACAGATACCATAAGTTGGTCCCCATCGATACCCACATACATTGTGCCACCGGGT

GATTATACCTTGACTCCTCTGTAACTCACTGTCCCTCGTGAGCGCGCCTAATTCATC.

TD-λ2 Protein Sequence (SEQ ID NO: 18)

MANVWGVRLADSLSSPTIETRTRQYTLHDLCSDLDANPGREPWKPLRN

QRTNNIVAVQLFRPLQGLVLDTQLYGFPGAFDDWERFMREKLRVLKYEVLRIYPISNY

SNEHVNVFVANALVGAFLSNQAFYDLLPLLIINDTMIGDLLGTGASLSQFFQSHGDVLE

VAAGRKYLQMENYSNDDDDPPLFAKDLSDYAKAFYSDTYEVLDRFFWTHDSSAGVL

VHYDKPTNGHHYLLGTLTQMVSAPPYIINATDAMLLESCLEQFSANVRARPAQPVTRL

DQCYHLRWGAQYVGEDSLTYRLGVLSLLATNGYQLARPIPRQLTNRWLSSFVSQIMS

DGVNETPLWPQERYVQIAYDSPSVVDGATQYGYVRKNQLRLGMRISALQSLSDTPSPV

QWLPQYTIDQAAMDEGDLMVSRLTQLPLRPDYGNIWVGDALSYYVDYNRSHRVVLS

SELPQLPDTYFDGDEQYGRSLFSLARKIGDRSLVKDTAVLKHAYQAIDPNTGKGYLRS

GQSVAYFGASAGHSGADQPLVIEPWIQKISGVPPPSSVRQFGYDVARGAIVDLARPFP

SGDYQFVYSDVDQVVDGHDDLSISSGLVESLLSSCMHATAPGGSFVVKINFPTRPVWH

YIEQKILPNITSYMLIKPFVTNNVELFFVAFGVHQHSSLTWTSGVYFFLVDHFYRYETLS

TISRQLPSFGYVDDGSSVTGIETISIENPGFSNMTQAARIGISGLCANVGNARKSIAIYES

HGARVLTITSRRSPASARRKSRLRYLPLIDPRSLEVQARTILPADPVLFENVSGASPHVC

LTMMYNFEVSSAVYDGDVVLDLGTGPEAKILELIPATSPVTCVDIRPTAQPSGCWNVR

TTFLELDYLSDGWITGVRGDIVTCMLSLGAAAAGKSMTFDAAFQQLIKVLSKSTANVV

LVQVNCPTDVVRSIKGYLEIDSTNKRYRFPKFGRDEPYSDMDALEKICRTAWPNCSIT

-continued

WVPLSYDLRWTRLALLESTTLSSASIRIAELMYKYMPEVIRIDIHGLPMEKRGNFIVGQN

CSLVIPGFNAQDVFNCYFNSALAFSTEDVNAAMIPQVSAQFDATKGEWTLDMVFSDA

GIYTMQALVGSNANPVSLGSFVVDSPDVDITDAWPAQLDFTIAGTDVDITVNPYYRLM

TFVRIDGQWQIANPDKFQFFSSASGTLVMNVKLDIADKYLLYYIRDVQSRDVGFYIQHP

LQLLNTITLPTNEDLFLSAPDMREWAVKESGNTICILNSQGFVLPQDWDVLTDTISWSP

SIPTYIVPPGDYTLTPL

TD-L3 Gene Sequence (SEQ ID NO: 38)

GCTAATCGTCAGGATGAAGCGGATTCCAAGGAAGACAAAGGGCAAA

TCCAGCGGAAAGGGCAATGACTCAACAGAGAGAGCGGACGATGGCTCGAGCCAAT

TAAGAGACAAGCAAAACAATAAGGCTGGCCCCGCCACTACGGAGCCTGGCACATC

CAACCGAGAGCAATACAAAGCTCGACCAGGTATTGCATCTGTGCAGAGGGCCACT

GAAAGTGCAGAAATGCCCATGAAGAATAATGACGAAGGGACGCCAGATAAGAAA

GGAAATACTAAGGGCGACCTAGTTAATGAGCATAGTGAGGCTAAAGACGAGGCGG

ATGAAGCGACGAAGAAGCAGGCAAAGGATACAGACAAAAGTAAAGCGCAAGTCA

CATATTCAGACACTGGTATCAATAATGCTAATGAACTGTCAAGATCTGGGAATGTG

GATAATGAGGGTGGAAGTAATCAGAAGCCGATGTCTACCAGAATAGCTGAGGCAA

CGTCTGCTATAGTGTCGAAACATCCTGCGCGTGTTGGGCTGCCACCTACCGCTAGC

AGTGGTCATGGGTATCAGTGCCATGTCTGTTCTGCAGTCCTGTTTAGTCCTTTAGAC

CTAGATGCCCACGTCGCCTCACATGGTTTGCATGGTAACATGACATTAACATCGAG

TGATATCCAGCGACATATAACTGAGTTCATCAGCTCATGGCAAAATCATCCTATTG

TTCAAGTTTCGGCTGATGTCGAAAATAAGAAAACTGCTCAATTGCTTCACGCTGAC

ACTCCTCGACTCGTCACTTGGGATGCTGGTTTGTGTACTTCATTCAAAATCGTCCCG

ATTGTGCCAGCTCAGGTGCCGCAGGATGTACTGGCCTATACGTTTTTCACCTCTTCA

TACGCTATCCAATCACCGTTTCCAGAGGCGGCAGTGTCTAGGATTGTGGTGCATAC

GAGATGGGCATCTAATGTTGACTTTGACCGAGACTCGTCTGTCATCATGGCGCCAC

CTACAGAAAACAATATCCATTTGTTTAAACAGTTACTAAATACTGAAACCCTGTCT

GTAAGGGGGGCTAATCCGCTAATGTTCAGGGCGAATGTGTTGCATATGTTGCTAGA

GTTCGTATTAGATAACTTGTATCTGAACAGACATACGGGATTCTCTCAAGACCACA

CGCCATTTACTGAGGGTGCTAATTTGCGTTCACTTCCTGGCCCCGATGCTGAGAAA

TGGTACTCGATTATGTATCCAACGCGCATGGGAACGCCGAATGTATCCAAAATATG

TAATTTCGTCGCCTCTTGTGTGCGAAATCGGGTTGGACGGTTTGATCGAGCACAGA

TGATGAACGGAGCTATGTCAGAGTGGGTGGATGTCTTCGAGACTTCAGACGCGCTA

ACCGTCTCCATTCGAGGTCGATGGATGGCTAGACTAGCTCGCATGAACATAAATCC

AACAGAGATCGAATGGGCATTGACTGAATGTGCACAAGGATATGTGACTGTCACA

AGTCCTTACGCTCCTATCGTAAATAGATTGATGCCCTATCGTATCTCCAACGCTGAG

CGGCAAATATCACAGATAATCAGGATCATGAACATTGGCAATAACGCGACGGTGA

TACAACCTGTTCTGCAAGATATTTCGGTACTCCTTCAACGCATATCACCACTCCAAA

TAGATCCAACTATTATTTCCAACACTATGTCAACAGTCTCGGAGTCTACTACTCAG

ACCCTCAGCCCCGCGTCCTCAATTTTGGGTAAACTACGACCAAGCAACTCAGATTT

TTCTAGTTTTAGAGTCGCGTTGGCTGGATGGCTTTATAATGGGGTTGTGACGACGG

TGATTGATGATAGTTCATATCCAAAAGACGGCGGCAGCGTGACCTCACTTGAAAAT

-continued

```
CTGTGGGATTTCTTCATCCTTGCGCTTGCTCTACCACTGACAACTGACCCCTGTGCA
CCTGTGAAAGCATTCATGACCCTAGCCAACATGATGGTTGGTTTCGAGACAATCCC
TATGGATAATCAGATCTATACTCAATCGAGACGCGCGAGTGCTTTCTCAACGCCTC
ACACGTGGCCACGATGCTTTATGAACATCCAGTTAATTTCTCCAATCGACGCTCCC
ATCTTGCGACAGTGGGCTGAAATTATTCATAGATACTGGCCTAACCCTTCACAGAT
TCGTTATGGTGCACCGAACGTTTTCGGCTCGGCAAATTTGTTCACTCCACCTGAGGT
GCTGTTATTGCCAATCGATCATCAACCAGCTAATGTAACAACGCCAACGCTGGACT
TCACCAATGAGTTAACTAATTGGCGCGCTCGTGTCTGTGAGCTTATGAAGAATCTC
GTTGATAATCAAAGATATCAACCTGGATGGACACAAAGTCTAGTCTCGTCAATGCG
CGGAACGCTAGACAAATTGAAGTTGATTAAATCGATGACACCAATGTATCTGCAAC
AGCTGGCTCCGGTAGAGTTAGCAGTGATAGCTCCCATGTTGCCTTTTCCACCTTTCC
AGGTGCCATACGTCCGTCTCGATCGTGACAGAGTTCCAACAATGGTTGGAGTAACA
CGACAGTCACGAGATACTATTACTCAGCCGGCGCTATCGCTGTCGACAACCAATAC
TACTGTTGGCGTGCCACTAGCTCTAGACGCGAGGGCTATCACCGTTGCGCTGTTGT
CAGGGAAATATCCGCCGGATTTGGTGACAAATGTATGGTACGCTGATGCCATTTAC
CCAATGTATGCAGACACGGAGGTGTTCTCTAATCTTCAGAGAGACATGATTACCTG
CGAGGCCGTGCAGACATTAGTGACTCTGGTGGCGCAAATATCAGAGACCCAGTAT
CCTGTAGATAGGTATCTTGATTGGATCCCATCACTGAGAGCATCGGCGGCGACGGC
GGCGACATTTGCTGAGTGGGTTAATACTTCAATGAAGACGGCGTTTGATTTGTCTG
ATATGCTGTTAGAGCCTCTCCTAAGCGGTGATCCGAGGATGACTCAACTAGCGATT
CAGTATCAGCAGTACAATGGCAGAACGTTTAATATCATACCTGAAATGCCAGGTTC
AGTAATTGCTGACTGCGTTCAATTAACAGCAGAAGTCTTTAATCACGAATATAACC
TGTTTGGGATTGCGCGGGGTGATATCATCATTGGCCGTGTTCAGTCGACACATTTGT
GGTCACCGCTGGCTCCTCCACCTGACCTGGTGTTTGATCGTGATACCCCTGGTGTTC
ACATCTTCGGACGAGATTGCCGTATATCGTTTGGAATGAATGGCGCCGCGCCAATG
ATTAGAGATGAGACTGGACTGATGGTGCCTTTTGAAGGAAATTGGATTTTCCCACT
GGCGCTTTGGCAAATGAATACACGATATTTTAATCAACAGTTCGACGCGTGGATTA
AGACAGGAGAGTTGCGAATCCGCATTGAGATGGGCGCGTATCCATATATGTTGCAT
TACTATGATCCACGTCAGTACGCTAATGCATGGAATTTAACATCCGCCTGGCTTGA
AGAAATTACGCCGACGAGCATCCCATCCGTGCCTTTCATGGTGCCCATTTCAAGTG
ATCATGACATTTCCTCTGCCCCAGCTGTCCAATATATCATTTCAACTGAATATAATG
ATCGGTCTCTGTTCTGCACTAACTCATCATCTCCCCAAACCATCGCTGGACCAGAC
AAACACATTCCAGTTGAGAGATATAACATTCTGACCAACCCCGACGCTCCACCCAC
GCAGATACAACTGCCTGAAGTCGTTGACTTGTACAACGTCGTCACACGCTATGCGT
ATGAGACTCCGCCTATTACCGCTGTTGTTATGGGTGTTCCTTGATCCTCATCCTCCC
AACAGGTGCTAGAGCATTGCGCTCAATGCTAGTTGGGCCGATTCATC.
```

TD-λ1 Protein Sequence (SEQ ID NO: 19)

MKRIPRKTKGKSSGKGNDSTERADDGSSQLRDKQNNKAGPATTEPGTS

NREQYKARPGIASVQRATESAEMPMKNNDEGTPDKKGNTKGDLVNEHSEAKDEADE

ATKKQAKDTDKSKAQVTYSDTGINNANELSRSGNVDNEGGSNQKPMSTRIAEATSAIV

-continued

SKHPARVGLPPTASSGHGYQCHVCSAVLFSPLDLDAHVASHGLHGNMTLTSSDIQRHI

TEFISSWQNHPIVQVSADVENKKTAQLLHADTPRLVTWDAGLCTSFKIVPIVPAQVPQD

VLAYTFFTSSYAIQSPFPEAAVSRIVVHTRWASNVDFDRDSSVIMAPPTENNIHLFKQLL

NTETLSVRGANPLMFRANVLHMLLEFVLDNLYLNRHTGFSQDHTPFTEGANLRSLPGP

DAEKWYSIMYPTRMGTPNVSKICNFVASCVRNRVGRFDRAQMMNGAMSEWVDVFET

SDALTVSIRGRWMARLARMNINPTEIEWALTECAQGYVTVTSPYAPIVNRLMPYRISN

AERQISQIIRIMNIGNNATVIQPVLQDISVLLQRISPLQIDPTIISNTMSTVSESTTQTLSPAS

SILGKLRPSNSDFSSFRVALAGWLYNGVVTTVIDDSSYPKDGGSVTSLENLWDFFILAL

ALPLTTDPCAPVKAFMTLANMMVGFETIPMDNQIYTQSRRASAFSTPHTWPRCFMNIQ

LISPIDAPILRQWAEIIHRYWPNPSQIRYGAPNVFGSANLFTPPEVLLLPIDHQPANVTTP

TLDFTNELTNWRARVCELMKNLVDNQRYQPGWTQSLVSSMRGTLDKLKLIKSMTPM

YLQQLAPVELAVIAPMLPFPPFQVPYVRLDRDRVPTMVGVTRQSRDTITQPALSLSTTN

TTVGVPLALDARAITVALLSGKYPPDLVTNVWYADAIYPMYADTEVFSNLQRDMITCE

AVQTLVTLVAQISETQYPVDRYLDWIPSLRASAATAATFAEWVNTSMKTAFDLSDML

LEPLLSGDPRMTQLAIQYQQYNGRTFNIIPEMPGSVIADCVQLTAEVFNHEYNLFGIAR

GDIIIGRVQSTHLWSPLAPPPDLVFDRDTPGVHIFGRDCRISFGMNGAAPMIRDETGLM

VPFEGNWIFPLALWQMNTRYFNQQFDAWIKTGELRIRIEMGAYPYMLHYYDPRQYAN

AWNLTSAWLEEITPTSIPSVPFMVPISSDHDISSAPAVQYIISTEYNDRSLFCTNSSSPQTI

AGPDKHIPVERYNILTNPDAPPTQIQLPEVVDLYNVVTRYAYETPPITAVVMGVP

TD-M1 Gene Sequence (SEQ ID NO: 33)
GCTATTCGCGGTCATGGCTTACATCGCAGTTCCTGCGGTGGTGGATTC

ACGTTCGAGTGAGGCTATTGGACTGCTAGAATCGTTTGGAGTAGACGCTGGGGCTG

ACGCGAATGACGTTTCATATCAAGATCATGACTATGTGTTGGATCAGTTACAGTAC

ATGTTAGATGGATATGAGGCTGGTGACGTTATCGATGCACTCGTCCACAAGAATTG

GTTACATCACTCTGTCTATTGCTTGTTGCCACCCAAAAGTCAACTATTAGAGTATTG

GAAAAGTAATCCTTCAGCGATACCGGACAACGTTGATCGTCGGCTTCGTAAACGAC

TAATGCTAAAGAAAGATCTCAGGAAAGATGATGAATACAATCAGCTAGCGCGTGC

TTTCAAGATATCGGATGTCTACGCACCTCTCATCTCATCCACGACGTCACCGATGA

CAATGATACAGAACTTGAATCAAGGCGAGATCGTGTACACCACGACGGACAGGGT

AATAGGGGCTAGAATCTTGTTATATGCTCCTAGAAAGTACTATGCGTCAACTCTGT

CATTTACTATGACTAAGTGCATCATTCCGTTTGGTAAAGAGGTGGGTCGTGTTCCTC

ACTCTCGATTTAATGTTGGCACATTTTCGTCAATTGCTACCCCGAAATGTTTTGTCA

TGAGTGGGGTTGATATTGAGTCCATCCCAAATGAATTTATCAAGTTGTTTTACCAG

CGCGTCAAGAGTGTTCACGCTAACATACTAAATGACATATCTCCTCAGATCGTCTC

TGACATGATAAACAGAAAGCGTCTGCGCGTTCATACTCCATCAGATCGTCGAGCCG

CGCAGTTGATGCATTTGCCTTACCATGTTAAACGAGGAGCGTCTCACGTCGACGTT

TACAAGGTGGATGTTGTAGACATGTTGTTCGAGGTAGTGGATGTGGCCGATGGGTT

GCGCAACGTATCTAGGAAACTAACTATGCATACCGTTCCGGTATGTATTCTTGAAA

TGTTGGGTATTGAGATTGCGGACTATTGCATTCGTCGAGAGGATGGAATGCTCACA

GATTGGTTCCTACTTTTAACCATGCTATCTGATGGCTTGACTGATAGAAGGACGCA

TTGTCAATACTTGATTAATCCGTCAAGTGTGCCTCCTGATGTGATACTTAACATCTC

-continued

```
AATTACTGGATTTATAAATAGACATACAATCGATGTCATGCCTGACATATATGACT

TTGTTAAACCCATTGGCGCTGTGCTGCCTAAGGGATCATTTAAATCAACAATTATG

AGAGTTCTTGATTCAATATCAATATTAGGAATCCAAATCATGCCGCGCGCGCATGT

AGTTGACTCAGATGAGGTGGGCGAGCAAATGGAGCCTACGTTTGAGCAGGCGGTT

ATGGAGATATACAAAGGGATTGCTGGCGTTGACTCGCTGGATGATCTCATCAAGTG

GGTGCTGAACTCGGATCTCATTCCGCATGATGACAGGCTTGGTCAATTATTTCAAG

CGTTTTTGCCTCTCGCAAAGGACTTATTAGCTCCAATGGCCAGAAAGTTTTATGATA

ACTCAATGAGTGAGGGTAGATTGCTAACATTCGCTCATGCCGACAGTGAGTTGCTG

AACGCAAATTATTTTGGTCATTTATTGCGACTAAAAATACCATATATTACAGAGGT

TAATCTGATGATTCGCAAGAATCGTGAGGGTGGAGAGCTATTTCAGCTTGTGTTAT

CTTATCTATATAAAATGTATGCTACTAGCGCGCAGCCTAAATGGTTTGGATCATTAT

TGCGATTGTTAATATGTCCCTGGTTACATATGGAGAAATTAATAGGAGAAGCAGAC

CCGGCATCTACGTCGGCTGAAATTGGGTGGCATATCCCTCGTGAACAGCTGATGCA

AGATGGATGGTGTGGATGTGAAGACGGATTCATTCCCTATGTTAGCATACGTGCGC

CAAGACTGGTTATAGAGGAGTTGATGGAGAAGAACTGGGGCCAATATCATGCCCA

AGTTATTGTCACTGATCAGCTTGTCGTAGGCGAACCGCGGAGGGTATCTGCTAAGG

CTGTGATCAAGGGTAACCACTTACCAGTTAAGTTAGTTTCACGATTTGCATGTTTCA

CATTGACGGCGAAGTATGAGATGAGGCTTTCGTGCGGCCATAGCACTGGACGTGG

AGCTGCATACAGTGCGAGACTAGCTTTCCGATCTGACTTGGCGTGATCCGTGACAT

GCGTAGTGTGACACCTGCTCCAGGTCAATGGGGGTAGGGGGCGGGCTAAGACTA

CGTACGCGCTTCATC
```

TD-µ2 Protein Sequence (SEQ ID NO: 14)

```
MAYIAVPAVVDSRSSEAIGLLESFGVDAGADANDVSYQDHDYVLDQLQ

YMLDGYEAGDVIDALVHKNWLHHSVYCLLPPKSQLLEYWKSNPSAIPDNVDRRLRKR

LMLKKDLRKDDEYNQLARAFKISDVYAPLISSTTSPMTMIQNLNQGEIVYTTTDRVIGA

RILLYAPRKYYASTLSFTMTKCIIPFGKEVGRVPHSRFNVGTFSSIATPKCFVMSGVDIES

IPNEFIKLFYQRVKSVHANILNDISPQIVSDMINRKRLRVHTPSDRRAAQLMHLPYHVK

RGASHVDVYKVDVVDMLFEVVDVADGLRNVSRKLTMHTVPVCILEMLGIEIADYCIR

REDGMLTDWFLLLTMLSDGLTDRRTHCQYLINPSSVPPDVILNISITGFINRHTIDVMPD

IYDFVKPIGAVLPKGSFKSTIMRVLDSISILGIQIMPRAHVVDSDEVGEQMEPTFEQAVM

EIYKGIAGVDSLDDLIKWVLNSDLIPHDDRLGQLFQAFLPLAKDLLAPMARKFYDNSM

SEGRLLTFAHADSELLNANYFGHLLRLKIPYITEVNLMIRKNREGGELFQLVLSYLYKM

YATSAQPKWFGSLLRLLICPWLHMEKLIGEADPASTSAEIGWHIPREQLMQDGWCGCE

DGFIPYVSIRAPRLVIEELMEKNWGQYHAQVIVTDQLVVGEPRRVSAKAVIKGNHLPV

KLVSRFACFTLTAKYEMRLSCGHSTGRGAAYSARLAFRSDLA
```

TD-M2 Protein Sequence (SEQ ID NO: 34)

```
GCTAATCTGCTGACCGTTACTCTGCAAAGATGGGAACGCTTCCTCT

ATCGTTCAGACGATCAACGTCACTGGAGATGGCAATGTATTTAAACCATCAGCTGA

AACTTCATCTACCGCTGTACCATCGTTAAGCTTATCACCTGGAATGCTGAATCCCG

GAGGGGTACCATGGATTGCTGTTGGAGATGAGACATCTGTGACTTCACCAGGCGCA
```

```
TTACGTCGAATGACGTCAAAGGACATCCCGGAAACGGCAATAATCAACACAGACA
ATTCATCAGGCGCCGTGCCAAGCGAATCAGCCTTGGTGCCCTACATCGATGAGCCG
CTGGTAGTGGTTACAGAGCATGCTATTACCAACTTCACCAAAGCTGAGATGGCACT
TGAATTCAATCGTGAGTTCCTTGACAAGATGCGTGTGCTGTCAGTGTCACCAAAAT
ATTCGGATCTTCTGACCTATGTTGACTGCTACGTCGGTGTGTCTGCTCGTCAGGCTT
TAAACAATTTTCAGAAACAAGTGCCTGTGATTACACCTACTAGGCAGACGATGTAT
GTCGACTCGATACAAGCGGCCTTGAAAGCTTTAGAAAAGTGGGAGATTGATCTGA
GAGTGGCTCAAACGTTGCTGCCTACGAACGTTCCGATTGGAGAAGTCTCTTGTCCA
ATGCAGTCGGTAGTGAAACTGCTGGATGATCAGCTGCCAGATGACAGCCTGATAC
GGAGGTATCCCAAGGAAGCCGCCGTCGCTTTGGCTAAACGAAACGGGGGAATACA
ATGGATGGACGTATCAGAAGGCACCGTGATGAACGAGGCTGTCAACGCTGTTGCA
GCTAGTGCACTGGCACCTTCAGCATCAGCCCCACCCTTAGAAGAGAAGTCAAAGTT
AACCGAACAAGCGATGGATCTCGTGACCGCGGCTGAGCCTGAGATAATTGCCTCA
CTCGCGCCAGTTCCCGCACCCGTGTTTGCCATACCACCTAAACCAGCAGATTATAA
TGTGCGTACTCTGAGGATCGACGAGGCCACTTGGCTGCGAATGATTCCAAAATCAA
TGAACACACCTTTTCAAATCCAGGTGACTGATAACACAGGAACTAATTGGCATCTC
AATTTGAGGGGGGGGACTCGTGTAGTGAATCTGGACCAAATCGCTCCGATGCGGTT
TGTATTAGATTTAGGGGGAAAGAGTTATAAAGAGACGAGCTGGGATCCAAACGGC
AAGAAGGTCGGATTCATCGTTTTTCAATGAAGATACCATTCGAACTTTGGACTGC
TGCTTCACAGATCGGTCAAGCCACGGTGGTTAACTATGTCCAACTATACGCTGAAG
ACAGCTCATTTACCGCGCAGTCTATCATTGCTACTACCTCTTTGGCTTATAACTATG
AGCCTGAGCAGTTGAATAAGACTGACCCTGAGATGAATTATTATCTTTTGGCGACC
TTTATAGACTCAGCCGCTATAACGCCAACGAATATGACACAGCCTGATGTTTGGGA
TGCCTTGCTGACGATGTCCCCACTATCAGCTGGCGAGGTGACAGTGAAGGGTGCGG
TAGTGAGTGAAGTAGTCCCTGCAGACTTGATAGGTAGCTACACTCCAGAATCCCTA
AACGCCTCACTTCCGAATGATGCTGCTAGATGCATGATCGATAGAGCTTCGAAGAT
AGCCGAAGCAATCAAGATTGATGATGATGCTGGACCAGATGAATATTCCCCAAAC
TCTGTACCAATTCAAGGTCAGCTTGCTATCTCGCAACTCGAAACTGGATATGGTGT
GCGAATATTCAACCCTAAAGGGATCCTTTCTAAAATTGCATCTAGGGCAATGCAGG
CTTTCATTGGTGACCCGAGCACAATCATCACGCAGGCGGCGCCAGTGTTATCAGAC
AAGAATAATTGGATTGCATTGGCACAGGGAGTGAAAACTAGTCTGCGTACTAAAA
GTCTATCAGCGGGAGTGAAGACTGCAGTGAGTAAGCTGAGCTCATCTGAGTCTATC
CAGAATTGGACTCAAGGATTCTTGGATAAAGTGTCAGCGCATTTTCCAGCACCAAA
GCCCGATTGTCCGACTAGCGGAGATAGTGGTGAATCGTCTAATCGCCGAGTGAAGC
GCGACTCATACGCAGGAGTGGTCAAACGTGGGTACACACGTTAGGCCGCTCGCCCT
GGTGACGCGGGGTTAAGGGATGCAGGCAAATCATC
```

TD-μ1 Protein Sequence (SEQ ID NO: 15)

MGNASSIVQTINVTGDGNVFKPSAETSSTAVPSLSLSPGMLNPGGVPWIA

VGDETSVTSPGALRRMTSKDIPETAIINTDNSSGAVPSESALVPYIDEPLVVVTEHAITNF

TKAEMALEFNREFLDKMRVLSVSPKYSDLLTYVDCYVGVSARQALNNFQKQVPVITP

TRQTMYVDSIQAALKALEKWEIDLRVAQTLLPTNVPIGEVSCPMQSVVKLLDDQLPDD

-continued

SLIRRYPKEAAVALAKRNGGIQWMDVSEGTVMNEAVNAVAASALAPSASAPPLEEKS

KLTEQAMDLVTAAEPEIIASLAPVPAPVFAIPPKPADYNVRTLRIDEATWLRMIPKSMN

TPFQIQVTDNTGTNWHLNLRGGTRVVNLDQIAPMRFVLDLGGKSYKETSWDPNGKKV

GFIVFQSKIPFELWTAASQIGQATVVNYVQLYAEDSSFTAQSIIATTSLAYNYEPEQLNK

TDPEMNYYLLATFIDSAAITPTNMTQPDVWDALLTMSPLSAGEVTVKGAVVSEVVPA

DLIGSYTPESLNASLPNDAARCMIDRASKIAEAIKIDDDAGPDEYSPNSVPIQGQLAISQL

ETGYGVRIFNPKGILSKIASRAMQAFIGDPSTIITQAAPVLSDKNNWIALAQGVKTSLRT

KSLSAGVKTAVSKLSSSESIQNWTQGFLDKVSAHFPAPKPDCPTSGDSGESSNRRVKRD

SYAGVVKRGYTR

TD-M3 Gene Sequence (SEQ ID NO: 35)

GCTAAAGTGACCGTGGTCATGGCTTCATTCAAGGGATTCTCCGCCAA

CACTGTTCCAGTTTCTAAGGCCAAGCGTGACATATCATCTCTTGCCGCTACTCCTGG

ACTTCGTTCACAATCCTTCACTCCGTCTGTGGATATGTCTCAATCGCGTGAATTCCT

CACAAAGGCAATTGAGCAAGGGTCCATGTCTATACCTTATCAGCATGTGAATGTAC

CGAAAGTTGATCGTAAAGTTGTTAGCCTGGTAGTGCGACCTTTCTCTTCAGGTGCTT

TCTCTATCTCTGGAGTGATTTCGCCAGCCCATGCCTATCTACTAGAGTGTCTACCCC

AGCTTGAGCAGGCGATGGCTTTTGTTGCTTCACCTGAGTCTTTCCAGGCTTCCGACG

TCGCGAAGCGCTTTGCCATAAAGCCAGGTATGAGCCTCCAGGATGCCATCACTGCC

TTTATTAACTTTGTGTCCGCGATGCTGAAAATGACGGTGACTCGTCAAAACTTTGA

CGTTATTGTGGCTGAGATCGAGAGGCTTGCTTCAACCAGCGTGTCCGTCAGGACTA

AAGAAGCGAAGGTTGCTGATGAGGAGCTAATGCTATTCGGGTTAGATCATAGAGG

GCCACAGCAGCTGGATGTTTCTGACGCTAAAGGGATAATGAAGGCTGCTGATATTC

AGACAACTCATGATGTCCATTTGGCACCAGGCGTTGGTAATATTGATCCTGAAATC

TATAACGAGGGGCGGTTCATGTTCATGCAGCACAAGCCACTTGCGGCGGATCAATC

GTATTTCACCTTGGAGACTGCGGATTATTTCAAGATTTATCCAACATACGATGAAC

ATGATGGCAGGATGGCTGACCAAAAGCAGTCGGGATTGATACTGTGTACTAAGGA

CGAGGTATTGGCTGAGCAAACTATATTTAAACTGGACGCCCCTGATGACAAGACTG

TTCATCTGTTGGATCGCGATGACGACCACGTTGTTGCCAGATTTACTAAGGTATTTA

TAGAGGACGTGGCTCCCGGGCATCATGCTGCTCAAAGATCGGGACAACGCTCTGTG

CTTGATGACCTATATGCGAATACGCAAGTGATTTCCATTACTTCTGCTGCTTTAAAG

TGGGTGGTCAAGCACGGCGTATCTGATGGAATCGTGAACAGGAAGAATGTCAAAG

TGTGTGTTGGTTTTGACCCCCTGTACACCTTGTCTACACATAACGGGGTGTCCTTAT

GTGCCCTGCTGATGGACGAAAAACTCTCTGTGCTGAACAGTGCGTGTCGTATGACG

TTACGCTCACTCATGAAGACCGGACGCGACGTTGATGCACACAGAGCTTTTCAGCG

AGTCCTCTCTCAAGGATACACATCGCTAATGTGCTACTATCATCCTTCACGGAAGTT

GGCATATGGTGAGGTGCTCTTTCTAGAACGATCCAATGACGTGACAGATGGGATCA

AGCTTCAGTTGGACGCATCTAGACAGTGTCATGAATGTCCTGTGTTGCAGCAGAAA

GTGGTTGAGTTAGAGAAACAGATTATTATGCAGAAGTCAATCCAGTCAGACCCTAC

CCCAGTGGCGCTGCAACCATTGTTGTCTCAGTTGCGTGAGTTGTCTAGTGAAGTTA

CTAGGCTACAGATGGAGTTGAGTCGAGCTCAGTCCCTGAATGCTCAGTTGGAGGCG

-continued

```
GATGTCAAGTCAGCTCAATCATGTAGCTTGGATATGTATCTGAGACACCACACTTG

CATTAATGGTCATGCTAAAGAAGATGAATTGCTTGACGCTGTGCGTGTCGCGCCGG

ATGTGAGGAGAGAAATCATGGAAAAGAGGAGTGAAGTGAGACAAGGTTGGTGCG

AACGTATTTCTAAGGAAGCAGCTGCCAAATGTCAAACTGTTATTGATGACCTGACT

TTGATGAATGGAAAGCAAGCACAAGAGATAACAGAATTACGTGATTCGGCTGAAA

AATATGAGAAACAGATTGCAGAGCTGGTGAGTACCATCACCCAAAACCAGATAAC

GTATCAGCAAGAGCTACAAGCCTTGGTAGCGAAAAATGTGGAATTGGACGCGTTG

AATCAGCGTCAGGCTAAGTCTTTGCGTATTACTCCCTCTCTTCTATCAGCCACTCCT

ATCGATTCAGCTGATGGTGTTGCTGACTTAATTGATTTCTCTGTTCCAACTGATGAG

TTGTAAATAATCCGTGATGCAGTGTTGCCCTAATCCCTTAAGCCTTCCCGACCCCCA

TTCATC
```

TD-µNS Protein Sequence
(SEQ ID NO: 16)

```
MASFKGFSANTVPVSKAKRDISSLAATPGLRSQSFTPSVDMSQSREFLTK

AIEQGSMSIPYQHVNVPKVDRKVVSLVVRPFSSGAFSISGVISPAHAYLLECLPQLEQA

MAFVASPESFQASDVAKRFAIKPGMSLQDAITAFINFVSAMLKMTVTRQNFDVIVAEIE

RLASTSVSVRTKEAKVADEELMLFGLDHRGPQQLDVSDAKGIMKAADIQTTHDVHLA

PGVGNIDPEIYNEGRFMFMQHKPLAADQSYFTLETADYFKIYPTYDEHDGRMADQKQ

SGLILCTKDEVLAEQTIFKLDAPDDKTVHLLDRDDDHVVARFTKVFIEDVAPGHHAAQ

RSGQRSVLDDLYANTQVISITSAALKWVVKHGVSDGIVNRKNVKVCVGFDPLYTLSTH

NGVSLCALLMDEKLSVLNSACRMTLRSLMKTGRDVDAHRAFQRVLSQGYTSLMCYY

HPSRKLAYGEVLFLERSNDVTDGIKLQLDASRQCHECPVLQQKVVELEKQIIMQKSIQS

DPTPVALQPLLSQLRELSSEVTRLQMELSRAQSLNAQLEADVKSAQSCSLDMYLRHHT

CINGHAKEDELLDAVRVAPDVRREEVIEKRSEVRQGWCERISKEAAAKCQTVIDDLTL

MNGKQAQEITELRDSAEKYEKQIAELVSTITQNQITYQQELQALVAKNVELDALNQRQ

AKSLRITPSLLSATPIDSADGVADLIDFSVPTDEL
```

TD-S1
(SEQ ID NO: 30)

```
GCTATTGGTCGGATGGATCCTCGCCTACGTGAAGAAGTAGTACGGCT

GATAATCGCATTAACGAGTGATAATGGAGTATCACTGTCAAAAGGGCTTGAATCA

AGGGTCTCGGCGCTCGAGAAGACGTCTCAAATACACTCTGATACTATCCTCCGGAT

CACCCAGGGACTCGATGATGCAAACAAACGAATCATCGCTCTTGAGCAAAGTCGG

GATGACTTGGTTGCATCAGTCAGTGATGCTCAACTTGCAATCTCCAGATTGGAAAG

CTCTATCGGAGCCCTCCAAACAGTTGTCAATGGACTTGATTCGAGTGTTACCCAGT

TGGGTGCTCGAGTGGGACAACTTGAGACAGGACTTGCAGAGCTACGCGTTGATCA

CGACAATCTCGTTGCGAGAGTGGATACTGCAGAACGTAACATTGGATCATTGACCA

CCGAGCTATCAACTCTGACGTTACGAGTAACATCCATACAAGCGGATTTCGAATCT

AGGATATCCACATTAGAGCGCACGGCGGTCACTAGCGCGGGAGCTCCCCTCTCAAT

CCGTAATAACCGTATGACCATGGGATTAAATGATGGACTCACGTTGTCAGGGAATA

ATCTCGCCATCCGATTGCCAGGAAATACGGGTCTGAATATTCAAATGGTGGACTT

CAGTTTCGATTTAATACTGATCAATTCCAGATAGTTAATAATAACTTGACTCTCAAG

ACGACTGTGTTTGATTCTATCAACTCAAGGATAGGCGCAACTGAGCAAAGTTACGT

GGCGTCGGCAGTGACTCCCTTGAGATTAAACAGTAGCACGAAGGTGCTGGATATG
```

-continued

```
CTAATAGACAGTTCAACACTTGAAATTAATTCTAGTGGACAGCTAACTGTTAGATC

GACATCCCCGAATTTGAGGTATCCGATAGCTGATGTTAGCGGCGGTATCGGAATGA

GTCCAAATTATAGGTTTAGGCAGAGCATGTGGATAGGAATTGTCTCCTATTCTGGT

AGTGGGCTGAATTGGAGGGTACAGGTGAACTCCGACATTTTTATTGTAGATGATTA

CATACATATATGTCTTCCAGCTTTTGACGGTTTCTCTATAGCTGACGGTGGAGATCT

ATCGTTGAACTTTGTTACCGGATTGTTACCACCGTTACTTACAGGAGACACTGAGC

CCGCTTTTCATAATGACGTGGTCACATATGGAGCACAGACTGTAGCTATAGGGTTG

TCGTCGGGTGGTACGCCTCAGTATATGAGTAAGAATCTGTGGGTGGAGCAGTGGCA

GGATGGAGTACTTCGGTTACGTGTTGAGGGGGTGGCTCAATTACGCACTCAAACA

GTAAGTGGCCTGCCATGACCGTTTCGTACCCGCGTAGTTTCACGTGAGGATCAGAC

CACCCCGCGGCACTGGGGCATTTCATC
```

TD-σ1
(SEQ ID NO: 11)
```
MDPRLREEVVRLIIALTSDNGVSLSKGLESRVSALEKTSQIHSDTILRITQ

GLDDANKRIIALEQSRDDLVASVSDAQLAISRLESSIGALQTVVNGLDSSVTQLGARVG

QLETGLAELRVDHDNLVARVDTAERNIGSLTTELSTLTLRVTSIQADFESRISTLERTAV

TSAGAPLSIRNNRMTMGLNDGLTLSGNNLAIRLPGNTGLNIQNGGLQFRFNTDQFQIVN

NNLTLKTTVFDSINSRIGATEQSYVASAVTPLRLNSSTKVLDMLIDSSTLEINSSGQLTV

RSTSPNLRYPIADVSGGIGMSPNYRFRQSMWIGIVSYSGSGLNWRVQVNSDIFIVDDYI

HICLPAFDGFSIADGGDLSLNFVTGLLPPLLTGDTEPAFHNDVVTYGAQTVAIGLSSGG

TPQYMSKNLWVEQWQDGVLRLRVEGGGSITHSNSKWPAMTVSYPRSFT
```

TD-S2
(SEQ ID NO: 31)
```
GCTATTCGCTGGTCAGTTATGGCTCGCGCTGCGTTCCTATTCAAGACT

GTTGGGTTTGGTGGTCTGCAAAATGTGCCAATTAACGACGAACTATCTTCACATCT

ACTCCGAGCTGGTAATTCACCATGGCAGTTAACACAGTTTTTAGACTGGATAAGCC

TTGGGAGGGGTTTAGCTACATCGGCTCTCGTTCCGACGGCTGGGTCAAGATACTAT

CAAATGAGTTGCCTTCTAAGTGGCACTCTCCAGATTCCGTTCCGTCCTAACCACCG

ATGGGGAGACATTAGGTTCTTACGCTTAGTGTGGTCAGCTCCTACTCTCGATGGAT

TAGTCGTAGCTCCACCACAAGTTTTGGCTCAGCCCGCTTTGCAAGCACAGGCAGAT

CGAGTGTACGACTGCGATGATTATCCATTTCTAGCGCGTGATCCAAGATTCAAACA

TCGGGTGTATCAGCAATTGAGTGCTGTAACTCTACTTAACTTGACAGGTTTTGGCCC

GATTTCCTACGTTCGAGTGGATGAAGATATGTGGAGTGGAGATGTGAACCAGCTTC

TCATGAACTATTTCGGGCACACGTTTGCAGAGATTGCATACACATTGTGTCAAGCC

TCGGCTAATAGGCCTTGGGAATATGACGGTACATATGCTAGGATGACTCAGATTGT

GTTATCCTTGTTCTGGCTATCGTATGTCGGTGTAATCCATCAGCAGAATACGTATCG

GACATTCTATTTTCAGTGTAATCGGCGAGGTGACGCCGCTGAGGTGTGGATTCTTT

CTTGTTCGTTGAACCATTCCGCACAAATTAGACCGGGTAATCGTAGCTTATTCGTTA

TGCCAACTAGCCCAGATTGAACATGGACGTCAATTTGATCCTGAGTTCAACGTTG

ACGGGGTGTTTGTGTTCGGGTTCACAGCTGCCACTGATTGACAATAATTCAGTACC

TGCAGTGTCGCGCAACATCCATGGCTGGACTGGTAGAGCTGGTAACCAATTGCATG

GGTTCCAGGTGAGACGAATGGTGACTGAATTTTGTGACAGGTTGAGACGCGATGGT
```

-continued

```
GTCATGACCCAAGCTCAGCAGAATCAAGTTGAAGCGTTGGCAGATCAGACTCAAC

AGTTTAAGAGGGACAAGCTCGAAACGTGGGCGAGAGAAGACGATCAATATAATCA

GGCTCATCCCAACTCCACAATGTTCCGTACGAAACCATTTACGAATGCGCAATGGG

GACGAGGTAATACGGGGGCGACTAGTGCCGCGATTGCAGCCCTTATCTGATCGTCT

TGGAGTGAGGGGGTCCCCCCACACCCCTCACGACTGACCACACATTCATC
```

TD-σ2

(SEQ ID NO: 12)

```
MARAAFLFKTVGFGGLQNVPINDELSSHLLRAGNSPWQLTQFLDWISLG

RGLATSALVPTAGSRYYQMSCLLSGTLQIPFRPNHRWGDIRFLRLVWSAPTLDGLVVA

PPQVLAQPALQAQADRVYDCDDYPFLARDPRFKHRVYQQLSAVTLLNLTGFGPISYVR

VDEDMWSGDVNQLLMNYFGHTFAEIAYTLCQASANRPWEYDGTYARMTQIVLSLFW

LSYVGVIHQQNTYRTFYFQCNRRGDAAEVWILSCSLNHSAQIRPGNRSLFVMPTSPDW

NMDVNLILSSTLTGCLCSGSQLPLIDNNSVPAVSRNIHGWTGRAGNQLHGFQVRRMVT

EFCDRLRRDGVMTQAQQNQVEALADQTQQFKRDKLETWAREDDQYNQAHPNSTMF

RTKPFTNAQWGRGNTGATSAAIAALI
```

TD-S4

(SEQ ID NO: 32)

```
GCTATTTTTGCCTCTTCCCAGACGTTGTCGCAATGGAGGTGTGCTTGC

CCAACGGTCATCAGGTCGTGGACTTGATTAACAACGCTTTTGAAGGTCGTGTATCA

ATCTACAGCGCGCAAGAGGGATGGGACAAAACAATCTCAGCACAGCCAGATATGA

TGGTATGTGGTGGCGCCGTCGTTTGCATGCATTGTCTAGGTGTTGTCGGATCTCTAC

AACGCAAGCTGAAGCATTTGCCTCACCATAGATGTAATCAACAGATCCGTCATCAG

GATTACGTCGATGTACAGTTCGCAGACCGTGTTACTGCTCACTGGAAGCGGGGTAT

GCTGTCCTTCGTTGCGCAGATGCACGAGATGATGAATGACGTGTCGCCAGATGACC

TGGATCGTGTGCGTACTGAGGGAGGTTCACTAGTGGAGCTGAACTGGCTTCAGGTT

GACCCAAATTCAATGTTTAGATCAATACACTCAAGTTGGACAGATCCTTTGCAGGT

GGTGGACGACCTTGACACTAAGCTGGATCAGTACTGGACAGCCTTAAACCTGATGA

TCGACTCATCCGACTTGATACCCAACTTTATGATGAGAGACCCATCACACGCGTTC

AATGGTGTGAAACTGGGGGGAGATGCTCGTCAAACCCAATTCTCCAGGACTTTTGA

TTCGAGATCGAGTTTGGAATGGGGTGTGATGGTTTATGATTACTCTGAGCTGGAGC

ATGATCCATCGAAGGGCCGTGCTTACAGAAAGGAATTGGTGACGCCAGCTCGAGA

TTTCGGTCACTTTGGATTATCCCATTATTCTAGGGCGACTACCCCAATCCTTGGAAA

GATGCCGGCCGTATTCTCAGGAATGTTGACTGGGAACTGTAAAATGTATCCATTCA

TTAAAGGAACGGCTAAGCTGAAGACAGTGCGCAAGCTAGTGGAGGCAGTCAATCA

TGCTTGGGGTGTCGAGAAGATTAGATATGCTCTTGGGCCAGGTGGCATGACGGGAT

GGTACAATAGGACTATGCAACAGGCCCCCATTGTGCTAACTCCTGCTGCTCTCACA

ATGTTCCCAGATACCATCAAGTTTGGGGATTTGAATTATCCAGTGATGATTGGCGA

TCCGATGATTCTTGGCTAAACACCCCCATCTTCACAGCGCCGGGCTTGACCAACCT

GGTGTGACGTGGGACAGGCTTCATTCATC
```

TD-σ3

(SEQ ID NO: 13)

```
MEVCLPNGHQVVDLINNAFEGRVSIYSAQEGWDKTISAQPDMMVCGGA

VVCMHCLGVVGSLQRKLKHLPHHRCNQQIRHQDYVDVQFADRVTAHWKRGMLSFV

AQMHEMMNDVSPDDLDRVRTEGGSLVELNWLQVDPNSMFRSIHSSWTDPLQVVDDL
```

-continued

DTKLDQYWTALNLMIDSSDLIPNFMMRDPSHAFNGVKLGGDARQTQFSRTFDSRSSLE

WGVMVYDYSELEHDPSKGRAYRKELVTPARDFGHFGLSHYSRATTPILGKMPAVFSG

MLTGNCKMYPFIKGTAKLKTVRKLVEAVNHAWGVEKIRYALGPGGMTGWYNRTMQ

QAPIVLTPAALTMFPDTIKFGDLNYPVMIGDPMILG

Genetically Modified T3D$^{PL}$ Reovirus with Improved Oncolytic Activity

In addition to reassortant viruses described in the foregoing section, modified reovirus that include genetic mutations that result in production of a mutant protein are also disclosed. In certain cases, the modified reovirus may be produced from a naturally occurring virus that has been genetically modified to alter the amino acid sequence of a protein expressed by the virus. In certain cases, the modified reovirus may be produced from a reassortant virus, such as, the reassortant viruses disclosed herein which may be further modified to include one or more genetic modifications that alter the amino acid sequence of one or more proteins expressed by the reassortant virus.

Proteins comprising mutations that improve oncolytic activity of a reovirus expressing one or more of such proteins are provided. Reoviruses expressing one or more of such proteins are also disclosed.

Mutant σ3 Protein

A T3D$^{PL}$ reovirus genetically modified to express a T3D$^{PL}$ reovirus σ3 protein comprising a substitution of lysine at position 198, where the numbering of the amino acid position is with reference to the amino acid sequence of T3D$^{PL}$ reovirus σ3 protein set forth in SEQ ID NO:4 is disclosed. In certain embodiments, a genetically modified T3D$^{PL}$ reovirus may express a T3D$^{PL}$ reovirus σ3 protein comprising a substitution of lysine at position 198 while the other proteins expressed by the genetically modified T3D$^{PL}$ reovirus may have the same sequence as that of the proteins expressed by the parental unmodified T3D$^{PL}$ reovirus strain. For example, the T3D$^{PL}$ reovirus may express PL σ1, PL σ1s, PL σ2, PL σNS, PL σ3 (comprising the substitution at position 198), PL μ2, PL μ1, PL μNS, PL λ3, PL λ2, and PL λ1.

In certain embodiments, the lysine at position 198 in the σ3 may be substituted with an amino acid other than a positively charged amino acid. In certain embodiments, the substitution at position 198 may be non-conservative substitution where the lysine is substituted with gly, ala, val, ile, leu; asp, glu; asn, gln; ser, thr; or phe, tyr. In certain embodiments, the substitution at position 198 may be K198G/A/V/I/L. In certain embodiments, the substitution at position 198 may be K198G or K198A.

In certain cases, the σ3 protein may include an additional substitution, such as, a substitution of aspartic acid at position 229, where the numbering of the amino acid position is with reference to the amino acid sequence of T3D$^{PL}$ reovirus σ3 protein set forth in SEQ ID NO:4. In certain cases, the substitution may be the substitution D229E or D229A or D229G.

In certain cases, the modified T3D$^{PL}$ reovirus may express PL proteins having sequences as provided herein and where the PL σ3 protein expressed by the modified T3D$^{PL}$ reovirus has the amino acid sequence as set forth in SEQ ID NO:4 and comprises a substitution of the lysine at position 198, and optionally at position 229, where the numbering of the amino acid positions is with reference to the amino acid sequence of T3D$^{PL}$ reovirus σ3 protein set forth in SEQ ID NO:4. Such a modified reovirus may be used as an optimal base vector that may be combined with the additional mutations disclosed here to provide an array of modified reoviruses with superior oncolytic activity.

Additional mutants of PL σ3 that improve reovirus mediated oncolysis are also provided. Some of these mutants reduce the number of σ1 protein per virion while some mutations do not affect the number of σ1 protein per virion but improve post-entry steps.

In certain cases, the PL σ3 protein may include a substitution of histidine at position 230 with reference to the amino acid sequence of wild type T3D$^{PL}$ reovirus σ3 protein set forth in SEQ ID NO:4. The histidine may be replaced with any other amino acid, such as, Q, S, T, or N. A T3D$^{PL}$ reovirus expressing such a mutant PL σ3 may have reduced number of σ1 protein per virion. The T3D$^{PL}$ reovirus may also express other mutated proteins, such as, λ1, λ2, and/or λ3 having a mutation as provided herein. For example, a T3D$^{PL}$ reovirus having improved oncolytic activity may express a PL σ3 protein with a substitution at position 230 and a PL λ2 having a substitution at position 1274 and a PL λ3 protein having a substitution at position 892, e.g., expressing PL σ3 H230Q mutant and PL λ2 I1274T mutant and PL λ3 M892I mutant.

In certain cases, the PL σ3 may include a substitution of lysine at position 64 with reference to the amino acid sequence of wild type T3D$^{PL}$ reovirus σ3 protein set forth in SEQ ID NO:4. The lysine may be replaced with any other amino acid, such as, E or D. A T3D$^{PL}$ reovirus expressing such a mutant PL σ3 may have no effect on the number of σ1 protein per virion but may have improved post-entry steps. The T3D$^{PL}$ reovirus may also express other mutated proteins, such as, λ1, λ2, and/or λ3 having a mutation as provided herein. For example, a T3D$^{PL}$ reovirus having improved oncolytic activity may express a PL σ3 protein with a substitution at position 64 and a PL λ1 having a substitution at position 122 and a PL λ3 protein having a substitution at position 972, e.g., expressing PL σ3 K64E mutant and PL λ1 Y122H mutant and PL λ3 Q972R mutant.

Mutant σ2 Protein

Figure 6:
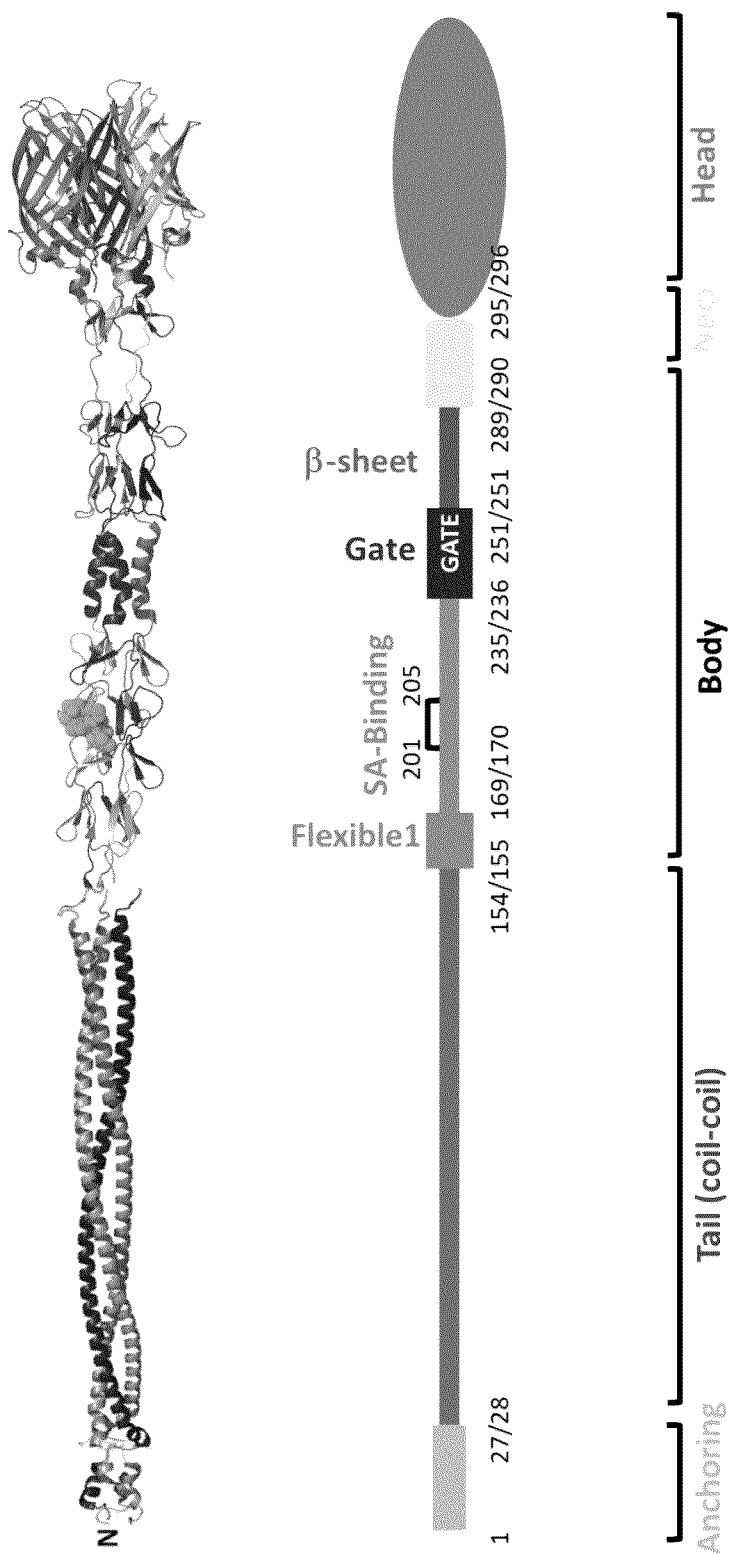
FIG. 6. Schematic of domains of reovirus σ1 protein.

The sequence of T3D$^{PL}$ reovirus σ1 protein is set forth in SEQ ID NO:1. The σf protein includes the domains as set out in Table 3 below and depicted in FIG. 6. As indicated in Table 3, T3D$^{PL}$ reovirus σ1 proteins that includes mutations in the anchoring domain, the tail, body, and/or head regions are disclosed. The head domain extends from amino acid 296-455, the body domain extends from amino acid 155-289, the tail domain extends from amino acid 28-154, and the numbering of the amino acid positions is with reference to the amino acid sequence of T3D$^{PL}$ reovirus σ1 protein set forth in SEQ ID NO:1. Reovirus, such as, a T3D$^{PL}$ reovirus expressing a mutant PL σ1 protein as disclosed herein has improved oncolytic activity.

TABLE 3

| σ1 Structure | Location of Mutation |
| --- | --- |
| Anchoring domain (amino acids 1-27) | 18 |
| Tail (coil-coil) (amino acids 28-154) | 28; 66; 114 |
| Body (amino acids 155-289) | 217; 219 |
| Neck (amino acids 290-295) | — |
| Head (amino acids 296-455) | 312 |

Provided herein is a T3D$^{PL}$ reovirus genetically modified to express a T3D$^{PL}$ reovirus σ1 protein comprising a mutation in the anchoring domain, tail, body, and/or head regions of the σ1 protein. The mutation may be a deletion, an insertion, and/or a substitution.

σ1 Anchoring Domain Mutant

In certain embodiments, the T3D$^{PL}$ reovirus may be genetically modified to express a T3D$^{PL}$ reovirus σ1 protein comprising an anchoring domain (the anchoring domain extends from amino acids 1-27 of SEQ ID NO:1) that includes a deletion or a substitution at or adjacent amino acid position 18, where the numbering of the position is with reference to the amino acid sequence of wild type T3D$^{PL}$ reovirus σ1 protein set forth in SEQ ID NO:1.

In certain cases, a T3D$^{PL}$ reovirus genetically modified to express a T3D$^{PL}$ reovirus σ1 protein comprising a mutation in the anchoring domain of the σ1 protein, such as, S18I or S18G or S18A, may additionally include a mutant σ3 protein, such as, a PL σ3 protein comprising a substitution at one or both of positions 198 and 229 (e.g., K198G or D229E), as described in the preceding section. In some cases, the serine at position 18 may be deleted.

In addition to expressing a PL σ1 protein with a deletion or substitution at position 18, the T3D$^{PL}$ reovirus may express a PL σ3 protein with substitutions at positions K198 and optionally at D229. As such, a T3D$^{PL}$ reovirus of the present disclosure may express PL σ3 protein with substitutions K198G and D229E and PL σ1 protein with the substation S18I.

σ1 Tail Domain Mutants

σ1 protein with mutations in the tail domain are disclosed. In certain cases, the mutation may be at or adjacent to amino acid position 28 and/or position 66, where the numbering of the position is with reference to the amino acid sequence of wild type T3D$^{PL}$ reovirus σ1 protein set forth in SEQ ID NO:1. In certain embodiments, the leucine at position 28 and/or serine at position 66 may be substituted with any of the other 19 amino acids.

In certain embodiments, a PL σ1 protein may include a substitution of the leucine at position 28 with phenylalanine, tyrosine, tryptophan, proline, or histidine. In certain embodiments, the PL σ1 protein may have the amino acid sequence set forth in SEQ ID NO:1 with a substitution of the leucine at position 28. For example, the PL σ1 protein may have the amino acid sequence set forth in SEQ ID NO:1 with the substitution L28P or L28G or L28A. A modified reovirus may express a mutant σ3 described in the preceding section and may further express a mutated PL σ1 protein comprising a substitution of the leucine at position 28 with another amino acid, e.g., with phenylalanine, tyrosine, tryptophan, proline, or histidine.

In certain embodiments, the PL σ1 protein may include a substitution of the serine at position 66 with alanine, valine, isoleucine, leucine, methionine, phenylalanine, tyrosine, tryptophan, proline, or histidine. In certain embodiments, the PL σ1 protein may have the amino acid sequence set forth in SEQ ID NO:1 with the substitution of the serine at position 66. For example, the PL σ1 protein may have the amino acid sequence set forth in SEQ ID NO:1 with the substitution S66I or S66G or S66A.

In certain embodiments, the PL σ1 protein may include substitutions at positions 28 and/or 66, e.g., L28P or L28G or L28A, and S66I or S66G or S66A. In certain cases, a modified T3D$^{PL}$ reovirus may express a mutant σ3 described in the preceding section (e.g., PL σ3 comprising substitutions K198G and D229E) and may further include a mutated PL σ1 protein comprising a mutation in the tail domain of the PL σ1 protein (e.g., L28P or L28G or L28A, and/or S66I or S66G or S66A). In certain cases, the reovirus is further genetically modified to express a T3D$^{PL}$ reovirus σ1 protein comprising a substitution of serine at position 18, and one or more of substitutions at positions 28 and 66, where the numbering of the amino acid position is with reference to the amino acid sequence of T3D$^{PL}$ reovirus σ1 protein set forth in SEQ ID NO:1. For example, the substitution at position 18 in the T3D$^{PL}$ reovirus σ1 protein comprises the substitution S18I.

In certain cases, reovirus comprising a mutation in the tail domain of σ1 protein may express reduced amount of σ1 protein per virion which may assist in improved entry of the virus into cells, such as, cancer cells as compared to a reovirus not having a mutation in the tail domain of σ1 protein.

In another embodiment, a T3D$^{PL}$ reovirus genetically modified to express a T3D$^{PL}$ reovirus σ1 protein comprising a mutation in the tail domain of the σ1 protein which does not result in reduced amount of σ1 protein per virion is disclosed. The mutation may be an insertion, deletion, or substitution at amino acid position 114 of PL σ1 protein. The threonine at position 114 may be replaced with any other amino acid, such as, an uncharged polar side chain (e.g., S, A, or Q), electrically charged side chain (e.g., H, K, D, or E), a hydrophobic side chain (e.g., A, V, I, L, M, F, Y, or W), or with G or P. In certain cases, the substitution may be T114P, T114S, T114R, T114A, T114Q, T114H, T114K, T114D, or T114E. In certain cases, the substitution may be T114P. This mutation in σ1 protein may be accompanied with a mutation in the body domain of the σ1 protein. For example, a substitution at position 219, where the numbering of the amino acid position is with reference to the amino acid sequence of T3D$^{PL}$ reovirus σ1 protein set forth in SEQ ID NO:1. In certain cases, the T3D$^{PL}$ reovirus may be genetically modified to express a T3D$^{PL}$ reovirus σ1 protein comprising a mutation in the tail domain and a mutation in the body domain along with the mutations in the PL σ3 protein as disclosed herein. For example, a T3D$^{PL}$ reovirus may express a PL σ1 protein having the sequence set forth in SEQ ID NO:1 and comprising the substitutions T114P and/or R219S and optionally a PL σ3 protein comprising the substitutions K198G and D229E.

σ1 Body Domain Mutants

In certain embodiments, the σ1 protein expressed by the T3D$^{PL}$ reovirus comprises a mutation in the body domain of the σ1 protein. The mutation may be an insertion, deletion, or substitution. In certain cases, the body domain of the PL σ1 protein comprises a substitution at or a deletion of the amino acid position 217 or 219 or adjacent to position 217 or 219 or comprises a deletion of amino acids 217 through 219 or a substitution at positions 217, 218, and/or 219.

In certain cases, the PL σ1 protein comprises a substitution at position 217. For example, the PL σ1 protein may comprise the substitution of Q217 with any of the other 19 amino acids, e.g., Q217 may be substituted with an amino acid with an electrically charged side chain (e.g., R, H, K, D, or E), a hydrophobic side chain (e.g., A, V, I, L, M, F, Y, or W), or with G or P. In certain cases, the substitution may be Q217R, Q217H, Q217K, Q217D, or Q217E. In certain cases, the substitution may be Q217H.

In certain cases, the PL σ1 protein comprises a substitution at position 219. For example, the PL σ1 protein may comprise the substitution of R219 with any of the other 19 amino acids, e.g., R219 may be substituted with an amino acid with an uncharged polar side chain (e.g., S, T, A, or Q), electrically charged side chain (e.g., H, K, D, or E), a hydrophobic side chain (e.g., A, V, I, L, M, F, Y, or W), or with G or P. In certain cases, the substitution may be R219S, R219T, R219A, R219Q, R219H, R219K, R219D, or R219E. In certain cases, the substitution may be R219S.

In certain cases, the PL σ1 protein comprises a substitution at both positions 217 and 219. For example, the PL σ1 protein comprises the substitutions Q217H and R219S.

A T3D$^{PL}$ reovirus expressing these PL σ1 protein mutants (e.g., substitutions at Q217, R219, and/or T114) may have same levels of σ1-per-virion as a T3D$^{PL}$ reovirus not having these mutations but may produce more proteins and viruses from an infection but due to improved post-entry steps required for virus replication.

In certain cases, a T3D$^{PL}$ reovirus may express a PL σ1 protein having the sequence set forth in SEQ ID NO:1 and comprising the substitutions Q217H and/or R219S and optionally a PL σ3 protein comprising the substitutions K198G and D229E.

σ1 Head Domain Mutants

In certain embodiments, the σ1 protein expressed by the T3D$^{PL}$ reovirus comprises a mutation in the head domain of the σ1 protein. The mutation may be an insertion, deletion, or substitution. In certain cases, the head domain of the PL σ1 protein comprises a substitution at or a deletion of the amino acid position 312. In certain cases, the PL σ1 protein comprises a substitution at position 312. For example, the PL σ1 protein may comprise the substitution of N312 with any of the other 19 amino acids, e.g., N312 may be substituted with an amino acid with an electrically charged side chain (e.g., R, H, K, D, or E), a hydrophobic side chain (e.g., A, V, I, L, M, F, Y, or W), or with G or P. In certain cases, the substitution may be N312R, N312H, N312K, N312D, or N312E. In certain cases, the substitution may be N312R. In certain cases, the T3D$^{PL}$ reovirus may express a PL σ1 protein having the amino acid sequence set forth in SEQ ID NO:1 and including a substitution at or adjacent (e.g. ±10 amino acids) position N312.

In certain examples, the T3D$^{PL}$ reovirus may further express a mutant μ2 protein such as a PL μ2 protein comprising a mutation, such as, a deletion or substitution at or adjacent (e.g. ±10 amino acids) position 612 or 613 with reference to the sequence set forth in SEQ ID NO:5.

λ2 Mutants

The sequence of T3D$^{PL}$ reovirus λ2 protein is set forth in SEQ ID NO:9. The λ2 protein includes the domains as set out in Table 4 below and depicted in FIG. 11. As indicated in Table 4, T3D$^{PL}$ reovirus λ2 proteins that include mutations in the bridge domain or the FLAP domain are disclosed. Reovirus, such as, a T3D$^{PL}$ reovirus expressing a mutant PL λ2 protein as disclosed herein has improved oncolytic activity as compared to a T3D$^{PL}$ reovirus expressing the native PL λ2 protein.

TABLE 4

| λ2 Structure | Location of Mutation |
| --- | --- |
| Guanylyltransferase (GTase) (amino acids 1-385) | — |
| Bridge (amino acids 386-433) | 408 |
| Methyltransferase (MTase1) (amino acids 434-691) | — |
| Bridge (amino acids 690-802) | — |
| Methyltransferase (MTase2) (amino acids 804-1022) | — |
| FLAP (amino acids 1023-1274) | 1101; 1148; and 1274 |

A T3D$^{PL}$ reovirus genetically modified to express a T3D$^{PL}$ reovirus λ2 protein comprising a mutation in a FLAP domain, where the FLAP domain comprises amino acids 1023-1274, where the numbering of the amino acids is with reference to the amino acid sequence of T3D$^{PL}$ reovirus λ2 protein as set forth in SEQ ID NO:9, where the reovirus expresses wild type T3D$^{PL}$ reovirus λ1 and λ3 proteins is provided.

Also provided herein are T3D$^{PL}$ reovirus genetically modified to express a T3D$^{PL}$ reovirus λ2 protein comprising a mutation at one or more of positions 1148 and 1274. The modified T3D$^{PL}$ reovirus may express other proteins that have the same sequence as that of the proteins expressed in an unmodified T3D$^{PL}$ reovirus or may express proteins that include one or more substitutions as disclosed herein.

A T3D$^{PL}$ reovirus genetically modified to express a T3D$^{PL}$ reovirus λ2 protein comprising a substitution of isoleucine at position 1274 or asparagine at position 1148 with reference to the amino acid sequence of wild type T3D$^{PL}$ reovirus λ2 protein set forth in SEQ ID NO:9 is provided.

The substitution at position 1274 may be a conservative substitution, e.g., I1274A/V/L/M/F/Y/W, or a non-conservative substitution such as, I1274S/T/N/Q or I1274G/P or I1274R/H/K/D/E. For example, the substitution at position 1274 may be I1274T or I1274M.

The substitution at position 1148 may be a conservative substitution, e.g., N1148S/T/Q, or a non-conservative substitution such as, N1148A/V/L/M/F/Y/W, or N1148G/P or N1148R/H/K/D/E. For example, the substitution at position N1148 may be N1148S.

A T3D$^{PL}$ reovirus genetically modified to express a PL λ2 protein with a mutation in the bridge region (amino acids 386-433) is also disclosed. The mutation may be a deletion or substitution in the bridge region, e.g., a substitution at or adjacent amino acid position 408 (±10 amino acids). In some cases, the PL λ2 protein may include a substitution at position 408, where the D at position 408 is substituted with N, S, T, or Q. The reovirus may include additional genetic modification that result in expression of mutated σ1 and/or μ2 proteins having mutations as disclosed herein.

In some cases, a modified T3D$^{PL}$ reovirus may express a PL λ2 D408N mutant, a σ1 Q217H mutant and a μ2 L112F, S613A mutant.

In addition or alternatively, these mutations may be combined with the other mutations disclosed herein.

λ3 Mutants

A T3D$^{PL}$ reovirus λ3 protein with a substitution of methionine at position 892 with reference to the amino acid sequence of wild type T3D$^{PL}$ reovirus λ3 protein set forth in SEQ ID NO:8 is disclosed. The substitution may be M892I/L/V/A.

A T3D$^{PL}$ reovirus λ3 protein with a substitution of methionine at position 972 with reference to the amino acid sequence of wild type T3D$^{PL}$ reovirus λ3 protein set forth in SEQ ID NO:8 is disclosed. The substitution may be Q972R/H/K.

λ1 Mutants

A T3D$^{PL}$ reovirus genetically modified to express a T3D$^{PL}$ reovirus λ1 protein comprising a mutation at or adjacent the amino acid position 962 and/or 122 of the λ1 protein, where the numbering of the amino acid positions is with reference to the amino acid sequence of T3D$^{PL}$ reovirus λ1 protein set forth in SEQ ID NO:10 is provided. The mutation may be a substitution. The substitution may be at amino acid position 962. The substitution may be A962S/T/N/Q. The substitution may be at amino acid position 122. The substitution may be Y122H/R/K.)

μ2 Mutants

A T3D$^{PL}$ reovirus genetically modified to express a T3D$^{PL}$ reovirus μ2 protein comprising a mutation at or adjacent amino acid position 112, 612, and/or 613, where the numbering of the amino acid positions is with reference to the amino acid sequence of T3D$^{PL}$ reovirus μ2 protein set forth in SEQ ID NO:5 is disclosed.

In some embodiments, a reovirus expressing a μ2 protein comprising a mutation, e.g., a deletion or substitution at or adjacent to (±10 amino acids) the position 612 or 613 may have improved oncolytic ability due to improved post-entry steps. In some embodiments, the amino acids at position 612 and/or 613 may be deleted. In some embodiments, the amino acids at position 612 and/or 613 may be substituted.

In one example, a T3D$^{PL}$ reovirus may be genetically modified to express a T3D$^{PL}$ reovirus μ2 protein with a substitution at position 612, e.g., A612V/I/L/M/F/Y/W.

In another example, a T3D$^{PL}$ reovirus may be genetically modified to express a T3D$^{PL}$ reovirus μ2 protein with a substitution at position 613, e.g., S613A/V/I/L/M/F/Y/W/G.

In another example, a T3D$^{PL}$ reovirus may be genetically modified to express a T3D$^{PL}$ reovirus μ2 protein with a substitution at position 112, e.g., L112F/Y/W/R/H/K.

In some embodiments, a T3D$^{PL}$ reovirus genetically modified to express a mutant μ2 protein as described herein may otherwise be wild type. In some embodiments, a T3D$^{PL}$ reovirus genetically modified to express a mutant μ2 protein as described herein may include additional genetic modification in other genes and express other mutant proteins, such as, σ1 and/or λ2.

In some embodiments, a T3D$^{PL}$ reovirus of the present disclosure is genetically modified to express PL μ2 A612V mutant. In some embodiments, a T3D$^{PL}$ reovirus of the present disclosure is genetically modified to express PL μ2 L112F, S613A mutant, PL σ1 Q217H mutant, and PL λ2 D408N mutant. In some embodiments, a T3D$^{PL}$ reovirus of the present disclosure is genetically modified to express PL μ2 A612V mutant and PL σ1 N312R mutant.

Metalloprotease Resistant Oncolytic Reovirus

Metalloprotease resistant oncolytic reovirus, such as a metalloprotease resistant T3D reovirus, are provided. Such a reovirus has improved oncolytic activity as compared to a wild type T3D reovirus since it is not inactivated by metalloproteases secreted by cancer cells. In certain embodiments, a metalloprotease resistant oncolytic T3D reovirus may include a mutation in the σ1 protein that renders the σ1 protein resistant to cleavage by a metalloprotease secreted by cancer cells, e.g., zinc dependent metalloproteases secreted by breast cancer cells, such as, polyoma virus middle T-antigen-derived mouse breast tumors. In certain aspects, the metalloprotease while having activity that cleaves of protein to generate a σ1N fragment does not have activity that generates infectious subviral particles (ISVPs), such as, activities required for cleavage of μ1C protein into 6. In certain embodiments, mutation may be located in the body domain of the σ1 protein. In some cases, the mutation may be at a region between amino acid positions 220-289 with reference to the PL σ1 protein sequence set out in SEQ ID NO:1. In some cases, the mutation is present within amino acids 222-251 of the body domain of the σ1 protein. In some cases, the mutation may be a substitution, insertion, or a deletion. In some cases, the mutation may be a substitution, such as, at position 249. In some cases, the substitution may be T249L/A/V/I/M/F/Y/W/G. The σ1 protein may be from a T3D reovirus such as, T3D$^{PL}$, T3D$^{TD}$, or T3D$^{KC}$.

In some cases, a metalloprotease resistant T3D reovirus may be a T3D$^{PL}$ reovirus that expresses a metalloprotease resistant σ1 protein having the amino acid sequence set forth in SEQ ID NO:1 and comprising a mutation in the region between amino acid positions 220-289, such as, within amino acids 222-251 of the body domain of the PL σ1 protein. In some cases, a metalloprotease resistant T3D reovirus may be a T3D$^{PL}$ reovirus that expresses a metalloprotease resistant σ1 protein having the amino acid sequence set forth in SEQ ID NO:1 and comprising a substitution at position 249, with reference to the PL of protein sequence set out in SEQ ID NO:1. In certain aspects, the substitution may be T249L/A/V/I/M/F/Y/W/G. In some aspects, the metalloprotease resistant T3D reovirus, e.g. metalloprotease resistant T3D$^{PL}$ reovirus may not express a wild type PL σ1 protein that is sensitive to degradation by a metalloprotease secreted by cancer cells, such as, cancer cells described herein. In some cases, T249 is substituted with any other amino acid other than N.

Also disclosed herein are methods for using the reovirus provided herein, such as, metalloprotease resistant T3D reovirus, e.g., T3D$^{PL}$ reovirus comprising a T249L/A/V/I/M/F/Y/W/G substitution in σ1 protein, for treating a cancer. The cancer may be intestinal cancer, breast cancer, or lung cancer. In certain aspects, the cancer may be a carcinoma (e.g., adenocarcinomas, squamous cell carcinomas, or basal cell carcinoma) or a sarcoma. In certain aspects, the cancer may be osteosarcoma or osteogenic sarcoma, chondrosarcoma, leiomyosarcoma, rhabdomyosarcoma, mesothelial sarcoma or mesothelioma, fibrosarcoma, angiosarcoma or hemangioendothelioma, liposarcoma, glioma or astrocytoma, myxosarcoma, or mesenchymous or mixed mesodermal, tumorsosteogenic sarcoma, chordoma, lymphangiosarcoma, synovioma, Ewing's tumor, colon carcinoma, pancreatic cancer, ovarian cancer, prostate cancer, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, Wilm's tumor, cervical cancer, uterine cancer, testicular cancer, small cell lung carcinoma, bladder carcinoma, epithelial carcinoma, glioma, astrocytoma, meduloblastoma, craniopharyngioma, pinealoma, hemangioblastoma, schwannoma, meningioma, melanoma, neuroblastoma, or retinoblastoma. The metalloprotease may be a matrix metalloprotease or a metalloprotease secreted by the cancer cells. In certain aspects, the cancer may include tumor cells having low sialic acid expression on cell surface. The method of treatment may include administering a therapeutically effective amount of the reovirus provided herein, such as, metalloprotease resistant T3D reovirus, e.g., T3D$^{PL}$ reovirus comprising a T249L/A/V/I/M/F/Y/W/G substitution in σ1 protein, to a patient having cancer.

In certain aspects, the T3D reovirus, e.g., T3D$^{PL}$ reovirus that comprises a mutant σ1 protein comprising a T249 substitution may also include the substitution S18I. In certain aspects, the T3D reovirus, e.g., T3D$^{PL}$ reovirus that comprises a mutant σ1 protein comprising a T249I substitution may not further comprise the substitution S18I.

In some aspects, the mutant σ1 protein may be resistant to cleavage that cleaves σ1 to a 22 kDa σ1N fragment.

As noted elsewhere herein, a metalloprotease resistant T3D reovirus, e.g., metalloprotease resistant T3D$^{PL}$ reovirus may include additional mutations that improve its oncolytic activity. Such mutations include those disclosed herein. In some cases, in addition to expressing a metalloprotease resistant σ1 protein having a modification as described herein, the T3D$^{PL}$ reovirus may also express a PL σ3 protein with the substitutions K198G and D229E.

Reoviruses disclosed herein may be include additional modifications, such as, modifications that reduce or eliminate an immune reaction to the reovirus. The modifications may include packaging of the reovirus in a liposome, a micelle or other vehicle to mask the reovirus from the host immune system. Alternatively, the outer capsid of the reovirus virion particle may be removed. In addition to reducing or eliminating immune responses, the modifications may also reduce non-specific uptake of the virus in normal tissues.

Treatment Methods with Tailored Cytokine Response

In certain aspects, a method for inducing a high interferon (IFN)-dependent cytokines response in a subject is provided. The method may include administering a therapeutically effective amount of a T3D$^{TD}$ to the subject, wherein high IFN cytokines response comprises an IFN cytokines response that is higher than that induced by T3D$^{PL}$.

In certain aspects, a method for inducing a low interferon (IFN)-dependent cytokines response in a subject is provided. The method may include administering a therapeutically effective amount of a T3D$^{PL}$ to the subject, wherein the low IFN cytokines response comprises an IFN cytokines response that is lower than that induced by T3D$^{TD}$.

The IFN-dependent cytokines response may include expression of one or more of Mx1, Cxcl10, Rsad2, Ccl4, Ifi44, and IL6.

In certain aspects, a method for inducing a high interferon (IFN)-independent, NF-κB-dependent cytokines response in a subject is provided. The method may include administering a therapeutically effective amount of a T3D$^{PL}$ to the subject, wherein the high IFN-independent, NF-κB-dependent cytokines response comprises a response that is higher than an IFN-independent, NF-κB-dependent cytokines response induced by T3D$^{TD}$.

In certain aspects, a method for inducing a high interferon (IFN)-independent, NF-κB-dependent cytokines response in a subject is provided. The method may include administering a therapeutically effective amount of a T3D$^{TD}$ genetically modified to express a σ3 protein of T3D$^{PL}$ to the subject, wherein the high IFN-independent, NF-κB-dependent cytokines response comprises a response higher than an IFN-independent, NF-κB-dependent cytokines response induced by T3D$^{TD}$ expressing a T3D$^{TD}$ σ3 protein.

In certain aspects, a method for inducing a low IFN-independent, NF-κB-dependent cytokines response in a subject is provided. The method may include administering a therapeutically effective amount of a T3D$^{TD}$ to the subject, wherein the low IFN-independent, NF-κB-dependent cytokines response comprises a IFN-independent, NF-κB-dependent cytokines response that is lower than that induced by T3D$^{PL}$.

In certain aspects, a method for inducing low IFN-independent, NF-κB-dependent cytokines response in subject is provided. The method may include administering a therapeutically effective amount of a T3D$^{PL}$ genetically modified to express a σ3 protein of T3D$^{TD}$ to the subject, wherein the low IFN-independent, NF-κB-dependent cytokines response comprises a IFN-independent, NF-κB-dependent cytokines response that is lower than that induced by T3D$^{PL}$ expressing a T3D$^{PL}$ σ3 protein. In certain aspects, the IFN-independent, NF-κB-dependent cytokines response comprises expression of one or more of Cxcl1, Csf2, Cxcl2, and Fas In certain aspects, the IFN-dependent cytokines response induced by the T3D$^{TD}$ reovirus in the subject may be at least 5% higher, 10% higher, 20% higher, 30% higher, 40% higher, 50% higher, or higher than the IFN-dependent cytokines response induced by T3D$^{PL}$ reovirus in the subject.

In certain aspects, the low IFN-dependent cytokines response induced by the T3D$^{PL}$ reovirus in the subject may be lower than IFN cytokines induced by T3D$^{TD}$ in a subject by at least 5%, 10%, 20%, 30%, 40%, 50%, or lower.

Tailored cytokine response may be useful in certain patient population, e.g., cancer patients, such as, immunocompromised cancer patients as well as cancer patients with autoimmune conditions.

In certain aspects, the subject may have a cancer having high levels of CCL2 or CCL4 in the tumor microenvironment. In such instances, the subject may be administered the T3DPL virus which does not induce increased expression of CCL4. For example, the subject may have lung adenocarcinoma having high levels of CCL2 or CCL4 in the tumor microenvironment.

In certain aspects, the subject may have a cancer having high levels of CCL5. In such instances, the subject may be administered the T3DPL virus which does not induce increased expression of CCL5 unlike T3DTD. For example, the subject may have pancreatic cancer having high levels of CCL5.

In certain aspects, the subject may have a cancer known to regress in response to CXCL10. In such instances, the subject may be administered the T3DTD to increase expression of CXCL10. For example, the subject may have high-grade serous ovarian cancer (HGSC).

In certain aspects, the subject may have a cancer known to regress in response to CXCL2. In such instances, the subject may be administered the T3DPL virus to increase expression of CXCL2. For example, the subject may have breast cancer or bladder cancer.

In certain aspects, the subject may have a cancer known to regress in response to GM-CSF. In such instances, the subject may be administered the T3DPL virus to increase expression of GM-CSF.

In certain aspects, the subject may have a cancer known to regress in response to FAS. In such instances, the subject may be administered the T3DPL virus to increase expression of FAS. In certain aspects, the subject may have a condition, e.g., cancer known to regress in response to increased expression of IFN-dependent cytokines. In such instances, the subject may be administered a therapeutically effective amount of a T3D$^{TD}$ to increase expression of IFN-dependent cytokines.

In certain aspects, the subject may have a condition, e.g., cancer known to regress in response to decreased expression of IFN-dependent cytokines. In such instances, the subject may be administered a therapeutically effective amount of a T3D$^{PL}$ to decrease expression of IFN-dependent cytokines.

In certain aspects, the subject may have a condition, e.g., cancer known to regress in response to increased expression of IFN-independent, NF-κB-dependent cytokines.

In such instances, the subject may be administered a therapeutically effective amount of a T3D$^{PL}$ or a T3D$^{TD}$ genetically modified to express a σ3 protein of T3D$^{PL}$ to increase expression of high IFN-independent, NF-κB-dependent cytokines.

In certain aspects, the subject may have a condition, e.g., cancer known to regress in response to decreased expression of IFN-independent, NF-κB-dependent cytokines. In such instances, the subject may be administered a therapeutically effective amount of a T3D$^{TD}$ or a T3D$^{PL}$ genetically modified to express a σ3 protein of T3D$^{TD}$ to decrease expression of IFN-independent, NF-κB-dependent cytokines.

Utility

The present disclosure provides compositions that find use inducing cell death in a neoplastic cell by cytolysis. The neoplastic cell may be in vitro or in vivo, such as, in a subject.

The present disclosure provides compositions that find use in treating cancer. The compositions include reoviruses described herein for administering to a subject in need thereof. Such compositions may include a therapeutically effective amount of an oncolytic reovirus described herein, optionally with a pharmaceutically acceptable vehicle. Such a composition may be administered once or several times and via the same or different routes.

A "therapeutically effective amount" corresponds to the amount of oncolytic reovirus that is sufficient for producing one or more beneficial results. Such a therapeutically effective amount may vary as a function of various parameters, in particular the mode of administration; the disease state; the age and weight of the subject; the ability of the subject to respond to the treatment; kind of concurrent treatment; the frequency of treatment; and/or the need for prevention or therapy. When prophylactic use is concerned, the oncolytic reovirus is administered at a dose sufficient to prevent or to delay the onset and/or establishment and/or relapse of a proliferative disease such as cancer, especially in a subject at risk. For "therapeutic" use, the oncolytic reovirus is administered to a subject diagnosed as having a proliferative disease such as cancer with the goal of treating the disease, optionally in association with one or more conventional therapeutic modalities. In particular, a therapeutically effective amount could be that amount necessary to cause an observable improvement of the clinical status over the baseline status or over the expected status if not treated, e.g. reduction in the tumor number; reduction in the tumor size, reduction in the number or extent of metastasis, increase in the period of remission, stabilization (i.e. absence of worsening) of the state of disease, delaying or slowing of disease progression or severity, amelioration or palliation of the disease state, prolonged survival, better response to the standard treatment, improvement of quality of life, reduced mortality, etc. A therapeutically effective amount could also be the amount sufficient to cause the development of an effective non-specific (innate) and/or specific anti-tumor immune response. Typically, development of an immune response in particular T cell response can be evaluated in vitro, in suitable animal models or using biological samples collected from the subject. For example, techniques routinely used in laboratories (e.g. flow cytometry, histology) may be used to perform tumor surveillance. An improvement of the clinical status can be easily assessed by any relevant clinical measurement typically used by physicians or other skilled healthcare staff.

The term "pharmaceutically acceptable vehicle" is intended to include any and all carriers, solvents, diluents, excipients, adjuvants, dispersion media, coatings, antibacterial and antifungal agents, absorption agents and the like compatible with administration in mammals and in particular, human subjects.

The oncolytic reovirus or the composition thereof can be placed in a solvent or diluent appropriate for human or animal use. The solvent or diluent may be isotonic, hypotonic or weakly hypertonic and may have a relatively low ionic strength. Representative examples include sterile water, physiological saline (e.g. sodium chloride), Ringer's solution, glucose, trehalose or saccharose solutions, Hank's solution, and other aqueous physiologically balanced salt solutions (see for example the most current edition of Remington: The Science and Practice of Pharmacy, A. Gennaro, Lippincott, Williams&Wilkins).

In one embodiment, the oncolytic reovirus composition is suitably buffered for human use. Suitable buffers include without limitation phosphate buffer (e.g. PBS), bicarbonate buffer and/or Tris buffer capable of maintaining a physiological or slightly basic pH (e.g. from approximately pH 7 to approximately pH 9).

The oncolytic reovirus compositions may also contain other pharmaceutically acceptable excipients for providing desirable pharmaceutical or pharmacodynamic properties, including for example osmolarity, viscosity, clarity, colour, sterility, stability, rate of dissolution of the formulation, modifying or maintaining release or absorption into an the human or animal subject, promoting transport across the blood barrier or penetration in a particular organ.

The oncolytic reovirus compositions can also include one or more adjuvant(s) capable of stimulating immunity (especially a T cell-mediated immunity) or facilitating infection of tumor cells upon administration, e.g., through toll-like receptors (TLR) such as TLR-7, TLR-8 and TLR-9, including without limitation alum, mineral oil emulsion such as, Fruend's complete and incomplete (IFA), lipopolysaccharide or a derivative thereof, saponins such as QS21, imidazoquinoline compounds, cytosine phosphate guanosine oligodeoxynucleotides such as CpG and cationic peptides such as IC-31.

In one embodiment, the oncolytic reovirus composition may be formulated with the goal of improving its stability in particular under the conditions of manufacture and long-term storage (i.e. for at least 6 months, with a preference for at least two years) at freezing (e.g. −70° C., −20° C.), refrigerated (e.g. 4° C.) or ambient temperatures. The oncolytic reovirus composition may be in a frozen form, liquid form or lyophilized form. For illustrative purposes, buffered formulations including NaCl and sugar are particularly adapted to the preservation of viruses (e.g. Tris 10 mM pH 8 with saccharose 5% (W/V), sodium glutamate 10 mM, and NaCl, 50 mM or phosphate-buffered saline with glycerol (10%) and NaCl).

In certain embodiments, the oncolytic virus composition can be formulated to ensure proper distribution or a delayed release in vivo. For example, it can be formulated in liposomes. Biodegradable, biocompatible polymers can be used, such as ethylene vinyl acetate, polyanhydrides, polyglycolic acid, collagen, polyorthoesters, and polylactic acid.

The appropriate dosage of oncolytic virus can be adapted as a function of various parameters and may be routinely determined by a practitioner in the light of the relevant circumstances. Suitable dosage for the oncolytic virus varies from approximately $10^5$ to approximately $10^{13}$ vp (viral particles), iu (infectious unit) or pfu (plaque-forming units) depending on the virus and the quantitative technique used. As a general guidance, reovirus doses from approximately $10^5$ to approximately $10^{13}$ pfu are suitable, preferably from approximately $10^5$ pfu to approximately $10^{11}$ pfu, e.g., from approximately $10^7$ pfu to approximately $5\times10^9$ pfu; or approximately $10^8$ pfu to approximately $10^9$ pfu. The quantity of virus present in a sample can be determined by routine titration techniques, e.g. by counting the number of plaques following infection of permissive cells using permissive cells (e.g. BHK-21 or CEF), immunostaining, by measuring the A260 absorbance (vp titers), or still by quantitative immunofluorescence (iu titers).

Administration

The oncolytic reovirus composition of the present disclosure may be administered in a single dose (e.g. bolus injection) or multiple doses. If multiple administrations are used, administrations may be performed by the same or different routes and may take place at the same site or at alternative sites. It is also possible to proceed via sequential cycles of administrations that are repeated after a rest period. Intervals between each administration can be from several hours to one year (e.g. 24 h, 20 h, 48 h, 72 h, weekly, every two weeks, monthly or yearly). Intervals can also be irregular (e.g. following tumor progression). The doses can vary for each administration within the range described above.

Any of the conventional administration routes are applicable in the context of the invention including parenteral, topical or mucosal routes. Parenteral routes are intended for administration as an injection or infusion. Common parenteral injection types are intravenous, intraarterial, intradermal, subcutaneous, intramuscular, and intratumoral (into tumor or at its close proximity). Infusions typically are given by intravenous route. Mucosal administrations include without limitation oral/alimentary, intranasal, intratracheal, intrapulmonary, intravaginal or intra-rectal route. Topical administration can also be performed using transdermal means (e.g. patch and the like). Administrations may use conventional syringes and needles or any compound or device available in the art capable of facilitating or improving delivery of the active agent(s) in the subject. In some cases, the oncolytic reovirus may be administered via intravenous or intratumoral route.

The oncolytic virus may be administered once or several time (e.g. 2, 3, 4, 5, 6, 7 or 8 times etc.) at a dose within the range of from $10^7$ to $5\times10^9$ pfu. The time interval between each administration can vary from approximately 1 day to approximately 8 weeks, advantageously from approximately 2 days to approximately 6 weeks, e.g., from approximately 3 days to approximately 4 weeks or from approximately 1 week to approximately 3 weeks (e.g. every two weeks for example). A therapeutic scheme involves from 2 to 5 (e.g. 3) intravenous or intratumoral administrations of $10^5$ or $10^9$ pfu of oncolytic reovirus at approximately 1 or 2 weeks interval.

The present disclosure also relates to a method for treating a proliferative disease such as cancer comprising administering an oncolytic virus as described herein to a subject in need thereof.

The present disclosure also relates to a method for inhibiting tumor cell growth in vivo comprising administering an oncolytic virus as described herein to a subject in need thereof.

The present disclosure also relates to a method for enhancing an immune response to tumor cells comprising administering an oncolytic virus as described herein to a subject in need thereof.

In one embodiment, the administration of the oncolytic virus stimulates and/or re-orients an immune response.

In one embodiment, the modified reovirus of the present disclosure provide a higher therapeutic efficacy than the one obtained in the same conditions with a reovirus not having the genetic modifications described herein. In some embodiments, the use of the modified reovirus of the present disclosure provides at least 5%, at least 10%, at least 15%, at least 20%, or at least 25% more therapeutic efficacy than either a parent reovirus from which the modified reovirus is derived. For example, use of the modified reovirus of the present disclosure provides at least 5%, at least 10%, at least 15%, at least 20%, or at least 25% longer survival of a cancer patient.

Examples of proliferative diseases that may be treated using the oncolytic reovirus, composition or methods described herein include bone cancer, liver cancer, pancreatic cancer, stomach cancer, colon cancer, cancer of the esophagus, oralpharyngeal cancer, lung cancer, cancer of the head or neck, skin cancer, melanoma, uterine cancer, cervix cancer, ovarian cancer, breast cancer, rectal cancer, cancer of the anal region, prostate cancer, lymphoma, cancer of the endocrine system, cancer of the thyroid gland, sarcoma of soft tissue, chronic or acute leukemias, cancer of the bladder, renal cancer, neoplasm of the central nervous system (CNS), glioma, etc. Non-limiting specific examples of cancers for treatment include melanoma (e.g. metastatic malignant melanoma), renal cancer (e.g. clear cell carcinoma), prostate cancer (e.g. hormone refractory prostate adenocarcinoma), breast cancer, colorectal cancer, lung cancer (e.g. non-small cell lung cancer) and liver cancer (e.g. hepatocarcinoma).

The oncolytic virus, composition or method disclosed herein can be associated with one or more substances or therapy effective in anticancer therapy. For example, the treatment methods of the present disclosure may include delivering to the subject of an additional cancer therapy. The additional cancer therapy may be surgery, radiation, chemotherapy, immunotherapy, hormone therapy or a combination thereof. Among pharmaceutical substances effective in anticancer therapy which may be used in association or in combination with the oncolytic virus, composition or method according to the present disclosure, may be S alkylating agents such as e.g. mitomycin C, cyclophosphamide, busulfan, ifosfamide, isosfamide, melphalan, hexamethylmelamine, thiotepa, chlorambucil, or dacarbazine; antimetabolites such as, e.g. gemcitabine, capecitabine, 5-fluorouracil, cytarabine, 2-fluorodeoxy cytidine, methotrexate, idatrexate, tomudex or trimetrexate; topoisomerase II inhibitors such as, e.g. doxorubicin, epirubicin, etoposide, teniposide or mitoxantrone; topoisomerase I inhibitors such as, e.g., irinotecan (CPT-11), 7-ethyl-10-hydroxy-camptothecin (SN-38) or topotecan; antimitotic drugs such as, e.g., paclitaxel, docetaxel, vinblastine, vincristine or vinorelbine; S platinum derivatives such as, e.g., cisplatin, oxaliplatin, spiroplatinum or carboplatinum; inhibitors of tyrosine kinase receptors such as sunitinib (Pfizer) and sorafenib (Bayer); anti-neoplastic antibodies in particular antibodies that affect the regulation of cell surface receptors such as trastuzumab, cetuximab, panitumumab, zalutumumab, nimotuzumab, matuzumab, bevacizumab and ranibizumab; EGFR (for Epidermal Growth Factor Receptor) inhibitors such as gefitinib, erlotinib and lapatinib; and immunomodulatory agents such as, e.g. alpha, beta or gamma interferon, interleukin (in particular IL-2, IL-6, IL-10 or IL-12) or tumor necrosis factor.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Materials and Methods

Cell lines. L929, NIH/3T3, H1299, ID8, B16-F10 cells (Dr. Patrick Lee, Dalhousie University), Huh7.5 (Dr. Michael Houghton, University of Alberta) and BHK-21-BSR T7/5 (Dr. Ursula Buchholz, NIAID) were generous gifts. All media was supplemented with 1× antibiotic antimycotics (A5955, Millipore Sigma). Except for NIH/3T3 media that was supplemented with 10% NCS (N4637, Millipore Sigma), all other media was supplemented with 10% FBS (F1051, Millipore Sigma). L929 cells were cultured in MEM (M4655, Millipore Sigma) supplemented with 1× non-essential amino acids (M7145, Millipore Sigma) and 1 mM sodium pyruvate (S8636, Millipore Sigma). L929 cells in suspension were cultured in Joklik's modified MEM (M0518, Millipore Sigma) supplemented with 2 g/L sodium bicarbonate (BP328, Fisher Scientific), 1.2 g/L HEPES (BP310, Fisher Scientific), 1×non-essential amino acids (M7145, Millipore Sigma) and 1 mM sodium pyruvate (S8636, Millipore Sigma). H1299 and ID8 cells were cultured in RPMI (R8758, Millipore Sigma). NIH/3T3, B16-F10, Huh7.5 and BHK-21-BSR T7/5 cells were cultured in DMEM (D5796, Millipore Sigma) supplemented with 1 mM sodium pyruvate (S8636, Millipore Sigma). BHK-21-BSR T7/5 cells were passaged in media containing 1 mg/ml G418 (A1720, Millipore Sigma) every second passage. All cells were routinely assessed for mycoplasma contamination using Hoechst 33352 (0.5 ug/ml) (H1399, ThermoFisher Scientific).

Reovirus Stocks. Seed stock lysates of T1L, T2J, T3D-PL (Dr. Patrick Lee, Dalhousie University), T3D-KC (Dr. Kevin Coombs, University of Manitoba) and T3D-TD (Dr. Terence Dermody, University of Pittsburgh) were gifts in kind. Reoviruses were plaque purified and second passage L929 cell lysates were used as spinner culture inoculums. Reovirus extraction and purification were performed similar to previously described. Briefly, reovirus infected L929 spinner cultures at 60-70% cell death were collected by centrifugation, resuspended in HO buffer (10 mM Tris pH 7.4, 250 mM NaCl, 10 mM β-mercaptoethanol), and twice vortex extracted with Vertel XF (Dymar Chemicals Limited, ON, Canada). Reovirus containing suspensions were layered onto 1.2/1.44 g/ml CsCl gradients and ultracentrifuged for 6-8 hours. The genome-containing reovirus band was extracted and extensively dialyzed in virus dilution buffer (10 mM Tris pH 7.4, 15 mM $MgCl_2$, 150 mM NaCl).

Reovirus Plaque Assays. Reovirus dilutions were added to confluent L929 cells for 1 hour with gently rocking every 10 minutes, followed by addition of agar overlay (2% agar and 2× suspension L929 culture media in a 1:1 dilution). Overlays were allowed so solidify for 20 minutes at room temperature and transferred to 37° C. When plaques became visible (3-7 days post infection), agar overlays were incubated with 4% formaldehyde solution (33314, Alfa Aesar) for 30 minutes. Agar overlays were carefully scooped out and cells were further fixed with methanol for 5 min, stained with crystal violet solution (1% crystal violet (C581, Fisher Scientific) in 50% ethanol and 50% water) for 10 min and rinsed with water. For cell lines other than L929, after methanol staining, plaques were stained using immunocytochemistry with rabbit anti-reovirus pAb. Plaques were scanned on the ImageQuant LAS4010 imager (GE Healthcare Life Sciences), and plaque area was measured using ImageQuant TL software (GE Healthcare Life Sciences).

Primary and Secondary Antibodies. All antibodies were diluted as per manufacturer's recommendations in 3% BSA/TBS-T or 3% BSA/PBS/0.1% Triton X-100 for Western blots or immunocytochemistry, respectively.

Primary: Rabbit anti-reovirus pAb (Dr. Patrick Lee, Dalhousie University), rabbit anti-σ1C pAb (Dr. Roy Duncan, Dalhousie University), rabbit anti-μ2 pAb (in-house, ProSci Inc), mouse anti-σNS mAb (3E10, DSHB), mouse anti-σ3 mAb (10G10, DSHB), rabbit anti-RIG-I mAb (3743, CST), rabbit anti-IRF3 pAb (9082, SCBT), rabbit anti-P-IRF3 mAb (4947, CST) and mouse anti-β-actin mAb (47778, SCBT).

Secondary: Goat anti-rabbit HRP (111-035-144, JIR), goat anti-mouse HRP (115-035-146, JIR), goat anti-rabbit Alexa Fluor 647 (111-605-144, JIR), goat anti-rabbit Alexa Fluor 488 (111-545-144, JIR) goat anti-mouse Alexa Fluor 647 (115-605-146, JIR).

Immunocytochemistry. Prior to primary antibody incubation, cells were blocked and permeabilized with 3% BSA/PBS/0.1% Triton X-100 for 1 hour at room temperature. Samples were washed 3×5 minutes with PBS/0.1% Triton X-100 after antibody incubations.

Plaque assays: Following methanol fixation, samples were blocked and permeabilized and sequentially incubated with rabbit anti-reovirus pAb and goat anti-rabbit alkaline phosphatase. Plaques were visualized following exposure to NBT/BCIP substrate diluted in AP buffer (100 mM Tris pH 9.5, 100 mM NaCl, 5 mM $MgCl_2$). When plaques had stained a dark purple color, reactions were stopped using PBS/5 mM EDTA. 100× substrate stocks were diluted as follows in DMF (D4551, Millipore Sigma): NBT (30 mg/1 ml) (B8503, Millipore Sigma), BCIP (15 mg/1 ml) (N6639, Millipore Sigma).

Infectivity assay: Cells were washed with PBS and fixed with 4% paraformaldehyde for 30 minutes at 4° C. Cells were blocked and permeabilized and sequentially incubated with rabbit anti-reovirus pAb and goat anti-rabbit Alexa Fluor 488. Nuclei were stained with Hoechst 33352 (0.5 ug/ml) (H1399, ThermoFisher Scientific) for 15 min and stained samples were visualized and imaged using EVOS FL Auto Cell Imaging System (ThermoFisher Scientific). For confocal microscopy, cells were seeded on #1.5 thickness coverslips. Following staining, coverslips were mounted using SlowFade Diamond (S36967, ThermoFisher Scientific) and visualized using an Olympus IX-81 spinning disk confocal microscope (Quorum Technologies). Primary mAbs mouse anti-σNS and mouse-anti-σ3 were conjugated to Alexa Fluor 568 and Alexa Fluor 647, respectively, using APEX antibody labeling kits (ThermoFisher Scientific).

Flow cytometry: Cells were detached with trypsin, processed similar to the infectivity assays excluding Hoechst 33352 staining, and analyzed using FACSCanto (BD Biosciences)

RNA extraction and RT-PCR. Cells were lysed in TRI Reagent (T9424, Millipore Sigma) and aqueous phase was separated following chloroform extraction. Ethanol was mixed with the aqueous phase and RNA isolation protocol was continued as per GenElute Mammalian Total RNA Miniprep Kit (RTN350, Millipore Sigma). cDNA synthesis was performed with random primers (48190011, ThermoFisher Scientific) using M-MLV reverse transcriptase (28025013, ThermoFisher Scientific). Following a 1:8 cDNA dilution, RT-PCR reactions were executed as per SsoFast EvaGreen Supermix (1725204, Bio-Rad) instructions using a CFX96 system (Bio-Rad).

Western blot analysis. Cells were rinsed with PBS and lysed in RIPA buffer (50 mM Tris pH 7.4, 150 mM NaCl, 1% IGEPAL CA-630 (NP-40), 0.5% sodium deoxycholate) supplemented with protease inhibitor cocktail (11873580001, Roche) and phosphatase inhibitors (1 mM sodium orthovanadate, 10 mM β-glycerophosphate, 50 mM sodium fluoride).

Following addition of 5× PROTEIN sample buffer (250 mM Tris pH 6.8, 5% SDS, 45% glycerol, 9% β-mercaptoethanol, 0.01% bromophenol blue), samples were heated for 5 min at 100 C and loaded onto SDS-acrylamide gels. After SDS-PAGE, separated proteins were transferred onto nitrocellulose membranes using the Trans-Blot® Turbo™ Transfer System (Bio-Rad). Membranes were blocked with 3% BSA/TBS-T and incubated with primary and secondary antibodies as per manufacturer's recommendations. HRP-conjugated antibodies were exposed to ECL Plus Western Blotting Substrate (32132, ThermoFisher Scientific). Membranes were visualized using ImageQuant LAS4010 imager (GE Healthcare Life Sciences), and densitometric analysis was performed by using ImageQuant TL software (GE Healthcare Life Sciences).

Double-stranded genomic RNA visualization. RNA was extracted from CsCl purified reovirus preparations (~1×10$_{10}$ virus particles) using TRI Reagent LS (T3934, Millipore Sigma) as per manufacturer's protocol. Purified RNA was diluted in 4× Laemmli sample buffer (1610747, Bio-Rad), and separated on an 8% SDS-acrylamide gel for 22 hours at 6 mA (per gel) at 4° C. RNA was stained using ethidium bromide and gels were imaged on ImageQuant LAS4010 imager (GE Healthcare Life Sciences).

Reovirus binding assay. L929 cells (5×10$_{10}$ cells/sample) were detached with CellStripper (Corning) and bound with normalized virions at 4° C. for 1 hour. Unbound virus was washed off and cell-bound virus was quantified using flow cytometry (FACSCanto, BD Biosciences) following sequential binding with rabbit anti-reovirus pAb and goat anti-rabbit Alexa Fluor 488. All steps were performed at 4° C. and FACS buffer (PBS/5% FBS) was used as the diluent.

Agarose gel separation of reovirus. Purified virions (5×10$_{10}$ virus particles) diluted in 5% Ficoll and 0.05% bromophenol blue were run on a 0.7% agarose gel in TAE buffer (40 mM Tris, 5 mM sodium acetate, 1 mM EDTA [pH 7.5]) for 12 hours at room temperature, stained with ethidium bromide and visualized on the ImageQuant LAS4010 imager (GE Healthcare Life Sciences)

In-vitro core transcription assay. Reovirus cores were generated by incubating purified virions with chymotrypsin (CHT) (C3142, Millipore Sigma) at 14 μg/ml for 2 hours at 37 C. CHT digest reactions were halted by adding protease inhibitor cocktail (11873580001, Roche) and incubating at 4° C. Reovirus cores were pelleted by centrifugation at 100,000 g for 2 hours at 4° C., and reconstituted in 100 mM Tris pH 8. Transcription reactions were assembled on ice to include 100 mM Tris pH 8, 10 mM MgCl$_2$, 100 μg/ml pyruvate kinase (P7768, Millipore Sigma), 3.3 mM phosphoenol pyruvate (P0564, Millipore Sigma), 0.32 units/μl RNaseOUT (Ser. No. 10/777,019, ThermoFisher Scientific), 0.2 mM rATP, 0.2 mM rCTP, 0.2 mM rGTP, 0.2 mM rUTP and 1×10$_{11}$ virus cores per 150 μl reaction. Negative control samples were set up without rATP. Reactions were allowed to proceed at 40° C. and at indicated timepoints, 40 μl transcription aliquots were added to 400 μl TRI Reagent LS (T3934, Millipore Sigma) containing 3 ng of mouse GAPDH RNA (in-vitro transcribed using T7 RiboMAX (Promega), as per manufacturer's protocol). Using 10 μg glycogen (R0551, ThermoFisher Scientific) as a carrier according to manufacturer's instructions, RNA was purified, converted to cDNA (28025013, ThermoFisher Scientific) using random primers (48190011, ThermoFisher Scientific) and RT-PCR (1725204, Bio-Rad) performed to quantify reovirus S4, reovirus M2 and mouse GAPDH. Values were standardized to GAPDH and plotted relative to 0 hours post transcription. For high throughput transcription assays, reactions were set up similar to before but spiked with 10× final SYBR Green II (S7564, ThermoFisher Scientific) and capped with ultra-clear caps. Relative fluorescence was measured at 5-minute intervals for 2 hours in a CFX96 system (Bio-Rad).

In vivo oncolysis experiments. Fifteen six-week-old female C57BL/6 mice were injected subcutaneously in the hind flank with 1×10$_5$B16-F10 cells per 100 ul per mouse. When tumors become palpable (~14 days post B16-F10 cell injection), a total of 3 equivalent doses (5×10$_8$ pfu/100 ul) were inoculated intratumorally at 2-day intervals. The negative control group was inoculated with PBS. Tumor volumes were measured in 3 dimensions using digital calipers every 2 days. Mice were sacrificed when either tumors became too large (200 mm$_3$), and/or tumors had visible signs of necrosis and ulceration.

Example 1: Identification of T3D$^{PL}$ as a Having Superior Oncolytic Activity

Oncolytic activity of laboratory strains of Serotype 3 Dearing (T3D) reoviruses was compared both in vitro and in vivo. The viruses tested included T3D Patrick Lee lab strain (T3D$^{PL}$), Terry Dermody lab strain (T3D$^{TD}$), Kevin Coombs lab strain (T3D$^{KC}$), and ATCC strain (T3D$^{ATCC}$). T3D$^{PL}$ was found to be superior to other laboratory strains with respect to oncolytic activity both in vitro and in vivo. See FIGS. 1A and 1B.

For in vitro test, the size of plaques generated by the virus, on tumorigenic cells, was used as a reflection of the virus' ability to replicate and disseminate on tumor cells. Data in FIG. 1A demonstrates that T3D$^{PL}$ is more oncolytic in vitro than T3D$^{TD}$ and T3D$^{KC}$ (and also T3D$^{ATCC}$, data not shown).

Assessment of in vivo oncolytic activity of these viruses was performed using animal models with tumors. Tumors were generated in immunocompetent mice by injecting 15 mice with B16 mouse melanoma cells. Mice were separated into 3 groups with similar tumor size representation. Mice were injected intratumorally with equivalent PFU/ml per virus, 3 times, 2 days apart. Tumor size was followed over time, to determine the ability of viruses to reduce tumor burden. Each line in FIG. 1B represents a single mouse in the group until time of death or euthanasia. In two T3D$^{PL}$-treated animals, tumors were small but become scabs (predicted to be necrotic) and were euthanized to prevent open flesh wounds and discomfort. Remaining mice were euthanized at 600 mm$^3$ tumor. As shown in FIG. 1B, T3D$^{PL}$ was more effective in reducing tumor load as compared to T3D$^{TD}$ (and T3D$^{KC}$, data not shown).

Figure 1B:
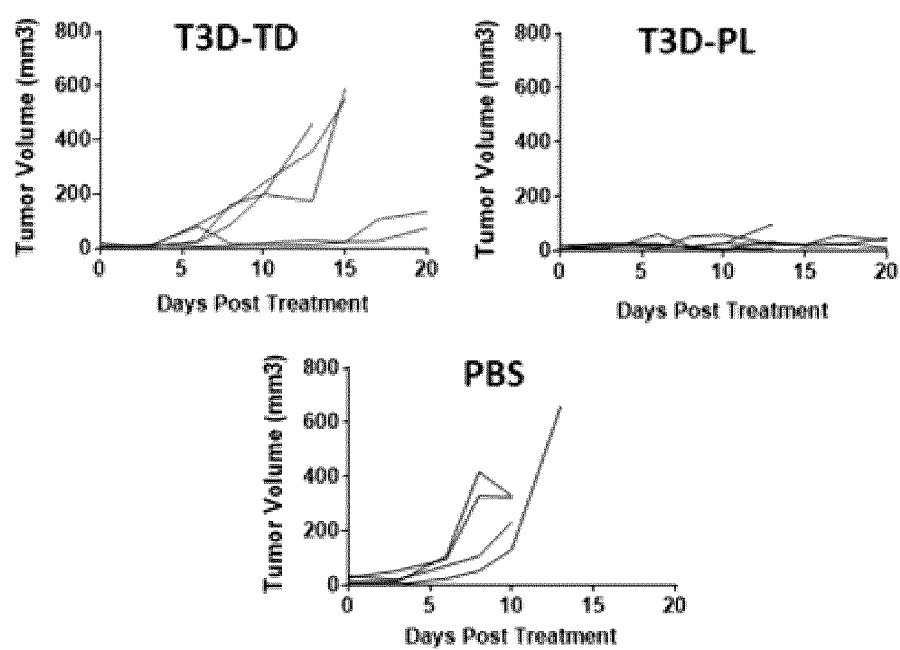
FIG. 1B. In vivo oncolysis by $T3D^{PL}$, $T3D^{TD}$ or PBS negative control.

FIG. 1A. Plaque size comparison of T3D PL, KC and TD laboratory strains obtained from Dr. Patrick Lee, Kevin Coombs, and Terry Dermody respectively. T3D$^{PL}$ causes larger plaques on human and mouse cancer cells.

FIG. 1B. In vivo oncolysis by T3D$^{PL}$, T3D$^{TD}$ or PBS negative control.

Example 2: Identification of Basis for Superior Oncolytic Activity of T3D$^{PL}$ We show that genes controlling post-entry steps of virus replication which allow it to rapidly establish robust amplification in tumor cells provide enhanced oncolysis activity to the T3D$^{PL}$ laboratory strain relative to T3D$^{TD}$ or T3D$^{KC}$.

Figure 2:
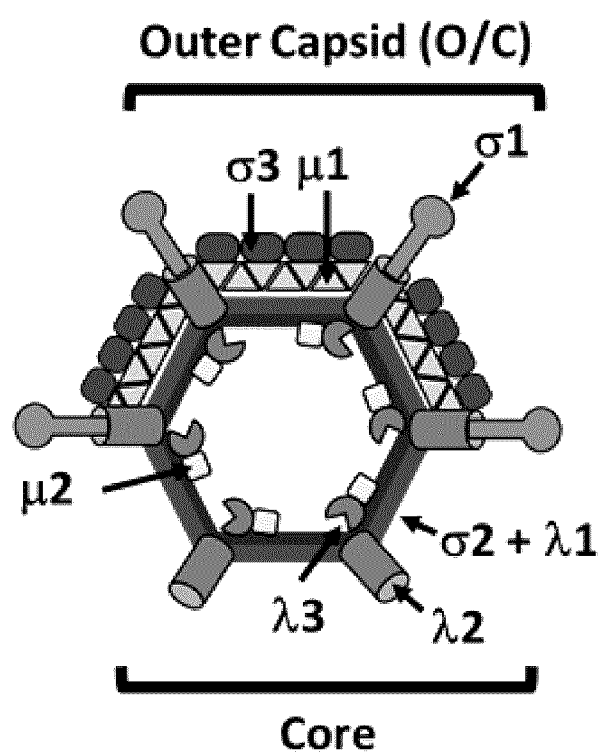
FIG. 2. Schematic of a reovirus showing a partial view of the outer capsid (O/C) and the core structure enclosed by the O/C.

A schematic of a reovirus showing a partial view of the outer capsid (O/C) and the core structure enclosed by the O/C is presented in FIG. 2. DNA and amino acid sequences of the genes in T3D$^{PL}$ virus and the proteins encoded by these genes are provided herein. Differences in the amino acid sequences of proteins expressed by various T3D$^{PL}$ and T3D$^{TD}$ strains are listed in Tables 5-7.

TABLE 5

| Gene | S1 | | | S2 | S3 | S4 | | |
|---|---|---|---|---|---|---|---|---|
| Protein | σ1 | | σ1s | σ2 | σNS | σ3 | | |
| T3D Strain\ Amino Acid Position | 22 | 408 | 77 | NONE | NONE | 133 | 198 | 229 |
| PL | A | A | H | | | R | K | D |
| TD | V | T | Y | | | W | G | E |

TABLE 6

| Gene | | | M1 | | M2 | | M3 | |
|---|---|---|---|---|---|---|---|---|
| Protein | | | μ2 | | μ1 | | μNS | |
| T3D Strain\ Amino Acid Position | 150 | 208 | 342 | 528 | 73 | 180 | 705 | 707 |
| PL | R | P | Q | S | D | E | V | D |
| TD | Q | S | R | A | E | K | A | G |

TABLE 7

| Gene | L1 | L2 | | L3 | | |
|---|---|---|---|---|---|---|
| Protein | λ3 | λ2 | | λ1 | | |
| T3D Strain\ Amino Acid Position | 979 | 1045 | 1048 | 504 | 500 | 852 |
| PL | L | R | S | E | S | H |
| TD | M | S | N | G | I | Q |

Figure 3A:
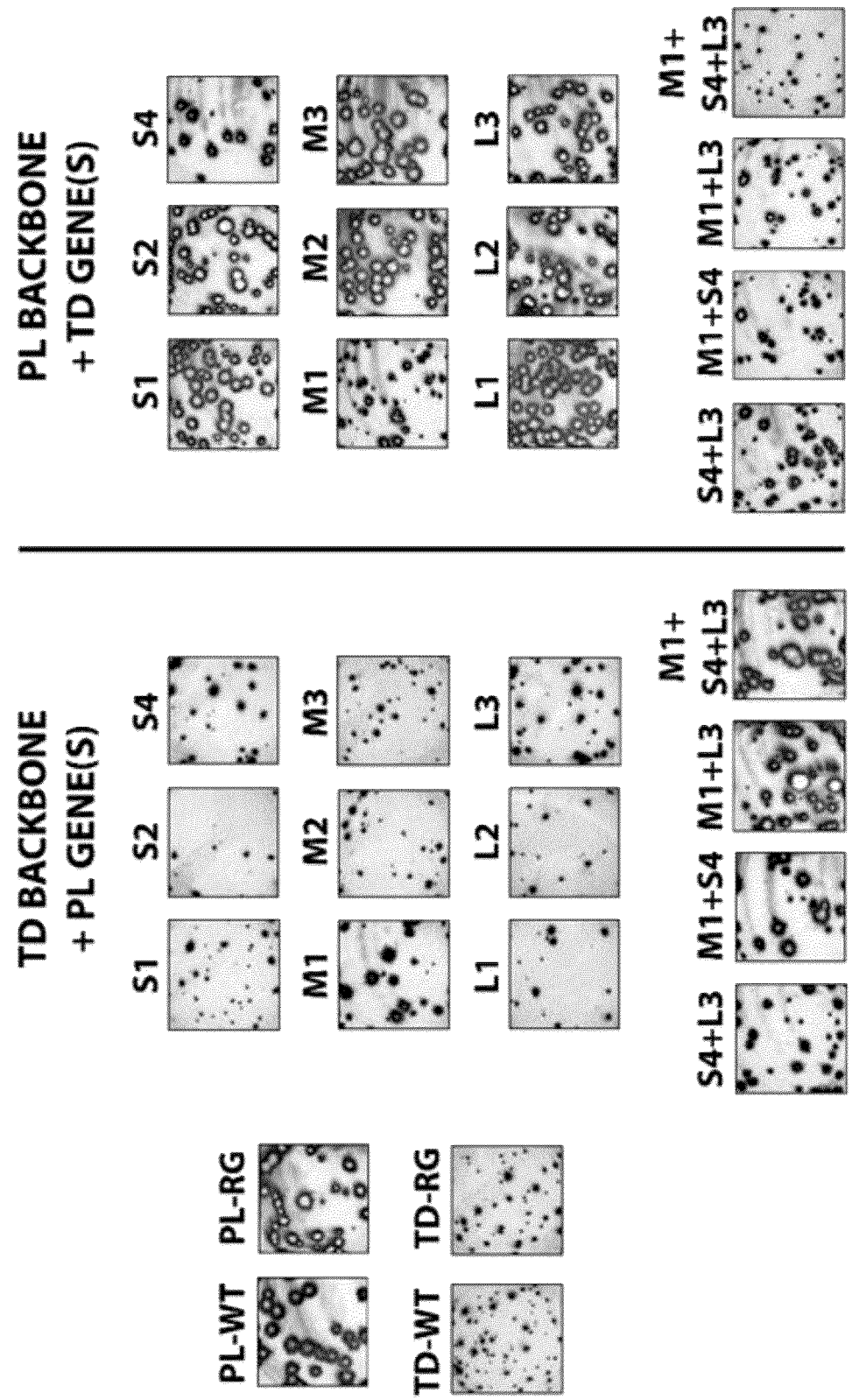
FIG. 3A-3B. Each of 10 genome segments from $T3D^{PL}$ and $T3D^{TD}$ were cloned into the reovirus reverse genetics system and used to generate viruses with mixed genomes.
Figure 3B:
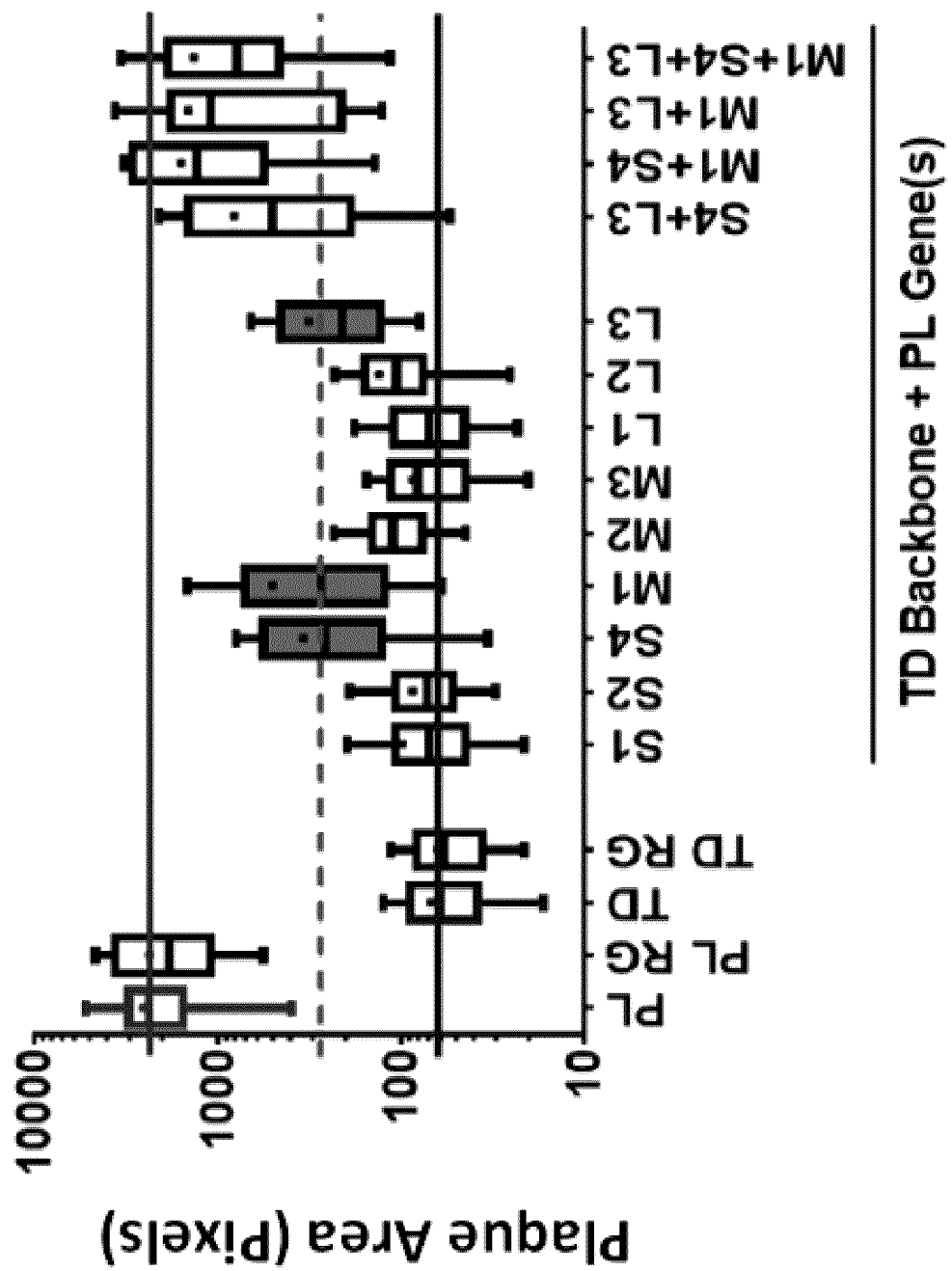

To identify which genome segments in T3D$^{PL}$ account for its superiority, reassortant viruses between T3D$^{PL}$ versus T3D$^{TD}$ were generated using reverse genetics and assayed in vivo and in vitro. 9 of 10 genome segments from T3D$^{PL}$ and T3DTD were cloned into the reovirus reverse genetics system and used to generate viruses with mixed genomes. S4, M1, and L3 genes were found to confer the superior oncolytic activity of T3D$^{PL}$. See FIGS. 3A-3B. FIG. 3B. Box and whisker plots showing the distribution of plaque size. S4 (σ3-encoding), M1 (μ2-encoding) and L3 (λ1 encoding) genes segregate with larger plaque size individually (grey) and even larger plaque size when combined.

Figure 4A:
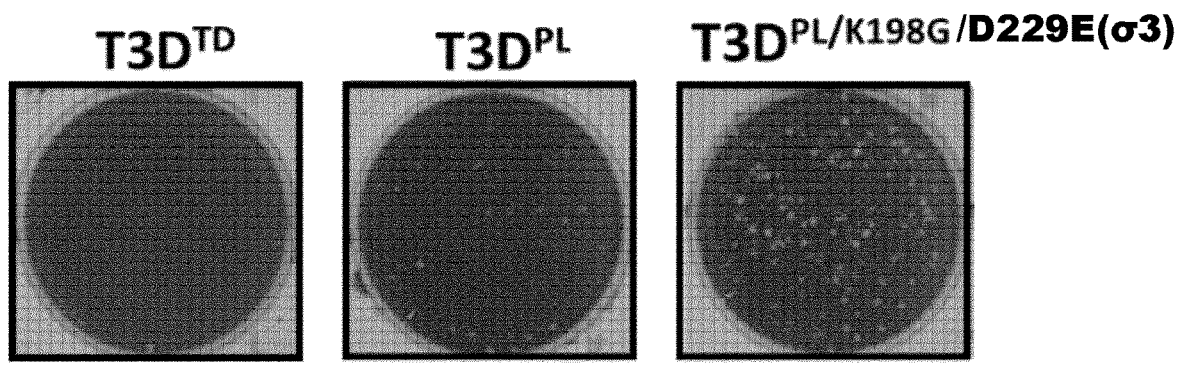
FIG. 4A. Plaque size produced by $T3D^{TD}$, $T3D^{PL}$, and $T3D^{PL}$ virus expressing PL σ3 protein comprising substitutions K198G and D229E.
Figure 4B:
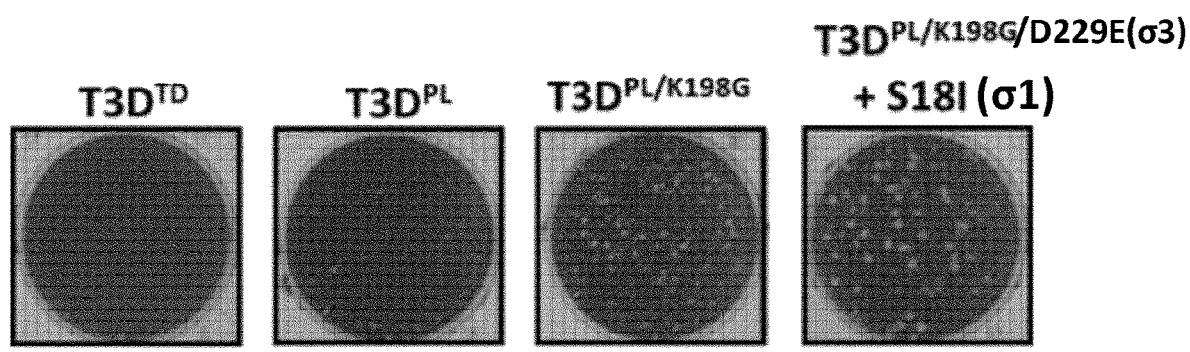
FIG. 4B. Plaque size produced by $T3D^{TD}$, $T3D^{PL}$, and $T3D^{PL}$ virus expressing PL σ3 protein comprising substitutions K198G and D229E and PL σ1 protein comprising the substitution S18I.

Example 3: Identification of Optimal Base Vector for Oncolytic Reovirus Production S4, M1, and L3 genes from T3D$^{PL}$ and T3D$^{TD}$ were compared to determine the basis for the superiority of these S4, M1, and L3 genes from T3D$^{PL}$ strain. Surprisingly, T3D$^{PL}$ S4 gene mutated to introduce two amino acid substitutions in the encoded protein σ3, which substitutions involved replacing the lysine at position 198 of the T3D$^{PL}$ σ3 protein with glycine (K198G) present at the corresponding position in T3D$^{TD}$ σ3 protein and the aspartic acid at position 229 with glutamic acid (D229E) present at the corresponding position in T3D$^{TD}$ σ3 protein dramatically improved oncolytic activity of the T3D$^{PL}$ strain (see FIG. 4A). Thus, a base vector for generation of a modified reovirus with improved oncolytic activity may include 9 of the 10 genes from T3D$^{PL}$ strain and a T3D$^{PL}$ S4 gene mutated to introduce in the encoded protein at positions 198 and 229, amino acids present at the corresponding positions in the T3D$^{TD}$ S4 gene.

Example 4: Modified Reovirus with Improved Entry into Cancer Cells or with Improved Post Entry Steps in Cancer Cells In order to identify mutations that further improve reovirus mediated oncolysis, we subjected reovirus to mutagens and selected viruses with larger plaques on various cancer cells. These larger-plaque mutants are referred to as "variants" (e.g., T3v1=variant 1 of T3D$^{PL}$). We then characterized the mechanisms of the variants, which led us to identify ways to improve the entry and post-entry steps of reovirus infection in cancer cells. Importantly, the variants maintained specificity towards cancer cells (i.e. they remain harmless to non-transformed cells).

Our previously published work (Mohamed, A. et al., J. Virol 89, 4319-4334, doi:JVI.03651-14 [pii]; 10.1128/JVI.03651-14 [doi] (2015); Mohamed, A. et al., Viruses 7, 6251-6278, doi:10.3390/v7122936 (2015); and Shmulevitz, M., et al. J Virol 86, 7403-7413 (2012)) shows the mechanisms for improved oncolysis by T3v1 and T3v2. These variants can more-efficiently enter cancer cells and establish an infection, because they can more-efficiently remove their σ1 cell attachment protein after entry which is a necessary step for them to initiate an infection. The key feature of these variants is that they have fewer σ1-per-virus, resulting in faster removal of σ1. In the natural site of reovirus infection, the intestine, digestive enzymes facilitate this entry step. But when reovirus is used to infect cancer cells instead of the intestine, this entry step is inefficient. Thus, T3v1 and T3v2 are better adapted for infecting cancer cells and hence are more oncolytic in animal cancer models. T3v2 has a single mutation in the cell attachment protein σ1 (S18I). T3v1 has a key mutation (M1101I) in the λ2 protein which anchors σ1 in virions, but also mutations in λ3 (P400S) and λ1 (N138D) that help support T3v2 activity.

We found that adding the σ1 (S18I) mutation from T3v2 into the "best base vector" T3D$^{PL/K198G/D229E}$ further improves oncolysis of cancer cells as evidenced by plaque size. See FIG. 3B.

We have identified new mutations that can reduce the level of σ1 and thereby promote reovirus oncolysis. We have also identified the domains important for assembly of σ1 on virions. Mutations in these domains reduce σ1-per-virion and improve entry. In addition, we have identified mutations that promote post-entry steps of virus replication, such that while these variants bind, enter, uncoat (shed proteins like σ1) as efficiently as wild-type, these variants produce more proteins and viruses upon infecting cancer cells. These variants with improved post-entry activity have the same levels of σ1-per-virion as wild type virus and therefore are unique from the variants having mutations that decrease levels of σ1-per-virion.

Figure 5A:
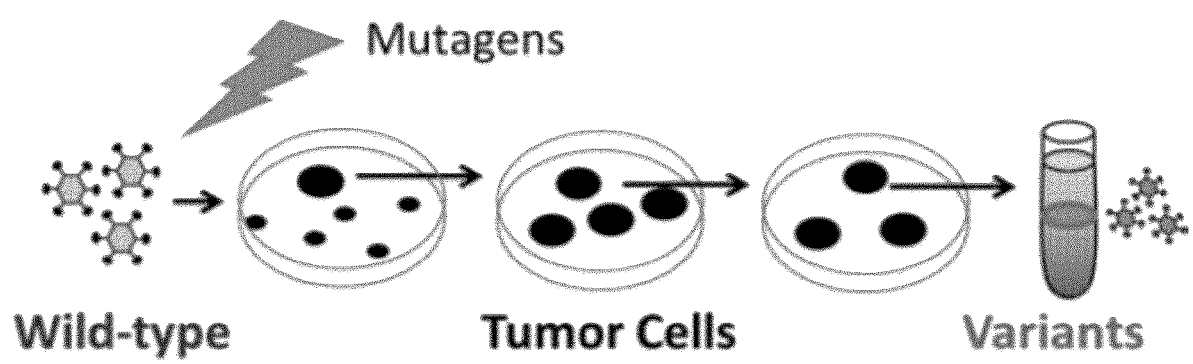
FIG. 5A-5J. Reovirus mutants with improved replication and/or dissemination in cancer cells.
Figure 5B:
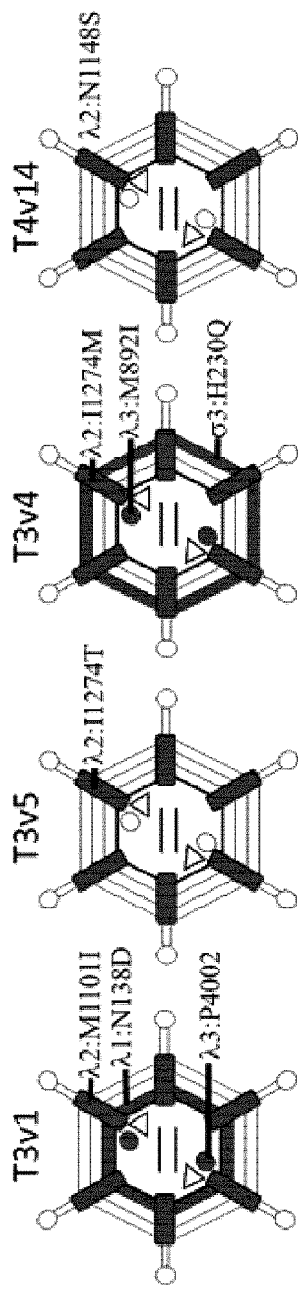
Figure 5B:
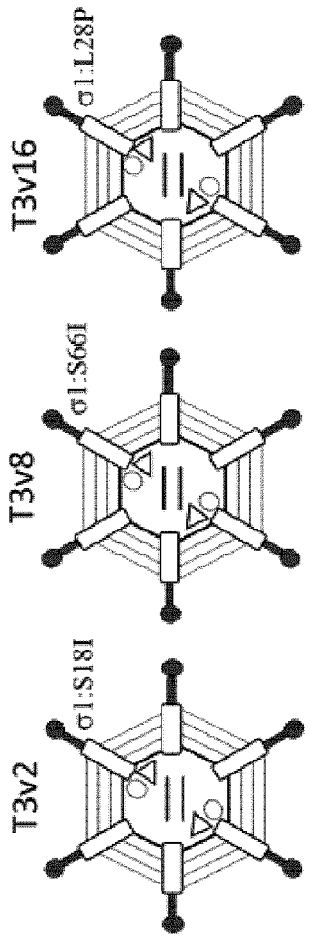
Figure 5B:
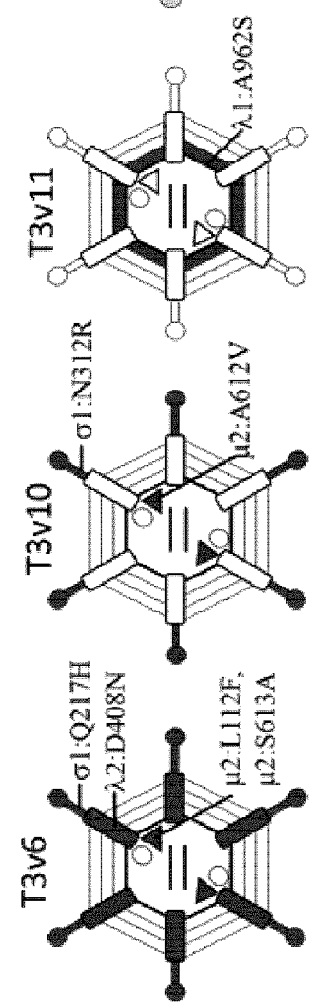

Strategy for selecting reovirus mutants with improved replication and/or dissemination in cancer cells is depicted in FIG. 5A. Large plaques were plaque-purified 3 times, propagated and purified. FIG. 5B shows the location of mutations in the variants.

Figure 5C:
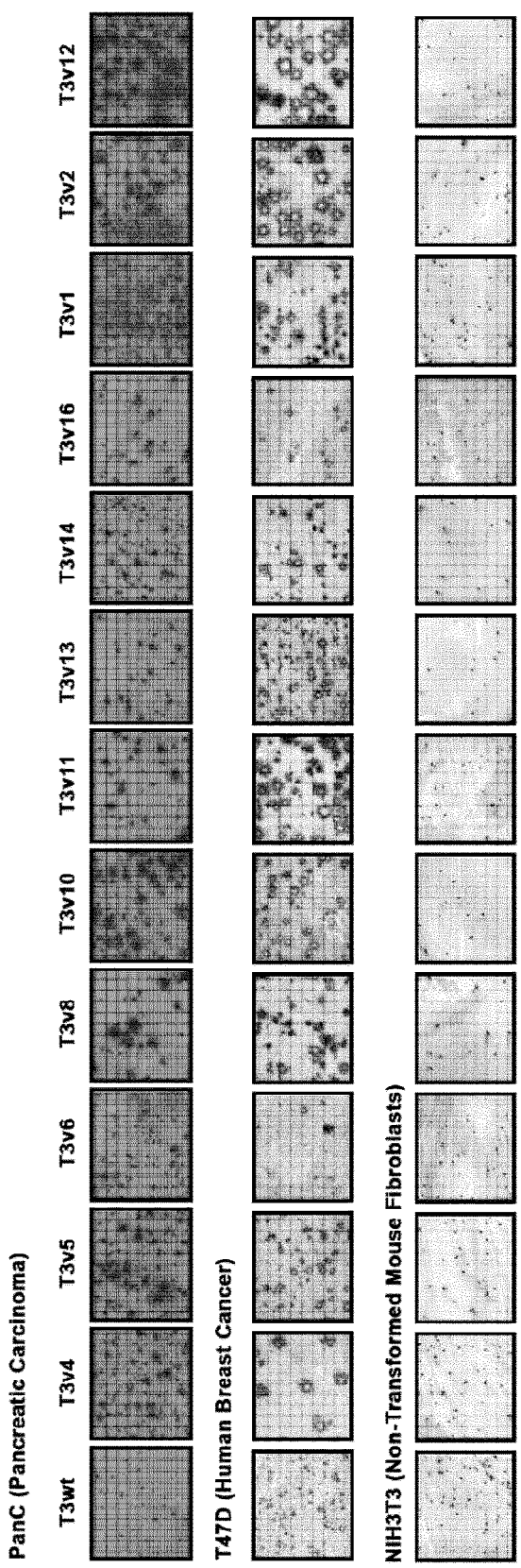
Figure 5D:
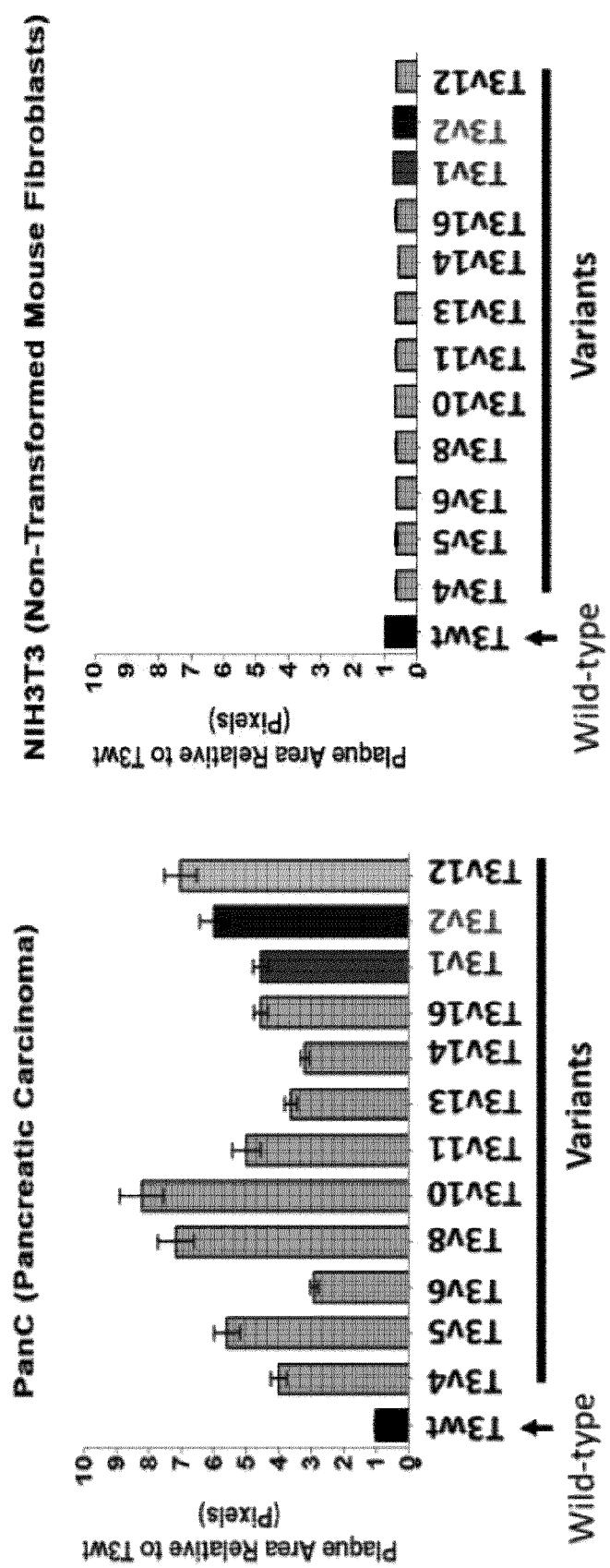

FIG. 5C, reovirus variants (T3v1-T3v16) produce larger plaques relative to wild type T3D$^{PL}$ (T3 wt) on two human cancer cell lines, but continue to produce only 1-3-cell foci on non-transformed cells showing retained specificity for cancer cells. Plaques were detected by immunocytochemistry with polyclonal anti-reovirus antibodies. FIG. 5D shows average plaque size for 4 independent experiments, >50 plaques minimum, with SD.

Figure 5E:
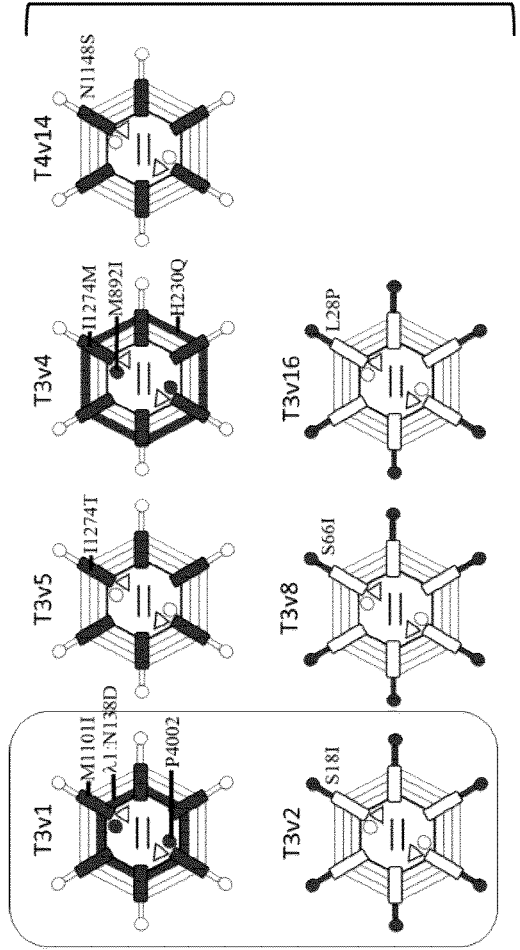
Figure 5E:
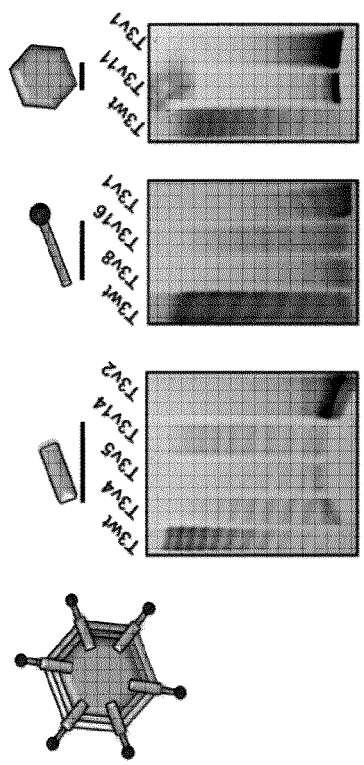

FIG. 5E shows position of mutations in variants T3v1, T3v2, T3v4, T3v5, T3v8, T3v14, T3v16 and characterization of levels of λ2, σ1, and core protein in T3 wt and variants, T3v2, T3v4, T3v5, and T3v14.

Data for characterization of mutants, T3v10 and T3v10$^{M1}$ (the μ2 A612V mutation isolated from T3v10) are provided. T3v10 includes two mutations, one in the S1 gene segment encoding a mutant σ1 protein with the substitution N312R and one in the M1 gene segment encoding a mutant μ2 protein with the substitution A612V. T3v10$^{M1}$ only includes the mutation in the M1 gene segment encoding the mutant μ2 protein with the substitution A612V while the S1 gene segment is not mutated. T3v10 and T3v10$^{M1}$ showed equal efficiency at early steps (FIGS. 5F-5H) but benefits at post-entry steps (FIGS. 5I-5J).

Figure 5F:
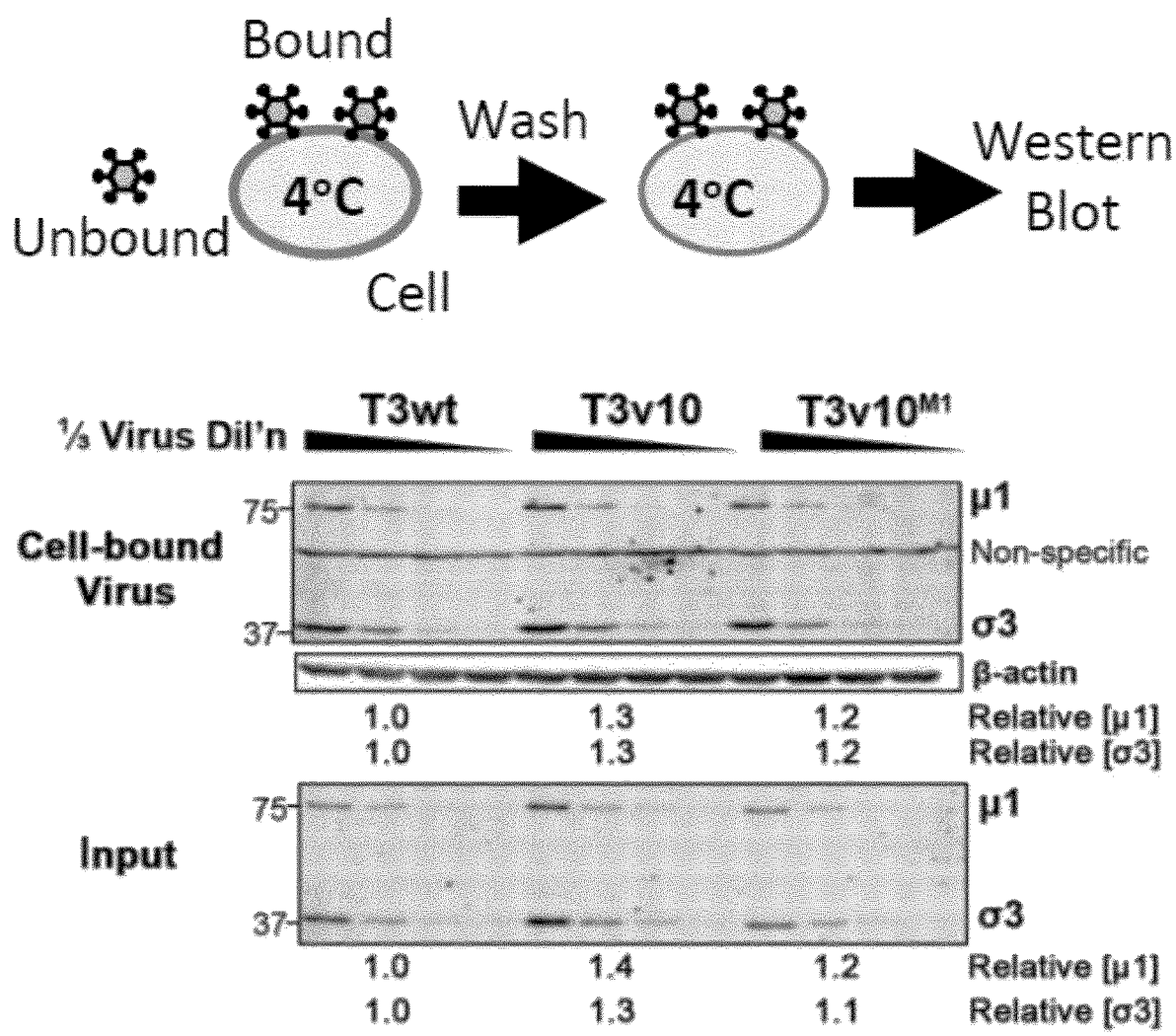

FIG. 5F. For binding experiments, L929 mouse tumor cells were exposed to equal number of particles of T3 wt versus variants at 4° C. for 1 hr, then washed extensively. Input (bottom) or cell-bound virus (top) was detected by western blot analysis with anti-reovirus antibodies.

Figure 5G:
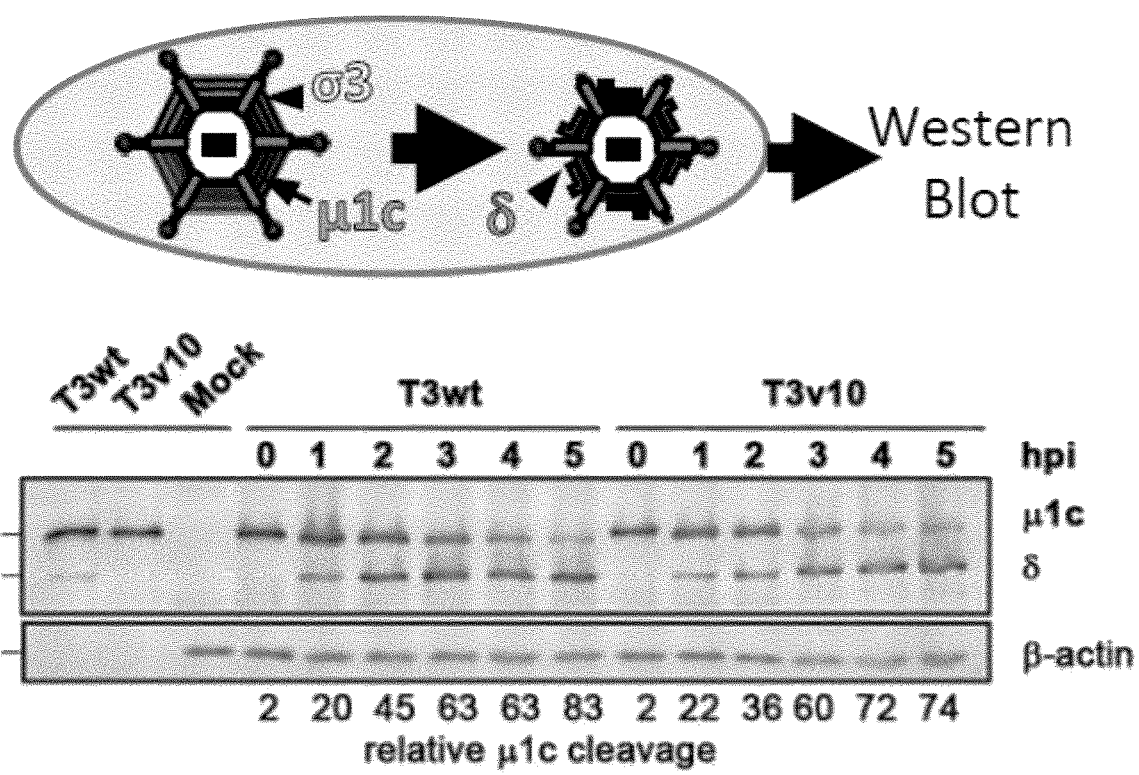

FIG. 5G. Outercapsid uncoating was monitored in L929 cells exposed to equivalent dose of viruses at 1-5 hours post incubation at 37° C. Cleavage of μ1 protein (μ1C) to δ is a hallmark of uncoating.

Figure 5H:
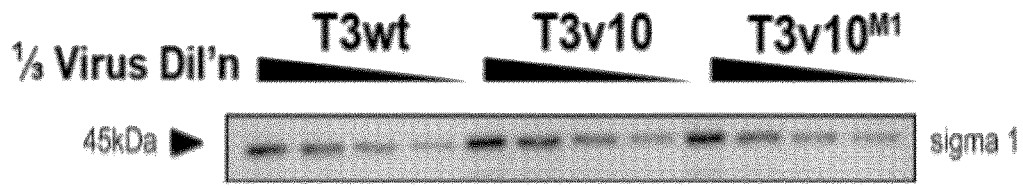
Figure 5I:
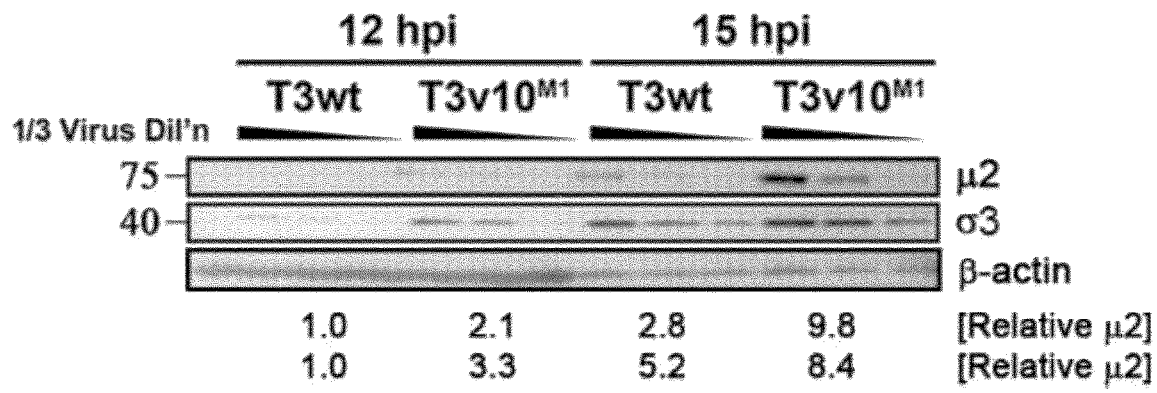
Figure 5J:
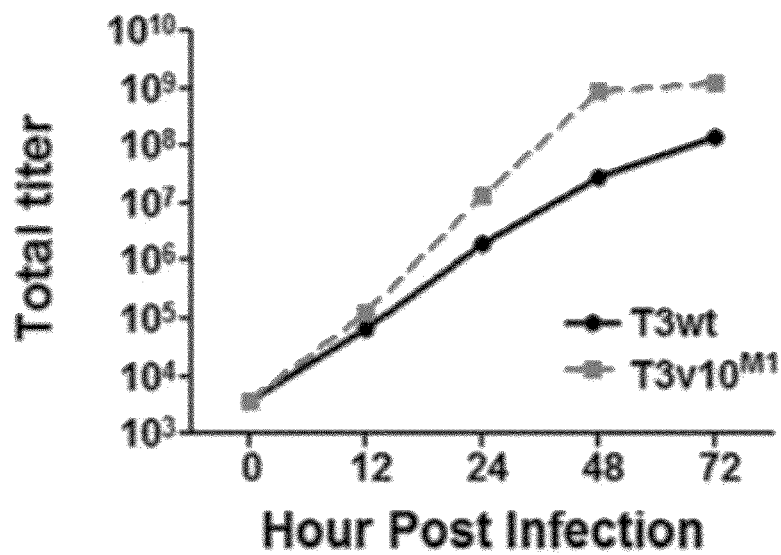

FIG. 5H. Levels of σ1 on purified virions was assessed with anti-σ1 immunoblotting. Unlike T3v1 and T3v2 that have decreased σ1-pervirion levels, T3v10/T3v10M1 have equivalent σ1 levels as T3 wt.

FIG. 5I. Levels of reovirus proteins at 12 and 15 hours post-infection were assessed by wester blotting and found to be higher in T3v10$^{M1}$ than wild-type.

FIG. 5J. Reovirus titers (MOI 0.01) are higher in T3v10 then T3 wt in the first (24 h) round and subsequent rounds (24-72 h) of infection (n=3, error bars too small at log scale to see). All results are representative of at least 3 independent experiments.

Example 5: Modified Reovirus Resistant to Inactivation by Tumor-Associated Extracellular Proteases Reovirus σ1 cell attachment protein has the following domains from the N-terminus to the C-terminus: a 27 amino acids long anchoring domain; a coil-coil tail domain (extending from amino acids 28-154); a body domain which includes a flexible linker (amino acids 155-169), SA-binding region (amino acids 170-235), GATE domain (amino acids 236-251), β-sheet region (amino acids 251-289); a neck domain (amino acids 290-295); and a head domain (amino acids 296-455). The tail domain binds sialic acid and the head domain binds JAM-1. See FIG. 6.

Tumors release many proteases into their extracellular environment. We analyzed breast cancer tumors from mice and isolated the extracellular proteins by diffusion. We found that reovirus treated with tumor extracellular extract (TE) lost 99% of their activity of infection cancer cells. Moreover, we found out that this loss-of-activity was due to metal-dependent proteases-mediated removal of the σ1 "head" and leaving the viruses with the tail domain for binding to cells via sialic acids. On cancer cells where sialic acids were limited, the viruses could no longer bind.

It was previously found that some naturally occurring reoviruses have a mutation in σ1 (T249L) that makes it resistant to proteases found in the gut (Chappell, J. D. et al. J Virol 72, 8205-8213 (1998)). We found that T249L, when introduced into T3D$^{PL}$, made σ1 resistant to tumor-associated proteases. Therefore we propose that oncolytic reovirus will be improved if mutated to resist cleavage by tumor-associated proteases.

Figure 7:
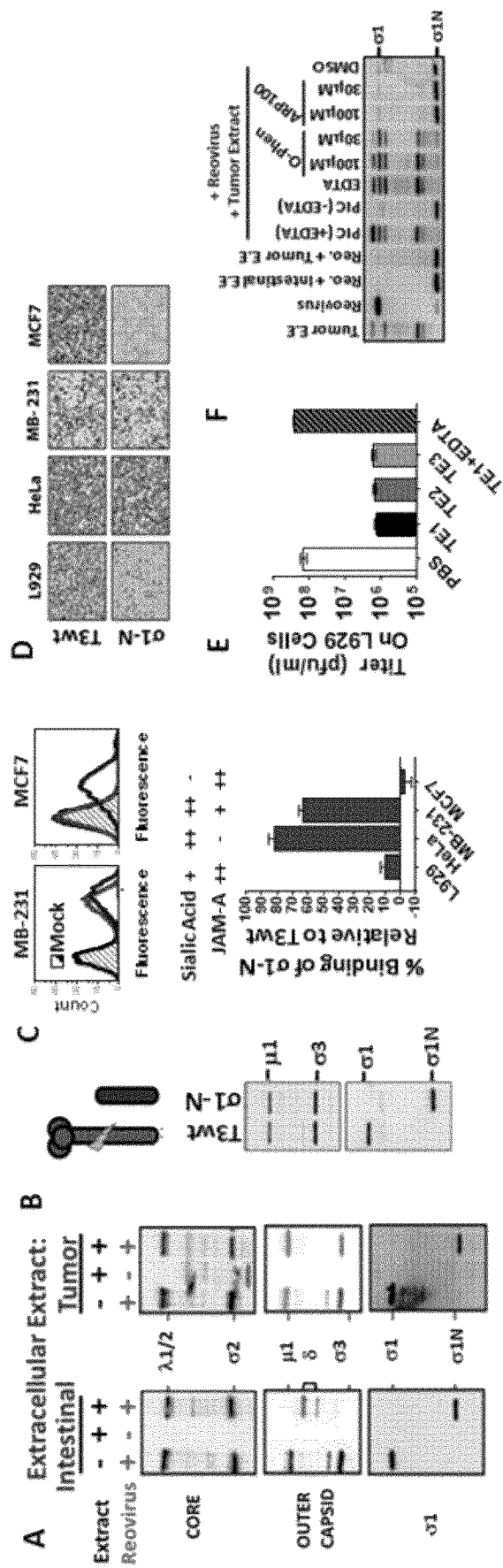
FIG. 7. Panels A-F. Tumor Extracellular Extract (TEE) cleaves reovirus σ1 and truncation of reovirus σ1 impairs binding to cells with low sialic acid levels.
Figure 8:
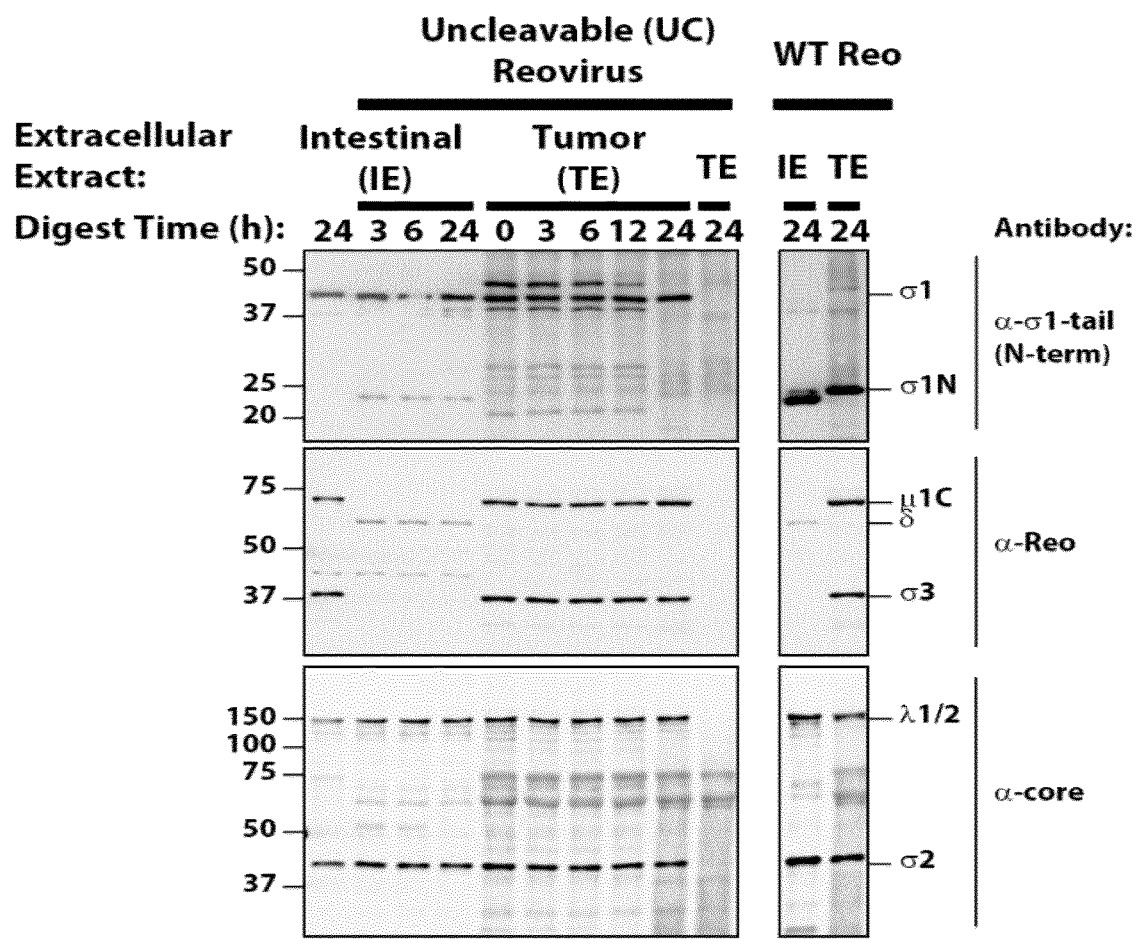
FIG. 8. Analysis of effect of Tumor Extract (TE) and Intestinal Extract (IE) on digestion of σ1, σ3, σ2, μ1, λ1, and λ2 proteins.

FIG. 7. Tumor Extracellular Extract (TEE) cleaves reovirus σ1 and truncation of reovirus σ1 impairs binding to cells with low sialic acid levels. (A) Reovirus treated with TEE or Intestinal Extracellular Extract (IEE) for 24 h at 37° C. were subjected to western blot analysis for reovirus proteins as indicated. (B) Diagram showing the full-length σ1 on T3 wt versus the truncated σ1 on σ1-N mutant virus. (Bottom) Western blot analysis confirms σ1 is truncated to σ1-N (tail domain) in σ1-N virus. (C) Measuring virus-cell binding. Cells were incubated with reovirus at 4° C. for 1 hr, washed, and bound virus was measured using anti-reovirus antibodies and flow cytometric analysis relative to mock-treated (Mock). (Top) Results for MB-232 and MCF7 cells. (Bottom) Histogram shows average ±SD for 4 independent experiments, with previously published relative levels of sialic acid and JAM-A for each cell line. (E) Immunohistochemical staining for reovirus protein expression shows reduced infectivity of σ1-N that corresponds to reduced binding potential on SA-low cells. BC Tumor Protease(s) that cleave reovirus σ1 are metalloproteases (MMP) that reduce infectivity by 100× on sialic-acid lowL929 cells. Reovirus was untreated, or treated with TEE or IEE in the presence or absence of various general inhibitors of metalloproteases (EDTA, 0-Phen) or specific MMP2/9 inhibitor ARP100. (E) Reovirus treated with TEEs from 3 independent mouse tumors shows 100× reduced infectivity towards L929 cells by plaque assay titration. Inclusion of EDTA with TEE1 and reovirus overcomes reovirus titer reduction. (F) Western blot analysis shows σ1 cleavage under different treatment conditions. See also FIG. 8.

Proteolysis of reovirus by intestinal proteases chymotrypsin and trypsin was previously shown to occur in the flexible protease-hypersensitive region (residues 219-264) in σ1 (FIG. 9A). This flexible protease-hypersensitive region (residues 219-264) is referred to as "neck" domain. If tumor-associated metalloproteases also cleaved in the neck domain, then the σ1N fragments generated by tumor extracellular extract (T.E.E.), intestinal extracellular extract (I.E.E.), trypsin, and chymotrypsin should share a similar molecular weight. Indeed, the tail (σ1N) and head (σ1C) fragments detected by Western blot analysis with σ1N- and σ1C-specific antibodies (respectively) were similar when reovirus was treated with T.E.E., I.E.E., trypsin, or chymotrypsin (FIG. 9B). Since chymotrypsin and trypsin cleavage sites are six amino acids apart but the size of their σ1 cleavage fragments are not resolved, it was inferred that the tumor-associated MP cleaves in the same general vicinity as the gut proteases.

It was previously observed that a change from threonine to isoleucine at position 249 of σ1 can prevent cleavage by both chymotrypsin and trypsin despite their different cleavage locations in the neck domain (Chappell J D, et al., J Virol. 1998 October; 72(10):8205-13). These findings suggested that the T249I modification eliminated cleavage susceptibility by altering the secondary structure of the neck domain, thereby altering the exposure of the hyper-cleavage domain. Accordingly, we predicted that mutation of T249 to isoleucine in T3D could also prevent cleavage by tumor-associated metalloproteases. Using reverse genetics, we introduced the T249I mutation into T3D and assessed the fate of σ1T249I after treatment with I.E.E. (FIG. 9C) or T.E.E. (FIG. 9D). As predicted, the T249I mutation impeded cleavage of σ1 by both I.E.E. and T.E.E.

Our previous studies showed that a mutation in the domain that anchors σ1 in virions, σ1-S18I, reduces the number of σ1 fibers per reovirus particle to ~4 (instead of 12 on wild-type T3D). We and others further showed that 3 σ1 trimers were sufficient to allow maximal binding to L929 and other tumorigenic cells. Moreover, having 4-7 (but fewer than 12) σ1 trimers promotes uncoating of σ1 during virus entry into tumor cells, and thereby increases reovirus oncolysis in vitro and in vivo (Mohamed A. et al., Journal of Virology 1026 2015, 89(8):4319-4334; Shmulevitz M, et al., J Virol. 2012 July; 86(13):7403-13). Having now learned about the cleavage of σ1 by breast tumor-associated metalloproteases, we reasoned that having fewer σ1 fibers would make T3DS18I hypersensitive to tumor-associated protease inactivation of JAM binding; in other words, that maintaining full-length σ1 would become less-likely if there were fewer σ1 fibers to begin with. We therefore also incorporated the T249I mutation into T3DS18I to generate a double-mutant T3DS18I/T249I. As expected, both T3DS18I and T3DS18I/T249I showed lower σ1 levels relative to T3D or T3DT249I (FIGS. 9C and 9D). Importantly however, while σ1 of T3DS18I was cleaved by I.E.E. and T.E.E., the σ1 T3DS18I/T249I was refractory to cleavage by either extracellular extract. In summary, localizing the σ1 cleavage site to the residues 219-264, and subsequently introducing a T249I mutation, allowed us to successfully generate T3D and T3DS18I variants that withstand proteolysis by breast tumor-associated metalloproteases.

It is possible that cleavage 27 of σ1 might promote virus entry, endocytosis, or uncoating; for example, a cleaved σ1 might bring viruses into closer proximity to membranes facilitating integrin binding for endocytosis or membrane penetration. To test this, L929 cells were exposed to equivalent particle doses of T3D, T3DT249I, T3DS18I or T3DS18I/T249I at 4° C., washed extensively, then incubated at 37° C. for 0-9 hours. At every hour, cells were fixed, stained for specific reovirus proteins, then analyzed by flow cytometry to follow the fate of input reovirus particles versus de novo reovirus protein expression. First, flow cytometry with λ2-specific antibodies, which cannot detect input virions (i.e., λ2 epitopes are hidden in the virion) but can detect de novo λ2 protein expression, demonstrated new virus protein expression at 8 hours post-infection (hpi). Importantly, T3D and T3DT249I demonstrated similar de novo protein synthesis levels, suggesting similar kinetics of infection (FIG. 9E). T3DS18I was similar to T3DS18I/T249I with respect to de novo λ2 expression. As expected from previous studies showing that S18I increases reovirus infectivity, both T3DS18I and T3DS18I/T249I exhibited ~3-fold more de novo λ2 expression relative to T3D and T3DT249I.

Next, polyclonal anti-reovirus antibodies and monoclonal antibodies towards σ3 that detect both input virions and de-novo virus protein synthesis, confirmed equivalent input levels for all four viruses, yet increased infectivity (or rate of infectivity) of variants containing the previously-characterized S18I mutation (FIG. 9F). Again, it is important to note that the T249I mutation did not impact the efficiency of establishing infection. Finally, antibodies directed to the tail domain of σ1 confirmed that input virions containing the S18I mutation contained ~3-fold less σ1 but produced more de-novo proteins (FIG. 9G). Altogether these results indicate that the T249I mutation does not negatively affect T3D reovirus infection whether in the context of wild-type T3D or the more oncolytic T3DS18I variant.

Since cleavage of σ1 by T.E.E. reduced attachment to SA-low cells and inhibited infectivity, we evaluated if the T249I mutation that prevents σ1 cleavage can facilitate reovirus infectivity in the presence of MPs. Accordingly, L929 cells were exposed to equivalent doses of T3D, T3DT249I, T3DS18I or T3DS18I/T249I that had been pre-treated with T.E.E., then binding was evaluated by flow cytometry (FIG. 9H), and infectivity evaluated by plaque assays (FIG. 9I). T3DT249I bound to L929 cells 16× more than T3D (FIG. 6H), indicating that it was resistant to protease cleavage. This increase in binding correlated with 16× higher virus production than T3D (FIG. 9I). T3DS18I showed lower binding and virus production than T3D probably because this mutant has reduced σ1 levels and is therefore hypersensitive to σ1 cleavage. Importantly, the dysfunction in binding and virus production was overcome by combining with the T249I mutation in T3DS18I/T249I. These results suggest that incorporating the T249I mutation into T3D generates a virus capable of resisting T.E.E.

Clinical trials using T3D as a monotherapy in several cancers have shown that T3D is a safe therapy but would benefit from enhanced efficacy (Phillips, M. B. et al., Oncolytic Virother. 2018 Jun. 14; 7:53-63). Little is known about the effects of the tumor environment on reovirus oncolytic performance. Having found that T.E.E. cleaves σ1 and reduces infectivity towards tumor cells with low sialic acid levels, and having developed σ1-"uncleavable" variants of T3D (T3DT249I and T3DS18I/T249I) (FIG. 9), we next sought to determine if these viruses can overcome attenuation by tumor proteases in vivo. We selected the MCF7 breast cancer model to test our variants, because our in vitro data showed that these cells secrete metalloprotease(s) that cleave wild-type σ1, and they are refractory to reovirus after σ1 has been cleaved.

Human MCF7 tumor xenografts were established in severely compromised NGS mice that lack mature T cells, B cells and natural killer (NK) cells. It is important to note that while reovirus is restricted to tumors and safety has been demonstrated in immunocompetent mice and in humans in clinical trials, in NSG mice the virus impairs circulation and causes black-foot syndrome owing to the severe reduction in immune restrictions. The onset of black-foot syndrome necessitates euthanasia, which prevented assessment of virus-mediated increase in long-term survival of MCF7 tumor-bearing mice. However, the MCF7 xenograft model allowed us to monitor three outcomes: (1) σ1-cleaving Zn-dependent metalloprotease activities in vivo, (2) whether σ1-uncleavable T3D variants pose any additional toxicity/safety concerns relative to T3D, and (3) the titers of σ1-uncleavable T3D variants versus wild-type T3D in tumors. In this experiment, MCF7 cells were implanted into the mammary fat pads of NSG mice. When tumors became palpable, five mice were injected intratumorally with either PBS, or plaque-forming-units (PFUs) of T3D, T3DT249I, T3DS18I or T3DS18I/T249I. Injections were repeated for a total of three times over a one week period. Mice were monitored and euthanized based on humane endpoints (first sign of black tail/black foot, or over 15% weight loss) or experimental endpoint at 45 days after the first PBS-injection.

The σ1-cleaving Zn-dependent metalloprotease activities was evaluated in MCF7 tumors excised from the 5 PBS-injected control mice at 45 days after the first PBS injection. Excised tumors were rinsed twice in PBS, cut into 4 pieces, and incubated at 4° C. in PBS for 2 hours to diffuse extracellular content. These tumor extracellular extracts (T.E.E.) were clarified by centrifugation and 0.45 um filtration. Reovirus was then exposed to the T.E.E.s and loss of full-length σ1 was monitored by Western blot analysis (FIG. 10A). Degradation of σ1 was T.E.E. dose-dependent and varied from ~10-90% depending on the tumor. Four of the five T.E.E.s showed >60% cleavage. Moreover, there seemed to be a relationship between the size of tumor and cleavage efficiency, although many more samples would be required to strengthen the correlation. Since cleavage was increased in the presence of Zn2+ and decreased in the presence of EDTA, a Zn-dependent metalloprotease is likely functioning in these tumors. However, since EDTA treatment did not completely prevent cleavage, it is also possible that additional ion-independent σ1-degrading proteases were active in MCF7 tumors.

The second objective of the in vivo experiment was to determine whether σ1-uncleavable T3D variants pose any additional safety concerns relative to wild-type T3D. As described above, reovirus causes black-foot syndrome and weight loss in NGS mice owing to dissemination to heart and circulatory system in these severely immunocompromised hosts (FIG. 10B). The onset of symptoms of toxicity for the different treatment groups is shown in FIG. 10C. Although time to symptoms varied between 25 and 32 days after the first virus inoculation, there were no significant differences among the virus treatments with respect to appearance of symptoms, although treatments with reovirus variants containing the S18I mutation trended toward longer survival. Reovirus titers in the hearts were also not significantly different between groups (FIG. 10D). Altogether, the experiment suggested that σ1-uncleavable T3D variants do not pose additional toxicity or safety concerns relative to wild-type T3D.

Finally, we assessed the relative infectious virus titers of σ1-uncleavable T3D variants versus wild-type T3D in tumors. The mean reovirus titers in homogenized tumors were $1.0 \times 10^7$, $1.6 \times 10^8$, $1.8 \times 10^8$, $3.5 \times 10^8$ PFUs for T3D, T3DT249I, T3DS18I and T3DS18I/T249I respectively (FIG. 10E). The trend suggested increasing titers for progressive addition of T249I and S18I mutations.

Figure 9:
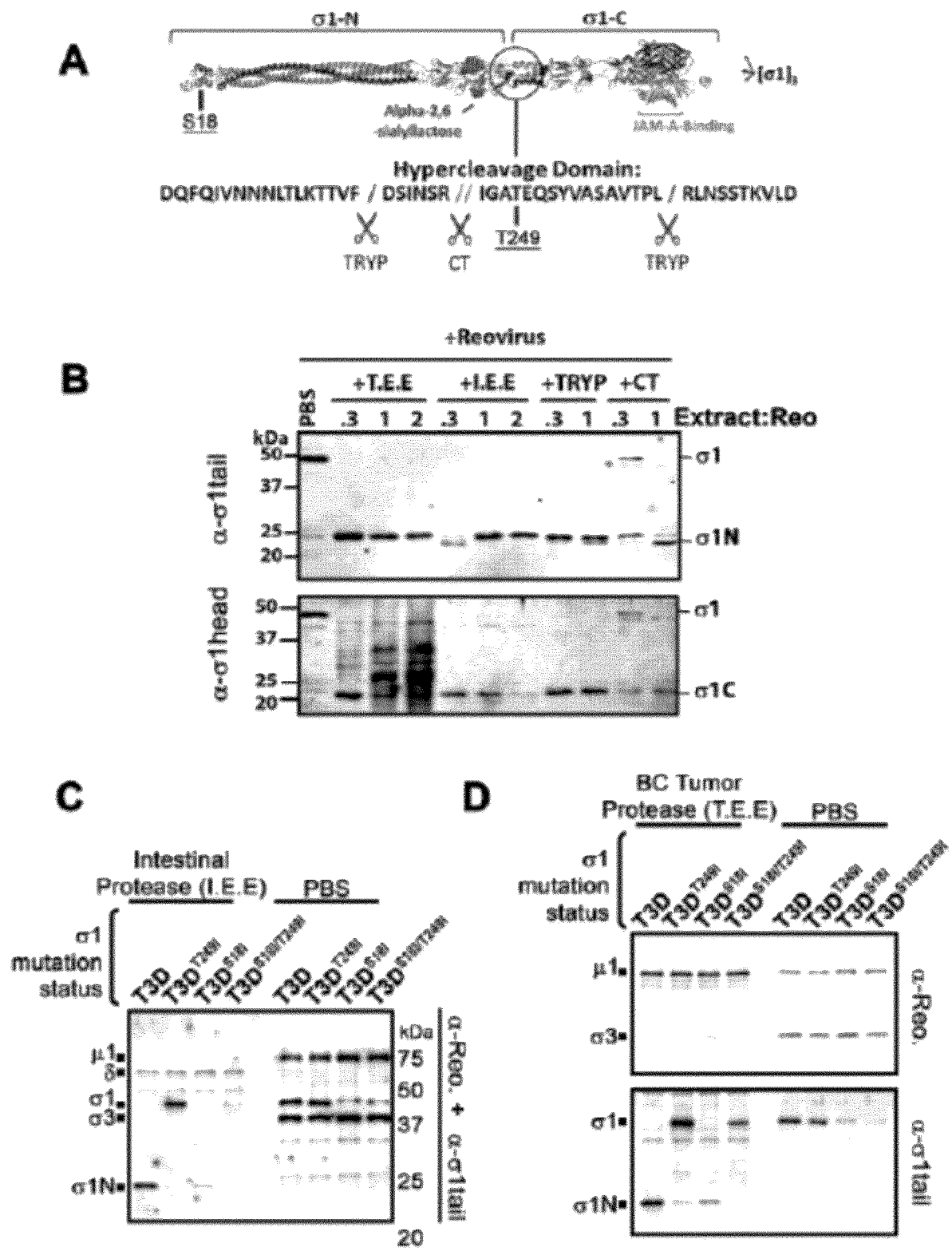
FIG. 9. Substitution of T249 in σ1 domain overcomes σ1 proteolysis by breast cancer metalloprotease.
Figure 9:
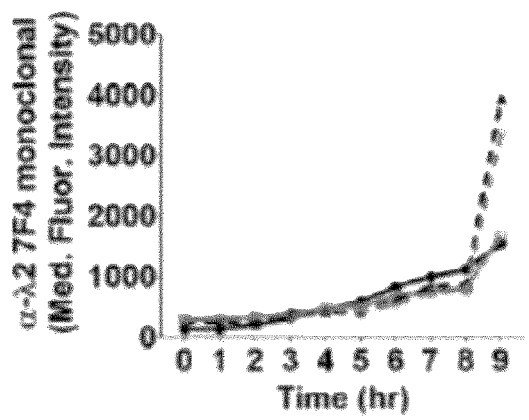
Figure 9:
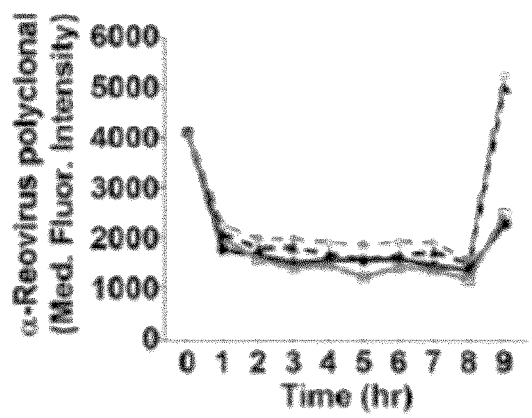
Figure 9:
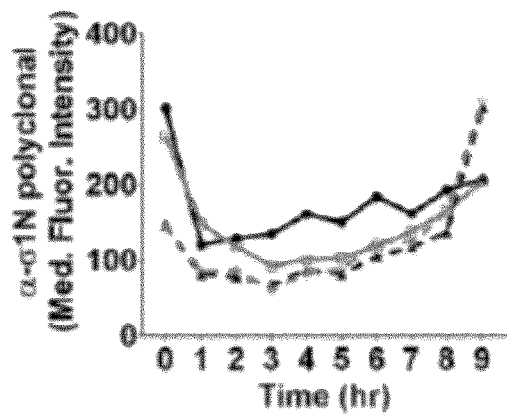
Figure 9:
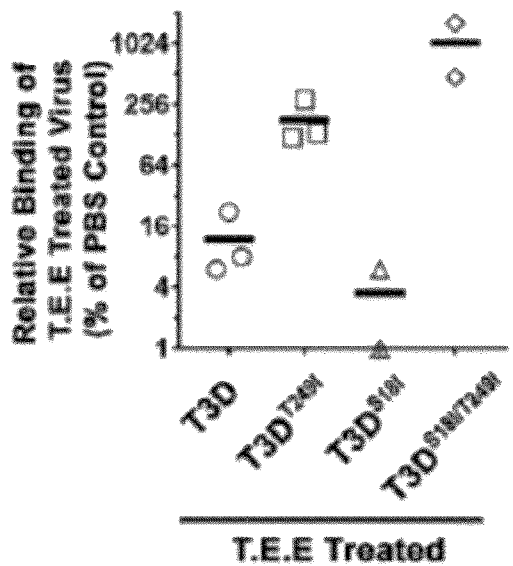
Figure 9:
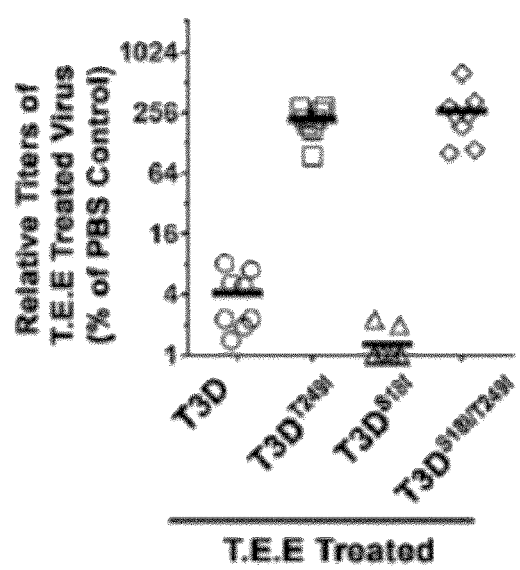

FIG. 9. Mutation at T249 in σ1 domain can overcome σ1 proteolysis by breast cancer metalloprotease. A. Diagrammatic depiction of σ1 with the protease-hypersensitive neck domain. B. Reovirus was treated with either T.E.E., I.E.E., chymotrypsin (CT) or trypsin (TRYP) for 24 hours at 37° C. and subjected to Western blot analysis with tail-(top) or head-(bottom) specific antibodies. C-D. CsCl-purified T3D, T3DT249I, T3DS18I or T3DS18I/T249I were treated with (C) PBS, I.E.E or (D) T.E.E. for 24 hours at 37° C. Western blot analysis with both polyclonal anti-reovirus antibodies and σ1N-specific antibodies demonstrate the levels of full-length σ1 and GIN. E-G. Reovirus infection dynamics of T3D, T3DT249I, T3DS18I or T3DS18I/T249I viruses. Flow cytometry was used to evaluate expression of reovirus proteins: (E) λ2, (F) σ3, (G) GIN, from 0 to 8 hours post infection. H. Binding assay as in FIG. 3 with reovirus mutants: T3D, T3DT249I, T3DS18I or T3DS18I/T249I treated with T.E.E. on L929 cells. I. Plaque titration of T.E.E. treated reovirus mutants (T3D, T3DT249I, T3DS18I or T3DS18I/T249I).

Figure 10:
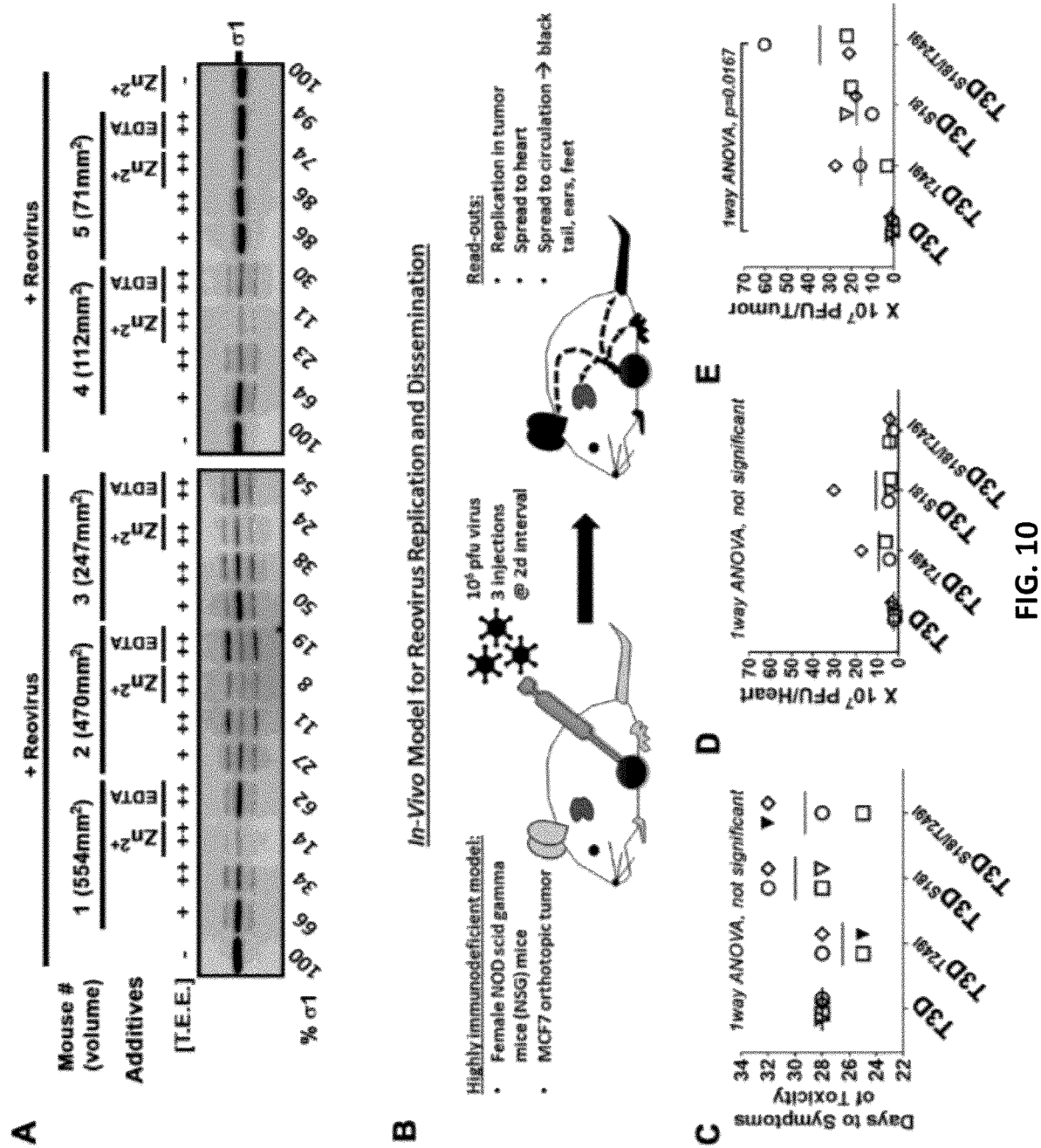
FIG. 10. Cancer metalloprotease resistant reovirus does not significantly increase toxicity and replicates efficiently in sialic acid-low cells in vivo.

FIG. 10. Uncleavable reovirus does not significantly increase toxicity and replicates efficiently in sialic acid-low cells in vivo. A. MCF7 tumors from control mice (PBS group) were excised after 45 days of in vivo tumor growth and T.E.E. was prepared. Reovirus was treated with T.E.E.s for 24 hours at 37° C., and subjected to Western blot analysis for full-length σ1. B. Diagrammatical representation of the in-vivo model used for C-F. C. Mice were euthanized when reovirus toxicity was observed (days to symptoms of toxicity), specifically when they showed first signs of blackfoot (and/or tail or ears) indicating circulation deficiencies, or lost more than 15% of body weight. We were unable to obtain tissues from the 2 mice indicated by solid-black triangles. In C-F, individual mice within each group have a unique symbol. D. Whole hearts were homogenized and subjected to plaque titration. Titers of reovirus in the heart provide a secondary measure of reovirus-induced toxicity. E. Reovirus titers in whole tumors as in D.

Example 6: Method for Controlling Types of Cytokines Induced by Reovirus in Cancer Cells We discovered that T3D$^{PL}$ and T3D$^{TD}$ stimulate very different expression profiles of cytokines. While T3D$^{TD}$ stimulates a high interferon (IFN)-dependent cytokines response, T3D$^{PL}$ stimulates a high IFN-independent, NFκB dependent cytokines response. We propose that depending on the cytokine profiles needed, one might want to use T3D$^{TD}$, T3D$^{PL}$, or reassortants (gene mixtures) between these.

Figure 11:
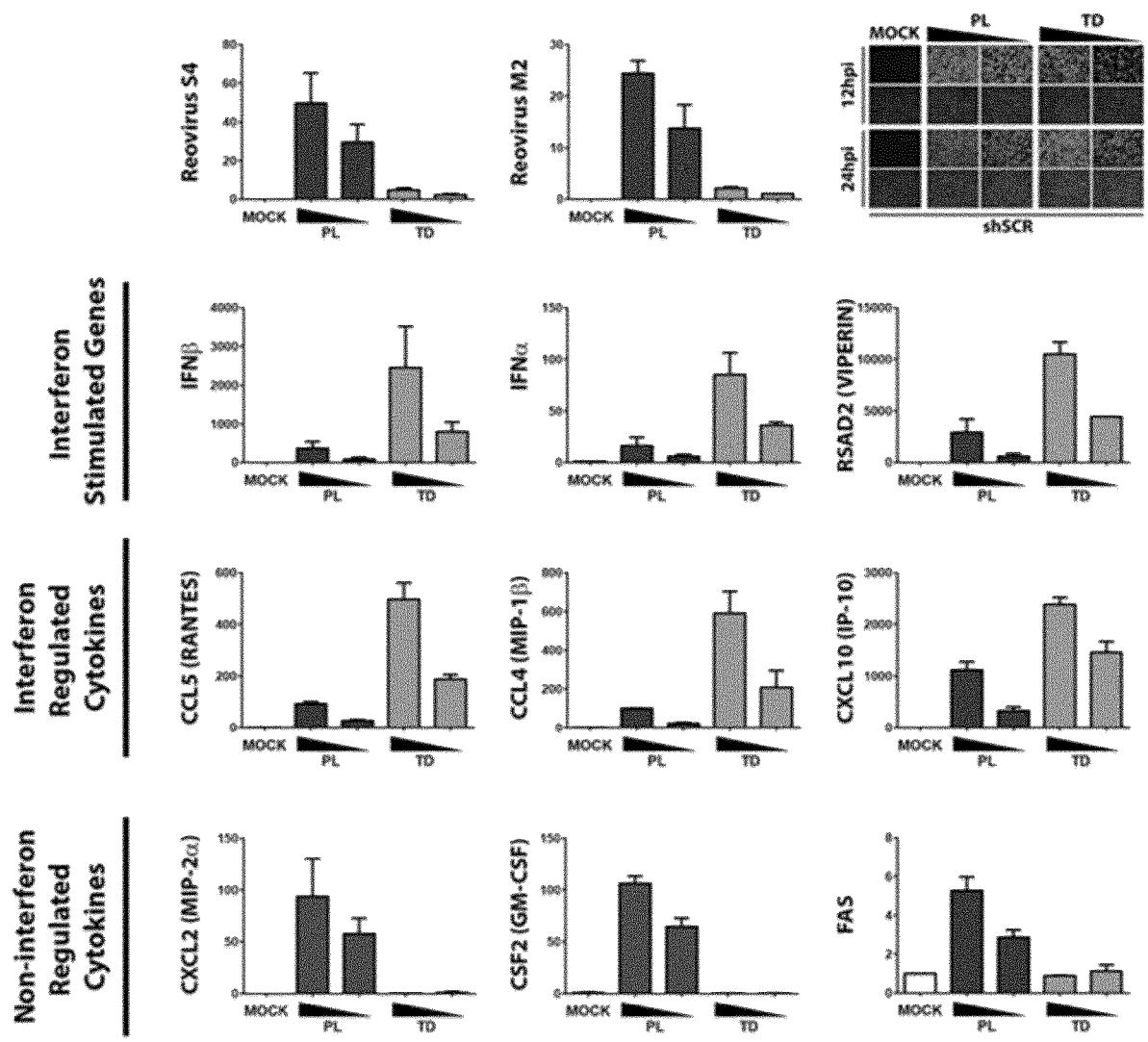
FIGS. 11 and 12. $T3D^{PL}$ but not $T3D^{TD}$ causes up regulation of some IFN-independent cytokines in a σ3-dependent manner.
Figure 12:
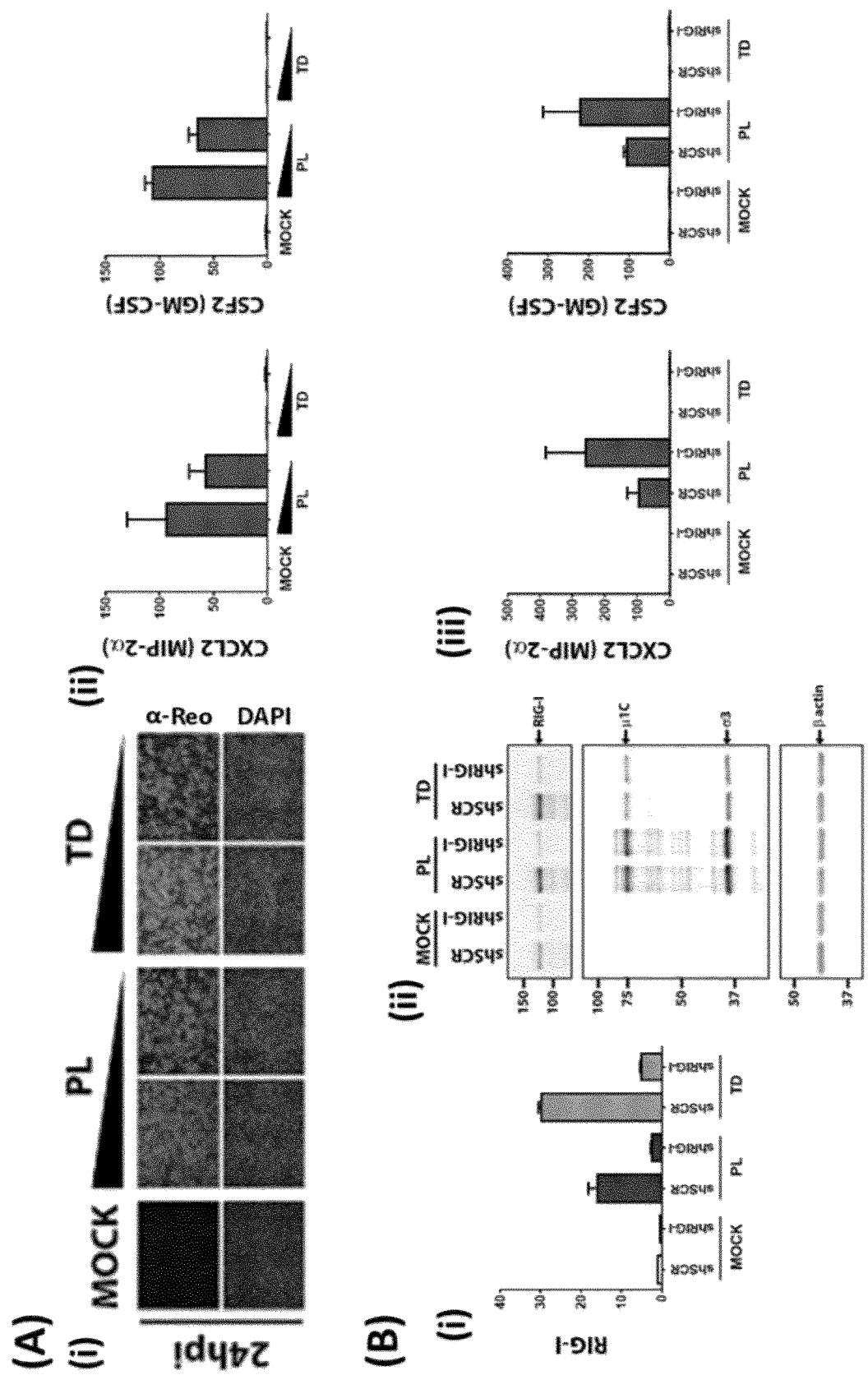
Figure 12:
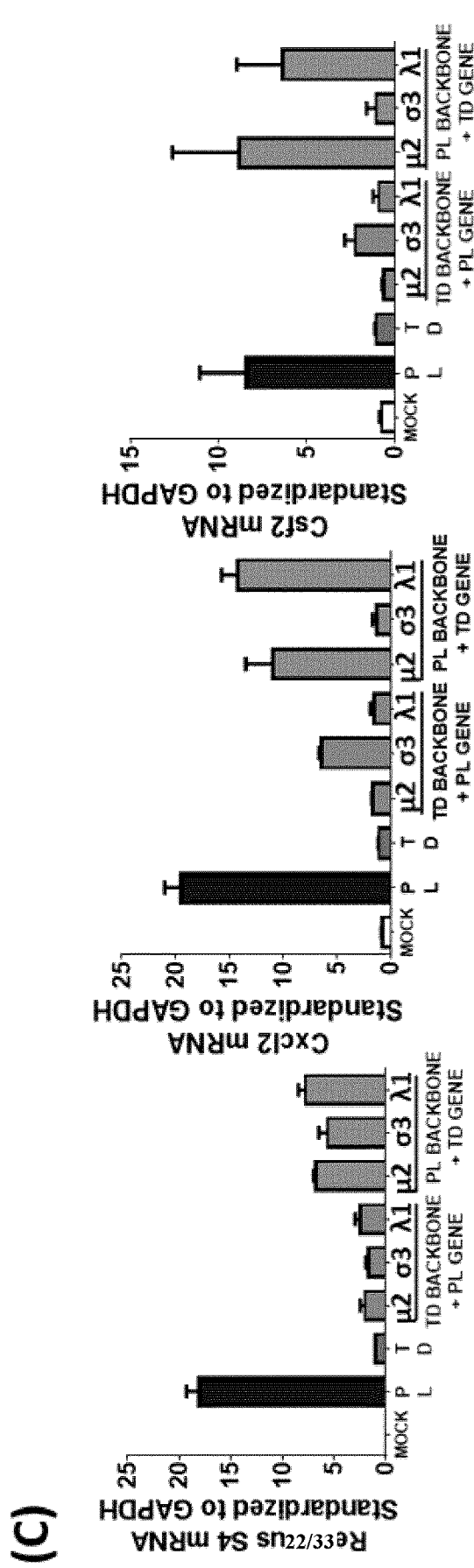

FIGS. 11 and 12. T3D$^{PL}$ but not T3D$^{TD}$ causes up regulation of IFN-independent, cytokines in a σ3-dependent manner. FIG. 12, (A) L929 tumorigenic mouse fibroblasts were infected with 2 concentrations T3D$^{PL}$ but not T3D$^{TD}$. (i) At 24 hours post infection, immunofluorescence with polyclonal anti-reovirus antibodies (α-Reo) shows similar percent of cells productively expressing reovirus proteins. DAPI shows all cell nuclei. (ii) Expression of CXCL2 and CSF2 was assessed by qRT-PCR. The ability of T3D$^{PL}$ but not T3D$^{TD}$ to upregulate CXCL2 and CSF2 was consistent among several human and mouse cell lines (data not shown). (B) Both CXCL2 and CSF2 lack interferon-regulatory promoter elements, but to confirm that these cytokines are IFN-independent, we tested their expression in NIH3T3 mouse fibroblasts silenced for RIG-I (shRIG-I) or containing scrambled shRNA control (shSCR). Note that we previously published evidence that RIG-I is necessary for T3DPL-induced IFN signalling. Knock-down of RIG-I was confirmed by qRT-PCR (i) and western blot analysis (ii), did not impact on reovirus protein expression (ii), and did not prevent upregulation of CXCL2 and CSF2. (C) Recombinant reo viruses were generated with mixed genotypes between T3DPL and T3DTD as indicated. When μ2, σ3, or λ1-encoding genome segments were mixed between PL and TD laboratory strains, each of these genes conferred intermediate phenotype with respect to reovirus mRNA levels (left, S4 reovirus mRNAs). However, transfer of the σ3-encoding genome segment was sufficient to control expression of CXCL2 and CSF2 as determined by qRT-PCR.

Activation of pathogen associated molecular pattern (PAMP) receptors, through a cascade of adaptor proteins and signaling events, results in phosphorylation (activation) and nuclear translocation of IRF3/7 and NFκB transcription factors, which subsequently induce expression of interferons (IFNs), antiviral interferon stimulated genes (ISGs) and inflammatory cytokines (FIG. 13A). Numerous studies have demonstrated the importance of the RIG-I/MDA5 signaling axis on reovirus mediated IFN production and subsequent paracrine suppression of reovirus spread to neighbouring cells (Goubau et al., 2014; Loo et al., 2008; Shmulevitz et al., 2010b). However, whether autocrine RIG-I/MDA5 and IFN signaling can reduce the initial round of reovirus infection is less clearly understood. We tested whether T3D$^{TD}$ induces more robust IFN signaling, and if so, whether this contributes to the reduced replication of T3D$^{TD}$ relative to T3D$^{PL}$.

First we determined if there were differences in IFN signalling between T3D laboratory strains. L929 cells were infected with T3DTD or T3DPL at a range of doses (MOI 1, 3, and 9), or mock infected. IFN signalling was then assessed at 12 hpi, an intermediate timepoint of virus replication when the potentially confounding effects of cell-cell spread of virus are minimal. IRF3 phosphorylation (activation) was strongly induced by T3DTD but not T3DPL, despite a reciprocal trend for reovirus protein expression (FIG. 13B). Moreover, while both T3D laboratory strains caused a dose-dependent increase in transcripts of IFN (Ifnα4, Ifnβ) and IFN-inducible genes (Mx1, Rsad2), T3DTD induced higher expression relative to T3DPL, as assessed by qRT-PCR (FIG. 13C). In other words, despite producing lower levels of viral proteins and transcripts, T3DTD induced elevated levels of antiviral signaling compared to T3DPL.

We considered two alternative explanations to account for increased IFN signalling by T3DTD: i) T3DTD might be a more potent inducer of antiviral signaling, or ii) T3DPL is a more potent inhibitor of antiviral signaling. To distinguish between these possibilities, L929 cells were co-infected with T3DPL and T3DTD at a high MOI of 9 (each) to ensure that most cells were infected with both viruses, and cell lysates were subjected to Western blot analysis for IRF3 phosphorylation. Phospho-IRF3 levels were similar between T3DTD and T3DPL/T3DTD coinfection (FIG. 13D), suggesting that T3DTD-dependent activation of IRF3 could not be overcome by the presence of T3DPL. Therefore, T3DTD is most likely a more potent activator of antiviral signaling than T3DPL. In other words, paradoxically, the less-prolific replicating variant is more dominant for IFN expression. Furthermore, the levels of reovirus proteins were either unchanged (FIG. 13D, σ3) or only marginally reduced (FIG. 13D, μ1/μ1C) in T3DPL/T3DTD co-infection compared to T3DPL despite high phospho-IRF3 levels, suggesting that IRF3 activation and downstream signaling may not play a major role in restricting the first round of reovirus replication.

Next, we determined if any of the 3 genes that segregated with the large plaque phenotype of T3DPL (i.e. S4, M1, and L3) contributed to the differential activation of IFN signalling between the two virus strains, by analyzing mono-reassortants. As previously noted, the mono-reassortants of S4, M1, and L3 produced intermediate viral RNA and protein levels compared to the T3DPL and T3DTD parental strains, reflecting their intermediate levels of replication. As for IFNs and IFN-induced genes, mono-reassortants also gave intermediate IFN signalling and no mono-reassortant fully reversed the phenotype of IFN signalling (FIG. 13E). For example, IFNβ was induced more by T3DTD than T3DPL parental strain, but individually adding S4, M1, or L3 from T3DTD into an otherwise T3DPL genomic background, did not increase IFNβ levels to those achieved by T3DTD. One possible interpretation of this data is that S4, M1, and L3 each independently contribute 'somewhat' to IFN signalling, such that mono-reassortants are insufficient to confer the full parental phenotype. Previous studies have indeed implicated these genes (and other genes such as S1) in affecting IFN signalling (Beattie et al., 1995; Lanoie and Lemay, 2018; Zurney et al., 2009). Of these IFN modulating viral proteins, the S4-encoded σ3 has been clearly demonstrated to sequester dsRNA, inhibit activation of PKR and rescue other viruses depleted of inhibitors of antiviral response (Beattie et al., 1995; Denzler and Jacobs, 1994; Yue and Shatkin, 1997). But it should be noted that most studies on reovirus genes that impact IFN signalling do not consider whether effects are direct (e.g. the gene or protein directly modulate IFN mediators), or whether instead the viral genes impact virus replication and thereby indirectly impact IFN induction. To consider the differences in virus replication kinetics between parental and mono-reassortant viruses, we determined the relationship between IFN signaling (IFNβ mRNA) and measures of virus replication (progeny titers) (FIG. 13E right). A strong negative correlation (R2=0.86) between virus replication proficiency and IFN signalling was found, suggesting that S4, M1, or L3 could contribute to differences in IFN signalling between T3DTD and T3DPL indirectly, by affecting the extent of virus replication. Specifically, we propose that incoming cores establish viral RNA and protein expression, and factory formation around the core, with sufficient speed to prevent detection of foreign virus patterns by the host.

Given that T3DTD induced more IFN signalling than T3DPL, the pivotal question became whether IFN signalling contributed to reduced replication of T3DTD relative to T3DPL. While it is well established that IFN signalling can prevent dissemination of reovirus to neighboring cells through paracrine signalling (Shmulevitz et al., 2010b), it is unknown whether IFN signalling can affect the initial infection of reovirus in an autocrine manner. To address this question, we made use of double knock-out (DKO) mouse embryo fibroblasts (MEFs) lacking both RIG-I and MDA5 (Errett et al., 2013; Loo et al., 2008). We reasoned that if IFN signalling can impact the first round of virus infection, then the DKO cells should demonstrate increased infection by reovirus at an intermediate timepoint of 12 hpi where cell-cell spread is minimal. Wild-type (WT) and DKO MEFs were exposed to T3DPL or T3DTD at MOIs of 0.7, 2, and 6 (based on WT MEF titers) and flow cytometric analysis was conducted to measure the number of cells positive for reovirus antigen expression (FIG. 13F). At 12 hpi, WT and DKO cells showed equivalent infection at matched MOIs, indicating that IFN signalling likely does not affect the first round of infection. As expected, at 24 hpi when reovirus already spreads to new cells, the DKO cells showed enhanced infection relative to WT, supporting the paracrine contribution of IFNs to reducing virus dissemination. To confirm the absence of IFN signalling in DKO cells, qRT-PCR was conducted at 12 hpi for IFNs (Ifnb1, Ifnα4) and IFN-induced gene Rsad2; all demonstrated a strong inhibition (>97%) of IFN signaling relative to WT cells following infection by either T3DPL or T3DTD (FIG. 13G). Analysis of reovirus transcript levels by qRT-PCR confirmed that WT and DKO cells supported equal levels of virus replication during the initial round of infection.

While having minimal-to-no effect on the first round of T3D reovirus infection, IFN signalling did have the predicted activity on restricting cell-cell spread of reovirus. Specifically, when plaque assays were used to assess the overall replication and spread of T3DPL and T3DTD, both viruses produced the same number of reovirus infected cell foci on DKO MEFs versus wildtype MEFs (FIG. 10H), suggesting that the initial round of infection was independent of IFN signaling. Plaques for both T3DPL and T3DTD were larger on DKO MEFs relative to wildtype MEFs, supporting the importance of IFN signalling during cell-cell spread. Importantly however, plaque size of T3DTD remained much smaller than T3DPL even on DKO MEFs; this supports the model that the oncolytic advantage of T3DPL relative to T3DTD is not dependent of IFN signalling, but rather dependent on differences in virus replication as described herein. Similar results were obtained in the NIH/3T3 mouse fibroblast cell line in which RIG-I was knocked down using shRNA. Altogether these results strongly suggest that RIG-I signaling does not affect the first round of reovirus replication for either T3D laboratory strain. However, the differences in IFN signalling appear to impact subsequent rounds of infection, permitting T3DPL to disseminate more efficiently. Furthermore, the finding that T3DTD induces more IFN signalling than T3DPL is likely to also indirectly affect the landscape of anti-tumor and anti-viral immune cells and therefore is an impactful discovery for understanding the contribution of virus genetics on the immunotherapeutic aspect of virus oncolysis.

T3DPL S4-Encoded σ3 Stimulates Expression of NFκB-Dependent but IFN-Independent Cytokines.

MAPK/ERK, p38 stress-activated kinase, and NF-κB pathways have all been implicated in replication of an assortment of viruses (Bonjardim, 2017; Lim et al., 2016; Mohamed and McFadden, 2009; Schmitz et al., 2014). As for reovirus specifically, ERK, p38, and NF-κB signalling were positively associated with reovirus oncolytic activities (Norman et al., 2004; Shmulevitz et al., 2010b; Thirukkumaran et al., 2017). Western blot analysis was therefore conducted to monitor total levels versus phosphorylation status of ERK p42 and p44 subunits, p38, and NF-κB factor IκBα, at 12 hpi following infection at MOI=1 (FIG. 14A). Whereas phosphorylation of p42/p44 and p38 are a direct indication of kinase activity, the phosphorylation of IκBα results its degradation from the NF-κB complex and facilitates NF-κB nuclear translocation and subsequent activity.

Densitometric analysis for three independent experiments showed that T3DPL induced higher levels of phosphop38, phospho-ERK, and phospho-IκBα. Of the three signalling proteins assessed, only IκBα became differentially phosphorylated by T3D laboratory strains in a gene-dependent manner. Specifically, T3DPL induced accumulation of phosphorylated IκBα while T3DTD did not. Moreover, the phosphorylation of IκBα corresponded with the T3DPL-derived S4/σ3, since addition of this T3DPL gene into an otherwise T3DTD background was sufficient for NF-κB activation. The σ3 protein has two well characterized activities; it functions as an outer-capsid protein and it sequesters viral RNAs away from cellular dsRNA-detecting signalling molecules such as PKR and RIG-I (Denzler and Jacobs, 1994; Yue and Shatkin, 1997). Our data now suggested that σ3 may contribute to NF-κB activation. Serving as transcription factors, NF-κB subunits ultimately stimulate expression of a plethora of NF-κB dependent genes. The discovery that T3DPL activated RIG-I, IRF3, and IFN-dependent genes less robustly than T3DTD (FIG. 13), but reciprocally may activate NF-κB more than T3DTD (FIG. 14), raised the possibility that T3DPL (but not T3DTD) activated NF-κB-dependent yet RIG-I/IFN-independent genes. This possibility was exciting because NF-κB signalling is typically characterized as being downstream of RIG-I activation, whereas our data potentially introduces a RIG-I independent NF-κB signalling cascade that is differentially stimulated by strains of reovirus with distinct oncolytic potencies. To test this possibility, it was essential that the western blot data be corroborated by data indicating that NF-κB-dependent (and RIG-I independent) genes are indeed stimulated by T3DPL but not T3DTD. Microarray and bioinformatics analysis was therefore conducted to identify T3DPL- and NF-κB-regulated genes that were RIG-I and IFN-independent. First, we conducted whole genome microarray analysis for NIH3T3 cells that were mock infected, or infected with T3DPL (MOI=60), and focused on genes that were up-regulated by ≥2-fold in T3DPL infected cells relative to mock infection. Microarray analysis was also conducted for T3DPL-infected NIH3T3 cells s 572 tably transduced with shRIG-I, and genes upregulated by reovirus were further subdivided into those whose expression was suppressed by RIG-I knock-down (RIG-I-dependent, cluster 1) versus those that were independent of RIG-I status (RIG-I-independent, cluster 2). To then determine which genes in each cluster are NF-κB-dependent, we made use of a publically available microarray dataset where lipopolysaccharide (LPS) was used to induce both NF-κB and IFN pathways. The database compared LPS-induced gene expression in wild-type MEFs versus MEFs with NF-κB p65/c-Rel subunit knock-out or with IFN receptor (IFNAR) knock-out, to distinguish NF-κB-dependent versus IFN dependent genes ((Cheng et al., 2017), GEO: GSE35521). Using this public dataset, we further classified T3DPL upregulated genes into four groups: genes that are RIG-I-dependent, NF-κB-dependent, and IFNAR-dependent (cluster 4), RIG-I-dependent, NF-κB-dependent, and IFNAR-independent (cluster 3), RIG-I-independent, NF-κB dependent, and IFNAR-dependent (cluster 5), and RIG-I-independent, NF-κB-dependent, and IFNAR independent (cluster 6). Cluster 6 represented T3DPL-upregulated genes predicted to be independent of both RIG-I and IFN signalling, but dependent on NF-κB activation, and was therefore chosen for empirical analysis. Included in cluster 6 were Cxcl1, Csf2, Cxcl2, and Fas. To confirm that these four genes were independent of IFN, L929 cells were treated with IFNα or IFNβ for 12 hours, and gene expression monitored by qRT-PCR. As expected, IFN-dependent genes such as Mx1, Cxcl10, Rsad2, Ccl4, Ifi44 and IL6 were upregulated by exposure to IFNs. Conversely, Cxcl1, Csf2, Cxcl2, and Fas genes were not upregulated by IFN treatment, suggesting they are indeed IFN-independent genes as the bioinformatics analysis suggested. When levels of Cxcl1, Csf2, Cxcl2, and Fas were compared between L929 cells infected with T3D laboratory strains at MOIs of 1, 3, and 9 for 12 hpi, strong induction (up to 30-fold) was evident in a dose dependent manner during infection by T3DPL but not T3DTD (FIG. 14B). Cxcl1, Csf2, Cxcl2, and Fas induction was also RIG-I independent, since these genes were upregulated by T3DPL to similar extent in NIH3T3 cells transduced with shSCR or shRIG-I (FIG. 14C). Moreover, analysis of gene expression among S4, M1, and L3 mono-reassortants showed a clear correlation between expression of these NF-κB-dependent RIG-I/IFN independent genes and presence of the T3DPL-derived S4/σ3 (FIG. 14D). Most surprising about the findings, is that NFκB and IRF3 signalling are inversely activated by T3D laboratory strains; T3DPL caused high expression of NFκB-dependent genes and low expression of RIG-I/IFN-dependent genes, but the reciprocal scenario occurred for T3DTD. These two signalling pathways are often linked, for example it was recently shown that serotype 3 (T3D) activates both NFκB and IRF3 more than serotype 1 (T1L) (Stuart et al., 2018). While many studies show NFκB and IRF3 downstream of cytosolic sensors like RIG-I, our data suggests an independent source of NFκB signalling that is modulated by σ3. The inverse induction of NFκB-versus RIG-I/IFN-dependent genes by T3DPL versus T3DTD was recapitulated in all four cells lines that we evaluated, including NIH/3T3 (n=2), L929 (n=3), B16-F10 (n=2), and ID8 (n=1), suggesting a widespread phenomenon (data not shown). As will be extrapolated in the discussion, that minor modifications to viral genomes can produce distinct cytokine expression landscapes could be relevant for optimizing virus-induced antitumor immunity and for understanding how closely-related viruses cause distinct pathogenic outcomes.

Figure 13:
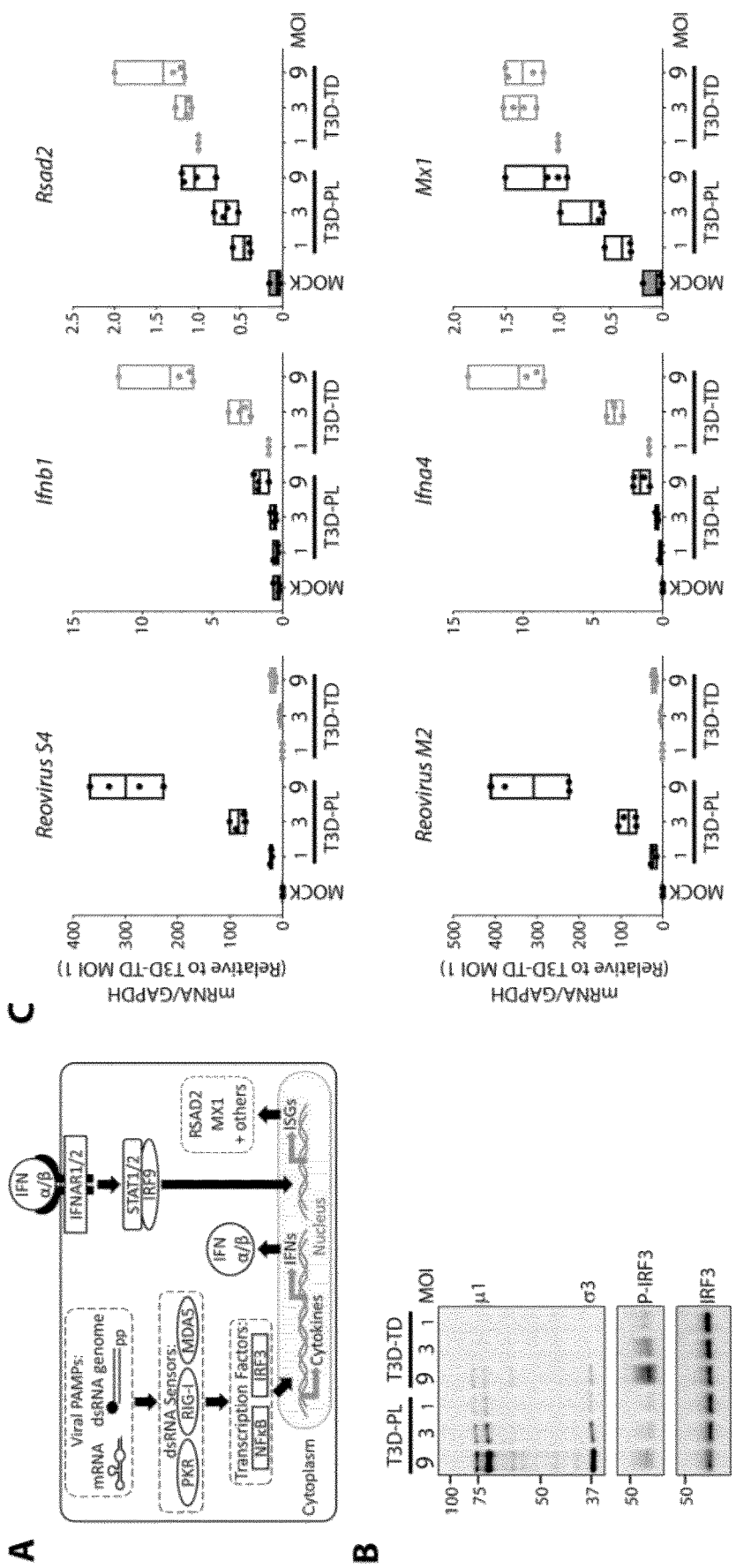
FIG. 13. T3DTD activates interferon signaling more than T3DPL, but IFN signaling does not impact the first round of reovirus infection.
Figure 13:
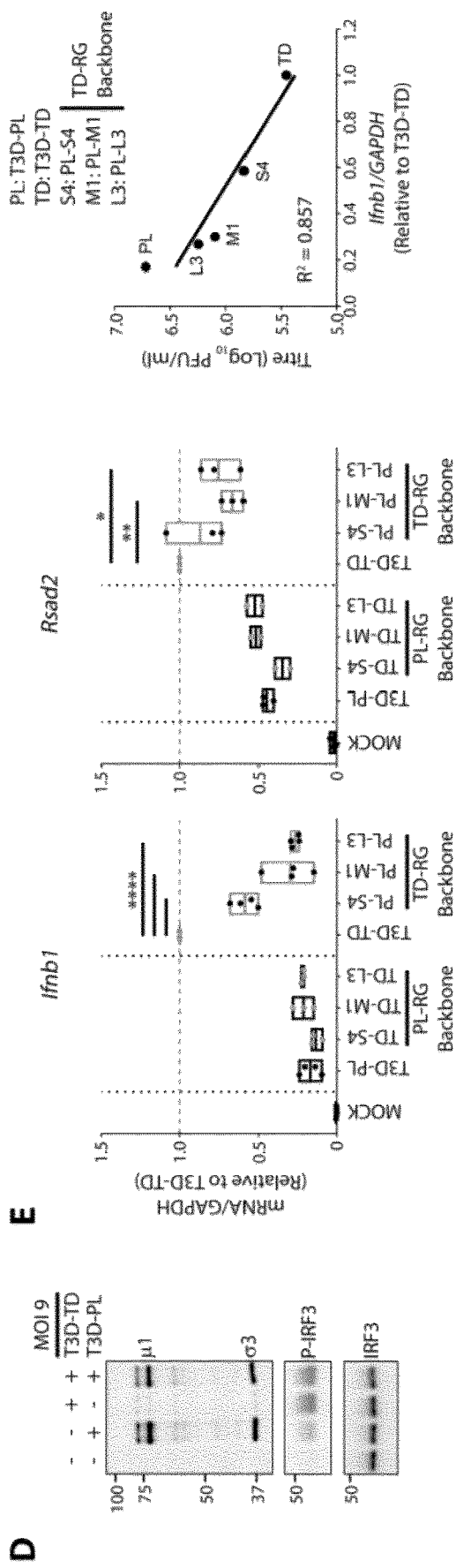
Figure 13:
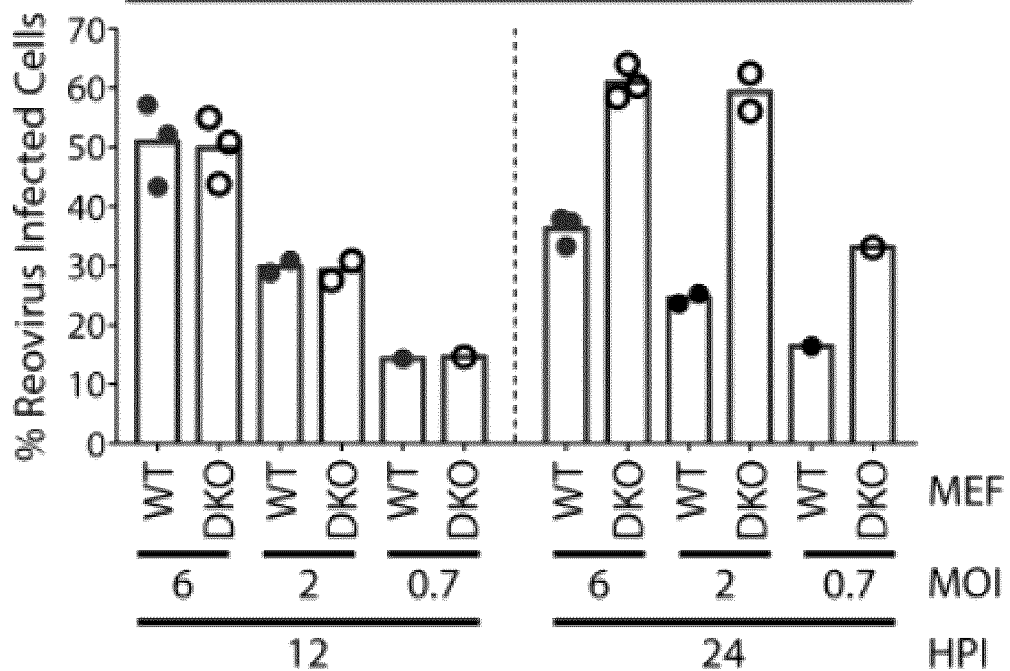
Figure 13:
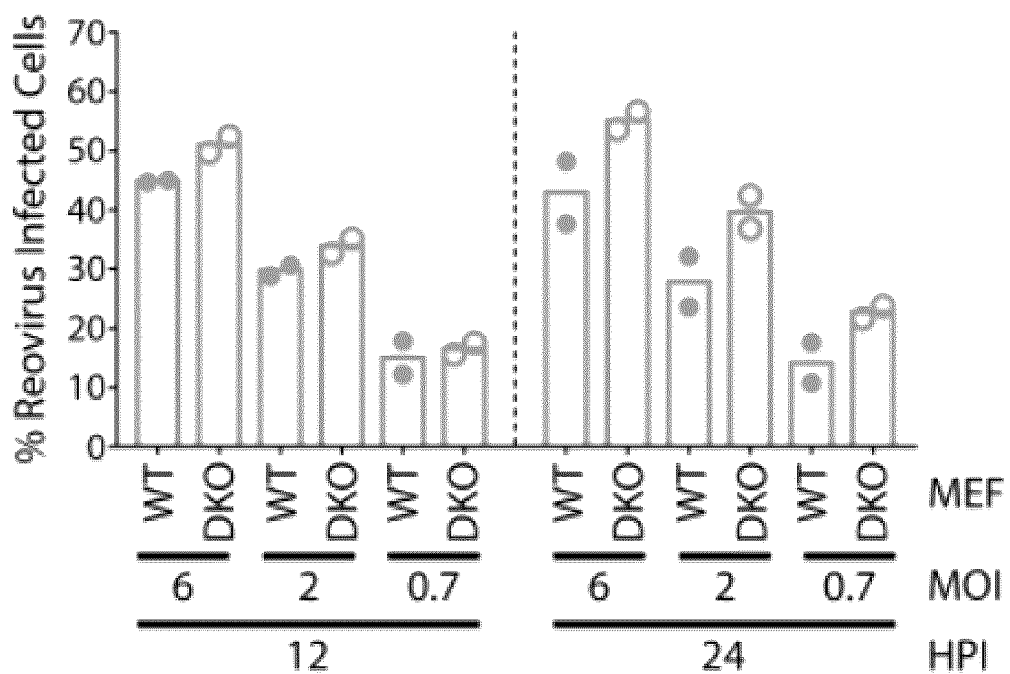
Figure 13:
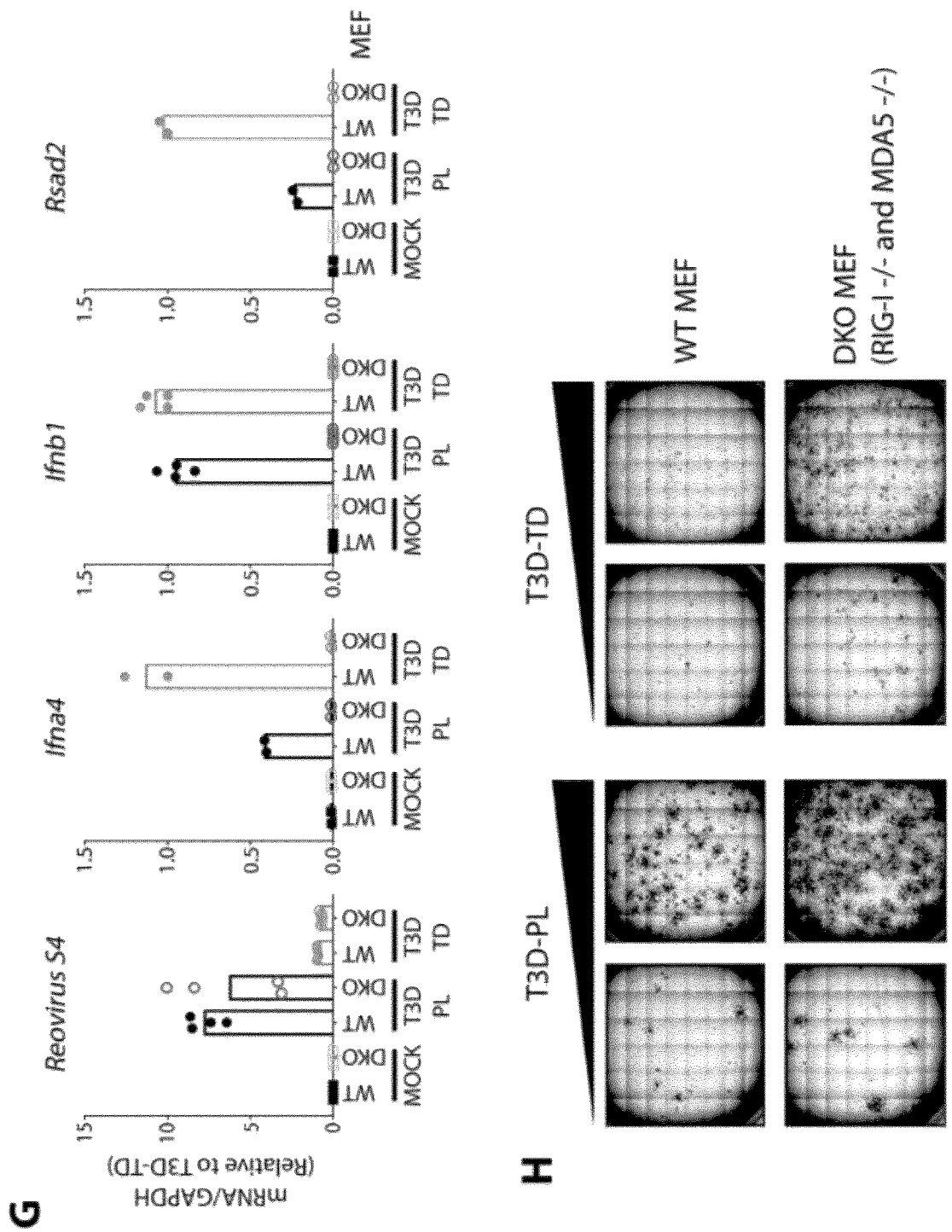
Figure 14:
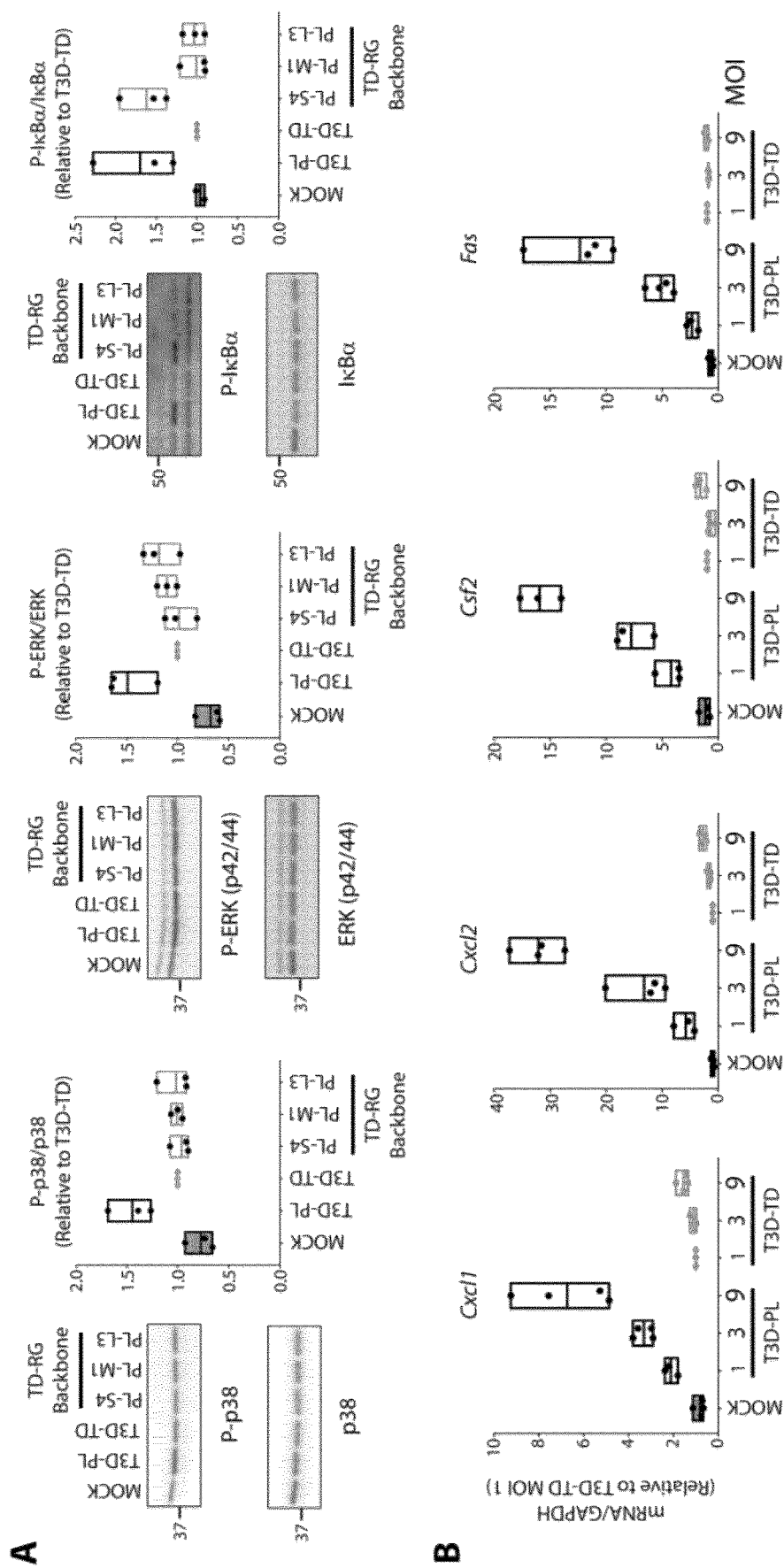
FIG. 14. T3DPL S4-encoded σ3 stimulates expression of NFκB-1650 dependent but IFN-independent cytokines.
Figure 14:
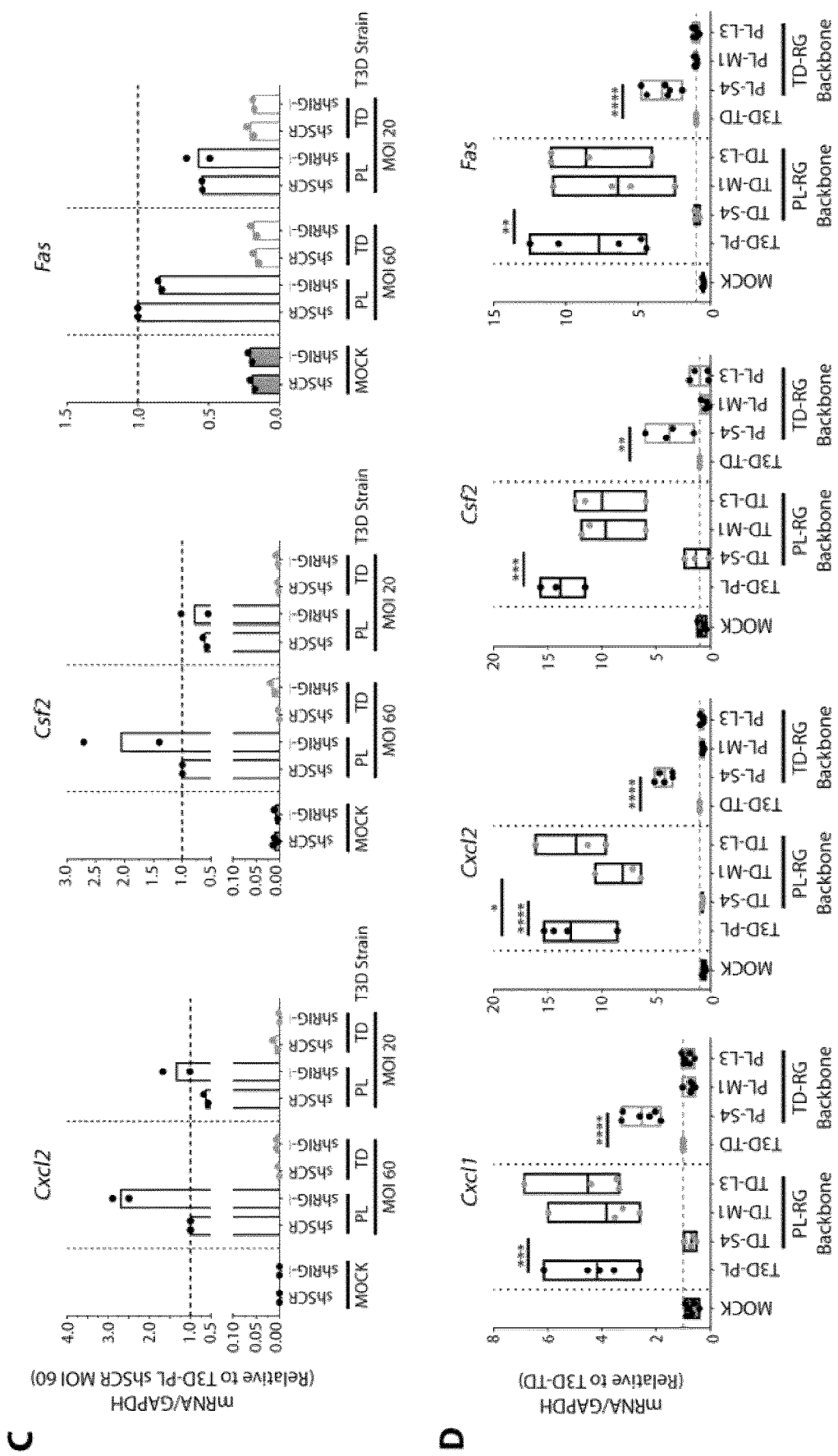
Figure 15:
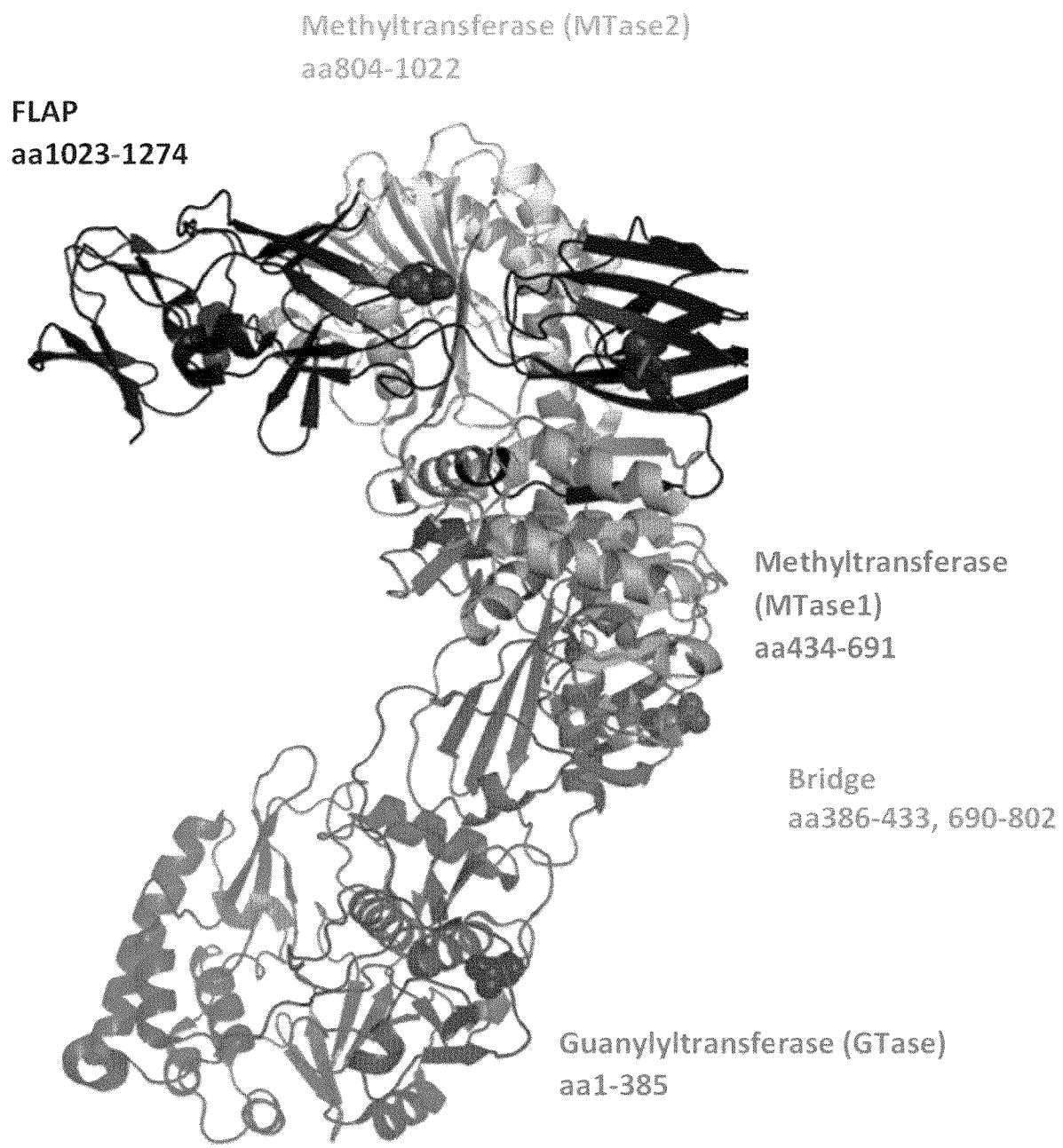
FIG. 15. Domains of PL-λ2 protein: Guanylyltransferase (GTase); bridge regions; Methyltransferase (MTase1); Methyltransferase (MTase2); and FLAP region.

FIG. 13. T3DTD activates interferon signaling more than T3DPL, but IFN signaling does not impact the first round of reovirus infection. (A) Overview of antiviral signaling induced during reovirus infection. (B-D) L929 cells were infected with T3DPL and/or T3DTD at indicated MOI and incubated at 37° C. for 12 hours. (B) and (D) Total proteins were separated using SDS PAGE and Western blot analysis with indicated antibodies. C) Total RNA was extracted, converted to cDNA and gene expression relative to housekeeping gene GAPDH was quantified using qRT-PCR. All values were normalized to T3DTD MOI 1. n=4. (E) Standardized for equal infection (MOI 3), L929 cells were infected with parental T3DPL or T3DTD, and S4, M1 and L3 gene monoreassortant PL-RG or TD-RG viruses. (Left) At 12 hpi, total RNA was extracted, converted to cDNA and gene expression relative to housekeeping gene GAPDH was quantified using qRT-PCR. All values were normalized to T3DTD. n≥3. Statistical significance determined using one-way ANOVA with Dunnett's multiple comparisons test, * p<0.05, * p<0.001, ** p<0.0001, ns>0.05. (Right) At 12 hpi, total viral titres at 12 hpi were plotted against Ifnb1 gene expression, followed by linear regression analysis. (F-H) WT or RIG-I/MDA5-/- double knockout (DKO) MEFs were infected with T3DPL or T3DTD. (F) At indicated MOIs and timepoints, percent reovirus infected cells were identified using reovirus specific primary antibody and Alexa Fluor 488 conjugated secondary antibody and quantified using flow cytometry. n=1-3, (G) For MOI 6 at 12 hpi, total RNA was extracted, converted to cDNA and gene expression relative to housekeeping gene GAPDH was quantified using qRT-PCR. All values were normalized to WT MEF T3DTD. n≥1-2, with experimental duplicates, (H) At 3 days post infection, reovirus infected cell foci were stained with colorimetric immunocytochemistry using primary polyclonal reovirus antibody, alkaline phosphatase secondary antibody and BCIP/NBT substrate.

FIG. 14. T3DPL S4-encoded σ3 stimulates expression of NFκB-1650 dependent but IFN-independent cytokines. (A) Standardized for equal infection (MOI 3), L929 cells were infected for 12 hrs with parental T3DPL or T3DTD, and S4, M1 and L3 gene monoreassortant TD-RG viruses. (Top) Total cell lysates were collected at 12 hpi for blot analysis using indicated antibodies to identify reovirus proteins. (Bottom) Densitometric band quantification of phosphorylated relative to total protein. n=3. (B) L929 cells were infected with T3DPL and/or T3DTD at indicated MOI and incubated at 37° C. for 12 hours. Total RNA was extracted, converted to cDNA and gene expression relative to housekeeping gene GAPDH was quantified using qRT-PCR. All values were normalized to T3DTD MOI 1. n=4. (C) NIH/ 3T3 cells stably transduced with scrambled (shSCR) or RIG-I (shRIG) lentivirus were infected with reovirus at indicated MOI (L929 cell line titres) and incubated at 37° C. Samples were collected at 12 hpi for RNA extraction, cDNA synthesis and qRT-PCR using gene-specific primers. Values were standardized to corresponding GAPDH and all samples were normalized to shSCR T3DPLMOI 60. n=2. (D) Similar experimental outline to (A) except the parental T3DPL or T3DTD, and S4, M1 and L3 gene monoreassortant for both PL-RG and TD-RG viruses were assessed. At 12 hpi, total RNA was assessed for reovirus S4 RNA expression relative to housekeeping gene GAPDH. n≥3. Statistical significance determined using one-way ANOVA with Dunnett's multiple comparisons test, * p<0.05, * p<0.001, ** p<0.0001, ns>0.05.

Example 7: Mutant Reovirus with Enhanced Oncolytic Activities

Immune-competent breast cancer mouse models are used to screen reovirus mutants for enhanced oncolytic activities in vivo. The mutant reovirus disclosed herein are used for treating cancer, such as, breast cancer. The mutant reovirus disclosed herein, e.g., a T3D virus genetically modified to express a mutant σ1 protein comprising a mutation in the region 220-289 of the σ1 protein (e.g., amino acids 222-251. Such as, position 249) relative to a wild type σ1 protein, where the mutation renders the mutant σ1 protein resistant to cleavage by the metalloprotease as compared to the wild type σ1 protein, is tested in the following mammary tumor cell line and/or mouse mammary tumor models:

| Cell Line | Mouse | |
|---|---|---|
| TUBO | BALB/c | J. Immunol. 2000 Nov. 1; 165(9): 5133-42 Mol. Ther. 2013 January; 21(1): 91-100 Mol. Ther. 2013 January; 21(1): 91-100 |
| MTV | FVB | jax.org/strain/002374 Nat Commun 2016 Jul. 13; 7: 12258 Cell Rep 2014 Mar. 27; 6(6): 992-9 Dis Model Mech 2015 March; 8(3): 237-51 Proc. Soc. Exp. Biol. Med. 1951 June; 77(2): 358-62 |
| E0771 | C57BL/6 | Anticancer Res. 25(6B): 3905-15 |
| EMT6 | BALB/c | J. Natl. Cancer Inst. 1972 September; 49(3): 735-49 J. Leukoc. Biol. 1985 November; 38(5): 573-85 Br. J. Cancer 1992 May; 65(5): 641-8 Cancer Res. 2010 Oct. 1; 70(19): 7431-41 |
| D2F2 | BALB/c | Cancer Gene Ther. 2012 April; 19(4): 282-91 |

For testing in animal models, three intratumoral injections (about $5 \times 10^8$ PFU per injection) are given. Oncolytic activity is monitored by animal survival, tumor size, metastasis, reovirus titer in primary tumor and metastasized tumor vs. other tissues, anti-tumor immune response (e.g., tumor-specific T-cell response).

Example 7: Reovirus with Multiple Genetic Modifications

The following mutations were tested individually and in certain combinations for improved infectivity:

| Mutation number | Mutated gene | Nucleotide mutation | Mutated protein | Amino acid change | Original reovirus variant |
|---|---|---|---|---|---|
| 2 | S1 | G-663-T | σ1 | Q-217-H | T3v6 |
| 3 | S1 | G-209-T | σ1 | S-66-I | T3v8 |
| 4 | S1 | A-946-G | σ1 | N-312-R | T3v10 |
| 5 | S1 | G-65-T | σ1 | S-18-I | T3v2, T3v12 |
| 6 | S1 | A-352-C | σ1 | T-114-P | T3v13 |
| 7 | S1 | G-668-A | σ1 | R-219-Q | T3v13 |

-continued

| Mutation number | Mutated gene | Nucleotide mutation | Mutated protein | Amino acid change | Original reovirus variant |
|---|---|---|---|---|---|
| 8 | S1 | T-95-G | σ1 | L-28-P | T3v16 |
| 9 | S4 | A-222-G | σ3 | K-64-E | T3v12 |
| 10 | S4 | T-722-G | σ3 | H-230-Q | T3v4 |
| 11 | M1 | C-347-T | μ2 | L-112-F | T3v6 |
| 12 | M1 | T-1850-G | μ2 | S-613-A | T3v6 |
| 13 | M1 | G-1848-T | μ2 | A-612-V | T3v10 |
| 14 | M2 | G-709-C | μ1 | S-227-T | T3MB-2 |
| 15 | L2 | A-3835-G | λ2 | I-1274-M | T3v4 |
| 16 | L2 | T-3834-G | λ2 | I-1274-T | T3v5 |
| 17 | L2 | G-1235-A | λ2 | D-408-N | T3v6 |
| 18 | L2 | A-3456-G | λ2 | N-1148-S | T3v14 |
| 19 | L2 | G-3316-A | λ2 | M-1101-I | T3v1 |
| 20 | L3 | G-2897-T | λ1 | A-962-S | T3v11 |
| 21 | L3 | T-377-C | λ1 | Y-122-H | T3v12 |
| 25 | L3 | A-425-G | λ1 | N-138-D | T3v1 |
| 22 | L1 | G-2694-A | λ3 | M-892-I | T3v4 |
| 23 | L1 | A-2933-G | λ3 | Q-972-R | T3v12 |
| 24 | L1 | C-1216-T | λ3 | P-400-S | T3vl |

Figure 16:
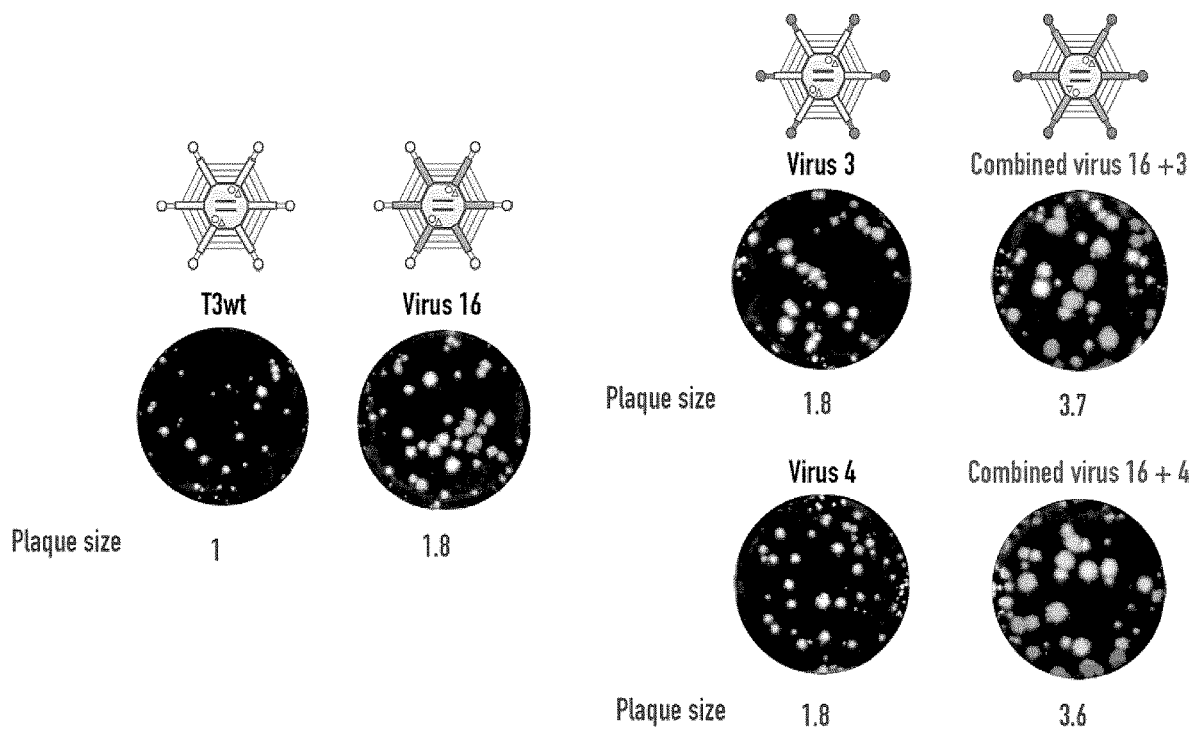
FIG. 16. Plaque size comparison between viruses with single mutations and viruses with combined mutations.

FIG. 16 demonstrates that a T3D$^{PL}$ virus genetically modified to express a T3D$^{PL}$ (i) λ2 protein comprising the substitution I1274T (Virus 16); (ii) σ1 protein comprising the substitution S66I (Virus 3); (iii) Virus 16+3; (iv) σ1 protein comprising the substitution N312R (Virus 4); (v) Virus 16+4 replicate and disseminate on tumor cells more efficiently as compared to wild type virus (T3 wt).

FIG. 16. Plaque size comparison between viruses with single mutations and viruses with combined mutations. Representative pictures of plaque size generated by combined viruses and their corresponding viruses with single mutations. Mean plaque size proportion of four independent experiments in duplicate is indicated. Plaque size was quantified with Fiji, ImageJ using Particle Analysis plugin.

Figure 17:
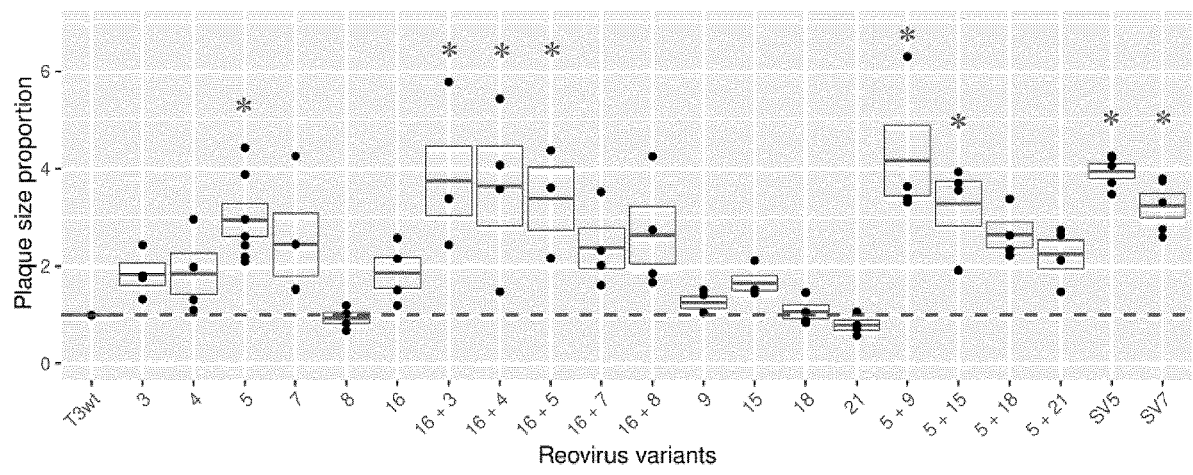
FIG. 17. Plaque size proportion between viruses with single mutations and viruses with combined mutations.

FIG. 17. Plaque size proportion between viruses with single mutations and viruses with combined mutations. Each point represents an independent experiment performed in duplicate. Dotted line corresponds to T3 wt. SV5 is a combination of the mutations=5+9+13+16+20. SV7 is a combination of the mutations=7+9+13+16+20. *p<0.05.

Figure 18:
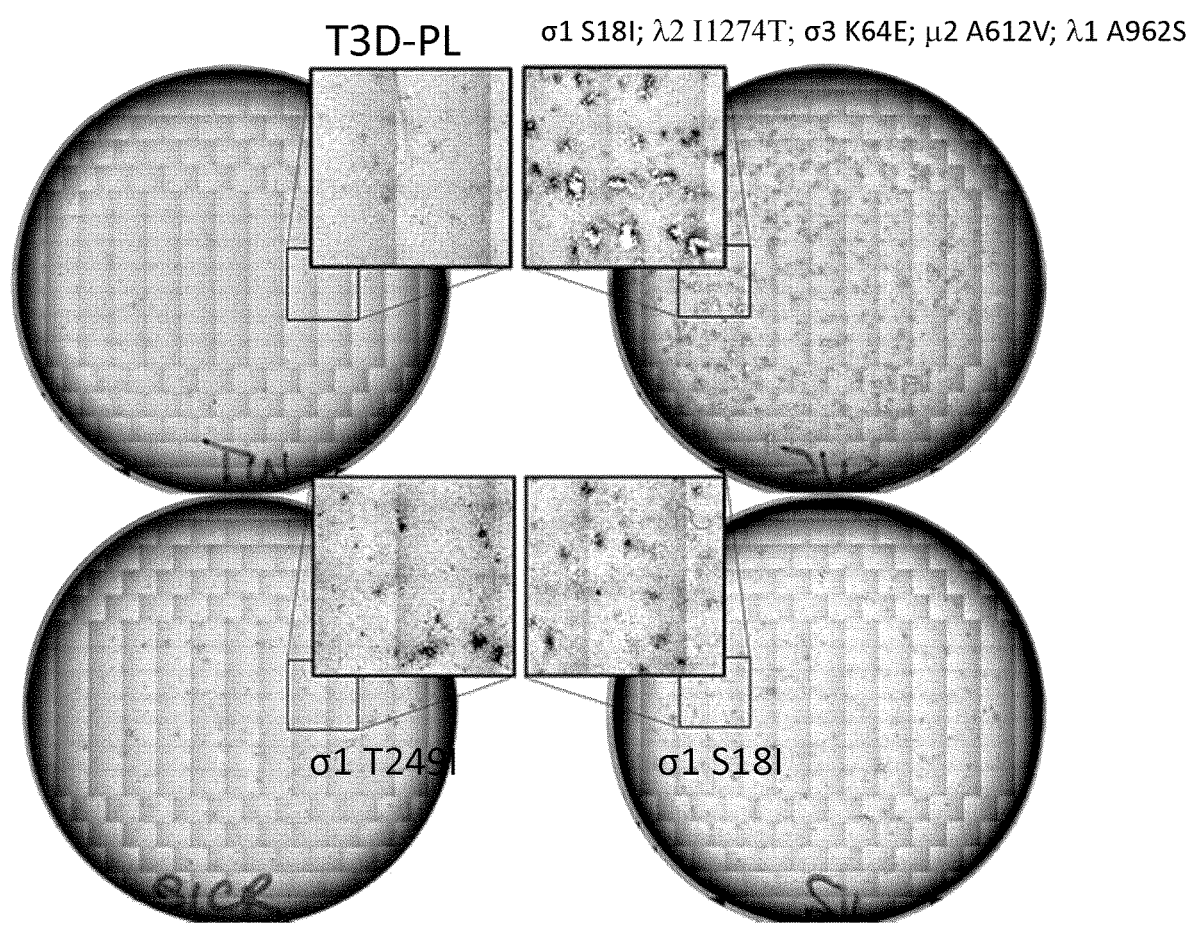
FIG. 18. Infection of TUBO breast cancer cell line by $T3D^{PL}$ virus genetically modified to have at least one genetic modification.

TUBO breast cancer cell line was used to assay infectivity of T3D$^{PL}$ virus genetically modified to have at least one genetic modification. T3D$^{PL}$. As shown in FIG. 18, T3DPL virus genetically modified to express a T3D$^{PL}$ (i) σ1 protein comprising the substitution S18I; (ii) σ1 protein comprising the substitution T249I; or (iii) σ1 protein comprising the substitution S18I, λ2 protein comprising the substitution I1274T, σ3 protein comprising the substitution K64E, μ2 protein comprising the substitution A612V, and λ1 protein comprising the substitution A962S, all showed improved infection of cancer cells as compared to the wild type T3D$^{PL}$ virus.

Figure 19:
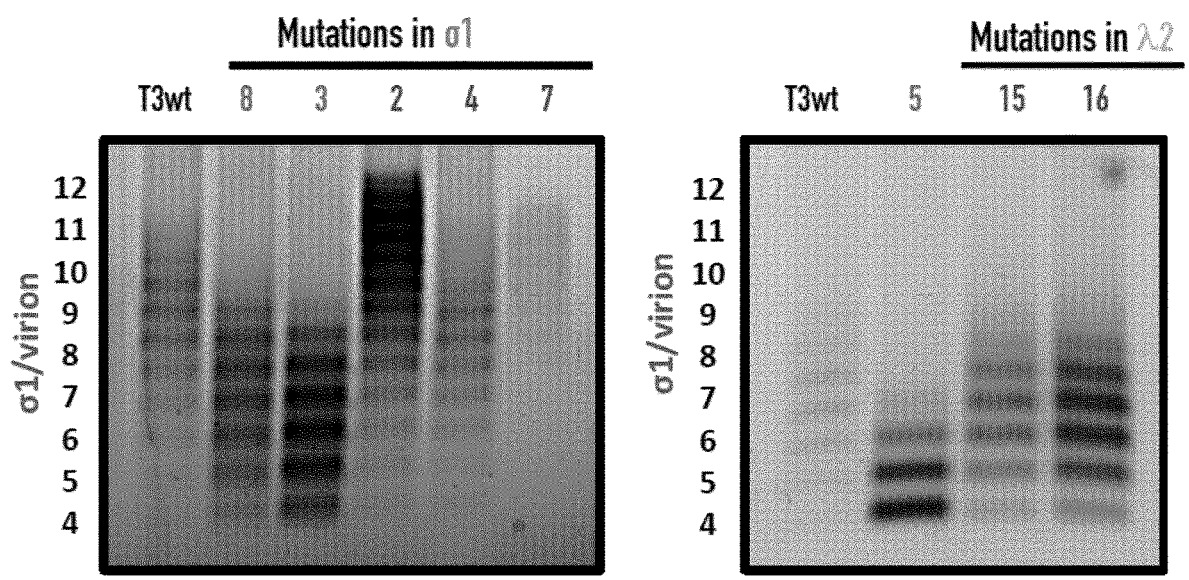
FIG. 19. σ1 mutations and λ2 mutations have the same mechanism, and reduce σ1 levels on virions.

FIG. 19 demonstrates that mutants 8 (L28P), 3 (S66I), and 5 (S18I) in σ1, as well mutations 15 (I1274M) and 16 (I1274T) in λ2, all have the same mechanism, and reduce σ1 levels on virions, which increases reovirus infectivity in tumor cells.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A T3D$^{PL}$ reovirus genetically modified to express a T3D$^{PL}$ reovirus λ2 protein comprising a mutation in a FLAP domain, wherein said mutation comprises a substitution of isoleucine at position 1274 in SEQ ID NO: 9, wherein the substitution is I1274M or I1274M.

2. The T3D$^{PL}$ reovirus of claim 1, further comprising a mutated μ2 protein comprising a substitution of alanine at position 612 with reference to the amino acid sequence of wild type T3D$^{PL}$ reovirus μ2 protein set forth in SEQ ID NO: 5.

3. The T3D$^{PL}$ reovirus of claim 2, wherein the substitution at position 612 is A612V.

4. The T3D$^{PL}$ reovirus of claim 2, further comprising a mutated σ3 protein with a substitution of lysine at position 64 with reference to the amino acid sequence of wild type T3D$^{PL}$ reovirus σ3 protein set forth in SEQ ID NO:4.

5. The T3D$^{PL}$ reovirus of claim 4, wherein the substitution at position 64 is K64E.

6. The T3D$^{PL}$ reovirus of claim 4, further comprising a mutated γ1 protein comprising substitution of alanine at position 962 with reference to the amino acid sequence of wild type T3D$^{PL}$ reovirus γ1 protein set forth in SEQ ID NO: 10.

7. The T3D$^{PL}$ reovirus of claim 6, wherein the substitution at position 962 is A962S.

8. The T3D$^{PL}$ reovirus of claim 6, further comprising a mutated σ1 protein comprising a substitution of serine at position 18 with reference to the amino acid sequence of wild type T3D$^{PL}$ reovirus protein set forth in SEQ ID NO:1.

9. The T3D$^{PL}$ reovirus of claim 8, wherein the substitution at position 18 is S18I.

10. The T3D$^{PL}$ reovirus of claim 1, wherein the T3D$^{PL}$ reovirus is genetically modified to express a T3D$^{PL}$ reovirus σ1 protein comprising the substitution S18I, a T3D$^{PL}$ reovirus σ1 protein comprising the substitution K64E, T3D$^{PL}$ reovirus μ2 protein comprising the substitution A612V, a T3D$^{PL}$ γ2 protein comprising the substitution I1274T, and a T3D$^{PL}$ γ1 protein comprising the substitution A962S.

11. The T3D$^{PL}$ reovirus of claim 10, further expressing a T3D$^{PL}$ reovirus σ3 protein comprising a substitution of T249.

12. The T3D$^{PL}$ reovirus of claim 11, wherein the substitution is T249I or T249L.

* * * * *